(12) United States Patent
Nakashima et al.

(10) Patent No.: US 9,101,140 B2
(45) Date of Patent: Aug. 11, 2015

(54) CYCLOHEXANONE COMPOUNDS AND HERBICIDES COMPRISING THE SAME

(75) Inventors: Yosuke Nakashima, Takarazuka (JP); Yoshinobu Jin, Kasai (JP); Masato Konobe, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 2 days.

(21) Appl. No.: 14/117,159

(22) PCT Filed: May 29, 2012

(86) PCT No.: PCT/JP2012/064349
§ 371 (c)(1),
(2), (4) Date: Nov. 12, 2013

(87) PCT Pub. No.: WO2012/165648
PCT Pub. Date: Dec. 6, 2012

(65) Prior Publication Data
US 2014/0228219 A1   Aug. 14, 2014

(30) Foreign Application Priority Data

May 30, 2011 (JP) ................................. 2011-120029
Dec. 20, 2011 (JP) ................................. 2011-277955

(51) Int. Cl.
| | | |
|---|---|---|
| *A01N 43/647* | (2006.01) | |
| *A01N 43/40* | (2006.01) | |
| *A01N 31/16* | (2006.01) | |
| *A01N 43/54* | (2006.01) | |
| *A01N 43/08* | (2006.01) | |
| *A01N 33/08* | (2006.01) | |
| *A01N 43/60* | (2006.01) | |
| *A01N 43/58* | (2006.01) | |
| *A01N 43/10* | (2006.01) | |
| *A01N 43/78* | (2006.01) | |
| *A01N 37/34* | (2006.01) | |

(Continued)

(52) U.S. Cl.
CPC .............. *A01N 43/647* (2013.01); *A01N 31/16* (2013.01); *A01N 33/08* (2013.01); *A01N 35/06* (2013.01); *A01N 37/02* (2013.01); *A01N 37/10* (2013.01); *A01N 37/24* (2013.01); *A01N 37/34* (2013.01); *A01N 41/04* (2013.01); *A01N 41/06* (2013.01); *A01N 41/10* (2013.01); *A01N 43/08* (2013.01); *A01N 43/10* (2013.01); *A01N 43/40* (2013.01); *A01N 43/54* (2013.01); *A01N 43/56* (2013.01); *A01N 43/58* (2013.01); *A01N 43/60* (2013.01); *A01N 43/78* (2013.01); *A01N 47/06* (2013.01); *C07C 49/747* (2013.01); *C07C 49/753* (2013.01); *C07C 69/157* (2013.01); *C07C 69/16* (2013.01); *C07C 69/24* (2013.01); *C07C 69/28* (2013.01); *C07C 317/24* (2013.01); *C07C 317/40* (2013.01); *C07C 323/22* (2013.01); *C07C 323/36* (2013.01); *C07C 323/42* (2013.01); *C07D 213/70* (2013.01); *C07D 237/18* (2013.01); *C07D 239/38* (2013.01); *C07D 241/18* (2013.01); *C07D 249/06* (2013.01); *C07D 277/36* (2013.01); *C07D 307/68* (2013.01); *C07D 333/34* (2013.01); *C07C 2101/02* (2013.01); *C07C 2101/16* (2013.01)

(58) Field of Classification Search
None
See application file for complete search history.

(56) References Cited

U.S. PATENT DOCUMENTS

| | | | |
|---|---|---|---|
| 4,209,532 A | 6/1980 | Wheeler | |
| 4,303,669 A | 12/1981 | D'Silva | |

(Continued)

FOREIGN PATENT DOCUMENTS

| | | |
|---|---|---|
| WO | 01/17972 A2 | 3/2001 |
| WO | 01/17972 A3 | 3/2001 |

(Continued)

OTHER PUBLICATIONS

International Search Report issued Sep. 20, 2012 in International (PCT) Application No. PCT/JP2012/064349.

(Continued)

*Primary Examiner* — Mina Haghighatian
*Assistant Examiner* — Erin Hirt
(74) *Attorney, Agent, or Firm* — Wenderoth, Lind & Ponack, L.L.P.

(57) ABSTRACT

The present invention provides a compound having an excellent efficacy for controlling weeds. A cyclohexanone compound of the formula (I): wherein m is an integer of 1, 2 or 3; n is an integer of any one of 1 to 5; X represents $CH_2$, O, S, S(O) or $S(O)_2$; $R^1$ represents a hydrogen atom or a methyl group; $R^2$ and $R^3$ represents a hydrogen atom, a $C_{1-6}$ alkyl group and the like; $R^4$ represents a $C_{6-10}$ aryl group or a five- to six-membered heteroaryl group; G represents a hydrogen atom and the like; Z represents a halogen atom, a cyano group, a nitro group, a phenyl group, a $C_{1-6}$ alkyl group and the like; is useful as an active ingredient for herbicides.

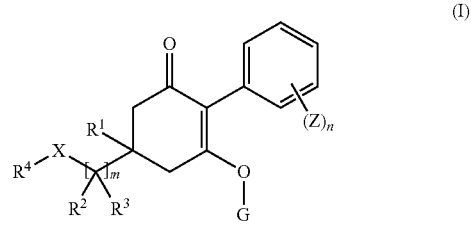

(I)

9 Claims, No Drawings

(51) Int. Cl.

| | | |
|---|---|---|
| *A01N 37/02* | (2006.01) | |
| *A01N 47/06* | (2006.01) | |
| *A01N 41/04* | (2006.01) | |
| *A01N 37/24* | (2006.01) | |
| *A01N 41/06* | (2006.01) | |
| *A01N 35/06* | (2006.01) | |
| *C07C 49/747* | (2006.01) | |
| *C07C 317/24* | (2006.01) | |
| *C07C 317/40* | (2006.01) | |
| *C07C 323/22* | (2006.01) | |
| *C07C 323/36* | (2006.01) | |
| *C07C 323/42* | (2006.01) | |
| *C07D 213/70* | (2006.01) | |
| *C07D 237/18* | (2006.01) | |
| *C07D 239/38* | (2006.01) | |
| *C07D 241/18* | (2006.01) | |
| *C07D 249/06* | (2006.01) | |
| *C07D 277/36* | (2006.01) | |
| *C07D 307/68* | (2006.01) | |
| *C07D 333/34* | (2006.01) | |
| *C07C 49/753* | (2006.01) | |
| *C07C 69/157* | (2006.01) | |
| *C07C 69/16* | (2006.01) | |
| *C07C 69/24* | (2006.01) | |
| *C07C 69/28* | (2006.01) | |
| *A01N 37/10* | (2006.01) | |
| *A01N 41/10* | (2006.01) | |
| *A01N 43/56* | (2006.01) | |

(56) References Cited

U.S. PATENT DOCUMENTS

| | | |
|---|---|---|
| 4,351,666 A | 9/1982 | Koerwer |
| 4,409,513 A | 10/1983 | D'Amato |
| 4,422,870 A * | 12/1983 | Wheeler ............... 504/313 |
| 4,659,372 A | 4/1987 | Wheeler |
| 6,894,005 B1 | 5/2005 | Maetzke et al. |
| 7,459,414 B2 | 12/2008 | Maetzke et al. |
| 7,605,111 B2 | 10/2009 | Maetzke et al. |
| 2005/0164883 A1 | 7/2005 | Maetzke et al. |
| 2005/0187110 A1 | 8/2005 | Maetzke et al. |

FOREIGN PATENT DOCUMENTS

| | | |
|---|---|---|
| WO | 03/059065 | 7/2003 |
| WO | 2008/110308 A2 | 9/2008 |
| WO | 2008/110308 A3 | 9/2008 |
| WO | 2010/046194 | 4/2010 |
| WO | 2010/081689 | 7/2010 |

OTHER PUBLICATIONS

International Preliminary Report on Patentability issued Dec. 2, 2013 and Written Opinion of the International Searching Authority issued Sep. 20, 2012 in International (PCT) Application No. PCT/JP2012/064349.

* cited by examiner

CYCLOHEXANONE COMPOUNDS AND HERBICIDES COMPRISING THE SAME

TECHNICAL FIELD

The present invention relates to cyclohexanone compounds and herbicides comprising the same.

BACKGROUND ART

Heretofore, some compounds that are useful as active ingredients in herbicides for controlling weeds have been widely developed and some compounds having an efficacy for controlling weeds have been found.

Some cyclohexanone compounds having herbicidal activity have been known (see e.g. U.S. Pat. No. 4,209,532, U.S. Pat. No. 4,303,669, U.S. Pat. No. 4,351,666, U.S. Pat. No. 4,409,513, U.S. Pat. No. 4,659,372, WO 2001/017972, WO 2003/059065, WO 2008/110308, WO 2010/046194 pamphlet).

DISCLOSURE of INVENTION

Problems to be Solved by Invention

An object of the present invention is to provide a compound having an excellent efficacy for controlling weeds.

Means to Solve Problems

The present inventors have intensively studied to find that cyclohexanone compounds of the following formula (I) (hereinafter, sometimes referred to as "the present compound") have an excellent efficacy for controlling weeds, which thus have completed the present invention.

Specifically, the present invention includes:
[1] A cyclohexanone compound of the formula (I):

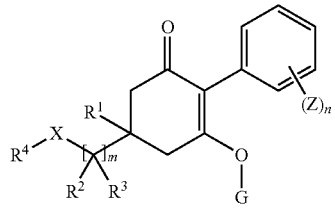

(I)

wherein
m is an integer of 1, 2 or 3;
n is an integer of any one of 1 to 5;
X represents $CH_2$, O, $NR^9$, S, S(O) or $S(O)_2$;
$R^1$ represents a hydrogen atom or a methyl group;
$R^2$ and $R^3$ represent independently of each other a hydrogen atom, a $C_{1-6}$ alkyl group, a $C_{1-6}$ haloalkyl group, a $C_{3-8}$ cycloalkyl group, a $C_{3-8}$ halocycloalkyl group, a $(C_{1-6}$ alkyl)$C_{3-8}$ cycloalkyl group, a $(C_{3-8}$ cycloalkyl)$C_{1-6}$ alkyl group, a $(C_{3-8}$ cycloalkyl)$C_{3-8}$ cycloalkyl group, a $(C_{3-8}$ halocycloalkyl)$C_{1-6}$ alkyl group or a $\{(C_{1-6}$ alkyl)$C_{3-8}$ cycloalkyl$\}C_{1-6}$ alkyl group, or $R^2$ and $R^3$ connect each other to represent a $C_{2-5}$ alkylene chain, or $R^2$ and $R^3$ combine each other to represent a $C_{1-3}$ alkylidene group optionally having one or more halogen atoms (with the proviso that when m is 2 or 3, two or three $R^2$ may be same or different to each other and two or three $R^3$ may be same or different to each other);

$R^4$ represents a $C_{6-10}$ aryl group or a five- to six-membered heteroaryl group (with the proviso that the $C_{6-10}$ aryl group and the five- or six-membered heteroaryl group may have one or more substituents selected from the group consisting of a halogen atom, a cyano group, a nitro group, an amino group, a $(C_{1-6}$ alkyl)amino group, a $(C_{1-6}$ alkyl)$(C_{1-6}$ alkyl)amino group, a benzoylamino group, an aminocarbonyl group, a $(C_{1-6}$ alkyl)aminocarbonyl group, a $(C_{1-6}$ alkyl)$(C_{1-6}$ alkyl)aminocarbonyl group, a pentafluorothio group, a $C_{1-6}$ alkyl group, a $C_{2-6}$ alkenyl group, a $C_{2-6}$ alkynyl group, a $C_{1-6}$ alkoxy group, a $C_{2-6}$ alkylthio group, a $C_{3-6}$ alkenyloxy group, a $C_{3-6}$ alkynyloxy group, a $C_{6-10}$ aryl group, a $C_{6-10}$ aryloxy group, a $C_{1-6}$ alkylsulfinyl group, a $C_{1-6}$ alkylsulfonyl group, a hydroxyl group, a $(C_{1-6}$ alkyl)carbonyl group, a hydroxycarbonyl group, a $(C_{1-6}$ alkoxy)carbonyl group and a $(C_{6-10}$ aryl) $C_{1-6}$ alkoxy group, and when two or more substituents exist, the substituents may be same or different to each other; and the $(C_{1-6}$ alkyl)amino group, the $(C_{1-6}$ alkyl)$(C_{1-6}$ alkyl) amino group, the benzoylamino group, the $(C_{1-6}$ alkyl)aminocarbonyl group, the $(C_{1-6}$ alkyl)$(C_{1-6}$ alkyl)aminocarbonyl group, the $C_{1-6}$ alkyl group, the $C_{2-6}$ alkenyl group, the $C_{2-6}$ alkynyl group, the $C_{1-6}$ alkoxy group, the $C_{1-6}$ alkylthio group, the $C_{3-6}$ alkenyloxy group, the $C_{3-6}$ alkynyloxy group, the $C_{6-10}$ aryl group, the $C_{6-10}$ aryloxy group, the $C_{1-6}$ alkylsulfinyl group, the $C_{1-6}$ alkylsulfonyl group, the $(C_{1-6}$ alkoxy) carbonyl group and the $(C_{6-10}$ aryl)$C_{1-6}$ alkoxy group may each have one or more halogen atoms or $C_{1-3}$ haloalkyl groups, and when two or more halogen atoms or $C_{1-3}$ haloalkyl groups exist, the halogen atoms or the $C_{1-3}$ haloalkyl groups may be same or different to each other respectively);

G represents a hydrogen atom or a group of any one of the following formulae:

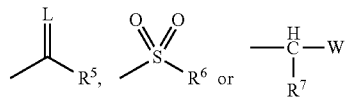

{wherein
L represents an oxygen atom or a sulfur atom;
$R^5$ represents a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a $(C_{6-10}$ aryl) $C_{1-6}$ alkyl group, a $C_{1-6}$ alkoxy group, a $C_{3-8}$ cycloalkoxy group, a $C_{3-6}$ alkenyloxy group, a $C_{3-6}$ alkynyloxy group, a $C_{6-10}$ aryloxy group, a $(C_{6-10}$ aryl)$C_{1-6}$ alkoxy group, a $(C_{1-6}$ alkyl)$(C_{1-6}$ alkyl)amino group, a $(C_{3-6}$ alkenyl) $(C_{3-6}$ alkenyl)amino group, a $(C_{1-6}$ alkyl)$(C_{6-10}$ aryl)amino group or a five- to six-membered heteroaryl group (with the proviso that these groups may each one or more halogen atoms, and when two or more halogen atoms exist, the halogen atoms may be same or different to each other; and the $C_{3-8}$ cycloalkyl group, the $C_{6-10}$ aryl group, an aryl moiety of the $(C_{6-10}$ aryl)$C_{1-6}$ alkyl group, a $C_{3-8}$ cycloalkoxy group, a $C_{6-10}$ aryloxy group, an aryl moiety of the $(C_{6-10}$ aryl)$C_{1-6}$ alkoxy group, an aryl moiety of the $(C_{1-6}$ alkyl)$(C_{6-10}$ aryl)amino group and a five- to six-membered heteroaryl group may each have one or more $C_{1-6}$ alkyl groups, and when two or more $C_{1-6}$ alkyl groups exist, the alkyl groups may be same or different to each other);

$R^6$ represents a $C_{1-6}$ alkyl group, a $C_{6-10}$ aryl group or a $(C_{1-6}$ alkyl)$(C_{1-6}$ alkyl)amino group (with the proviso that these groups may each have one or more halogen atoms and when two or more halogen atoms exist, the halogen atoms may be same or different to each other; and the $C_{6-10}$ aryl group may have one or more $C_{1-6}$ alkyl groups and when two or more $C_{1-6}$ alkyl groups exist, the alkyl groups may be same or different to each other);

$R^7$ represents a hydrogen atom or a $C_{1-6}$ alkyl group;

W represents a $C_{1-6}$ alkoxy group, a $C_{1-6}$ alkylthio group, a $C_{1-6}$ alkylsulfinyl group or a $C_{1-6}$ alkylsulfonyl group (with the proviso that these groups may each have one or more halogen atoms and when two or more halogen atoms exist, the halogen atoms may be same or different to each other)};

$R^9$ represents a hydrogen atom, a $C_{1-6}$ alkyl group, a $C_{6-10}$ aryl group, a $C_{6-10}$ arylthio group, a $C_{6-10}$ arylsulfinyl group, a $C_{6-10}$ arylsulfonyl group (with the proviso that the $C_{1-6}$ alkyl group may have one or more halogen atoms, and when two or more halogen atoms exist, the halogen atoms may be same or different to each other; the $C_{6-10}$ aryl group, the $C_{6-10}$ arylthio group, the $C_{6-10}$ arylsulfinyl group and the $C_{6-10}$ arylsulfonyl group may have one or more substituents selected from the group consisting of a halogen atom, a cyano group, a nitro group and an amino group);

Z represents a halogen atom, a cyano group, a nitro group, a $C_{1-6}$ alkyl group, a $C_{2-6}$ alkenyl group, a $C_{2-6}$ alkynyl group, a $C_{1-6}$ alkoxy group, a ($C_{1-6}$ alkyl)carbonyl group, a $C_{1-6}$ alkylthio group, a $C_{6-10}$ aryloxy group, a five- or six-membered heteroaryloxy group, a $C_{3-8}$ cycloalkyl group, a $C_{6-10}$ aryl group or a five- to six-membered heteroaryl group (with the proviso that the $C_{1-6}$ alkyl group, the $C_{2-6}$ alkenyl group, the $C_{2-6}$ alkynyl group, the $C_{1-6}$ alkoxy group, the ($C_{1-6}$ alkyl) carbonyl group and the $C_{1-6}$ alkylthio group may each have one or more halogen atoms, and when two or more halogen atoms exist, the halogen atoms may be same or different to each other; and the $C_{6-10}$ aryl group, a five- to six-membered heteroaryl group, a $C_{6-10}$ aryloxy group and the five- to six-membered heteroaryloxy group may each have one or more substituents selected from the group consisting of a halogen atom, a $C_{1-6}$ alkyl group and a $C_{1-6}$ haloalkyl group, and when two or more substituents exist, the substituents may be same or different to each other; and the $C_{3-8}$ cycloalkyl group may have one or more substituents selected from the group consisting of a halogen atom and a $C_{1-6}$ alkyl group, and when two or more substituents exist, the substituents may be same or different to each other; when n is an integer of 2 or more, Z may be same or different to each other).

[2] The cyclohexanone compound of [1] wherein n is an integer of any one of 1 to 3;

X represents $CH_2$, O, $NR^9$, S, S(O) or $S(O)_2$;

$R^1$ represents a hydrogen atom;

$R^2$ and $R^3$ represent independently of each other a hydrogen atom or a $C_{1-3}$ alkyl group, or $R^2$ and $R^3$ connect each other to represent a $C_{2-5}$ alkylene chain (with the proviso that when m is 2 or 3, two or three $R^2$ may be same or different to each other and two or three $R^3$ may be same or different to each other);

$R^4$ represents a phenyl group, a 2-pyridyl group, a 3-pyridyl group, a 4-pyridyl group, a 2-pyrimidinyl group, a 2-pyrazinyl group, a 3-pyridazinyl group, a 3-furyl group, a 2-thienyl group, a 2-thiazolyl group or a 1,2,3-triazolyl group (with the proviso that the phenyl group, the 2-pyridyl group, the 3-pyridyl group, the 4-pyridyl group, the 2-pyrimidinyl group, the 2-pyrazinyl group, the 3-pyridazinyl group, the 3-furyl group, the 2-thienyl group and the 2-thiazolyl group may each have one or more substituents selected from the group consisting of a halogen atom, a $C_{1-3}$ alkyl group, a hydroxyl group, a ($C_{1-3}$ alkyl)carbonyl group, a ($C_{1-3}$ alkoxy) carbonyl group, a $C_{1-3}$ alkoxy group, a $C_{1-3}$ haloalkyl group, a $C_{1-3}$ alkylthio group, a $C_{1-3}$ haloalkylthio group, a cyano group, a nitro group, an amino group, a pentafluorothio group, a benzoylamino group and a $C_{1-3}$ haloalkoxy group, and when two or more substituents exist, the substituents may be same or different to each other; and the 1,2,3-triazolyl group may be substituted with $C_{6-10}$ aryl group and the $C_{6-10}$ aryl group may have one or more halogen atoms or $C_{1-3}$ haloalkyl groups, and when two or more halogen atoms or $C_{1-3}$ haloalkyl groups exist, the halogen atoms or the $C_{1-3}$ haloalkyl groups may be same or different respectively);

G represents a hydrogen atom or a group of any one of the following formulae:

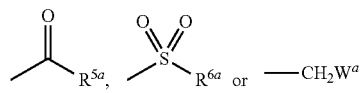

{wherein $R^{5a}$ represents a $C_{1-6}$ alkyl group, a $C_{6-10}$ aryl group, a $C_{1-6}$ alkoxy group, a $C_{3-6}$ alkenyloxy group, a $C_{3-6}$ alkynyloxy group or a $C_{6-10}$ aryloxy group;

$R^{6a}$ represents a $C_{1-6}$ alkyl group;

$W^a$ represents a $C_{1-3}$ alkoxy group};

$R^9$ represents a hydrogen atom, a $C_{1-6}$ alkyl group or a $C_{6-10}$ arylsulfonyl group (with the proviso that the $C_{1-6}$ alkyl group may have one or more halogen atoms, and when two or more halogen atoms exist, the halogen atoms may be same or different to each other; and the $C_{6-10}$ arylsulfonyl group may have one or more substituents selected from the group consisting of a halogen atom and a nitro group, and when two or more substituents exist, the substituents may be same or different to each other);

Z represents a halogen atom, a $C_{1-3}$ alkyl group, a $C_{2-6}$ alkenyl group, a $C_{2-6}$ alkynyl group, a $C_{1-3}$ alkoxy group, a $C_{3-8}$ cycloalkyl group, a nitro group, a phenyl group or a five- to six-membered heteroaryloxy group (with the proviso that the $C_{1-3}$ alkyl group, the $C_{2-6}$ alkenyl group, the $C_{2-6}$ alkynyl group, the $C_{1-3}$ alkoxy group, the phenyl group and the five- to six-membered heteroaryloxy group may have one or more halogen atoms, and when two or more halogen atoms exist, the halogen atoms may be same or different to each other.

[3] The cyclohexanone compound of [2] wherein m is 2;

X represents $CH_2$, O, $NR^9$, S, S(O) or $S(O)_2$;

$R^2$ and $R^3$ represents independently of each other a hydrogen atom, a methyl group or an ethyl group, or $R^2$ and $R^3$ connect each other to represent an ethylene chain (with the proviso that two $R^2$ may be same or different to each other and two $R^3$ may be same or different to each other);

$R^4$ represents a phenyl group, a 2-pyridyl group, a 3-pyridyl group, a 4-pyridyl group, a 2-pyrimidinyl group, a 2-pyrazinyl group, a 3-pyridazinyl group, a 3-furyl group, a 2-thienyl group, a 2-thiazolyl group or a 1,2,3-triazolyl group (with the proviso that the phenyl group, the 2-pyridyl group, the 3-pyridyl group, the 4-pyridyl group, the 2-pyrimidinyl group, the 2-pyrazinyl group, the 3-pyridazinyl group, the 3-furyl group, the 2-thienyl group and the 2-thiazolyl group have each one or more substituents selected from the group consisting of a chlorine atom, a bromine atom, an iodine atom, a fluorine atom, a methyl group, an ethyl group, an isopropyl group, a tert-butyl group, a methoxy group, a nitro group, an amino group, a cyano group, a hydroxyl group, an acetyl group, a methoxycarbonyl group, a pentafluorothio group, a pentafluoroethyl group, a difluoroethyl group, a heptafluoroisopropyl group, a trifluoromethylthio group, a benzoylamino group, a trifluoromethoxy group and a trifluoromethyl group; and the 1,2,3-triazolyl group may be substituted with a phenyl group, and the phenyl group has one or more substituents selected from the group consisting of a chlorine atom, a bromine atom, an iodine atom, a fluorine atom and a trifluoromethyl group);

G represents a hydrogen atom, an acetyl group, a propionyl group, a butyryl group, a benzoyl group, a methylsulfonyl group, a methoxycarbonyl group, an ethoxycarbonyl group, an allyloxycarbonyl group, a phenoxycarbonyl group, a methoxymethyl group or an ethoxymethyl group;

$R^9$ represents a hydrogen atom, a 2-nitrophenylsulfonyl group or a methyl group;

Z represents a methyl group, an ethyl group, a phenyl group, a vinyl group, a cyclopropyl group, a nitro group, a fluorine atom, a chlorine atom, a bromine atom, a methoxy group, a trifluoromethyl group, a 5-trifluoromethyl-2-chloropyridyloxy group or an ethynyl group.

[4] A cyclohexanone compound of the formula (II):

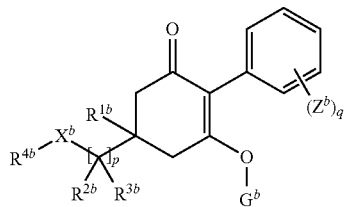

(II)

wherein p is an integer of 1, 2 or 3;

q is an integer of any one of 1 to 5;

$X^b$ represents $CH_2$, O, S, S(O) or $S(O)_2$;

$R^{1b}$ represents a hydrogen atom or a methyl group;

$R^{2b}$ and $R^{3b}$ represent independently of each other a hydrogen atom, a $C_{1-6}$ alkyl group, a $C_{1-6}$ haloalkyl group, a $C_{3-8}$ cycloalkyl group, a $C_{3-8}$ halocycloalkyl group, a ($C_{1-6}$ alkyl) $C_{3-8}$ cycloalkyl group, a ($C_{3-8}$ cycloalkyl) $C_{1-6}$ alkyl group, a ($C_{3-8}$ cycloalkyl) $C_{3-8}$ cycloalkyl group, a ($C_{3-8}$ halocycloalkyl) $C_{1-6}$ alkyl group or a {($C_{1-6}$ alkyl) $C_{3-8}$ cycloalkyl}$C_{1-6}$ alkyl group, or $R^{2b}$ and $R^{3b}$ connect each other to represent a $C_{2-5}$ alkylene chain, or $R^{2b}$ and $R^{3b}$ combine each other to represent a $C_{1-3}$ alkylidene group optionally having one or more halogen atoms (with the proviso that when p is 2 or 3, two or three $R^{2b}$ may be same or different to each other and $R^{3b}$ may be same or different to each other);

$R^{4b}$ represents a $C_{6-10}$ aryl group or a five- to six-membered heteroaryl group (with the proviso that the $C_{6-10}$ aryl group and the five- to six-membered heteroaryl group may have one or more substituents selected from the group consisting of a halogen atom, a cyano group, a nitro group, a pentafluorothio group, a $C_{1-6}$ alkyl group, a $C_{2-6}$ alkenyl group, a $C_{2-6}$ alkynyl group, a $C_{1-6}$ alkoxy group, a $C_{1-6}$ alkylthio group, a $C_{3-6}$ alkenyloxy group, a $C_{3-6}$ alkynyloxy group and a ($C_{6-10}$ aryl) $C_{1-6}$ alkoxy group, and when two or more substituents exist, the substituents may be same or different to each other; and the $C_{1-6}$ alkyl group, the $C_{2-6}$ alkenyl group, the $C_{2-6}$ alkynyl group, the $C_{1-6}$ alkoxy group, the $C_{1-6}$ alkylthio group, the $C_{3-6}$ alkenyloxy group, the $C_{3-6}$ alkynyloxy group and the ($C_{6-10}$ aryl) $C_{1-6}$ alkoxy group may have one or more halogen atoms, and when two or more halogen atoms exist, the halogen atoms may be same or different to each other);

$G^b$ represents a hydrogen atom or a group of any one of the following formulae:

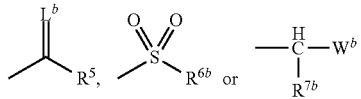

{wherein $L^b$ represents an oxygen atom or a sulfur atom;

$R^{5b}$ represents a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a ($C_{6-10}$ aryl) $C_{1-6}$ alkyl group, a $C_{1-6}$ alkoxy group, a $C_{3-8}$ cycloalkoxy group, a. $C_{3-6}$ alkenyloxy group, a $C_{3-6}$ alkynyloxy group, a $C_{6-10}$ aryloxy group, a ($C_{6-10}$ aryl) $C_{1-6}$ alkoxy group, a ($C_{1-6}$ alkyl)($C_{1-6}$ alkyl)amino group, a ($C_{3-6}$ alkenyl)($C_{3-6}$ alkenyl)amino group, a ($C_{1-6}$ alkyl)($C_{6-10}$ aryl)amino group or a five- to six-membered heteroaryl group (with the proviso that these groups may each have one or more halogen atoms, when two or more halogen atoms exist, the halogen atoms may be same or different to each other; and the $C_{3-8}$ cycloalkyl group, the $C_{6-10}$ aryl group, an aryl moiety of the ($C_{6-10}$ aryl) $C_{1-6}$ alkyl group, the $C_{3-8}$ cycloalkoxy group, the $C_{6-10}$ aryloxy group, an aryl moiety of the ($C_{6-10}$ aryl) $C_{1-6}$ alkoxy group, an aryl moiety of the ($C_{1-6}$ alkyl)($C_{6-10}$ aryl) amino group and a five- to six-membered heteroaryl group may each one or more $C_{1-6}$ alkyl groups, and when two or more $C_{1-6}$ alkyl groups exist, the alkyl groups may be same or different to each other);

$R^{6b}$ represents a $C_{1-6}$ alkyl group, a $C_{6-10}$ aryl group or a ($C_{1-6}$ alkyl)($C_{1-6}$ alkyl)amino group (with the proviso that these groups may have one or more halogen atoms, and when two or more halogen atoms exist, the halogen atoms may be same or different to each other; and the $C_{6-10}$ aryl group may have one or more $C_{1-6}$ alkyl groups, and when two or more $C_{1-6}$ alkyl groups exist, the alkyl groups may be same or different to each other);

$R^{7b}$ represents a hydrogen atom or a $C_{1-6}$ alkyl group;

$W^b$ represents a $C_{1-6}$ alkoxy group, a $C_{1-6}$ alkylthio group, a $C_{1-6}$ alkylsulfinyl group or a $C_{1-6}$ alkylsulfonyl group (with the proviso that these groups may each have one or more halogen atoms, and when two or more halogen atoms exist, the halogen atoms may be same or different to each other)};

$Z^b$ represents a halogen atom, a cyano group, a nitro group, a phenyl group, a $C_{1-6}$ alkyl group, a $C_{2-6}$ alkenyl group, a $C_{2-6}$ alkynyl group, a $C_{1-6}$ alkoxy group, a $C_{1-6}$ alkylthio group, a $C_{6-10}$ aryloxy group, a five- to six-membered heteroaryloxy group or a $C_{3-8}$ cycloalkyl group (with the proviso that the $C_{1-6}$ alkyl group, the $C_{2-6}$ alkenyl group, the $C_{2-6}$ alkynyl group, the $C_{1-6}$ alkoxy group and the $C_{1-6}$ alkylthio group may have one or more halogen atoms, and when two or more halogen atoms exist, the halogen atoms may be same or different to each other; and the phenyl group, the $C_{6-10}$ aryloxy group and the five- to six-membered heteroaryloxy group may have one or more substituents selected from the group consisting of a halogen atom, a $C_{1-6}$ alkyl group and a $C_{1-6}$ haloalkyl group, and when two or more substituents exist, the substituents may be same or different to each other; and the $C_{3-8}$ cycloalkyl group may have one or more substituents selected from the group consisting of a halogen atom and a $C_{1-6}$ alkyl group, and when two or more substituents exist, the substituents may be same or different to each other; when q is an integer of 2 or more, $Z^b$ may be same or different to each other).

[5] The cyclohexanone compound of [4] wherein n is an integer of any one of 1 to 3;

$R^{1b}$ represents a hydrogen atom;

$R^{2b}$ and $R^{3b}$ represent independently of each other a hydrogen atom or a $C_{1-3}$ alkyl group (with the proviso that when p is 2 or 3, two or three $R^{2b}$ may be same or different to each other and two or three $R^{3b}$ may be same or different to each other);

$R^{4b}$ represents a phenyl group or a 2-pyridyl group (with the proviso that the phenyl group and the 2-pyridyl group may have one or more substituents selected from the group consisting of a halogen atom, a $C_{1-3}$ alkyl group, a $C_{1-3}$ alkoxy group, a $C_{1-3}$ haloalkyl group, a nitro group, a pentafluorothio group and a $C_{1-3}$ haloalkoxy group, and when two or more substituents exist, the substituents may be same or different to each other;

$G^b$ represents a hydrogen atom or a group of any one of the following formulae:

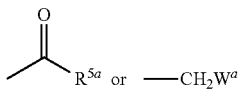

{wherein $R^{5a}$ represents a $C_{1-6}$ alkyl group, a $C_{6-10}$ aryl group, a $C_{1-6}$ alkoxy group, a $C_{3-6}$ alkenyloxy group, a $C_{3-6}$ alkynyloxy group or a $C_{6-10}$ aryloxy group; and $W^a$ represents a $C_{1-3}$ alkoxy group}; and $Z^b$ represents a $C_{1-3}$ alkyl group.

[6] The cyclohexanone compound of [5] wherein p is 2;

$R^{2b}$ and $R^{3b}$ represent independently of each other a hydrogen atom or a methyl group (with the proviso that two $R^{2b}$ may be same or different to each other and two $R^{3b}$ may be same or different to each other);

$R^{4b}$ represents a phenyl group or a 2-pyridyl group (with the proviso that the phenyl group and the 2-pyridyl group have one or more substituents selected from the group consisting of a chlorine atom, a fluorine atom, a methyl group, a methoxy group and a trifluoromethyl group);

$G^b$ represents a hydrogen atom, an acetyl group, a propionyl group, a benzoyl group, a methoxycarbonyl group, an ethoxycarbonyl group, an allyloxycarbonyl group, a phenoxycarbonyl group, a methoxymethyl group or an ethoxymethyl group; and $Z^b$ represents a methyl group or an ethyl group.

[7] The cyclohexanone compound of any one of [1] to [6] wherein G represents a hydrogen atom.

[8] A herbicide comprising a cyclohexanone compound of any one of [1] to [7] as an active ingredient and an inert carrier.

[9] A method for controlling weeds which comprises applying an effective amount of the cyclohexanone compound of any one of [1] to [7] to weeds or soil where weeds grow.

[10] Use of the cyclohexanone compound of any one of [1] to [7] for controlling weeds.

Effect of Invention

The compound of the present invention shows an efficacy for controlling weeds and is therefore useful as an active ingredient for herbicides.

MODE FOR CARRYING OUT THE INVENTION

Hereinafter, the present invention is explained in detail.

The substituent of the present invention is explained.

The "$C_{1-6}$ alkyl group" to be used herein means an alkyl group having 1 to 6 carbon atoms, and includes for example, a methyl group, an ethyl group, a normalpropyl group, an isopropyl group, a normalbutyl group, an isobutyl group, a sec-butyl group, a tert-butyl group, a normalpentyl group, a sec-pentyl group, an isopentyl group, a neopentyl group, a normalhexyl group and an isohexyl group.

The "$C_{1-6}$ haloalkyl group" to be used herein means a $C_{1-6}$ alkyl group substituted with one or more halogen atoms such as a fluorine atom, a chlorine atom, a bromine atom and an iodine atom, and includes for example, a trifluoromethyl group, a chloromethyl group, a 2,2,2-trichloroethyl group, a 2,2,2-trifluoroethyl group and a 2,2,2-trifluoro-1,1-dichloroethyl group.

The "$C_{3-8}$ cycloalkyl group" to be used herein means a cycloalkyl group having 3 to 8 carbon atoms and includes for example, a cyclopropyl group, a cyclopentyl group and a cyclohexyl group.

The "$C_{3-8}$ halocycloalkyl group" to be used herein means a cycloalkyl group having 3 to 8 carbon atoms substituted with one or more halogen atoms such as a fluorine atom, a chlorine atom, a bromine atom and an iodine atom and includes for example, a 2-chlorocyclopropyl group and a 4,4-difluorocyclohexyl group.

The "($C_{1-6}$ alkyl) $C_{3-8}$ cycloalkyl group" to be used herein means a cycloalkyl group having 3 to 8 carbon atoms substituted with an alkyl group having 1 to 6 carbon atoms and includes for example, an ethylcyclopropyl group, an isobutylcyclopropyl group, a 3-methylcyclopentyl group and a 4-methylcyclohexyl group.

The "($C_{3-8}$ cycloalkyl)$C_{1-6}$ alkyl group" to be used herein means an alkyl group having 1 to 6 carbon atoms substituted with a cycloalkyl group having 3 to 8 carbon atoms and includes for example, a cyclopropylmethyl group and a cyclopentylmethyl group.

The "($C_{3-8}$ cycloalkyl)$C_{3-8}$ alkyl group" to be used herein means a cycloalkyl group having 3 to 8 carbon atoms substituted with a cycloalkyl group having 3 to 8 carbon atoms and includes for example, a 2-cyclopropylcyclopropyl group and a 3-cyclopropylcyclopentyl group.

The "($C_{3-8}$ halocycloalkyl)$C_{1-6}$ alkyl group" to be used herein means an alkyl group having 1 to 6 carbon atoms substituted with a (cycloalkyl group having 3 to 8 carbon atoms substituted with one or more halogen atoms such as a fluorine atom, a chlorine atom, a bromine atom and an iodine atom) and includes for example, a 2-chlorocyclopropylmethyl group and a 3-chlorocyclopentylethyl group.

The "{($C_{1-6}$ alkyl)$C_{3-8}$ cycloalkyl}$C_{1-6}$ alkyl group" to be used herein means an alkyl group having 1 to 6 carbon atoms substituted with a (cycloalkyl group having 3 to 8 carbon atoms substituted with an alkyl group having 1 to 6 carbon atoms) and includes for example, a 2-methylcyclopropylmethyl group and a 3-methylcyclopentylmethyl group.

The "$C_{2-5}$ alkylene chain" to be used herein means an alkylene chain having 2 to 5 carbon atoms and includes for example, an ethylene chain, a propylene chain (i.e., a trimethylene chain), a butylene chain (i.e., a tetramethylene chain) and a pentylene chain (i.e., a pentamethylene chain).

When $R^2$ and $R^3$ or $R^{2b}$ and $R^{3b}$ connect each other respectively to represent a $C_{2-5}$ alkylene chain, $R^2$ and $R^3$ combine together with the carbon to which they are attached to form a $C_{3-6}$ cycloalkyl group. Also when $R^2$ and $R^3$ connect each other to represent an ethylene chain, $R^2$ and $R^3$ combine together with the carbon to which they are attached to form a $C_3$ cycloalkyl group, i.e. a cyclopropyl group.

The "$C_{1-3}$ alkylidene chain" to be used herein means an alkylidene chain having 1 to 3 carbon atoms and includes for example, a methylidene group, an ethylidene group and an isopropylidene group.

The "halogen atom" to be used herein includes for example, a fluorine atom, a chlorine atom, a bromine atom and an iodine atom.

The "$C_{2-6}$ alkenyl group" to be used herein means an alkenyl group having 2 to 6 carbon atoms and includes for example, a vinyl group, an allyl group, a 1-butene-3-yl group and a 3-butene-1-yl group.

The "$C_{2-6}$ alkynyl group" to be used herein means an alkynyl group having 2 to 6 carbon atoms and includes for example, an ethynyl group, a propargyl group and a 2-butynyl group.

The "$C_{1-6}$ alkoxy group" to be used herein means an alkoxy group having 1 to 6 carbon atoms and includes for example, a methoxy group, an ethoxy group, a normalpropyloxy group, an isopropyloxy group, a normalbutoxy group, an isobutoxy group, a sec-butoxy group, a tert-butoxy group, a normalpentyloxy group, a sec-pentyloxy group, an isopentyloxy group, a neopentyloxy group, a normalhexyloxy group and an isohexyloxy group.

The "$C_{1-6}$ alkylthio group" to be used herein means an alkylthio group having 1 to 6 carbon atoms and includes for example, a methylthio group, an ethylthio group and an isopropylthio group.

The "$C_{3-6}$ alkenyloxy group" to be used herein means an alkenyloxy group having 3 to 6 carbon atoms and includes for example, an allyloxy group and a 2-butenyloxy group.

The "$C_{3-6}$ alkynyloxy group" to be used herein means an alkynyloxy group having 3 to 6 carbon atoms and includes for example, a propargyloxy group and a 2-butynyloxy group.

The "($C_{6-10}$ aryl)$C_{1-6}$ alkoxy group" to be used herein means an alkoxy group having 1 to 6 carbon atoms substituted with an aryl group having 6 to 10 carbon atoms and includes for example, a benzyloxy group and a phenethyloxy.

The "($C_{6-10}$ aryl)$C_{1-6}$ alkyl group" to be used herein means an alkyl group having 1 to 6 carbon atoms substituted with an aryl group having 6 to 10 carbon atoms and includes for example, a benzyl group and a phenethyl group.

The "$C_{3-8}$ cycloalkoxy group" to be used herein means a cycloalkoxy group having 3 to 8 carbon atoms and includes for example, a cyclopropyloxy group, a cyclopentyloxy group and a cyclohexyloxy group.

The "($C_{1-6}$ alkyl)($C_{1-6}$ alkyl)amino group" to be used herein means an amino group substituted with two alkyl groups having 1 to 6 carbon atoms that may be same or different to each other and includes for example, a dimethylamino group, a diethylamino group and an ethylmethylamino group.

The "($C_{3-6}$ alkenyl)($C_{3-6}$ alkenyl)amino group" to be used herein means an amino group substituted with two alkenyl groups having 3 to 6 carbon atoms that may be same or different to each other and includes for example, a diallylamino group and a di(3-butenyl)amino group.

The "($C_{1-6}$ alkyl)($C_{6-10}$ aryl)amino group" to be used herein means an amino group substituted with an alkyl group having 1 to 6 carbon atoms and a $C_{6-10}$ aryl group and includes for example, a methylphenylamino group and an ethylphenylamino group.

The "$C_{1-6}$ alkylsulfinyl group" to be used herein means an alkylsulfinyl group having 1 to 6 carbon atoms and includes for example, a methylsulfinyl group, an ethylsulfinyl group and an isopropylsulfinyl group.

The "$C_{1-6}$ alkylsulfonyl group" to be used herein means an alkylsulfonyl group having 1 to 6 carbon atoms and includes for example, a methylsulfonyl group, an ethylsulfonyl group and an isopropylsulfonyl group.

The "$C_{6-10}$ aryl group" to be used herein means an aryl group having 6 to 10 carbon atoms and includes for example, a phenyl group and a naphthyl group.

The "five- to six-membered heteroaryl group" to be used herein means an aromatic five- or six-membered heterocyclic group having 1 to 3 heteroatoms selected from a nitrogen atom, an oxygen atom or a sulfur atom and includes for example, a 2-pyridyl group, a 4-pyridyl group, a 3-furyl group, a pyrimidinyl group, a 3-thienyl group and a 1-pyrazolyl group.

The "$C_{6-10}$ aryloxy group" to be used herein means an aryloxy group having 6 to 10 carbon atoms and includes for example, a phenoxy group and a naphthyloxy group.

The "five- to six-membered heteroaryloxy group" to be used herein means an aromatic five- or six-membered heterocyclyloxy group having 1 to 3 heteroatoms selected from a nitrogen atom, an oxygen atom or a sulfur atom and includes for example, a 2-pyridyloxy group and a 3-pyridyloxy group.

The "($C_{1-6}$ alkoxy)carbonyl group" to be used herein means a carbonyl group substituted with an alkoxy group having 1 to 6 carbon atoms and includes for example, a methoxycarbonyl group and an ethoxycarbonyl group.

The "($C_{1-6}$ alkyl)amino group" to be used herein means an amino group substituted with an alkyl group having 1 to 6 carbon atoms and includes for example, a monomethylamino group and a monoethylamino group.

The "($C_{1-6}$ alkyl)aminocarbonyl group" to be used herein means an aminocarbonyl group substituted with an alkyl group having 1 to 6 carbon atoms and includes for example, a monomethylaminocarbonyl group and a monoethylaminocarbonyl group.

The "($C_{1-6}$ alkyl)($C_{1-6}$ alkyl)aminocarbonyl group" to be used herein means an aminocarbonyl group substituted with two alkyl groups having 1 to 6 carbon atoms that may be same or different to each other and includes for example, a dimethylaminocarbonyl group, a diethylaminocarbonyl group and an ethylmethylaminocarbonyl group.

The "($C_{1-6}$ alkyl)carbonyl group" to be used herein means a carbonyl group substituted with an alkyl group having 1 to 6 carbon atoms and includes for example, a methylcarbonyl group, an ethylcarbonyl group and an isopropylcarbonyl group.

The "$C_{6-10}$ arylthio group" to be used herein means an arylthio group having 1 to 6 carbon atoms and includes for example, a phenylthio group and a naphthylthio group.

The "$C_{1-3}$ alkyl group" to be used herein means an alkyl group having 1 to 3 carbon atoms and includes for example, a methyl group, an ethyl group, a normalpropyl group and an isopropyl group.

The "$C_{1-3}$ alkoxy group" to be used herein means an alkoxy group having 1 to 3 carbon atoms and includes for example, a methoxy group, an ethoxy group, a normalpropyloxy group and an isopropyloxy group.

The "$C_{1-3}$ haloalkyl group" to be used herein means a $C_{1-3}$ alkyl group substituted with one or more halogen atoms selected from a fluorine atom, a chlorine atom, a bromine atom or an iodine atom and includes for example, a trifluoromethyl group, a chloromethyl group, a 2,2,2-trichloroethyl group, a 2,2,2-trifluoroethyl group and a 2,2,2-trifluoro-1,1-dichloroethyl group.

The "$C_{1-3}$ haloalkoxy group" to be used herein means a $C_{1-3}$ alkoxy group substituted with one or more halogen atoms selected from a fluorine atom, a chlorine atom, a bromine atom or an iodine atom and includes for example, a trifluoromethoxy group, a 2,2,2-trichloroethoxy group, a 3,3-difluoropropyloxy group and a 2,2,2-trifluoroethoxy group.

The "$C_{1-3}$ haloalkylthio group" to be used herein means a $C_{1-3}$ alkylthio group substituted with one or more halogen atoms selected from a fluorine atom, a chlorine atom, a bromine atom or an iodine atom and includes for example, a trifluoromethylthio group, a chloromethylthio group, a 2,2,2-trichloroethylthio group, a 2,2,2-trifluoroethylthio group and a 2,2,2-trifluoro-1,1-dichloroethylthio group.

For the present compound, the cyclohexanone compounds of the formula (I) and (II) may form agronomically acceptable salts with inorganic bases or organic bases and the present invention may encompass the salt forms of the cyclohexanone compound. The salt includes for example, salts that are formed by mixing the compound with inorganic bases (for example, hydroxides, carbonates, hydrogen carbonates, acetates or hydrides of alkali metals (for example, lithium, sodium and potassium)), hydroxides or hydrides of alkaline-earth metals (for example, magnesium, calcium and barium) and ammonia), organic bases (for example, dimethylamine, triethylamine, piperazine, pyrrolidine, piperidine, 2-phenylethylamine, benzylamine, ethanolamine, diethanolamine, pyridine and collidine) or metal alkoxides (for example, sodium methoxide, potassium tert-butoxide and magnesium methoxide).

When the present compound has one or more asymmetric centers, two or more stereoisomers (for example, enantiomer and diastereomer) may exist. The present compound may encompass all these stereoisomers and a mixture of two or more arbitrary stereoisomers.

Also when the present compound contains geometric isomers due to a double bond and the like, two or more geometric isomers (for example, each E/Z or trans/cis isomer, each S-trans/S-cis isomer and the others) may exist. The present compound may encompass all these geometric isomers and a mixture of two or more arbitrary geometric isomers.

As an embodiment of the present compound, the following compounds are included for example.
a compound wherein m is 2;
a compound wherein n is 3;
a compound wherein m is 2 and n is 3;
a compound wherein X is S;
a compound wherein $R^2$ is a hydrogen atom;
a compound wherein $R^3$ is a hydrogen atom;
a compound wherein a moiety represented by the formula:

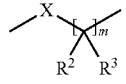

in the formula (I) represents —S—CH$_2$CH$_2$—, —S—CH$_2$CH(CH$_3$)—, —S—CH(CH$_3$)CH$_2$—, —O—CH$_2$CH$_2$—, —CH$_2$—CH$_2$CH$_2$—, —S(O)—CH$_2$CH$_2$—, —S(O)—CH$_2$CH(CH$_3$)—, —S(O)$_2$—CH$_2$CH$_2$—, —S(O)$_2$—CH$_2$CH(CH$_3$)—, —S—CH$_2$C(CH$_3$)$_2$—, —S—CH$_2$C (cyclopropyl)-, —S—CH$_2$CH(C$_2$H$_5$)—, —S—CH$_2$—, —S—CH$_2$CH$_2$CH$_2$—, —N(CH$_3$)—CH$_2$CH(CH$_3$)— or —N(CH$_3$)—CH$_2$CH$_2$—;

a compound wherein $R^4$ represents a phenyl group, a 2-pyridyl group, a 3-pyridyl group, a 4-pyridyl group, a 2-pyrimidinyl group, a 2-pyrazinyl group, a 3-pyridazinyl group or a 3-furyl group;

a compound wherein Z is a phenyl group or a $C_{1-6}$ alkyl group optionally having one or more halogen atoms;

a cyclohexanone compound wherein
m is an integer of 1, 2 or 3;
n is an integer of 1, 2 or 3;
X represents CH$_2$, O, S, S(O), S(O)$_2$ or N(CH$_3$);
$R^1$ represents a hydrogen atom;
$R^2$ and $R^3$ represent independently of each other a hydrogen atom or a $C_{1-6}$ alkyl group, or $R^2$ and $R^3$ connect each other to represent a $C_{2-5}$ alkylene chain;
$R^4$ represents a $C_{6-10}$ aryl group or a five- to six-membered heteroaryl group (with the proviso that the $C_{6-10}$ aryl group and the five- to six-membered heteroaryl group may have one or more substituents selected from the group consisting of a halogen atom, a cyano group, a nitro group, a pentafluorothio group, a $C_{1-6}$ alkyl group and a $C_{1-6}$ alkoxy group, and two or more substituents exist, the substituents may be same or different to each other), and the $C_{1-6}$ alkyl group and the $C_{1-6}$ alkoxy group may have one or more halogen atoms);
G represents a hydrogen atom or a group of any one of the following formulae:

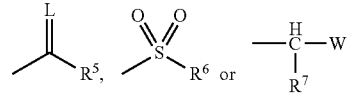

{wherein
L represents an oxygen atom;
$R^5$ represents a $C_{1-6}$ alkyl group, a $C_{1-6}$ alkoxy group, a $C_{3-6}$ alkenyloxy group or a $C_{6-10}$ aryloxy group;
$R^6$ represents a $C_{1-6}$ alkyl group;
$R^7$ represents a hydrogen atom;
W represents a $C_{1-6}$ alkoxy group};
Z represents a halogen atom, a phenyl group, a $C_{1-6}$ alkyl group, a $C_{2-6}$ alkenyl group, a $C_{2-6}$ alkynyl group or a six membered heteroaryloxy group (with the proviso that the phenyl group and the six membered heteroaryloxy group may have one or more substituents selected from the group consisting of a halogen atom and a $C_{1-6}$ haloalkyl group, and two or more substituents exist, the substituent may be same or different to each other)];
[1-1] a cyclohexanone compound of the formula (I):

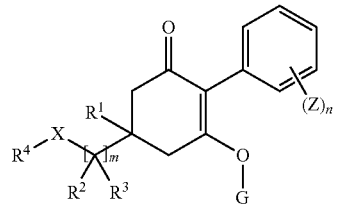

wherein
m is an integer of 1, 2 or 3;
n is an integer of any one of 1 to 5;
X represents CH$_2$, O, NR$^9$, S, S(O) or S(O)$_2$;
$R^1$ represents a hydrogen atom or a methyl group;
$R^2$ and $R^3$ represent independently of each other a hydrogen atom, a $C_{1-6}$ alkyl group, a $C_{1-6}$ haloalkyl group, a $C_{3-8}$ cycloalkyl group, a $C_{3-8}$ halocycloalkyl group, a ($C_{1-6}$ alkyl) $C_{3-8}$ cycloalkyl group, a ($C_{3-8}$ cycloalkyl) $C_{1-6}$ alkyl group, a ($C_{3-8}$ cycloalkyl) $C_{3-8}$ cycloalkyl group, a ($C_{3-8}$ halocycloalkyl) $C_{1-6}$ alkyl group or a {($C_{1-6}$ alkyl) $C_{3-8}$ cycloalkyl}$C_{1-6}$ alkyl group, or $R^2$ and $R^3$ connect each other to represent a $C_{2-5}$ alkylene chain, or $R^2$ and $R^3$ combine each other to represent a $C_{1-3}$ alkylidene group optionally having one or more halogen atoms (with the proviso that when m is 2 or 3, two or three $R^2$ may be same or different to each other and two or three $R^3$ may be same or different to each other);

$R^4$ represents a $C_{6-10}$ aryl group or a five- to six-membered heteroaryl group (with the proviso that the $C_{6-10}$ aryl group and the five- or six-membered heteroaryl group may have one or more substituents selected from the group consisting of a halogen atom, a cyano group, a nitro group, an amino group, a ($C_{1-6}$ alkyl)amino group, a ($C_{1-6}$ alkyl)($C_{1-6}$ alkyl)amino group, a benzoylamino group, an aminocarbonyl group, a ($C_{1-6}$ alkyl)aminocarbonyl group, a ($C_{1-6}$ alkyl)($C_{1-6}$ alkyl)aminocarbonyl group, a pentafluorothio group, a $C_{1-6}$ alkyl group, a $C_{2-6}$ alkenyl group, a $C_{2-6}$ alkynyl group, a $C_{1-6}$ alkoxy group, a $C_{1-6}$ alkylthio group, a $C_{3-6}$ alkenyloxy group, a $C_{3-6}$ alkynyloxy group, a $C_{6-10}$ aryl group, a $C_{6-10}$ aryloxy group, a $C_{1-6}$ alkylsulfinyl group, a $C_{1-6}$ alkylsulfonyl group, a hydroxycarbonyl group, a ($C_{1-6}$ alkoxy)carbonyl group and a ($C_{6-10}$ aryl) $C_{1-6}$ alkoxy group, and when two or more substituents exist, the substituents may be same or different to each other; and the ($C_{1-6}$ alkyl)amino group, the ($C_{1-6}$ alkyl)($C_{1-6}$ alkyl)amino group, the benzoylamino group, the ($C_{1-6}$ alkyl)aminocarbonyl group, the ($C_{1-6}$ alkyl)($C_{1-6}$ alkyl)aminocarbonyl group, the $C_{1-6}$ alkyl group, the $C_{2-6}$ alkenyl group, the $C_{2-6}$ alkynyl group, the $C_{1-6}$ alkoxy group, the $C_{1-6}$ alkylthio group, the $C_{3-6}$ alkenyloxy group, the $C_{3-6}$ alkynyloxy group, the $C_{6-10}$ aryl group, the $C_{6-10}$ aryloxy group, the $C_{1-6}$ alkylsulfinyl group, the $C_{1-6}$ alkylsulfonyl group, the ($C_{1-6}$ alkoxy)carbonyl group and the ($C_{6-10}$ aryl)$C_{1-6}$ alkoxy group may each have one or more halogen atoms, and when two or more halogen atoms exist, the halogen atoms may be same or different to each other respectively);

G represents a hydrogen atom or a group of any one of the following formulae:

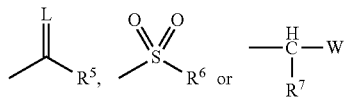

{wherein

L represents an oxygen atom or a sulfur atom;

$R^5$ represents a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a ($C_{6-10}$ aryl) $C_{1-6}$ alkyl group, a $C_{1-6}$ alkoxy group, a $C_{3-8}$ cycloalkoxy group, a $C_{3-6}$ alkenyloxy group, a $C_{3-6}$ alkynyloxy group, a $C_{6-10}$ aryloxy group, a ($C_{6-10}$ aryl)$C_{1-6}$ alkoxy group, a ($C_{1-6}$ alkyl)($C_{1-6}$ alkyl)amino group, a ($C_{3-6}$ alkenyl)($C_{3-6}$ alkenyl)amino group, a ($C_{1-6}$ alkyl)($C_{6-10}$ aryl)amino group or a five- to six-membered heteroaryl group (with the proviso that these groups may each one or more halogen atoms, and when two or more halogen atoms exist, the halogen atoms may be same or different to each other; and the $C_{3-8}$ cycloalkyl group, the $C_{6-10}$ aryl group, an aryl moiety of the ($C_{6-10}$ aryl) $C_{1-6}$ alkyl group, a $C_{3-8}$ cycloalkoxy group, a $C_{6-10}$ aryloxy group, an aryl moiety of the ($C_{6-10}$ aryl)$C_{1-6}$ alkoxy group, an aryl moiety of the ($C_{1-6}$ alkyl)($C_{6-10}$ aryl) amino group and a five- to six-membered heteroaryl group may each have one or more $C_{1-6}$ alkyl groups, and when two or more $C_{1-6}$ alkyl groups exist, the alkyl groups may be same or different to each other);

$R^6$ represents a $C_{1-6}$ alkyl group, a $C_{6-10}$ aryl group or a ($C_{1-6}$ alkyl)($C_{1-6}$ alkyl)amino group (with the proviso that these groups may each have one or more halogen atoms and when two or more halogen atoms exist, the halogen atoms may be same or different to each other; and the $C_{6-10}$ aryl group may have one or more $C_{1-6}$ alkyl groups and when two or more $C_{1-6}$ alkyl groups exist, the alkyl groups may be same or different to each other);

$R^7$ represents a hydrogen atom or a $C_{1-6}$ alkyl group;

W represents a $C_{1-6}$ alkoxy group, a $C_{1-6}$ alkylthio group, a $C_{1-6}$ alkylsulfinyl group or a $C_{1-6}$ alkylsulfonyl group (with the proviso that these groups may each have one or more halogen atoms and when two or more halogen atoms exist, the halogen atoms may be same or different to each other)};

$R^9$ represents a hydrogen atom, a $C_{1-6}$ alkyl group, a $C_{6-10}$ aryl group, a $C_{6-10}$ arylthio group, a $C_{6-10}$ arylsulfinyl group, a $C_{6-10}$ arylsulfonyl group (with the proviso that the $C_{1-6}$ alkyl group may have one or more halogen atoms, and when two or more halogen atoms exist, the halogen atoms may be same or different to each other; the $C_{6-10}$ aryl group, the $C_{6-10}$ arylthio group, the $C_{6-10}$ arylsulfinyl group and the $C_{6-10}$ arylsulfonyl group may have one or more substituents selected from the group consisting of a halogen atom, a cyano group, a nitro group and an amino group);

Z represents a halogen atom, a cyano group, a nitro group, a $C_{1-6}$ alkyl group, a $C_{2-6}$ alkenyl group, a $C_{2-6}$ alkynyl group, a $C_{1-6}$ alkoxy group, a ($C_{1-6}$ alkyl)carbonyl group, a $C_{1-6}$ alkylthio group, a $C_{6-10}$ aryloxy group, a five- or six-membered heteroaryloxy group, a $C_{3-8}$ cycloalkyl group, a $C_{6-10}$ aryl group or a five- to six-membered heteroaryl group (with the proviso that the $C_{1-6}$ alkyl group, the $C_{2-6}$ alkenyl group, the $C_{2-6}$ alkynyl group, the $C_{1-6}$ alkoxy group, the ($C_{1-6}$ alkyl) carbonyl group and the $C_{1-6}$ alkylthio group may each have one or more halogen atoms, and when two or more halogen atoms exist, the halogen atoms may be same or different to each other; and the $C_{6-10}$ aryl group, a five- to six-membered heteroaryl group, a $C_{6-10}$ aryloxy group and the five- to six-membered heteroaryloxy group may each have one or more substituents selected from the group consisting of a halogen atom, a $C_{1-6}$ alkyl group and a $C_{1-6}$ haloalkyl group, and when two or more substituents exist, the substituents may be same or different to each other; and the $C_{3-8}$ cycloalkyl group may have one or more substituents selected from the group consisting of a halogen atom and a $C_{1-6}$ alkyl group, and when two or more substituents exist, the substituents may be same or different to each other; when n is an integer of 2 or more, Z may be same or different to each other);

[2-1] The cyclohexanone compound of [1-1] wherein n is an integer of any one of 1 to 3;

X represents $CH_2$, O, $NR^9$, S, S(O) or $S(O)_2$;

$R^1$ represents a hydrogen atom;

$R^2$ and $R^3$ represent independently of each other a hydrogen atom or a $C_{1-3}$ alkyl group, or $R^2$ and $R^3$ connect each other to represent a $C_{2-5}$ alkylene chain (with the proviso that when m is 2 or 3, two or three $R^2$ may be same or different to each other and two or three $R^3$ may be same or different to each other);

$R^4$ represents a phenyl group, a 2-pyridyl group, a 3-pyridyl group, a 4-pyridyl group, a 2-pyrimidinyl group, a 2-pyrazinyl group, a 3-pyridazinyl group or a 3-furyl group (with the proviso that the phenyl group, the 2-pyridyl group, the 3-pyridyl group, the 4-pyridyl group, the 2-pyrimidinyl group, the 2-pyrazinyl group, the 3-pyridazinyl group or the 3-furyl group may each have one or more substituents selected from the group consisting of a halogen atom, a $C_{1-3}$ alkyl group, a $C_{1-3}$ alkoxy group, a $C_{1-3}$ haloalkyl group, a $C_{1-3}$ alkylthio group, a $C_{1-3}$ haloalkylthio group, a cyano group, a nitro group, an amino group, a pentafluorothio group, a benzoylamino group and a $C_{1-3}$ haloalkoxy group, and when two or more substituents exist, the substituents may be same or different to each other);

G represents a hydrogen atom or a group of any one of the following formulae:

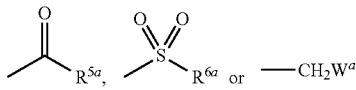

{wherein
$R^{5a}$ represents a $C_{1-6}$ alkyl group, a $C_{6-10}$ aryl group, a $C_{1-6}$ alkoxy group, a $C_{3-6}$ alkenyloxy group, a $C_{3-6}$ alkynyloxy group or a $C_{6-10}$ aryloxy group;
$R^{6a}$ represents a $C_{1-6}$ alkyl group;
$W^a$ represents a $C_{1-3}$ alkoxy group};
$R^9$ represents a hydrogen atom, a $C_{1-6}$ alkyl group or a $C_{6-10}$ arylsulfonyl group (with the proviso that the $C_{1-6}$ alkyl group may have one or more halogen atoms, and when two or more halogen atoms exist, the halogen atoms may be same or different to each other; and the $C_{6-10}$ arylsulfonyl group may have one or more substituents selected from the group consisting of a halogen atom and a nitro group, and when two or more substituents exist, the substituents may be same or different to each other);
Z represents a halogen atom, a $C_{1-3}$ alkyl group, a $C_{2-6}$ alkenyl group, a $C_{2-6}$ alkynyl group, a $C_{1-3}$ alkoxy group, a $C_{3-8}$ cycloalkyl group, a nitro group, a phenyl group or a five- to six-membered heteroaryloxy group (with the proviso that the $C_{1-3}$ alkyl group, the $C_{2-6}$ alkenyl group, the $C_{2-6}$ alkynyl group, the $C_{1-3}$ alkoxy group, the phenyl group and the five- to six-membered heteroaryloxy group may have one or more halogen atoms, and when two or more halogen atoms exist, the halogen atoms may be same or different to each other;
[3-1] a cyclohexanone compound of [2-1] wherein
  m is 2;
  X represents $CH_2$, O, $NR^9$, S, S(O) or $S(O)_2$;
  $R^2$ and $R^3$ represents independently of each other a hydrogen atom, a methyl group or an ethyl group, or $R^2$ and $R^3$ connect each other to represent an ethylene chain (with the proviso that two $R^2$ may be same or different to each other and two $R^3$ may be same or different to each other);
  $R^4$ represents a phenyl group, a 2-pyridyl group, a 3-pyridyl group, a 4-pyridyl group, a 2-pyrimidinyl group, a 2-pyrazinyl group, a 3-pyridazinyl group or a 3-furyl group (with the proviso that the phenyl group, the 2-pyridyl group, the 3-pyridyl group, the 4-pyridyl group, the 2-pyrimidinyl group, the 2-pyrazinyl group, the 3-pyridazinyl group and the 3-furyl group have each one or more substituents selected from the group consisting of a chlorine atom, a bromine atom, an iodine atom, a fluorine atom, a methyl group, a methoxy group, a nitro group, an amino group, a cyano group, a pentafluorothio group, a pentafluoroethyl group, a difluoroethyl group, a heptafluoroisopropyl group, a trifluoromethylthio group, a benzoylamino group, a trifluoromethoxy group and a tifluoromethyl group);
  G represents a hydrogen atom, an acetyl group, a propionyl group, a butyryl group, a benzoyl group, a methylsulfonyl group, a methoxycarbonyl group, an ethoxycarbonyl group, an allyloxycarbonyl group, a phenoxycarbonyl group, a methoxymethyl group or an ethoxymethyl group;
  $R^9$ represents a hydrogen atom, a 2-nitrophenylsulfonyl group or a methyl group;
  Z represents a methyl group, an ethyl group, a phenyl group, a vinyl group, a cyclopropyl group, a nitro group, a fluorine atom, a chlorine atom, a methoxy group, a trifluoromethyl group, a 5-trifluoromethyl-2-chloropyridyloxy group or an ethynyl group;

[4-1] a cyclohexanone compound of the formula (II):

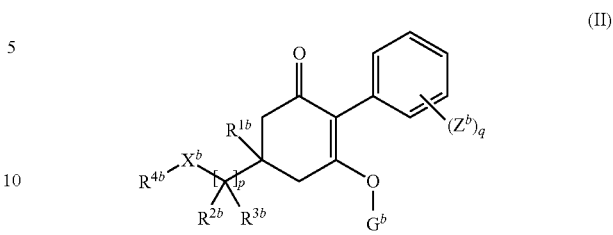

wherein
p is an integer of 1, 2 or 3;
q is an integer of any one of 1 to 5;
$X^b$ represents $CH_2$, O, S, S(O) or $S(O)_2$;
$R^{1b}$ represents a hydrogen atom or a methyl group;
$R^{2b}$ and $R^{3b}$ represent independently of each other a hydrogen atom, a $C_{1-6}$ alkyl group, a $C_{1-6}$ haloalkyl group, a $C_{3-8}$ cycloalkyl group, a $C_{3-8}$ halocycloalkyl group, a ($C_{1-6}$ alkyl)$C_{3-8}$ cycloalkyl group, a ($C_{3-8}$ cycloalkyl)$C_{1-6}$ alkyl group, a ($C_{3-8}$ cycloalkyl)$C_{3-8}$ cycloalkyl group, a ($C_{3-8}$ halocycloalkyl) $C_{1-6}$ alkyl group or a {($C_{1-6}$ alkyl) $C_{3-8}$ cycloalkyl}$C_{1-6}$ alkyl group, or $R^{2b}$ and $R^{3b}$ connect each other to represent a $C_{2-5}$ alkylene chain, or $R^{2b}$ and $R^{3b}$ combine each other to represent a $C_{1-3}$ alkylidene group optionally having one or more halogen atoms (with the proviso that when p is 2 or 3, two or three $R^{2b}$ may be same or different to each other and $R^{3b}$ may be same or different to each other);
$R^{4b}$ represents a $C_{6-10}$ aryl group or a five- to six-membered heteroaryl group (with the proviso that the $C_{6-10}$ aryl group and the five- to six-membered heteroaryl group may have one or more substituents selected from the group consisting of a halogen atom, a cyano group, a nitro group, a pentafluorothio group, a $C_{1-6}$ alkyl group, a $C_{2-6}$ alkenyl group, a $C_{2-6}$ alkynyl group, a $C_{1-6}$ alkoxy group, a $C_{1-6}$ alkylthio group, a $C_{3-6}$ alkenyloxy group, a $C_{3-6}$ alkynyloxy group and a ($C_{6-10}$ aryl) $C_{1-6}$ alkoxy group, and when two or more substituents exist, the substituents may be same or different to each other; and the $C_{1-6}$ alkyl group, the $C_{2-6}$ alkenyl group, the $C_{2-6}$ alkynyl group, the $C_{1-6}$ alkoxy group, the $C_{1-6}$ alkylthio group, the $C_{3-6}$ alkenyloxy group, the $C_{3-6}$ alkynyloxy group and the ($C_{6-10}$ aryl) $C_{1-6}$ alkoxy group may have one or more halogen atoms, and when two or more halogen atoms exist, the halogen atoms may be same or different to each other);
$G^b$ represents a hydrogen atom or a group of any one of the following formulae:

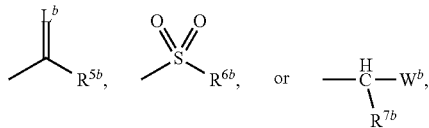

{wherein
$L^b$ represents an oxygen atom or a sulfur atom;
$R^{5b}$ represents a $C_{1-6}$ alkyl group, a $C_{3-9}$ cycloalkyl group, a $C_{2-6}$ alkenyl group, a $C_{2-6}$ alkynyl group, a $C_{6-10}$ aryl group, a ($C_{6-10}$ aryl) $C_{1-6}$ alkyl group, a $C_{1-6}$ alkoxy group, a $C_{3-8}$ cycloalkoxy group, a $C_{3-6}$ alkenyloxy group, a $C_{3-6}$ alkynyloxy group, a $C_{6-10}$ aryloxy group, a ($C_{6-10}$ aryl)$C_{1-6}$ alkoxy group, a ($C_{1-6}$ alkyl)($C_{1-6}$ alkyl)amino group, a ($C_{3-6}$ alkenyl) ($C_{3-6}$ alkenyl)amino group, a ($C_{1-6}$ alkyl)($C_{6-10}$ aryl)amino group or a five- to six-membered heteroaryl group (with the proviso that these groups may each have one or more halogen atoms, when two or more halogen atoms exist, the halogen atoms may be same or different to each other; and the $C_{3-8}$ cycloalkyl group, the $C_{6-10}$ aryl group, an aryl moiety of the $(C_{6-10}$ aryl)$C_{1-6}$ alkyl group, the $C_{3-8}$ cycloalkoxy group, the $C_{6-10}$ aryloxy group, an aryl moiety of the $(C_{6-10}$ aryl)$C_{1-6}$ alkoxy group, an aryl moiety of the $(C_{1-6}$ alkyl)($C_{6-10}$ aryl) amino group and a five- to six-membered heteroaryl group may each one or more $C_{1-6}$ alkyl groups, and when two or more $C_{1-6}$ alkyl groups exist, the alkyl groups may be same or different to each other);

$R^{6b}$ represents a $C_{1-6}$ alkyl group, a $C_{6-10}$ aryl group or a $(C_{1-6}$ alkyl)($C_{1-6}$ alkyl)amino group (with the proviso that these groups may have one or more halogen atoms, and when two or more halogen atoms exist, the halogen atoms may be same or different to each other; and the $C_{6-10}$ aryl group may have one or more $C_{1-6}$ alkyl groups, and when two or more $C_{1-6}$ alkyl groups exist, the alkyl groups may be same or different to each other);

$R^{7b}$ represents a hydrogen atom or a $C_{1-6}$ alkyl group;

$W^b$ represents a $C_{1-6}$ alkoxy group, a $C_{1-6}$ alkylthio group, a $C_{1-6}$ alkylsulfinyl group or a $C_{1-6}$ alkylsulfonyl group (with the proviso that these groups may each have one or more halogen atoms, and when two or more halogen atoms exist, the halogen atoms may be same or different to each other)};

$Z^b$ represents a halogen atom, a cyano group, a nitro group, a phenyl group, a $C_{1-6}$ alkyl group, a $C_{2-6}$ alkenyl group, a $C_{2-6}$ alkynyl group, a $C_{1-6}$ alkoxy group, a $C_{1-6}$ alkylthio group, a $C_{6-10}$ aryloxy group, a five- to six-membered heteroaryloxy group or a $C_{3-8}$ cycloalkyl group (with the proviso that the $C_{1-6}$ alkyl group, the $C_{2-6}$ alkenyl group, the $C_{2-6}$ alkynyl group, the $C_{1-6}$ alkoxy group and the $C_{1-6}$ alkylthio group may have one or more halogen atoms, and when two or more halogen atoms exist, the halogen atoms may be same or different to each other; and the phenyl group, the $C_{6-10}$ aryloxy group and the five- to six-membered heteroaryloxy group may have one or more substituents selected from the group consisting of a halogen atom, a $C_{1-6}$ alkyl group and a $C_{1-6}$ haloalkyl group, and when two or more substituents exist, the substituents may be same or different to each other; and the $C_{3-8}$ cycloalkyl group may have one or more substituents selected from the group consisting of a halogen atom and a $C_{1-6}$ alkyl group, and when two or more substituents exist, the substituents may be same or different to each other; when q is an integer of 2 or more, $Z^b$ may be same or different to each other);

[5-1] a cyclohexanone compound of [4-1] wherein
n is an integer of any one of 1 to 3;
$R^{1b}$ represents a hydrogen atom;
$R^{2b}$ and $R^{3b}$ represent independently of each other a hydrogen atom or a $C_{1-3}$ alkyl group (with the proviso that when p is 2 or 3, two or three $R^{2b}$ may be same or different to each other and two or three $R^{3b}$ may be same or different to each other);
$R^{4b}$ represents a phenyl group or a 2-pyridyl group (with the proviso that the phenyl group and the 2-pyridyl group may have one or more substituents selected from the group consisting of a halogen atom, a $C_{1-3}$ alkyl group, a $C_{1-3}$ alkoxy group, a $C_{1-3}$ haloalkyl group, a nitro group, a pentafluorothio group and a $C_{1-3}$ haloalkoxy group, and when two or more substituents exist, the substituents may be same or different to each other;

$G^b$ represents a hydrogen atom or a group of any one of the following formulae:

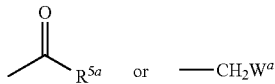

{wherein
$R^{5a}$ represents a $C_{1-6}$ alkyl group, a $C_{6-10}$ aryl group, a $C_{1-6}$ alkoxy group, a $C_{3-6}$ alkenyloxy group, a $C_{3-6}$ alkynyloxy group or a $C_{6-10}$ aryloxy group; and
$W^a$ represents a $C_{1-3}$ alkoxy group}; and
$Z^b$ represents a $C_{1-3}$ alkyl group;

[6-1] a cyclohexanone compound of [5-1] wherein
q is 2;
$R^{2b}$ and $R^{3b}$ represent independently of each other a hydrogen atom or a methyl group (with the proviso that two $R^{2b}$ may be same or different to each other and two $R^{3b}$ may be same or different to each other);
$R^{4b}$ represents a phenyl group or a 2-pyridyl group (with the proviso that the phenyl group and the 2-pyridyl group have one or more substituents selected from the group consisting of a chlorine atom, a fluorine atom, a methyl group, a methoxy group and a trifluoromethyl group);
$G^b$ represents a hydrogen atom, an acetyl group, a propionyl group, a benzoyl group, a methoxycarbonyl group, an ethoxycarbonyl group, an allyloxycarbonyl group, a phenoxycarbonyl group, a methoxymethyl group or an ethoxymethyl group; and
$Z^b$ represents a methyl group or an ethyl group;

[7-1] a cyclohexanone compound of any one of [1-1] to [6-1] wherein G represents a hydrogen atom.

The herbicide of the present invention comprises the present compound and inert carriers (hereinafter, sometimes referred to as "the present herbicide"). The present herbicide can be usually prepared by further adding auxiliary agents for formulation such as surfactants, stickers, dispersers and stabilizers to formulate into wettable powders, water dispersible granules, flowables, granules, dry flowables, emulsifiable concentrates, aqueous solutions, oil solutions, smoking agents, microcapsules and the others. The present herbicide usually contains the present compound in 0.1 to 80% by weight.

The inert carrier includes a solid carrier, a liquid carrier and a gaseous carrier.

Examples of the solid carrier include clays (for example, kaolin, diatomaceous earth, synthetic hydrated silicon dioxide, Fubasami clay, bentonite and acid clay), talcs or the other inorganic minerals (for example, sericite, quartz powder, sulfur powder, activated charcoal, calcium carbonate and hydrated silica) in the form of fine powders or particulates, and examples of the liquid carries include water, alcohols (for example, methanol and ethanol), ketones (for example, acetone and methyl ethyl ketone), aromatic hydrocarbons (for example, benzene, toluene, xylene, ethylbenzene and methyl naphthalene), aliphatic hydrocarbons (for example, n-hexane, cyclohexane and kerosene), esters (for example, ethyl acetate and butyl acetate), nitriles (for example, acetonitrile and isobutyronitrile), ethers (for example, dioxane and diisopropylether), acid amides (for example, N,N-dimethyl formamide and dimethylacetamide), halogenated hydrocarbons (for example, dichloroethane, trichloro ethylene and carbon tetrachloride) and the others.

Examples of the surfactants include alkyl sulfates, alkyl sulfonates, alkyl aryl sulfonates, alkyl aryl ethers and polyoxyethylenated compounds thereof, polyethylene glycol ethers, polyol esters and sugar alcohol derivatives Examples of other auxiliary agents for formulation include stickers and dispersers, specifically casein, gelatin, polysaccharides (for example, starch, gum arabic, cellulose derivatives and alginic acid), lignin derivatives, bentonite, sugars, water-soluble synthetic polymers (for example, polyvinyl alcohol, polyvinyl pyrrolidone and polyacrylic acids), PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, fatty acids or fatty acid esters thereof and the others.

The method for controlling weeds of the present invention comprises applying an effective amount of the present compound to weeds or to a soil where weeds grow (hereinafter, sometimes referred as to "the present weeds controlling method"). In the method for controlling weeds of the present invention, the present herbicide is usually used. The method of application comprises, for example, a foliage treatment of the weeds using the present herbicide, a treatment of the soil surface where the weeds grow, and a soil incorporation treatment of the soil where the weeds grow. In the present weeds controlling method, the present compound is applied in amount of usually 1 to 5000 g and preferably 10 to 1000 g per 10000 m² of area to be controlled weeds.

The present compound can be applied to an agricultural land and the others where "plant" as below-mentioned is cultivated.

"Plant":

Crops:

corn, rice, wheat, barley, rye, oat, sorghum, cotton, soybean, peanut, buckwheat, beet, rapeseed, sunflower, sugar cane, tobacco, hop, and the others;

Vegetables:

solanaceous vegetables (for example, eggplant, tomato, pimento, pepper and potato), cucurbitaceous vegetables (for example, cucumber, pumpkin, zucchini, water melon and melon), cruciferous vegetables (for example, Japanese radish, white turnip, horseradish, kohlrabi, Chinese cabbage, cabbage, leaf mustard, broccoli and cauliflower), asteraceous vegetables (for example, burdock, crown daisy, artichoke and lettuce), liliaceous vegetables (for example, green onion, onion, garlic and asparagus), ammiaceous vegetables (for example, carrot, parsley, celery and parsnip), chenopodiaceous vegetables (for example, spinach and Swiss chard), lamiaceous vegetables (for example, *Perilla frutescens*, mint and basil), strawberry, sweet potato, *Dioscorea japonica*, colocasia and the others;

Fruits:

pomaceous fruits (for example, apple, pear, Japanese pear, Chinese quince and quince), stone fleshy fruits (for example, peach, plum, nectarine, *Prunus mume*, cherry fruit, apricot and prune), citrus fruits (for example, *Citrus unshiu*, orange, lemon, lime and grapefruit), nuts (for example, chestnut, walnuts, hazelnuts, almond, pistachio, cashew nuts and *macadamia* nuts), berry fruits (for example, blueberry, cranberry, blackberry and raspberry), grape, kaki persimmon, olive, Japanese plum, banana, coffee, date palm, coconuts, oil palm and the others;

Trees Other than Fruit Trees:

tea, mulberry, flowering plant (for example, dwarf azalea, camellia, hydrangea, sasanqua, *Illicium anisatum*, cherry trees, tulip tree, crape myrtle and fragrant olive), roadside trees (for example, ash, birch, dogwood, Eucalyptus, *Ginkgo biloba*, lilac, maple, *Quercus*, poplar, Judas tree, *Liquidambar formosana*, plane tree, zelkova, Japanese arborvitae, fir wood, hemlock, juniper, *Pinus, Picea, Taxus cuspidate*, elm and Japanese horse chestnut),

*Sweet viburnum, Podocarpus macrophyllus*, Japanese cedar, Japanese cypress, croton, Japanese spindletree and *Photinia glabra*);

Others:

flowers (for example, rose, carnation, chrysanthemum, Eustoma, gypsophila, gerbera, marigold, salvia, petunia, verbena, tulip, aster, gentian, lily, pansy, cyclamen, orchid, lily of the valley, lavender, stock, ornamental cabbage, primula, poinsettia, gladiolus, cattleya, daisy, cymbidium and begonia), bio-fuel plants (for example, jatropha, safflower, *Camelina*, switch grass, *Miscanthus giganteus, Phalaris arundinacea, Arundo donax*, Kenaf (*Hibiscus cannabinus*), cassava (*Manihot esculenta*), willow (Salicaceae), etc.), and ornamental foliage plants, and the others.

The "crops" include genetically modified crops.

The present compound can be mixed or combined with other pesticides, miticides, nematicides, fungicides and/or synergists.

Examples of the active ingredient as the pesticides include the followings:

(1) Organophosphorous Compound acephate, butathiofos, chlorethoxyfos, chlorfenvinphos, chlorpyrifos, chlorpyrifos-methyl, cyanophos (abbrev. CYAP), diazinon, dichlofenthion (abbrev. ECP), dichlorvos (abbrev. DDVP), dimethoate, dimethylvinphos, disulfoton, EPN, ethion, ethoprophos, etrimfos, fenthion (abbrev. MPP), fenitrothion (abbrev. MEP), fosthiazate, formothion, isofenphos, isoxathion, malathion, mesulfenfos, methidathion (abbrev. DMTP), monocrotophos, naled (abbrev. BRP, oxydeprofos (abbrev. ESP), parathion, phosalone, phosmet (abbrev. PMP), pirimiphos-methyl, pyridafenthion, quinalphos, phenthoate (abbrev. PAP), profenofos, propaphos, prothiofos, pyraclorfos, salithion, sulprofos, tebupirimfos, temephos, tetrachlorvinphos, terbufos, thiometon, trichlorphon (abbrev. DEP), vamidothion, phorate, cadusafos.

(2) Carbamate Compounds alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb (abbrev. MIPC), metolcarb, methomyl, methiocarb, oxamyl, pirimicarb, propoxur (abbrev. PHC), XMC, thiodicarb, xylylcarb, aldicarb.

(3) Pyrethroid Compounds acrinathrin, allethrin, beta-cyfluthrin, bifenthrin, cycloprothrin, cyfluthrin, cyhalothrin, cypermethrin, empenthrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, Lambda-cyhalothrin, gamma-cyhalothrin, furamethrin, tau-fluvalinate, metofluthrin, profluthrin, dimefluthrin, 2,3,5,6-tetrafluoro-4-(methoxymethyl)benzyl 2,2-dimethyl-3-(2-cyano-1-propenyl)cyclopropanecarboxylate, 2,3,5,6-tetrafluoro-4-(methoxymethyl)benzyl 2,2,3,3-tetramethylcyclopropanecarboxylate, protrifenbute.

(4) Nereis Toxin Compounds
cartap, bensultap, thiocyclam, monosultap, bisultap.
(5) Neonicotinoid Compounds
imidacloprid, nitenpyram, acetamiprid, thiamethoxam, thiacloprid, dinotefuran, clothianidin.
(6) Benzoylurea Compounds
chlorfluazuron, bistrifluron, diflubenzuron, fluazuron, flucycloxuron, flufenoxuron, hexaflumuron, lufenuron, novaluron, noviflumuron, teflubenzuron, triflumuron.
(7) Phenylpyrazole Compounds
acetoprole, ethiprole, fipronil, vaniliprole, pyriprole, pyrafluprole.
(8) Bt Toxins
live spores and crystal toxins originated from *Bacillus thuringiensis* and a mixture thereof.
(9) Hydrazine Compounds
chromafenozide, halofenozide, methoxyfenozide, tebufenozide.
(10) Organochlorine Compounds
aldrin, dieldrin, chlordane, DDT, dienochlor, endosulfan, methoxychlor.
(11) Other Pesticide Active Ingredients
machine oil, nicotine-sulfate; avermectin-B, bromopropylate, buprofezin, chlorphenapyr, cyromazine, DCIP (dichlorodiisopropyl ether), D-D (1,3-Dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, aluminium phosphide, arsenous oxide, benclothiaz, calcium cyanamide, calcium polysulfide, DSP, flonicamid, flurimfen, formetanate, hydrogen phosphide, metam-ammonium, metam-sodium, methyl bromide, potassium oleate, spiromesifen, Sulfoxaflor, sulfur, metaflumizone, spirotetramat, pyrifluquinazone, spinetoram, chlorantraniliprole, tralopyril, diafenthiuron.

A compound of the formula (A):

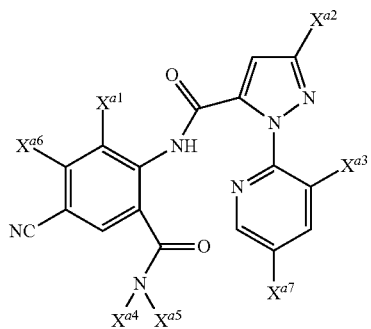

(A)

wherein $X^{a1}$ represents a methyl group, a chlorine atom, a bromine atom or a fluorine atom, $X^{a2}$ represents a fluorine atom, a chlorine atom, a bromine atom, a $C_1$-$C_4$ haloalkyl group or a $C_1$-$C_4$ haloalkoxy group, $X^{a3}$ represents a fluorine atom, a chlorine atom or a bromine atom, $X^{a4}$ represents an optionally substituted $C_2$-$C_4$ alkyl group, an optionally substituted $C_3$-$C_4$ alkenyl group, an optionally substituted $C_3$-$C_4$ alkynyl group, an optionally substituted $C_3$-$C_5$ cycloalkylalkyl group or a hydrogen atom, $X^{a5}$ represents a hydrogen atom or a methyl group, $X^{a6}$ represents a hydrogen atom, a fluorine atom or a chlorine atom, and $X^{a7}$ represents a hydrogen atom, a fluorine atom or a chlorine atom.

A compound of the formula (B):

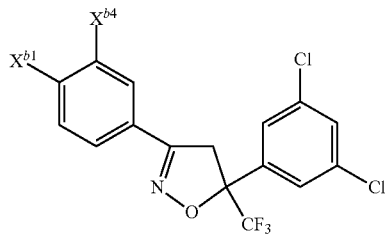

(B)

wherein $X^{b1}$ represents a $X^{b2}$—NH—C(=O) group, a $X^{b2}$—C(=O)—NH—CH$_2$ group, a $X^{b3}$—S(O) group, an optionally substituted pyrrol-1-yl group, an optionally substituted imidazol-1-yl group, an optionally substituted pyrazol-1-yl group or an optionally substituted 1,2,4-triazol-1-yl group, $X^{b2}$ represents an optionally substituted $C_1$-$C_4$ haloalkyl group such as a 2,2,2-trifluoroethyl group or an optionally substituted $C_3$-$C_6$ cycloalkyl group such as a cyclopropyl group, $X^{b3}$ represents an optionally substituted $C_1$-$C_4$ alkyl group such as a methyl group, and $X^{b4}$ represents a hydrogen atom, a chlorine atom, a cyano group or a methyl group.

A compound of the formula (C):

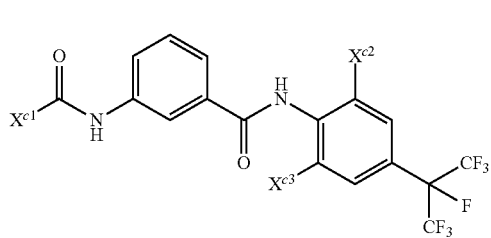

(C)

wherein $X^{c1}$ represents an optionally substituted $C_1$-$C_4$ alkyl group such as a 3,3,3-trifluoropropyl group, an optionally substituted $C_1$-$C_4$ alkoxy group such as a 2,2,2-trichloroethoxy group, an optionally substituted phenyl group such as a 4-cyanophenyl group or an optionally substituted pyridyl group such as a 2-chloro-3-pyridyl group, $X^{c2}$ represents a methyl group or a trifluoromethylthio group, and $X^{c3}$ represents a methyl group or a halogen atom.

Examples of the active ingredient as the miticides include the followings:

acequinocyl, amitraz, benzoximate, bifenazate, bromopropylate, chinomethionat, chlorobenzilate, CPCBS (chlorfenson), clofentezine, cyflumetofen, kelthane (which is also referred to as dicofol), etoxazole, fenbutatin oxide, fenothiocarb, fenpyroximate, fluacrypyrim, halfenprox, hexythiazox, propargite (abbrev. BPPS), polynactins, pyridaben, pyrimidifen, tebufenpyrad, tetradifon, spirodiclofen, spiromesifen, spirotetramat, amidoflumet and cyenopyrafen.

Examples of the active ingredient as the nematicides include the followings:

DCIP, fosthiazate, levamisol, methylsothiocyanate, morantel tartarate and imicyafos.

Examples of the active ingredient as the fungicides include the followings:
(1) Polyhaloalkylthio Compounds
captan, folpet and the others.
(2) Organophosphorous Compounds
IBP, EDDP, tolclofos-methyl and the others.
(3) Benzimidazole Compounds
benomyl, carbendazim, thiophanate-methyl, thiabendazole and the others.
(4) Carboxyamide Compounds
carboxin, mepronil, flutolanil, thifluzamid, furametpyr, boscalid, penthiopyrad and the others.
(5) Dicarboxylmide Compounds
procymidone, iprodione, vinclozolin and the others.
(6) Acylalanine compounds
Metalaxyl and the Others.
(7) Azole Compounds
triadimefon, triadimenol, propiconazole, tebuconazole, cyproconazole, epoxiconazole, prothioconazole, ipconazole, triflumizole, prochloraz, penconazole, flusilazole, diniconazole, bromuconazole, difenoconazole, metconazole, tetraconazole, myclobutanil, fenbuconazole, hexaconazole, fluquinconazole, triticonazole, bitertanol, imazalil, flutriafol and the others.
(8) Morpholine Compounds
dodemorph, tridemorph, fenpropimorph and the others.
(9) Strobilurin Compounds
azoxystrobin, kresoxim-methyl, metominostrobin, trifloxystrobin, picoxystrobin, pyraclostrobin, fluoxastrobin, dimoxystrobin and the others.
(10) Antibiotics
validamycin A, blasticidin S, kasugamycin, polyoxin and the others.
(11) Dithiocarbamate Compounds
mancozeb, maneb, thiuram and the others.
(12) The Other Fungicidal Active Ingredients
fthalide, probenazole, isoprothiolane, tricyclazole, pyroquilon, ferimzone, acibenzolar S-methyl, carpropamid, diclocymet, fenoxanil, tiadinil, diclomezine, teclofthalam, pencycuron, oxolinic acid, TPN, triforine, fenpropidin, spiroxamine, fluazinam, iminoctadine, fenpiclonil, fludioxonil, quinoxyfen, fenhexamid, silthiofam, proquinazid, cyflufenamid, bordeaux mixture, dichlofluanid, cyprodinil, pyrimethanil, mepanipyrim, diethofencarb, pyribencarb, famoxadone, fenamidone, zoxamide, ethaboxam, amisulbrom, iprovalicarb, benthiavalicarb, cyazofamid, mandipropamid, metrafenone, fluopiram, bixafen and the others.

Examples of the active ingredient as the synergists include the followings:
piperonyl butoxide, sesamex, sulfoxide, N-(2-ethylhexyl)-8,9,10-trinorborn-5-ene-2,3-dicarboximide (MGK 264), N-declyimidazole), WARF-antiresistan, TBPT, TPP, IBP, PSCP, methyl iodide ($CH_3I$), t-phenylbutenone, diethylmaleate, DMC, FDMC, ETP and ETN.

Examples of the subjects to be controlled by the present herbicide include the followings:
Weeds:
*Digitaria ciliaris, Eleusine indica, Setaria viridis, Setaria faberi, Setaria glauca, Echinochloa crus-galli, Panicum dichotomiflorum, Panicum texanum, Brachiaria platyphylla, Brachiaria plantaginea, Brachiaria decumbens, Sorghum halepense, Andropogon sorghum, Cynodon dactylon, Avena fatua, Lolium multiflorum, Alopecurus myosuroides, Bromus tectorum, Bromus sterilis, Phalaris minor, Apera spica-venti, Poa annua, Agropyron repens, Cyperus iria, Cyperus rotundus, Cyperus esculentus, Portulaca oleracea, Amaranthus retroflexus, Amaranthus hybridus, Amaranthus palmeri, Amaranthus rudis, Abutilon theophrasti, Sida spinosa, Fallopia convolvulus, Polygonum scabrum, Persicaria pennsylvanica, Persicaria vulgaris, Rumex crispus, Rumex obtusifolius, Fallopia japonica, Chenopodium album, Kochia scoparia, Polygonum longisetum, Solanum nigrum, Datura stramonium, Ipomoea purpurea, Ipomoea hederacea, Ipomoea hederacea* var. *integriuscula, Ipomoea lacunosa, Convolvulus arvensis, Lamium purpureum, Lamium amplexicaule, Xanthium pensylvanicum, Helianthus annuus, Matricaria perforata* or *inodora, Matricaria chamomilla, Chrysanthemum segetum, Matricaria matricarioides, Ambrosia artemisiifolia, Ambrosia trifida, Erigeron canadensis, Artemisia princeps, Solidago altissima, Conyza bonariensis, Sesbania exaltata, Cassia obtusifolia, Desmodium tortuosum, Trifolium repens, Pueraria lobata, Vicia angustifolia, Commelina communis, Commelina benghalensis, Galium aparine, Stellaria media, Raphanus raphanistrum, Sinapis arvensis, Capsella bursa-pastoris, Veronica persica, Veronica hederifolia, Viola arvensis, Viola tricolor, Papaver rhoeas, Myosotis scorpioides, Asclepias syriaca, Euphorbia helioscopia, Chamaesyce nutans, Geranium carolinianum, Erodium cicutarium, Equisetum arvense, Leersia japonica, Echinochloa oryzicola, Echinochloa crus-galli* var. *formosensis, Leptochloa chinensis, Cyperus difformis, Fimbristylis miliacea, Eleocharis acicularis, Scirpus juncoides, Scirpus wallichii, Cyperus serotinus, Eleocharis kuroguwai, Bolboschoenus koshevnikovii, Schoenoplectus nipponicus, Monochoria vaginalis, Lindernia procumbens, Dopatrium junceum, Rotala indica, Ammannia multiflora, Elatine triandra, Ludwigia epilobioides, Sagittaria pygmaea, Alisma canaliculatum, Sagittaria trifolia, Potamogeton distinctus, Oenanthe javanica, Callitriche palustris, Lindernia micrantha, Lindernia dubia, Eclipta prostrata, urdannia keisak, Paspalum distichum, Leersia oryzoides* and the others;
Aquatic Plants:
*Alternanthera philoxeroides, Limnobium spongia, Ceratopteris* (*Salvinia* sp.), *Pistia stratiotes, Hydrotyle verticillata* (*Hydrocotyle* sp.), filamentous algae (*Pithophora* sp., *Cladophora* sp.), *Ceratophyllum demersum*, duckweed (*Lemna* sp.), *Cabomba caroliniana, Hydrilla verticillata, Najas guadalupensis*, pond weeds (*Potamogeton crispus, Potamogeton illinoensis, Potamogeton pectinatus* and the like), watermeals (*Wolffia* sp.), watermillfoils (*Myriophyllum spicatum, Myriophyllum heterophyllum* and the like), *Eichhornia crassipes* and the others;
Moss, Liverworts, Hornworts;
Cyanobacterium;
Ferm;
Sucher of perennial plants (such as pomaceous fruits, stone fleshy fruits, berry fruits, nuts, citrus fruits, hop and grape).

The present compound can be prepared for example, according to the below-mentioned process.
Process 1
The present compound of the formula (1a) wherein G represents a hydrogen atom can be prepared by reacting the compound of the formula (2) and the compound of the formula (3) in the presence of a base.

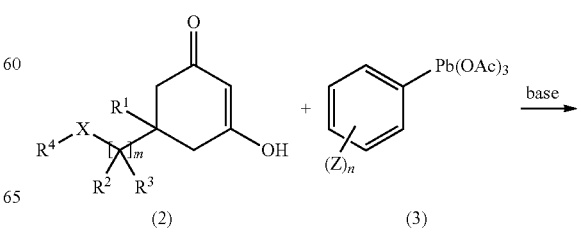

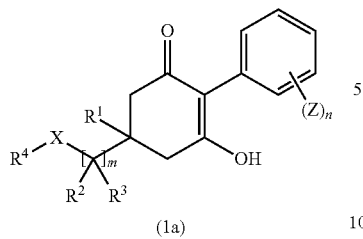

(1a)

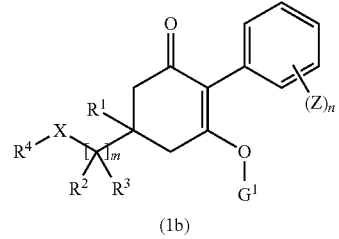

(1b)

[wherein G represents a group of any one of the formulae:

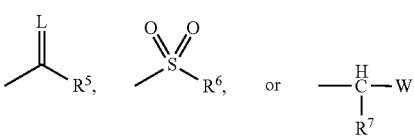

(wherein L, $R^5$, $R^6$, $R^7$ and W are the same as defined above)

$X^1$ represents a halogen atom (for example, a chlorine atom, a bromine atom, an iodine atom and the like) or a $C_{1-3}$ alkylsulfonyloxy group optionally substituted with one or more halogen atoms (for example, a methylsulfonyloxy group, a trifluoromethylsulfonyloxy group) or a group of the formula: $OG^1$ (with the proviso that when $G^1$ represents a group of the formula:

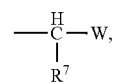

$X^1$ represents a halogen atom or a $C_{1-3}$ alkylsulfonyloxy group optionally substituted with one or more halogen atoms), $R^1$, $R^2$, $R^3$, $R^4$, X, n, m and Z are the same as defined above]

[wherein, $R^1$, $R^2$, $R^3$, $R^4$, X, n, m and Z are the same as defined above]

This reaction is usually carried out in a solvent. Examples of the solvent that can be used include aromatic hydrocarbons such as benzene, toluene and xylene; ethers such as diethyl ether, diisopropylether, dioxane, tetrahydrofuran and dimethoxyethane; halogenated hydrocarbons such as dichloromethane, chloroform and 1,2-dichloroethane; amides such as dimethylformamide and dimethylacetamide; sulfones such as sulfolane; and mixed solvents thereof.

Examples of the base to be used in this reaction includes organic bases such as triethylamine, tripropylamine, pyridine, dimethylaminopyridine, 1,8-diazabicyclo[5.4.0]-7-undecene. The amount used of the base is usually within a range of 1 to 10 molar equivalents and preferably within a range of 2 to 5 molar equivalents of the amount of the compound of the formula (2). The amount used of the compound of the formula (3) is usually within a range of 1 to 3 molar equivalents of the amount of the compound of the formula (2).

The reaction temperature is usually within a range of −60 to 180° C. and preferably within a range of −10 to 100° C. The reaction period of this reaction is usually within a range of 10 minutes to 30 hours.

The completion of this reaction can be confirmed by sampling a part of the reaction mixtures followed by performing analytical means such as thin-layer chromatography and high-performance liquid chromatography. When this reaction is completed, for example, the reaction mixtures is acidified with an acid, mixed with water, extracted with an organic solvent and the resulting organic layers are treated (for example, drying and concentration) to obtain the compound of the formula (1a).

Process 2

The present compound of the formula (1b) wherein G represents a group other than a hydrogen atom can be prepared by reacting the compound of the formula (1a) and the compound of the formula $G^1$-$X^1$.

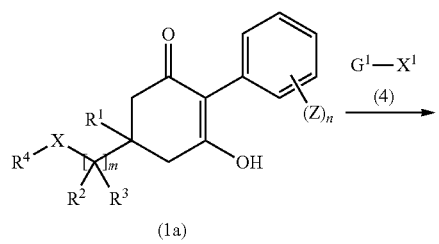

(1a)

This reaction can be carried in a solvent. Examples of the solvent that can be used includes aromatic hydrocarbons such as benzene and toluene; ethers such as diethyl ether, diisopropylether, dioxane, tetrahydrofuran and dimethoxyethane; halogenated hydrocarbons such as dichloromethane, chloroform and 1,2-dichloroethane; amides such as dimethylformamide and dimethylacetamide; sulfoxides such as dimethyl sulfoxide; sulfones such as sulfolane; and mixed solvents thereof.

Examples of the compound of the formula (4) to be used in this reaction include carboxylic halides such as acetyl chloride, propionyl chloride, isobutyryl chloride, pivaloyl chloride, benzoyl chloride and cyclohexanecarboxylic acid chloride; carboxylic anhydrides such as acetic anhydride and trifluoroacetic anhydride; halides of carbonate half ester such as methyl chloroformate, ethyl chloroformate and phenyl chloroformate; carbamic halides such as dimethylcarbamoyl chloride; sulfonic halides such as methanesulfonyl chloride and p-toluenesulfonyl chloride; sulfonic anhydrides such as methanesulfonic anhydride and trifluoromethanesulfonic anhydride; alkyl halogenoalkyl ethers such as chloromethyl methyl ether and ethyl chloromethyl ether. The amount used of the compound of the formula (4) is usually within a range of 1 molar equivalent or more and preferably within a range of 1 to 3 molar equivalents of the amount of the compound of the formula (1a).

This reaction is usually carried out in the presence of a base. Examples of the base to be used in this reaction include organic bases such as triethylamine, tripropylamine, pyridine, dimethylaminopyridine, 1,8-diazabicyclo[5.4.0]-7-undecene; and inorganic bases such as sodium hydroxide, potassium hydroxide, calcium hydroxide, sodium carbonate, potassium carbonate, sodium hydrogen carbonate, calcium carbonate and sodium hydride. The amount used of the base is usually within a range of 0.5 to 10 molar equivalents and preferably within a range of 1 to 5 molar equivalents of the amount of the compound of the formula (1a).

The reaction temperature is usually within a range of −30 to 180° C. and preferably within a range of −10 to 50° C. The reaction period of this reaction is usually within a range of 10 minutes to 30 hours.

The completion of this reaction can be confirmed by sampling a part of the reaction mixtures followed by performing analytical means such as thin-layer chromatography and high-performance liquid chromatography. When this reaction is completed, for example, the reaction mixtures is mixed with water and extracted with an organic solvent and the resulting organic layers are treated (for example, drying and concentration) to obtain the compound of the formula (1b).

The compound of the formula (4) is a known compound, or may be prepared from a known compound.

Process 3

The present compound wherein X represents S(O) can be prepared by oxidizing the compound wherein X represents S. When an alkylthio group, an alkylsulfinyl group, a haloalkylthio group and/or a haloalkylsulfinyl group is/are contained at any position other than X in the compound of the formula (1c), these groups may be oxidized.

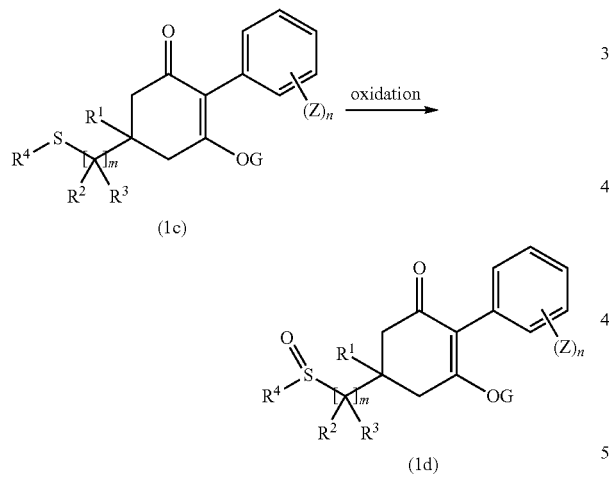

[wherein $R^1$, $R^2$, $R^3$, $R^4$, G, n, m and Z are the same as defined above]

An oxidizing agent is used in this reaction. Examples of the oxidizing agent includes hydrogen peroxide; peracids such as peracetic acid, perbenzoic acid and m-chloroperbenzoic acid; sodium periodate, ozone, selenium dioxide, chromic acid, dinitrogen tetraoxide, acetyl nitrate, iodine, bromine, N-bromosuccinimide and iodosylbenzene. The oxidizing agent is used usually within a range of 0.8 to 1.2 moles opposed to 1 mole of the compound of the formula (1c).

The reaction is carried out in a solvent. Examples of the solvent to be used in the reaction include saturated hydrocarbons such as hexane, heptane, octane and cyclohexane; aromatic hydrocarbons such as benzene, toluene, xylene, chlorobenzene and dichlorobenzene; halogenated hydrocarbons such as dichloromethane, chloroform, 1,2-dichloroethane and carbon tetrachloride; alcohols such as methanol, ethanol and propanol; nitriles such as acetonitrile; amides such as dimethylformamide and dimethylacetamide; sulfones such as sulfolane; organic acids such as acetic acid and propionic acid; and mixed solvents thereof.

The reaction temperature is usually within a range of −50 to 100° C. and preferably within a range of 0 to 50° C.

The reaction period of this reaction is usually within a range of 10 minutes to 100 hours. The completion of the reaction can be confirmed by analyzing a part of the reaction mixtures on analytical means such as thin-layer chromatography and high-performance liquid chromatography. When this reaction is completed, for example, the reaction mixtures is mixed with water and extracted with an organic solvent and the resulting organic layers are treated (for example, drying and concentration) to obtain the compound of the formula (1d).

Process 4

The present compound wherein X represents $S(O)_2$ can be prepared by oxidizing the compound wherein X represents S or S(O). When an alkylthio group, an alkylsulfinyl group, a haloalkylthio group and/or a haloalkylsulfinyl group is/are contained at any position other than X in the compound of the formula (1e), these groups may be oxidized.

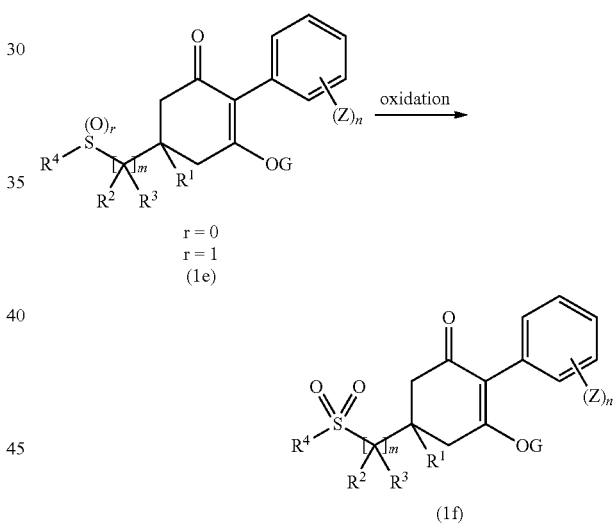

[wherein r is an integer of 0 or 1, and $R^1$, $R^2$, $R^3$, $R^4$, G, n, m and Z are the same as defined above]

An oxidizing agent is used in the reaction. Examples of the oxidizing agent include hydrogen peroxide; peracids such as peracetic acid, perbenzoic acid and m-chloroperbenzoic acid; sodium periodate, ozone, selenium dioxide, chromic acid, dinitrogen tetraoxide, acetyl nitrate, iodine, bromine, N-bromosuccinimide, iodosylbenzene, a combination of hydrogen peroxide and tungsten catalyst, a combination of hydrogen peroxide and vanadium, and potassium permanganate. When the compound of the formula (1e) wherein r is 0 is used, the amount of the oxidizing agent is usually within a range of 2 to 10 moles and preferably within a range of 2 to 4 moles opposed to 1 mole of the compound. Also when the compound of the formula (1e) wherein r is 1 is used, the amount of the oxidizing agent is usually within a range of 1 to 10 moles and preferably within a range of 1 to 3 moles opposed to 1 mole of the compound.

The reaction is carried out in a solvent. Examples of the solvent to be used in the reaction include saturated hydrocarbons such as hexane, heptane, octane and cyclohexane; aromatic hydrocarbons such as benzene, toluene, xylene, chlorobenzene and dichlorobenzene; halogenated hydrocarbons such as dichloromethane, chloroform, 1,2-dichloroethane and carbon tetrachloride; alcohols such as methanol, ethanol and propanol; nitriles such as acetonitrile; amides such as dimethylformamide and dimethylacetamide; sulfones such as sulfolane; organic acids such as acetic acid and propionic acid; water; and mixed solvents thereof.

The reaction temperature is usually within a range of 0 to 200° C. and preferably 20 to 150° C. The reaction period of the reaction is usually within a range of 30 minutes to 100 hours. The completion of the reaction can be confirmed by analyzing a part of the reaction mixtures on analytical means such as thin-layer chromatography and high-performance liquid chromatography. When this reaction is completed, for example, the reaction mixtures is mixed with water and extracted with an organic solvent and the resulting organic layers are treated (for example, drying and concentration) to obtain the compound of the formula (1f).

Process 5

The present compound of the formula (1a) wherein G represents a hydrogen atom can be prepared by reacting the compound of the formula (2) and the compound of the formula (31) in the presence of a base.

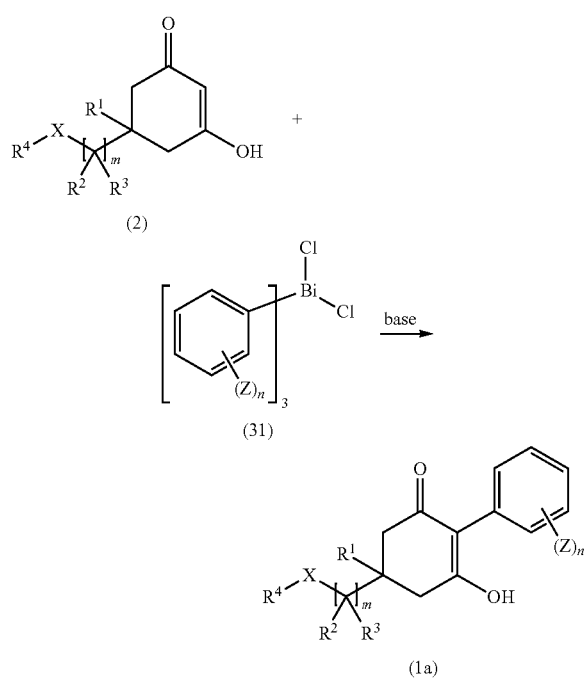

[wherein, R—, R—, R—, R—, X, n, m and Z are the same as defined above]

The reaction is usually carried out in a solvent.

Examples of the solvent that can be used include aromatic hydrocarbons such as benzene, toluene and xylene; ethers such as diethyl ether, diisopropylether, dioxane, tetrahydrofuran and dimethoxyethane; halogenated hydrocarbons such as dichloromethane, chloroform and 1,2-dichloroethane; amides such as dimethylformamide and dimethylacetamide; sulfones such as sulfolane; and mixed solvents thereof.

Examples of the base to be used in the reaction include organic bases such as triethylamine, tripropylamine, pyridine, dimethylaminopyridine, 1,8-diazabicyclo[5.4.0]-7-undecene. The amount used of the base is usually within a range of 1 to 10 molar equivalents and preferably within a range of 1 to 5 molar equivalents of the amount of the compound of the formula (2). The amount used of the compound of the formula (31) is usually within a range of 1 to 3 molar equivalents of the amount of the compound of the formula (2).

The reaction temperature is usually within a range of −60 to 180° C. and preferably within a range of −10 to 100° C. The reaction period of this reaction is usually within a range of 10 minutes to 30 hours. The completion of the reaction can be confirmed by analyzing a part of the reaction mixtures on analytical means such as thin-layer chromatography and high-performance liquid chromatography. When the reaction is completed, for example, after an acid is added to the reaction mixtures, the reaction mixtures is mixed with water and extracted with an organic solvent and the resulting organic layers are treated (for example, drying and concentration) to obtain the compound of the formula (1a).

Process 6

The present compound of the formula (1g) can be prepared by reacting the compound of the formula (22) and the compound of the formula (21) in the presence of a phosphine.

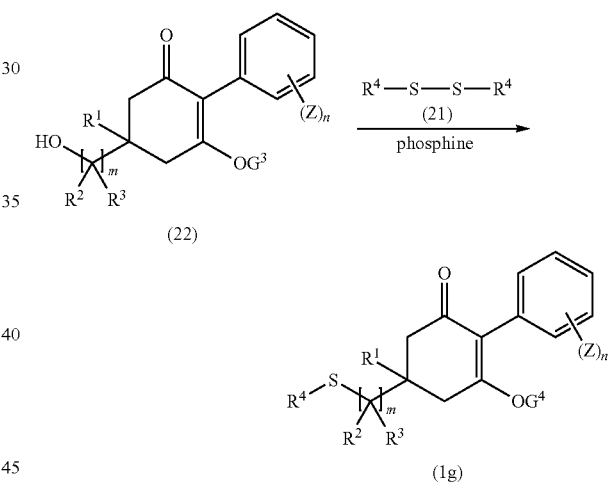

[wherein $G^3$ represents a group of the formula:

(wherein L and $R^5$ are the same as defined above), $G^4$ represents a hydrogen atom or a group of the formula:

(wherein L and $R^5$ are the same as defined above), and $R^1$, $R^2$, $R^3$, $R^4$, n, m and Z are the same as defined above]

The reaction is usually carried out in a solvent. Examples of the solvent include ethers such as diethyl ether, diisopropylether, dioxane, tetrahydrofuran and dimethoxyethane; halogenated hydrocarbons such as dichloromethane, chloroform and 1,2-dichloroethane; and mixed solvents thereof.

Examples of the phosphine include trinormalbutylphosphine and triphenylphosphine. The amount used of the phosphine to be used in the reaction is usually within a range of 1 mole or more and preferably within a range of 1 to 3 moles opposed to 1 mole of the compound of the formula (22). The amount used of the compound of the formula (21) to be used in the reaction is usually within a range of 1 mole or more and preferably within a range of 1 to 3 moles opposed to 1 mole of the compound of the formula (22).

The reaction temperature is usually within a range of −60 to 180° C. and preferably within a range of −10 to 100° C. The reaction period of this reaction is usually within a range of 10 minutes to 30 hours. The completion of the reaction can be confirmed by analyzing a part of the reaction mixtures on analytical means such as thin-layer chromatography and high-performance liquid chromatography. When the reaction is completed, for example, after an acid is added to the reaction mixtures, the reaction mixtures is mixed with water and extracted with an organic solvent and the resulting organic layers are treated (for example, drying and concentration) to obtain the compound of the formula (1g).

Process 7

The present compound of the formula (1g) can be prepared by reacting the compound of the formula (34) and the compound of the formula (10).

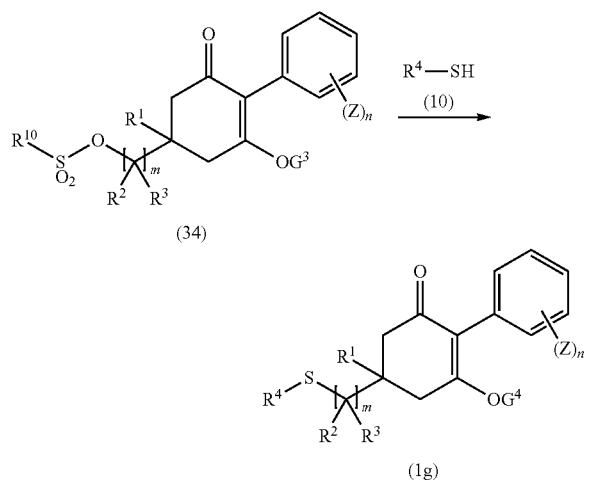

[wherein
$R^{10}$ represents a $C_{1-6}$ alkyl group or a $C_{6-10}$ aryl group (with the proviso that the $C_{1-6}$ alkyl group and the $C_{6-10}$ aryl group may have one or more halogen atoms, and when two or more halogen atoms exist, the halogen atoms may be same or different to each other; and the $C_{6-10}$ aryl group may have one or more $C_{1-6}$ alkyl groups and when two or more $C_{1-6}$ alkyl groups exist, the alkyl groups may be same or different to each other;

$R^1$, $R^2$, $R^3$, $R^4$, n, m, Z, $G^3$ and $G^4$ are the same as defined above]

The reaction is usually carried out in a solvent. Examples of the solvent include ethers such as diethyl ether, diisopropylether, dioxane, tetrahydrofuran and dimethoxyethane; halogenated hydrocarbons such as dichloromethane, chloroform and 1,2-dichloroethane; amides such as dimethylformamide and dimethylacetamide; and mixed solvents thereof.

The amount used of the compound of the formula (10) to be used in the reaction is usually within a range of 1 mole or more and preferably within a range of 1 to 5 moles opposed to 1 mole of the compound of the formula (34).

The reaction temperature is usually within a range of −60 to 180° C. and preferably within a range of −10 to 100° C. The reaction period of this reaction is usually within a range of 10 minutes to 30 hours. The completion of the reaction can be confirmed by analyzing a part of the reaction mixtures on analytical means such as thin-layer chromatography and high-performance liquid chromatography. When the reaction is completed, for example, after an acid is added to the reaction mixtures, the reaction mixtures is mixed with water and extracted with an organic solvent and the resulting organic layers are treated (for example, drying and concentration) to obtain the compound of the formula (1g).

Process 8

The present compound of the formula (1h) can be prepared by hydrolyzing the compound of the formula (1g) in the presence of a base.

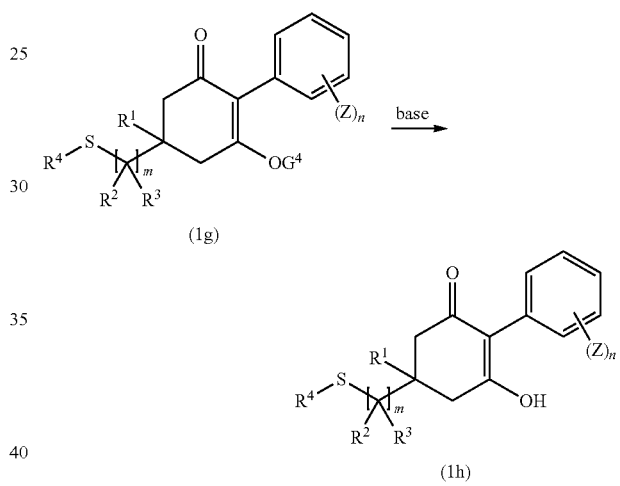

[wherein $R^1$, $R^2$, $R^3$, $R^4$, n, m, Z and $G^4$ are the same as defined above]

The reaction is usually carried out in a solvent.

Examples of the solvent include ethers such as diethyl ether, diisopropylether, dioxane, tetrahydrofuran and dimethoxyethane; alcohols such as methanol and ethanol; amides such as dimethylformamide and dimethylacetamide; and mixed solvents thereof.

Examples of the base to be used in the reaction include lithium hydroxide, sodium hydroxide, potassium hydroxide, sodium methoxide and sodium ethoxide. The amount used of the base is usually within a range of 1 to 10 molars and preferably within a range of 1 to 5 molars opposed to 1 mole of the compound of the formula (1g).

The reaction temperature is usually within a range of −60 to 180° C. and preferably within a range of −10 to 100° C. The reaction period of this reaction is usually within a range of 10 minutes to 30 hours.

The completion of the reaction can be confirmed by analyzing a part of the reaction mixtures on analytical means such as thin-layer chromatography and high-performance liquid chromatography. When the reaction is completed, for example, after an acid is added to the reaction mixtures, the reaction mixtures is mixed with water and extracted with an organic solvent and the resulting organic layers are treated (for example, drying and concentration) to obtain the compound of the formula (1h).

Process 9

The present compound of the formula (1i) can be prepared by reacting the compound of the formula (35) and the compound of the formula (11) in the presence of cupper sulfate and sodium ascorbate.

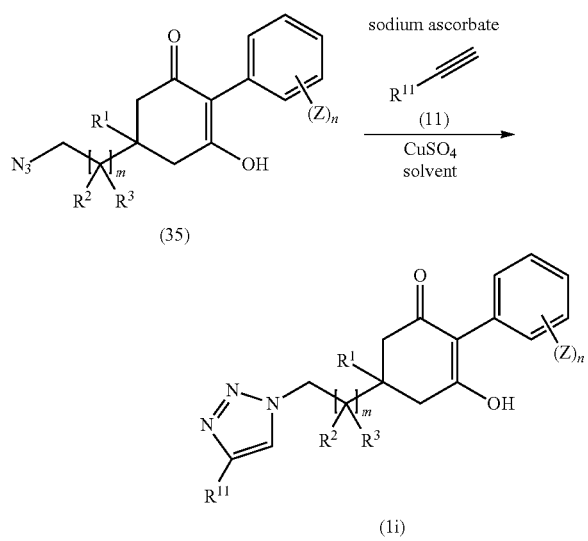

[wherein
$R^{11}$ represents a $C_{6-10}$ aryl group (with the proviso that the $C_{6-10}$ aryl group may have one or more halogen atoms or $C_{1-3}$ haloalkyl groups, and when two or more halogen atoms or $C_{1-3}$ haloalkyl groups exist, the halogen atoms or the $C_{1-3}$ haloalkyl groups may be same or different to each other respectively);
$R^1$, $R^2$, $R^3$, n, m and Z are the same as defined above]

The reaction is usually carried out in a solvent. Examples of the solvent include nitriles such as acetonitrile; amides such as dimethylformamide; sulfoxides such as dimethyl sulfoxide; and mixed solvents thereof.

The amount used of the compound of the formula (11) is usually within a range of 1 to 10 molar equivalents and preferably within a range of 1 to 3 molar equivalents of the amount of the compound of the formula (35). The amount used of copper sulfate is usually within a range of 0.02 to 0.2 molar equivalents of the amount of the compound of the formula (35). The amount used of sodium ascorbate is usually within a range of 0.05 to 0.5 molar equivalents of the amount of the compound of the formula (35).

The reaction temperature is usually within a range of 20 to 100° C. The reaction period of this reaction is usually within a range of 10 minutes to 30 hours.

The completion of the reaction can be confirmed by analyzing a part of the reaction mixtures on analytical means such as thin-layer chromatography and high-performance liquid chromatography. When the reaction is completed, for example, after an acid is added to the reaction mixtures, the reaction mixtures is mixed with water and extracted with an organic solvent and the resulting organic layers are treated (for example, drying and concentration) to obtain the compound of the formula (1i).

The compounds that are prepared according to the above-mentioned processes 1 to 9 may be isolated and/or purified by other known means such as concentration, concentration under reduced pressure, extraction, re-extraction, crystallization, recrystallization and chromatography.

Reference Process 1

The compound of the formula (3) can be prepared for example, by reacting the compound of the formula (5) and lead tetraacetate in the presence of a base according to a method described in Journal of Chemical Society Perkin Transion 1 (1990) p. 721 by Marie-Luise Huber and John T. Pinhey.

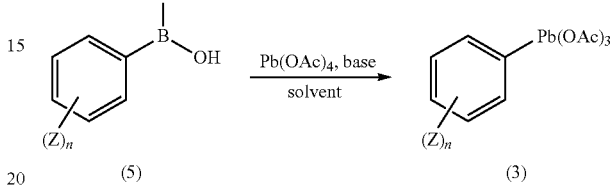

[wherein Z and n are the same as defined above]

The compound of the formula (5) is a known compound, or may be prepared from a known compound. The compound can be prepared for example, according to the method described in JP 2008-133252 A or the similar method thereof.

Reference Process 2

The compound of the formula (2) can be prepared for example, according to the below-mentioned reaction scheme.

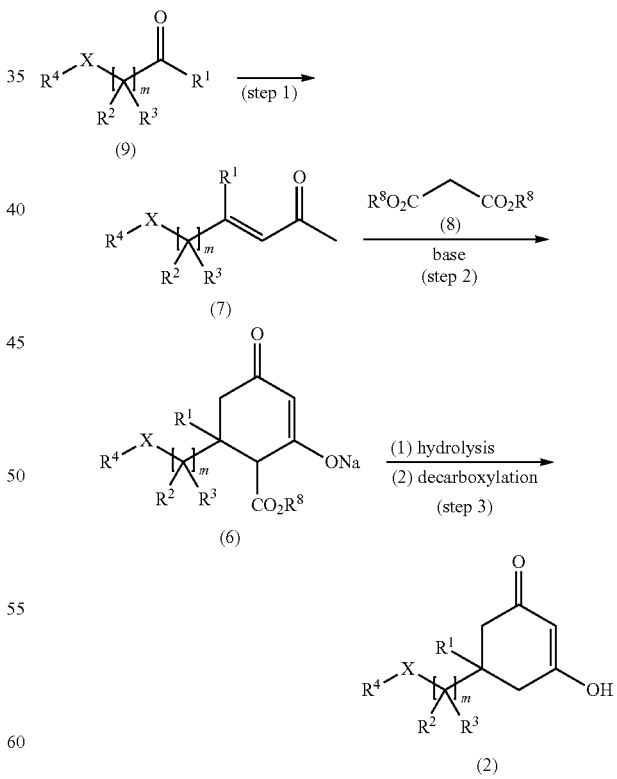

[wherein $R^8$ represents a $C_{1-3}$ alkyl group, and X, m, $R^1$, $R^2$, $R^3$, $R^4$ and n are the same as defined above]

The compound of the formula (2) can be prepared for example, according to a method described in JP 63-146856.

In the step 1, the present compound of the formula (7) can be prepared by Wittig Reaction between the compound of the formula (9) and 1-triphenylphosphoranylidene-2-propanone.

In the step 2, the compound of the formula (6) can be prepared by reacting the compound of the formula (7) and the compound of the formula (8) under basic condition. Among the compound of the formula (8), the dimethyl malonate or diethyl malonate is preferred. This reaction is carried out in an appropriate solvent such as tetrahydrofuran, methanol, ethanol and toluene.

In the step 3, the compound of the formula (6) is hydrolyzed and then decarboxylated to prepare the compound of the formula (2).

The compound of the formula (9) is a known compound, or may be prepared from a known compound, and may be prepared for example, according to the method described in Tetrahedron letter 28 (1987) 2893-2894, Tetrahedron letter 47 (2006) 5869-5873, Tetrahedron 42 (1986) 6071-6095 or JP 63-146856 or the similar methods thereof.

Reference Process 3

The compound of the formula (3-1) can be prepared for example, according to the below-mentioned methods.

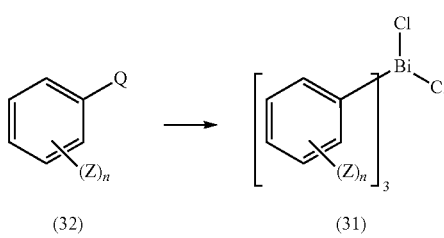

(32)   (31)

[wherein Q represents a halogen atom, and Z and n are the same as defined above]

The compound of the formula (31) can be prepared for example, from the compound of the formula (3-2) according to the method described in Bull. Chem. Soc. Jpn., 65, 3504-3506 (1992).

The compound of the formula (32) is a known compound, or may be prepared from a known compound, and may be prepared for example, according to the method described in WO 2010102761 or WO 2006084663 or the similar methods thereof.

Reference Preparation Example 4

The compound of the formula (22) can be prepared for example, according to the below-mentioned method.

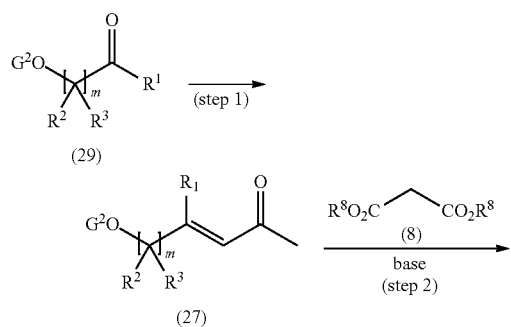

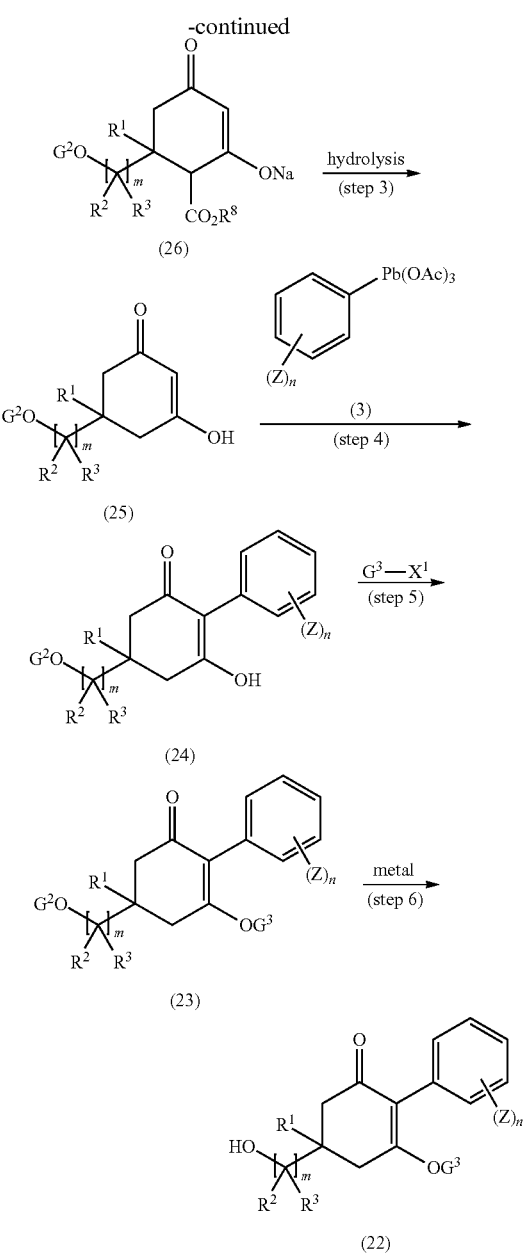

[wherein $G^2$ represents a benzyl group or a para-methoxybenzyl group, and $G^3$, m, $R^1$, $R^2$, $R^3$, $R^8$, Z, $X^1$ and n are the same as defined above]

The compound of the formula (25) can be prepared for example, according to the method described in JP 63-146856 A.

Step 1

The compound of the formula (27) can be prepared by Wittig Reaction between the compound of the formula (29) and 1-triphenylphosphoranylidene-2-propanone.

Step 2

The compound of the formula (26) can be prepared by reacting the compound of the formula (27) and the compound of the formula (8) under basic condition.

Examples of the compound of the formula (8) include dimethylmalonate or diethylmalonate. Examples of the solvent to be used in the reaction include tetrahydrofuran, methanol, ethanol and toluene.

Step 3
The compound of the formula (25) can be prepared by hydrolyzing the compound of the formula (26) followed by decarboxylation.

Step 4
The compound of the formula (24) can be prepared by reacting the compound of the formula (25) and the compound of the formula (3) in the presence of a base.

The reaction is usually carried out in a solvent.

Examples of the solvent include aromatic hydrocarbons such as benzene, toluene and xylene; ethers such as diethyl ether, diisopropylether, dioxane, tetrahydrofuran and dimethoxyethane; halogenated hydrocarbons such as dichloromethane, chloroform and 1,2-dichloroethane; amides such as dimethylformamide and dimethylacetamide; sulfones such as sulfolane; and mixed solvents thereof.

Examples of the base to be used in the reaction include organic bases such as triethylamine, tripropylamine, pyridine, dimethylaminopyridine and 1,8-diazabicyclo[5.4.0]-7-undecene. The amount used of the base is usually within a range of 1 to 10 molars and preferably within a range of 2 to 5 molars opposed to 1 mole of the compound of the formula (25). The amount used of the compound of the formula (3) is usually within a range of 1 to 3 molar equivalents of the amount of the compound of the formula (25).

The reaction temperature is usually within a range of −60 to 180° C. and preferably within a range of −10 to 100° C. The reaction period of this reaction is usually within a range of 10 minutes to 30 hours.

The completion of the reaction can be confirmed by analyzing a part of the reaction mixtures on analytical means such as thin-layer chromatography and high-performance liquid chromatography. When the reaction is completed, for example, after an acid is added to the reaction mixtures, the reaction mixtures is mixed with water and extracted with an organic solvent and the resulting organic layers are treated (for example, drying and concentration) to obtain the compound of the formula (24).

Step 5
The compound of the formula (23) can be prepared by reacting the compound of the formula (24) and the compound of $G^3$-$X^1$ in the presence of a base. The reaction is usually carried out in a solvent. Examples of the solvent include aromatic hydrocarbons such as benzene and toluene; ethers such as diethyl ether, diisopropylether, dioxane, tetrahydrofuran and dimethoxyethane; halogenated hydrocarbons such as dichloromethane, chloroform and 1,2-dichloroethane; amides such as dimethylformamide and dimethylacetamide; sulfoxides such as dimethyl sulfoxide; sulfones such as sulfolane; and mixed solvents thereof.

Examples of the compound of $G^3$-$X^1$ to be used in the reaction include carboxylic halides such as acetyl chloride, propionyl chloride, isobutyryl chloride, pivaloyl chloride, benzoyl chloride, cyclohexanecarboxylic acid chloride; carboxylic anhydrides such as acetic anhydride and trifluoroacetic anhydride; halides of carbonate ester such as methyl chloroformate, ethyl chloroformate and phenyl chloroformate; carbamic halides such as dimethylcarbamoyl chloride; sulfonic halides such as methanesulfonyl chloride and p-toluenesulfonyl chloride; sulfonic anhydrides such as methanesulfonic anhydride and trifluoromethanesulfonic anhydride; alkyl halogenoalkyl ethers such as chloromethyl methyl ether and ethyl chloromethyl ether.

The amount used of the compound of $G^3$-$X^1$ to be used in the reaction is usually within a range of 1 mole or more and preferably within a range of 1 to 3 moles opposed to 1 mole of the compound of the formula (24).

Examples of the base to be used in the reaction include organic bases such as triethylamine, tripropylamine, pyridine, dimethylaminopyridine and 1,8-diazabicyclo[5.4.0]-7-undecene; and inorganic bases such as sodium hydroxide, potassium hydroxide, calcium hydroxide, sodium carbonate, potassium carbonate, sodium hydrogen carbonate, calcium carbonate and sodium hydride.

The amount used of the base is usually within a range of 0.5 to 10 moles and preferably within a range of 1 to 5 moles opposed to 1 mole of the compound of the formula (24).

The reaction temperature is usually within a range of −30 to 180° C. and preferably within a range of −10 to 50° C. The reaction period of this reaction is usually within a range of 10 minutes to 30 hours.

The completion of the reaction can be confirmed by analyzing a part of the reaction mixtures on analytical means such as thin-layer chromatography and high-performance liquid chromatography. When the reaction is completed, for example, the reaction mixtures is mixed with water and extracted with an organic solvent and the resulting organic layers are treated (for example, drying and concentration) to obtain the compound of the formula (23).

The compound of $G^3$-$X^1$ is a known compound, or may be prepared from a known compound.

Step 6
The compound of the formula (22) can be prepared by reacting the compound of the formula (23) in the presence of a metal.

The reaction is usually carried out in a solvent.

Examples of the solvent include aromatic hydrocarbons such as benzene and toluene; ethers such as diethyl ether, diisopropylether, dioxane, tetrahydrofuran and dimethoxyethane; alcohols such as methanol and ethanol; esters such as ethyl acetate; and mixed solvents thereof.

Examples of the metal to be used in the reaction include palladium and platinum. The amount used of the metal to be used in the reaction is usually within a range of 0.01 mole or more and preferably within a range of 0.01 to 0.5 mole opposed to 1 mole of the compound of the formula (23).

The reaction temperature is usually within a range of −30 to 180° C. and preferably within a range of −10 to 50° C. The reaction period of this reaction is usually within a range of 10 minutes to 30 hours.

The completion of the reaction can be confirmed by analyzing a part of the reaction mixtures on analytical means such as thin-layer chromatography and high-performance liquid chromatography. When the reaction is completed, for example, the reaction mixtures is filtered through Celite (registered trademark) and the resulting filtrates are treated (for example, concentration under reduced pressure) to obtain the compound of the formula (22).

Reference Preparation Example 5

The compound of the formula (34) can be prepared by reacting the compound of the formula (22) and the compound of the formula (35).

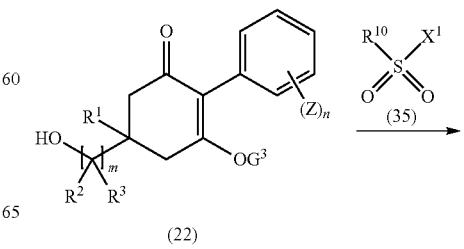

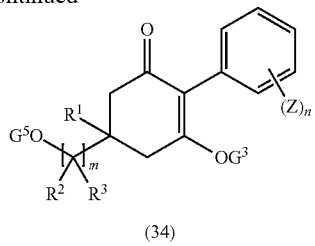

(34)

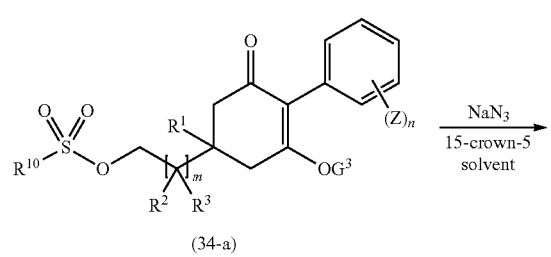

(34-a)

[wherein $R^{10}$, $X^1$, $R^1$, $R^2$, $R^3$, n, m and Z are the same as defined above]

The reaction is usually carried out in a solvent. Examples of the solvent include aromatic hydrocarbons such as benzene and toluene; ethers such diethyl ether, diisopropylether, dioxane, tetrahydrofuran and dimethoxyethane; halogenated hydrocarbons such as dichloromethane, chloroform and 1,2-dichloroethane; amides such as dimethylformamide and dimethylacetamide; sulfoxides such as dimethyl sulfoxide; sulfones such as sulfolane; and mixed solvents thereof.

Examples of the compound of the formula (35) to be used in the reaction include sulfonic halides such methanesulfonyl chloride and p-toluenesulfonyl chloride; sulfonic anhydrides such as methanesulfonic anhydride and trifluoromethanesulfonic anhydride. The amount used of the compound of the formula (35) to be used in the reaction is usually within a range of 1 mole or more and preferably within a range of 1 to 3 moles opposed to 1 mole of the compound of the formula (22).

The reaction is usually carried out in the presence of a base. Examples of the based to be used in this reaction include organic bases such as triethylamine, tripropylamine, pyridine, dimethylaminopyridine and 1,8-diazabicyclo[5.4.0]-7-undecene; and inorganic bases such as sodium hydroxide, potassium hydroxide, calcium hydroxide, sodium carbonate, potassium carbonate, sodium hydrogen carbonate, calcium carbonate and sodium hydride. The amount used of the base is usually within a range of 0.5 to 10 moles and preferably within a range of 1 to 5 moles opposed to 1 mole of the compound of the formula (22).

The reaction temperature is usually within a range of −30 to 180° C. and preferably within a range of −10 to 50° C. The reaction period of this reaction is usually within a range of 10 minutes to 30 hours.

The completion of the reaction can be confirmed by analyzing a part of the reaction mixtures on analytical means such as thin-layer chromatography and high-performance liquid chromatography.

When the reaction is completed, for example, the reaction mixtures is mixed with water and extracted with an organic solvent and the resulting organic layers are treated (for example, drying and concentration) to obtain the compound of the formula (34).

The compound of the formula (35) is a known compound, or may be prepared from a known compound.

Reference Preparation Example 6

The compound of the formula (35) can be prepared by reacting the compound of the formula (34-a) and sodium azide in the presence of 15-crown-5-ether.

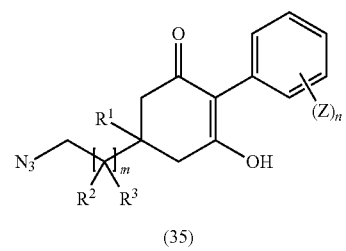

(35)

[wherein $R^{10}$, $R^1$, $R^2$, $R^3$, $G^3$, n, m and Z are the same as defined above]

The reaction is usually carried out in a solvent. Examples of the solvent include amides such as dimethylformamide and dimethylacetamide; sulfoxides such as dimethyl sulfoxide; and mixed solvents thereof. The amount used of the sodium azide is usually within a range of 1 to 20 molar equivalents and preferably within a range of 2 to 10 molar equivalents of the amount of the compound of the formula (34-a). The amount used of the 15-crown-5 is usually within a range of 0.02 to 0.2 molar equivalents of the amount of the compound of the formula (34-a).

The reaction temperature is usually within a range of −10 to 120° C. The reaction period of this reaction is usually within a range of 10 minutes to 30 hours.

The completion of the reaction can be confirmed by analyzing a part of the reaction mixtures on analytical means such as thin-layer chromatography and high-performance liquid chromatography.

When the reaction is completed, for example, the reaction mixtures are concentrated to obtain the compound of the formula (35).

The compound of the formula (34) can be prepared for example, according to the methods described in the Reference Preparation Example 5.

Some examples of the present compounds that can be prepared according to the above-mentioned processes are shown below.

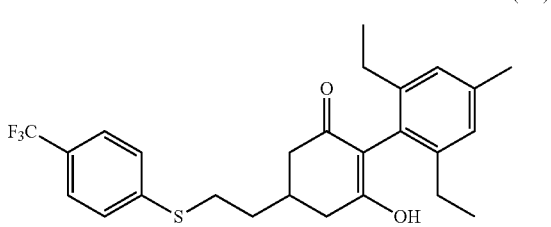

(1-1)

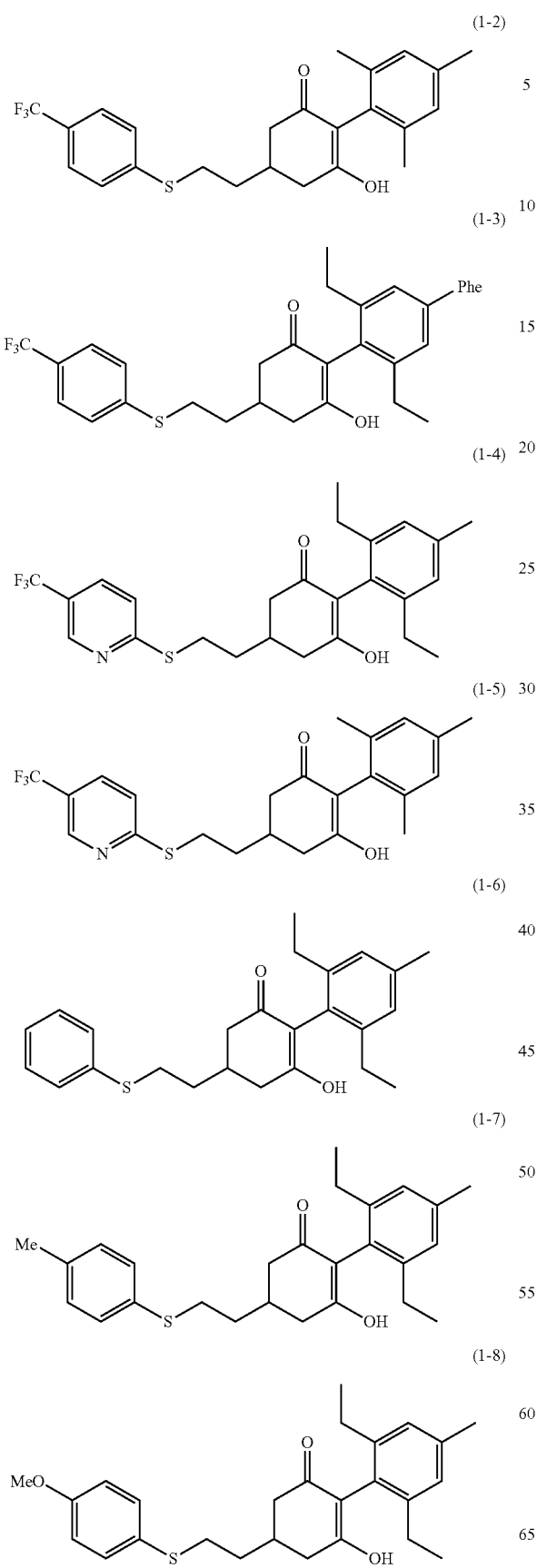
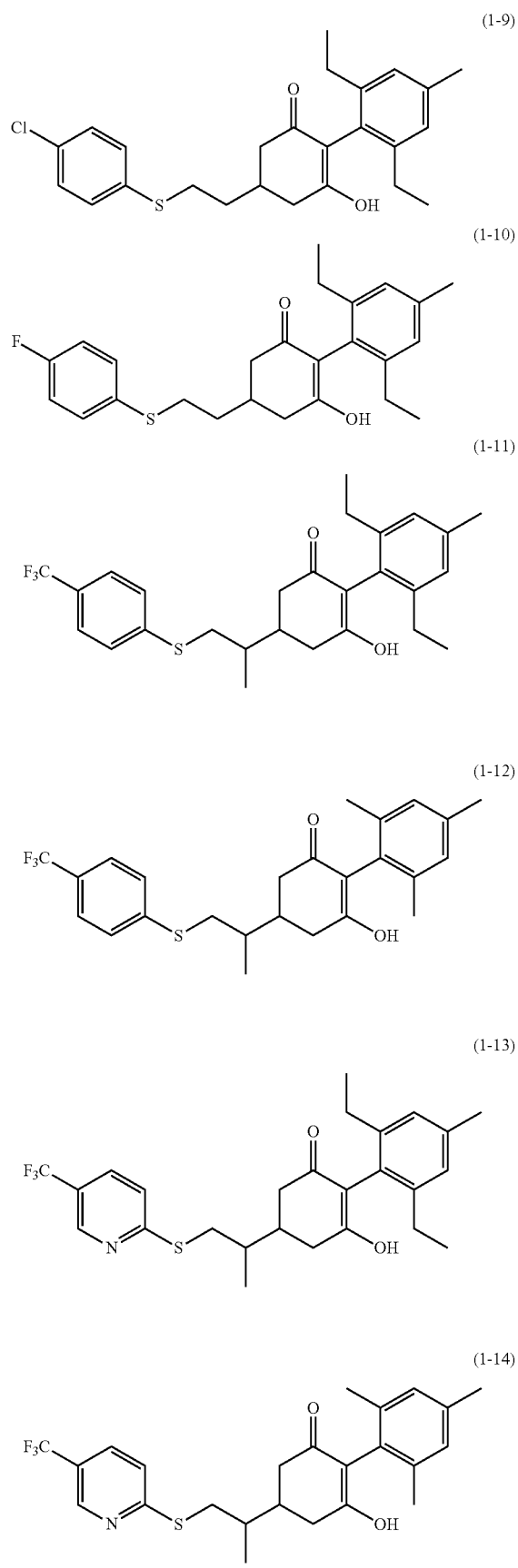

(1-15)
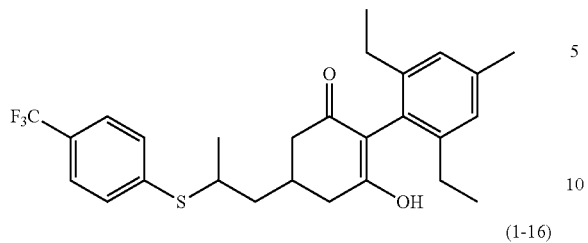
(1-16)
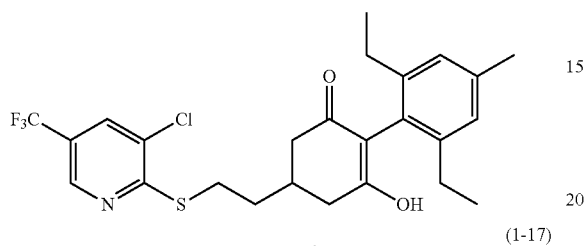
(1-17)
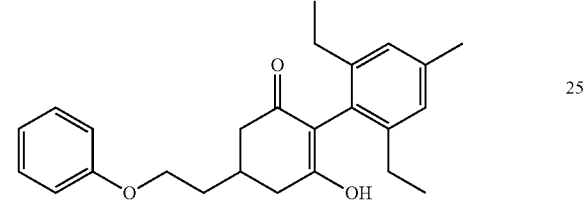
(1-18)
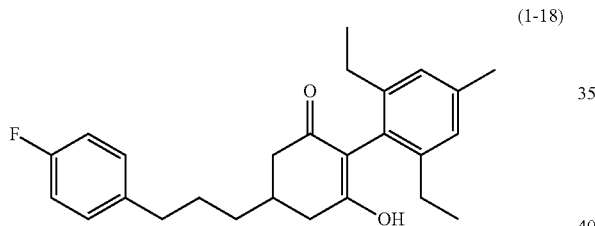
(1-19)
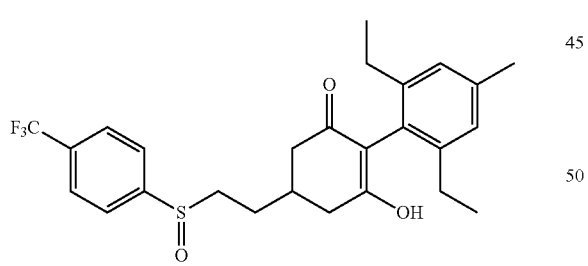
(1-20)
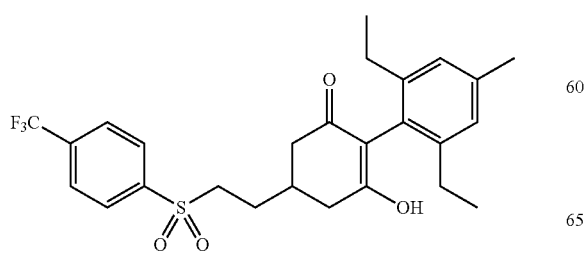
(1-21)
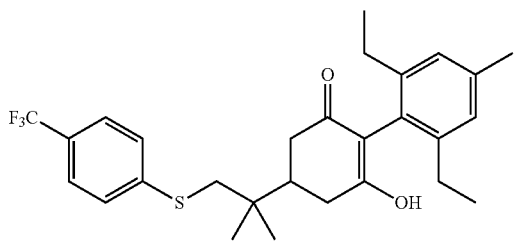
(1-22)
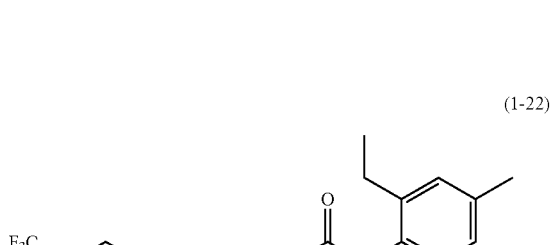
(1-23)
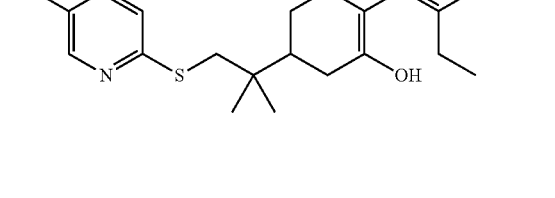
(1-24)
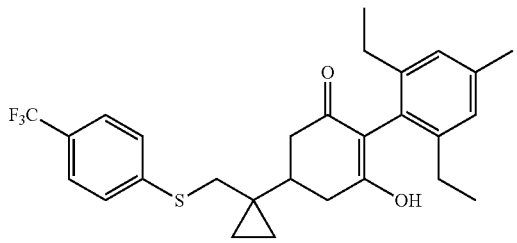
(1-25)
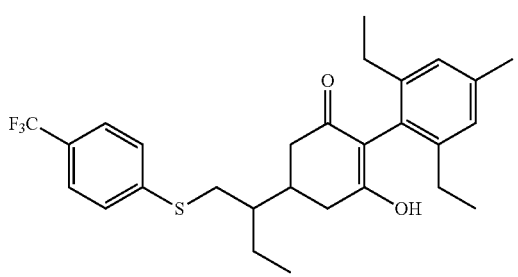

(1-26) (1-27) (1-28) (1-29) (1-30) (1-31) (1-32) (1-33) (1-34) (1-35) (1-36) (1-37) (1-38)

(1-39)
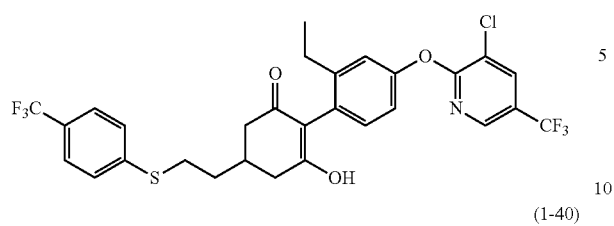
(1-40)
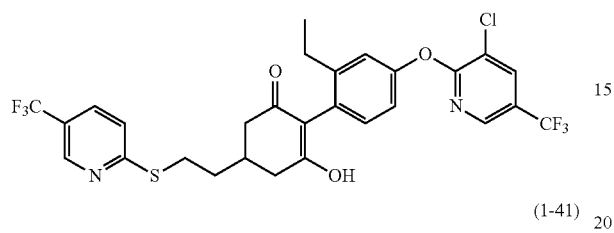
(1-41)
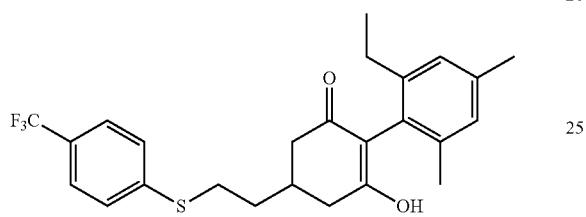
(1-42)
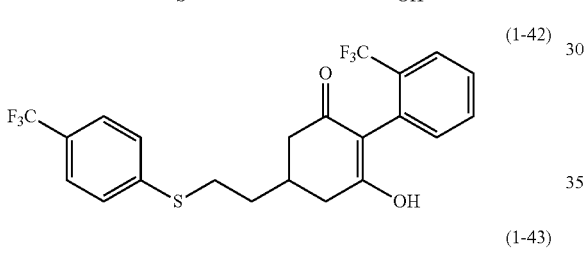
(1-43)
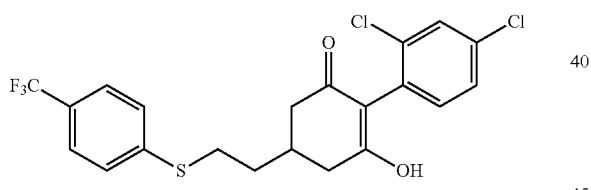
(1-44)
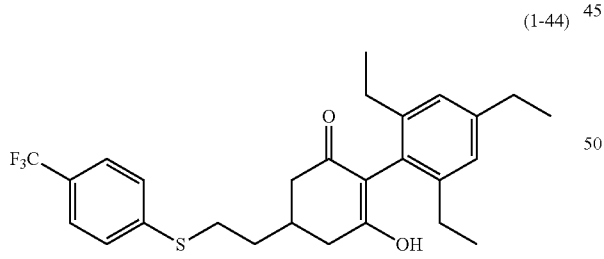
(1-45)
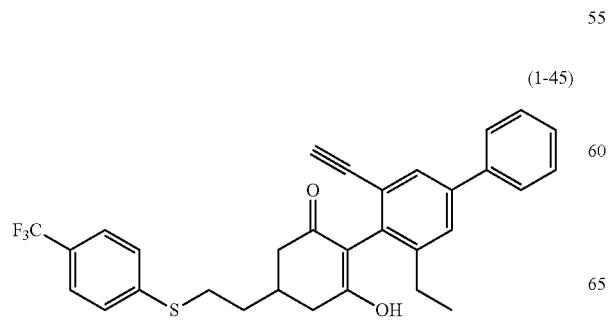
(1-46)
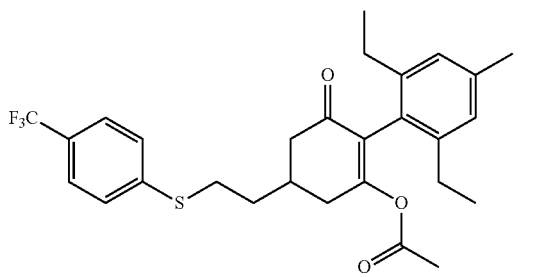
(1-47)
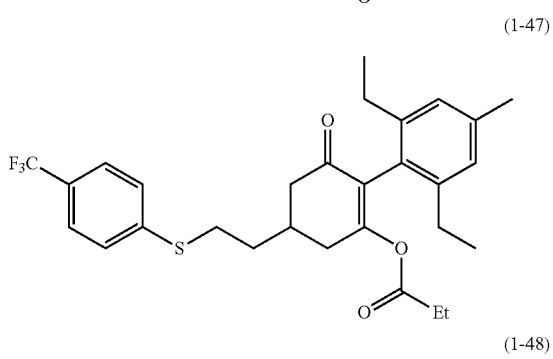
(1-48)
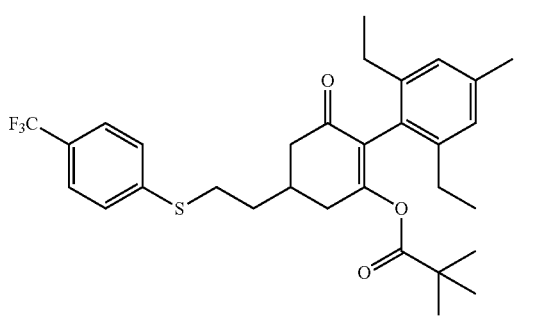
(1-49)
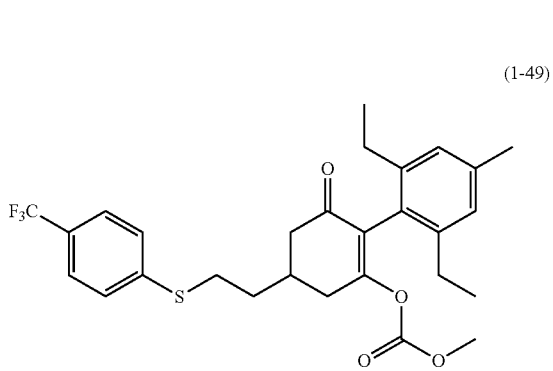
(1-50)
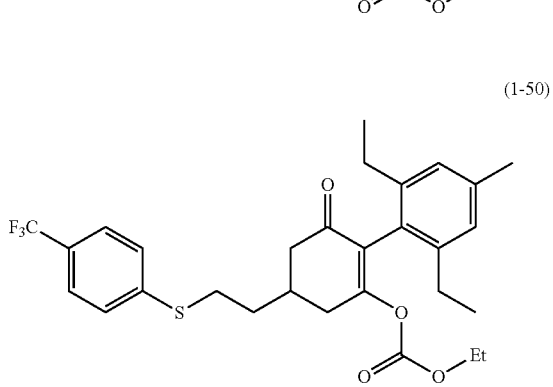

(1-51)
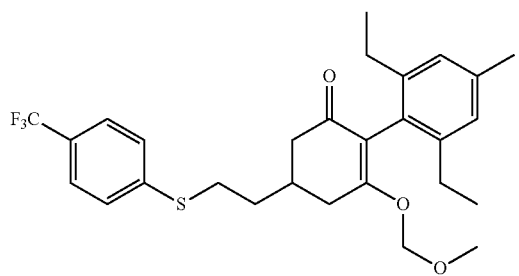
(1-52)
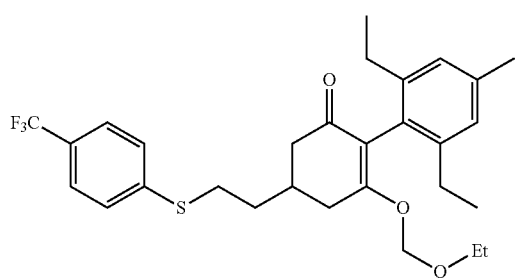
(1-53)
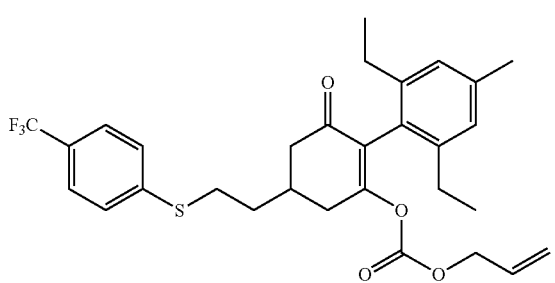
(1-54)
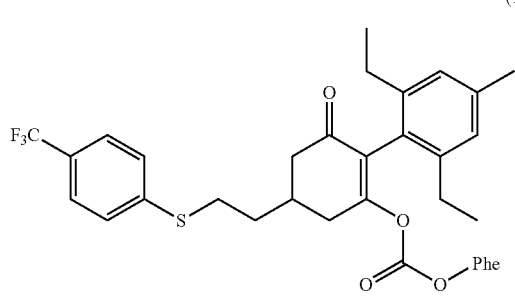
(1-55)
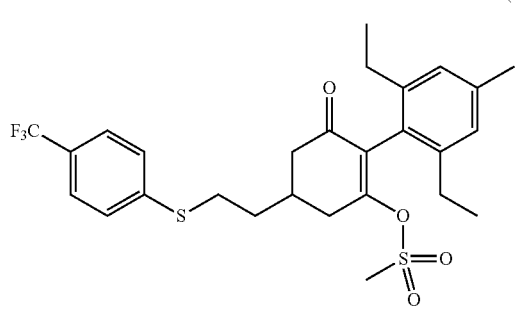
(1-56)
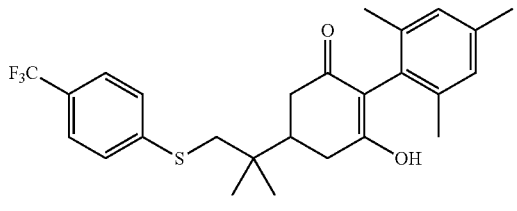
(1-57)
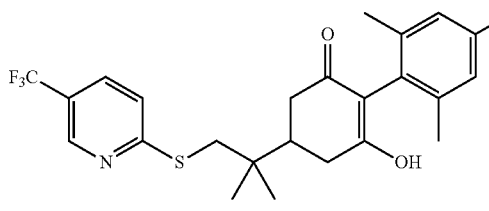
(1-58)
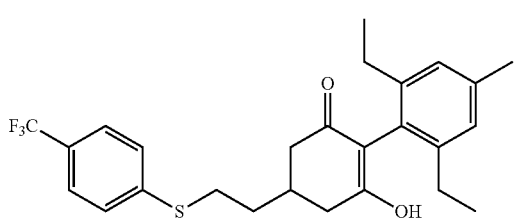
(1-59)
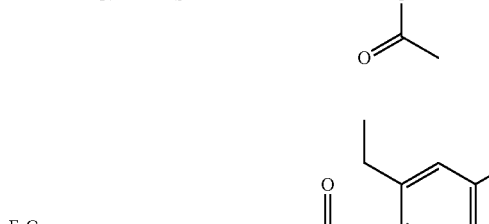
(1-60)
(1-61)
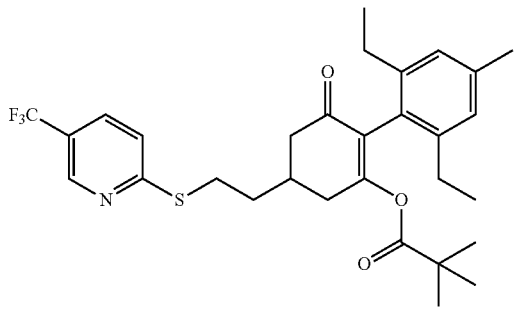

(1-62)
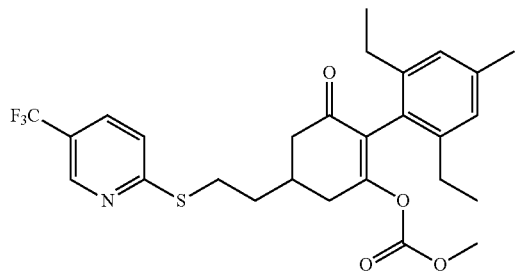
(1-63)
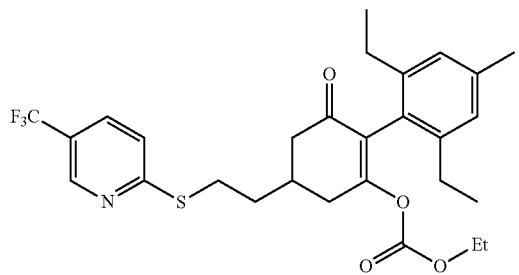
(1-64)
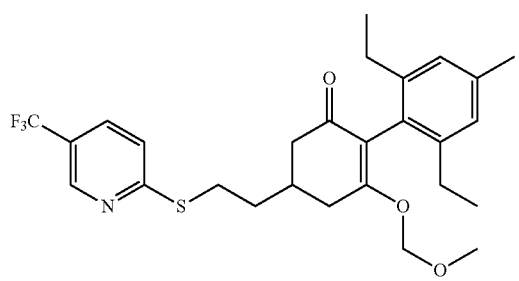
(1-65)
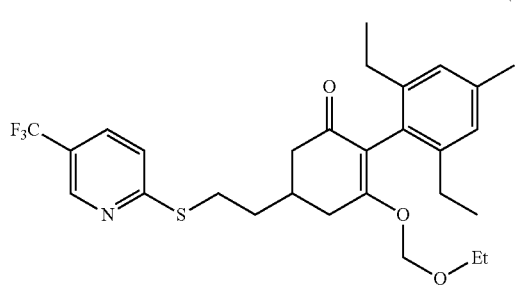
(1-66)
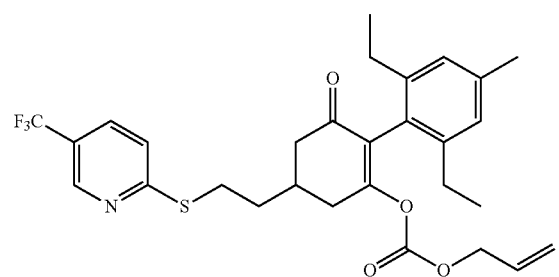
(1-67)
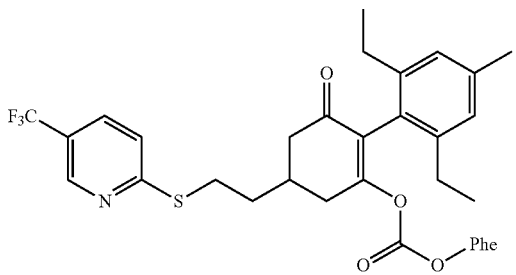
(1-68)
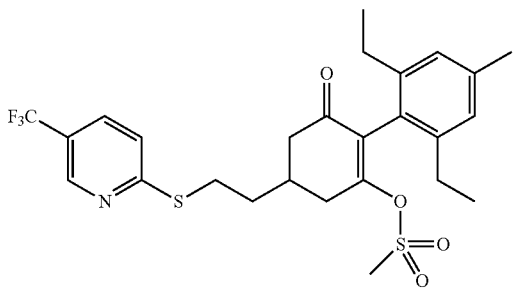
(1-69)
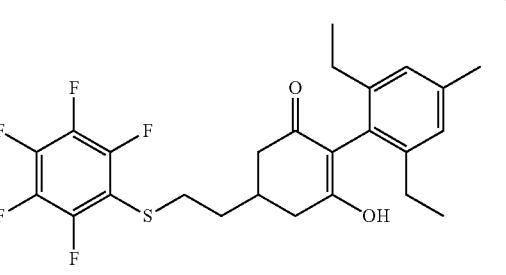
(1-70)
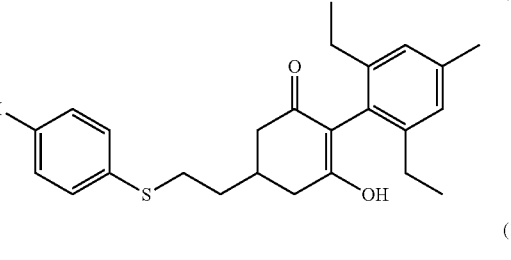
(1-71)
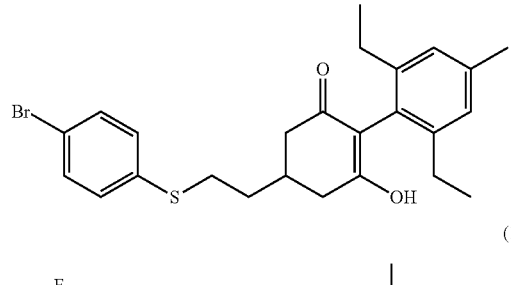
(1-72)
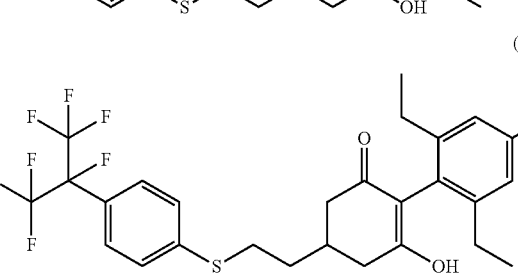

-continued
(1-73)
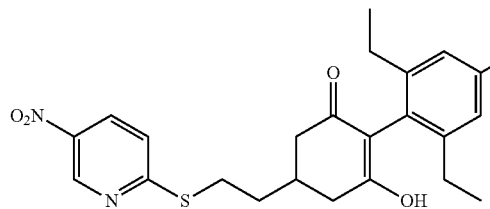
(1-74)
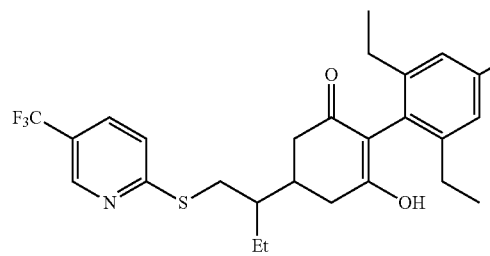
(1-75)
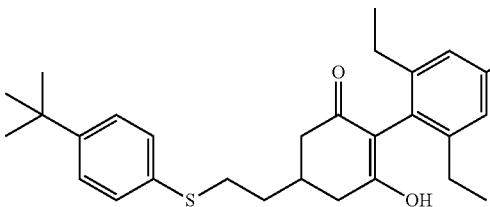
(1-76)
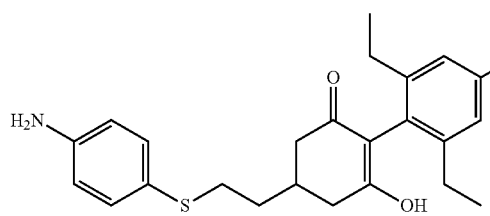
(1-77)
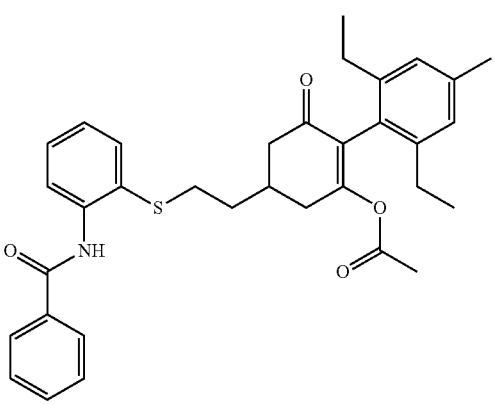
(1-78)
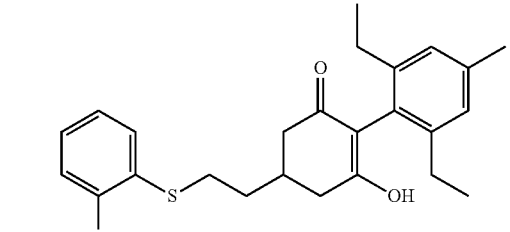
(1-79)
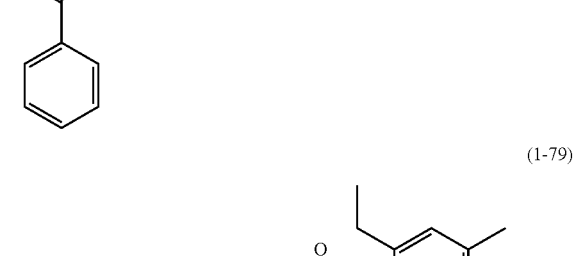
(1-80)
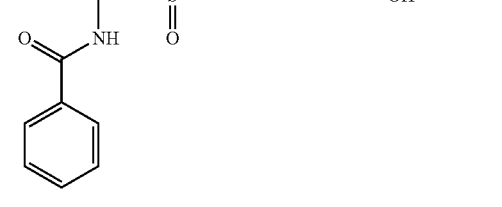
(1-81)
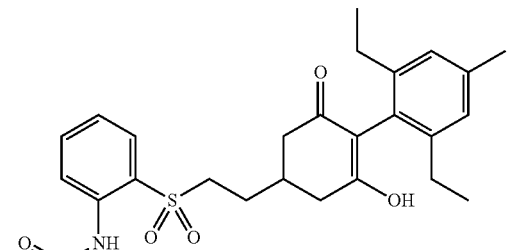

-continued
(1-82)
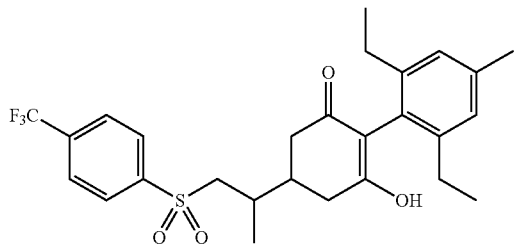
(1-83)
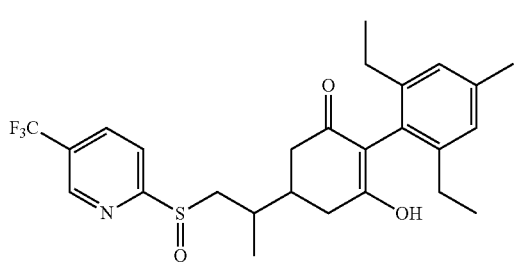
(1-84)
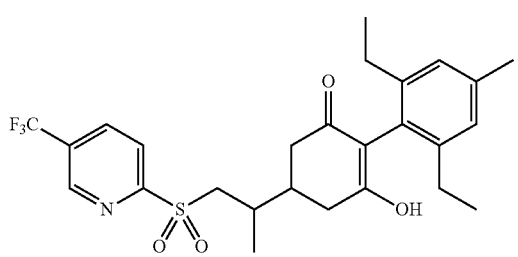
(1-85)
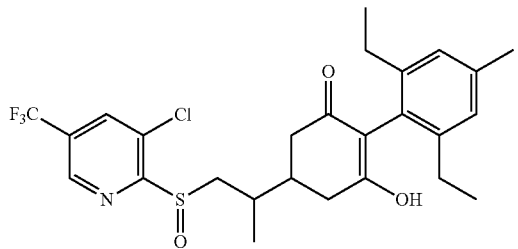
(1-86)
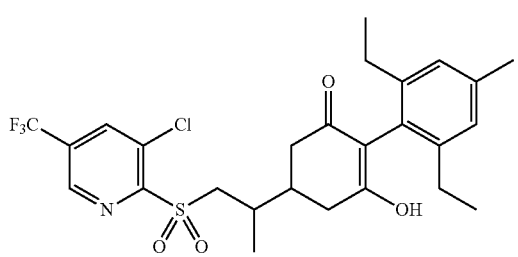
-continued
(1-87)
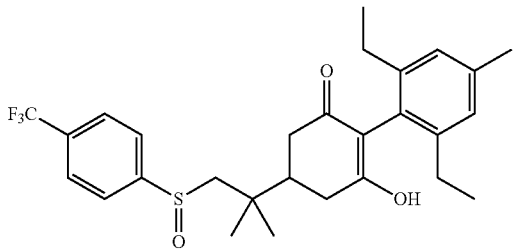
(1-88)
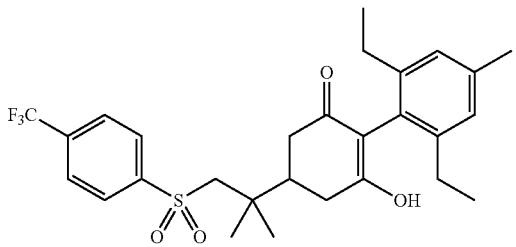
(1-89)
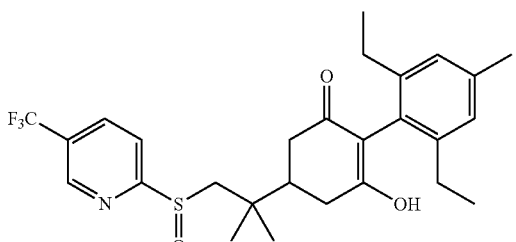
(1-90)
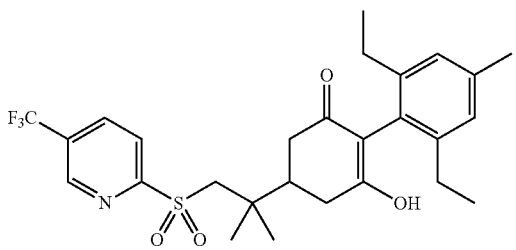
(1-91)
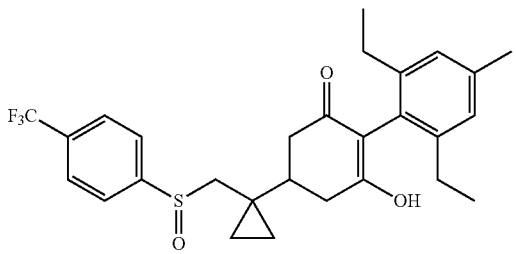
(1-92)
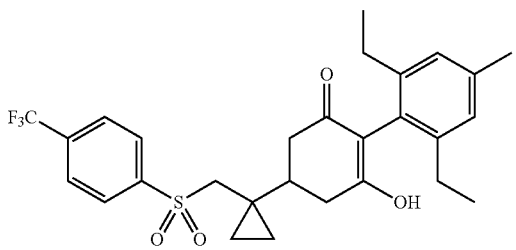

-continued
(1-93)
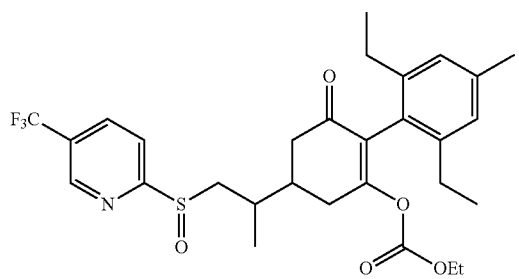
(1-94)
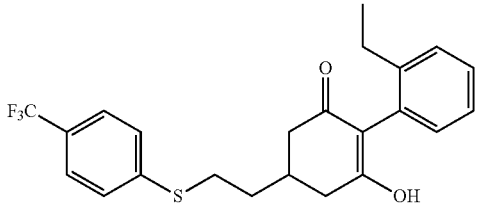
(1-95)
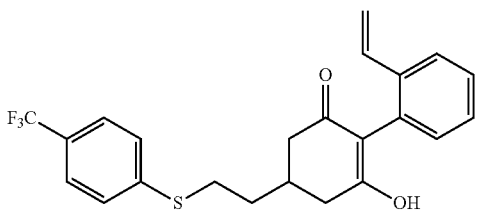
(1-96)
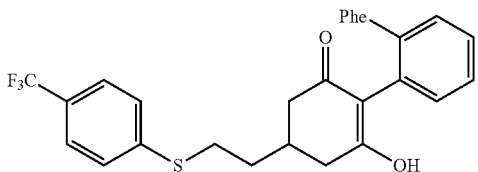
(1-97)
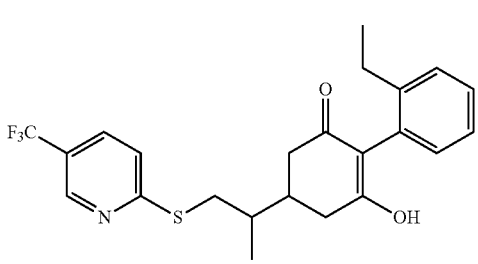
(1-98)
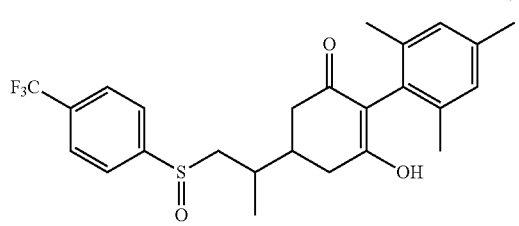
(1-99)
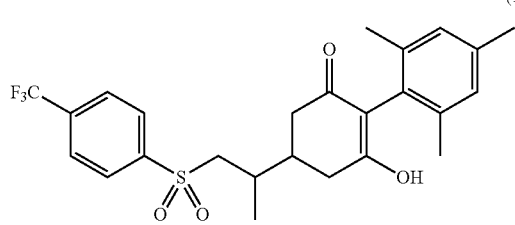
-continued
(1-100)
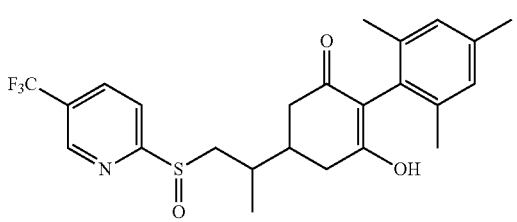
(1-101)
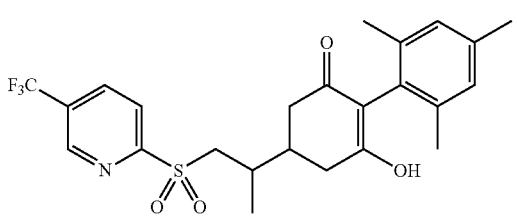
(1-102)
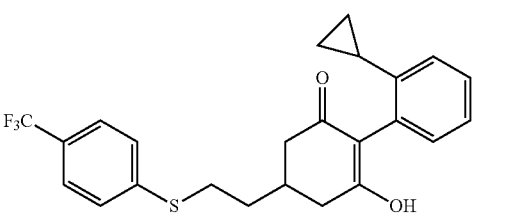
(1-103)
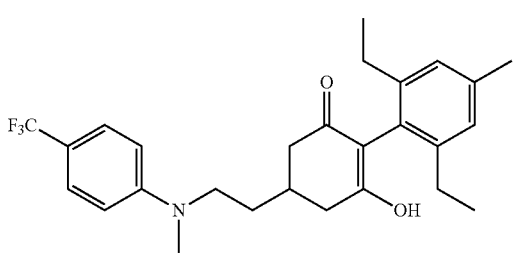
(1-104)
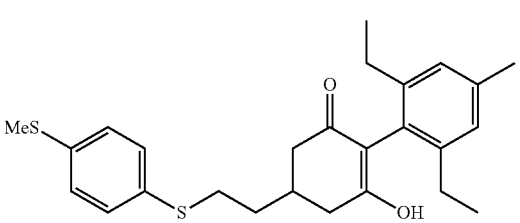
(1-105)
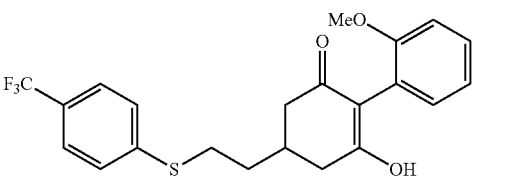

(1-106)
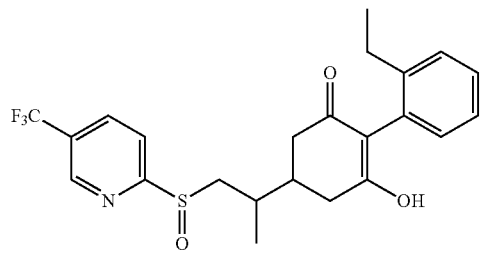
(1-107)
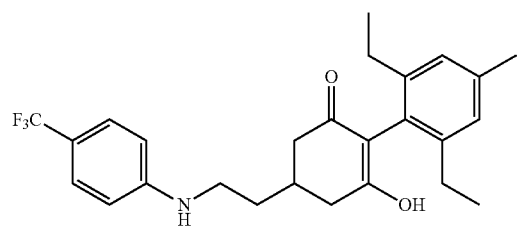
(1-108)
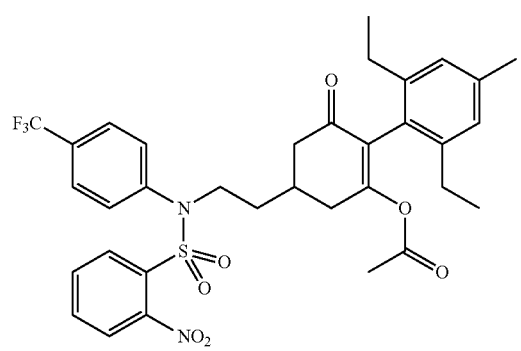
(1-109)
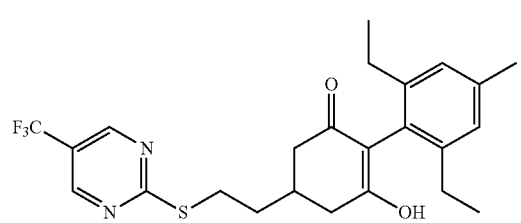
(1-110)
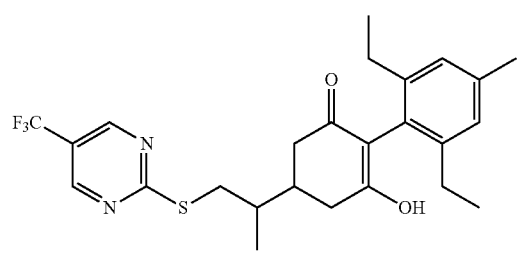
(1-111)
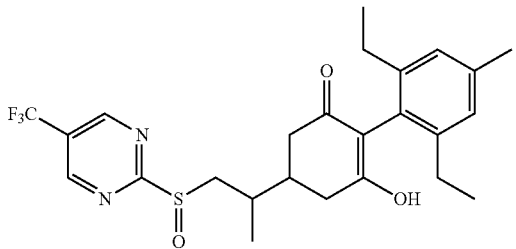
(1-112)
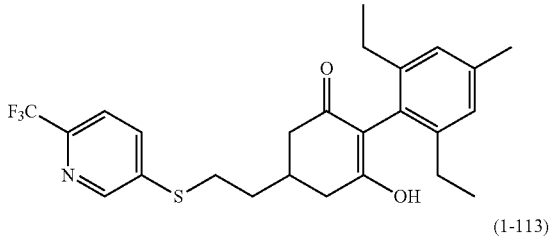
(1-113)
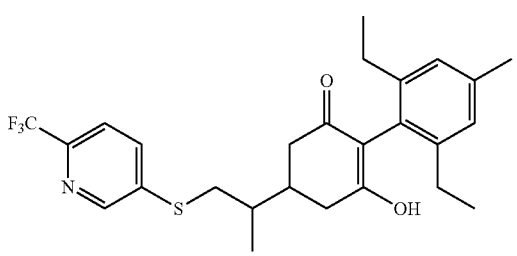
(1-114)
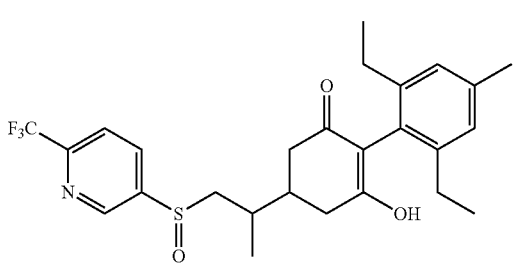
(1-115)
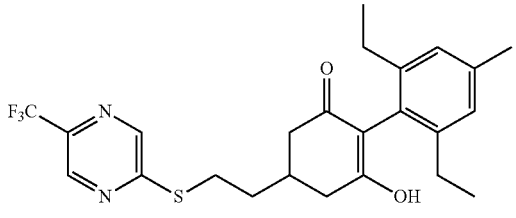
(1-116)
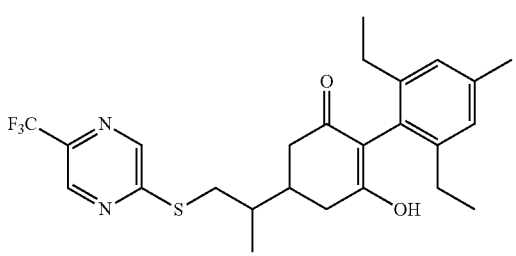

(1-117)
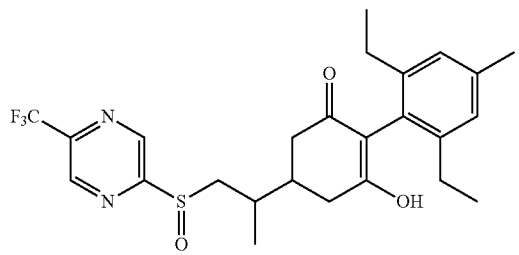
(1-118)
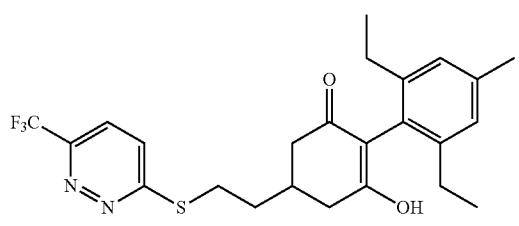
(1-119)
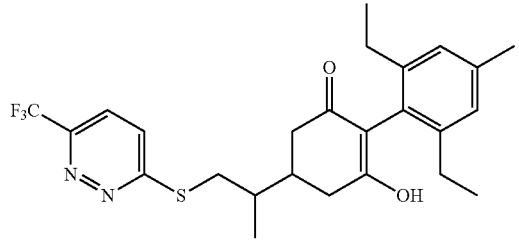
(1-120)
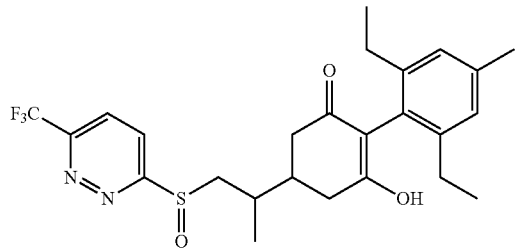
(1-121)
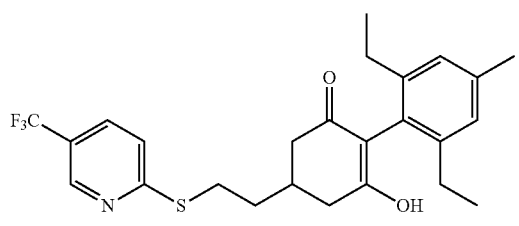
(1-122)
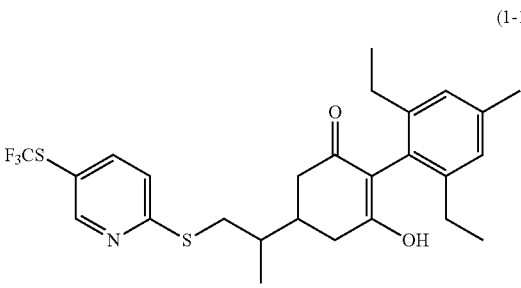
(1-123)
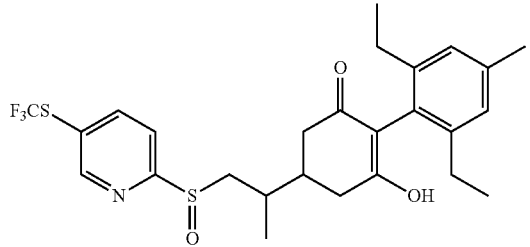
(1-124)
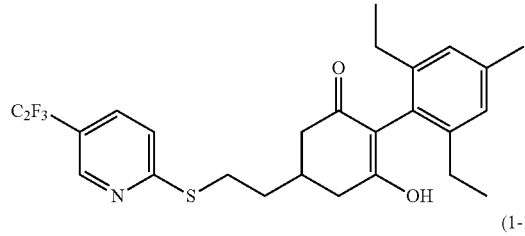
(1-125)
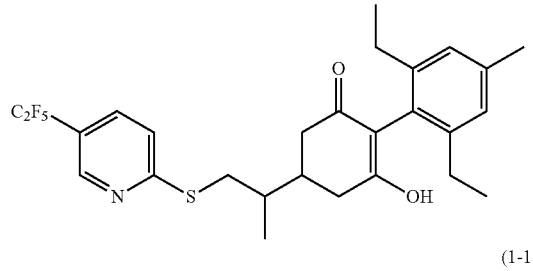
(1-126)
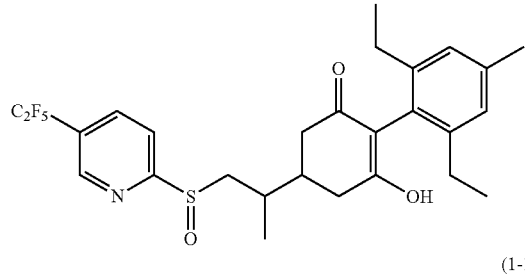
(1-127)
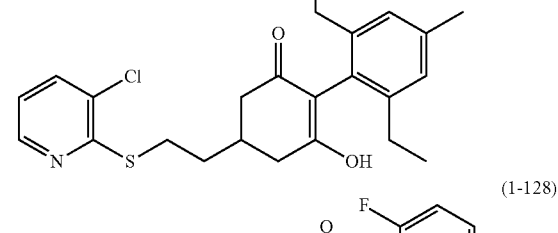
(1-128)
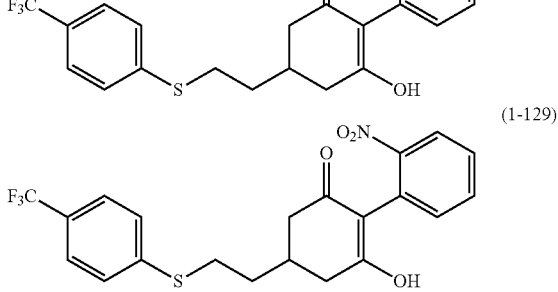
(1-129)

(1-130)
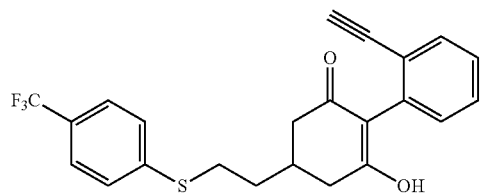
(1-131)
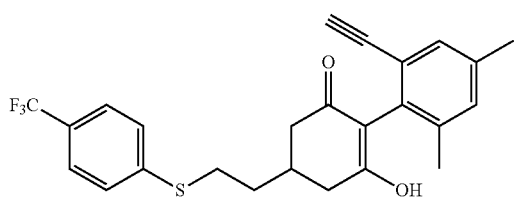
(1-132)
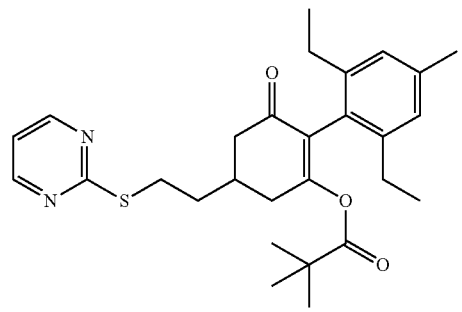
(1-133)
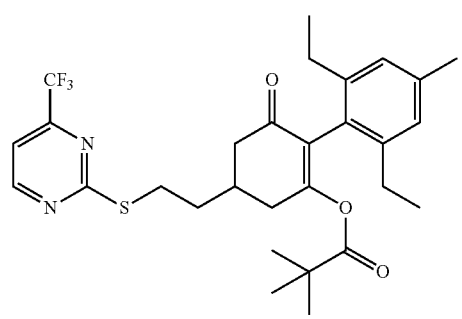
(1-134)
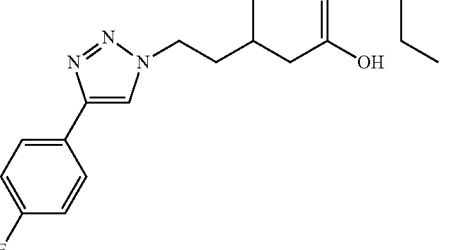
(1-135)
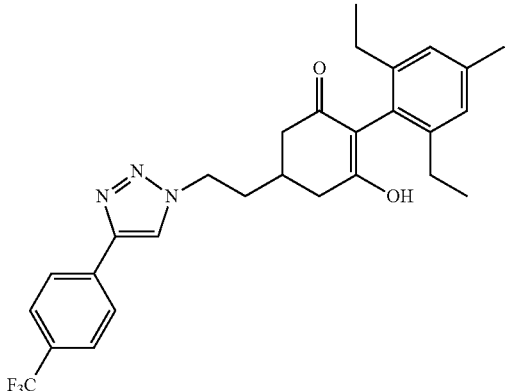
(1-136)
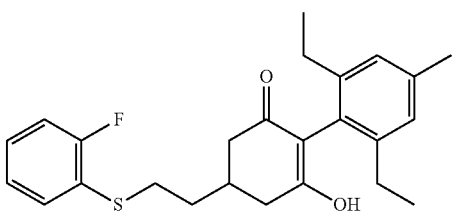
(1-137)
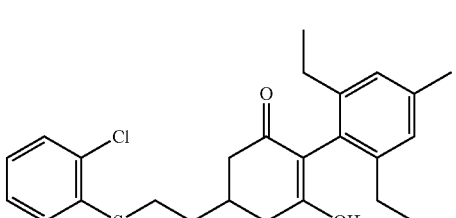
(1-138)
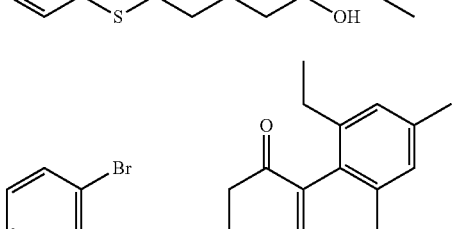
(1-139)
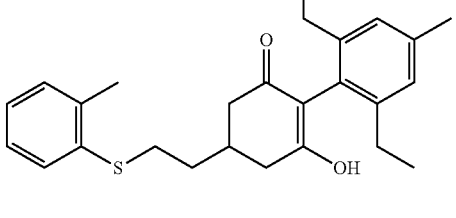
(1-140)
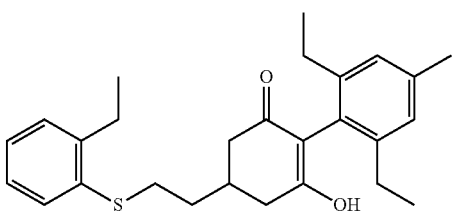

(1-141)
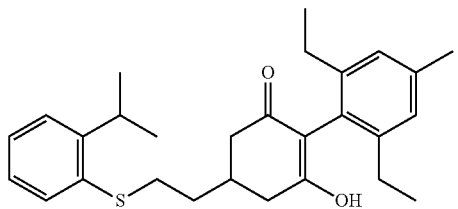
(1-142)
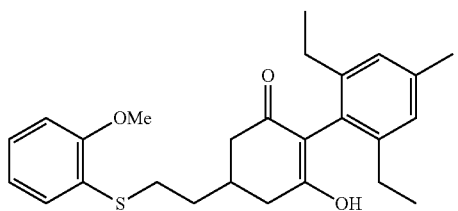
(1-143)
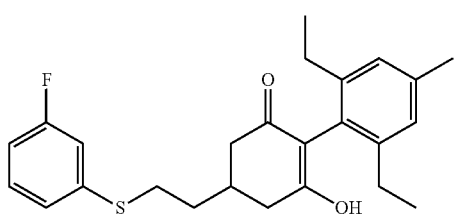
(1-144)
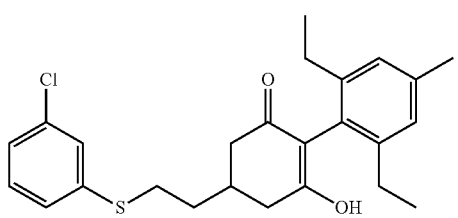
(1-145)
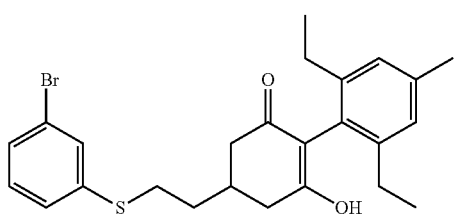
(1-146)
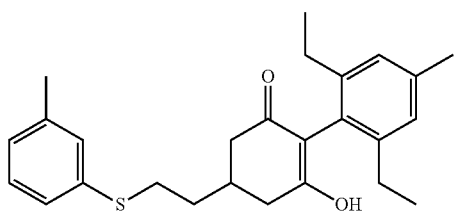
(1-147)
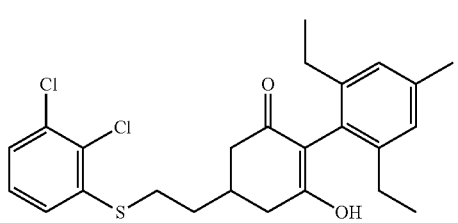
(1-148)
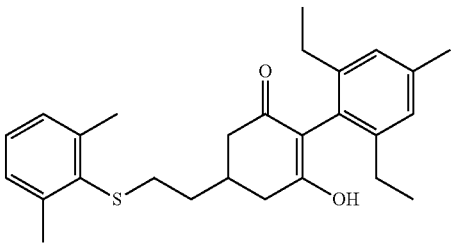
(1-149)
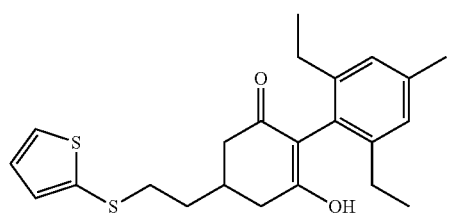
(1-150)
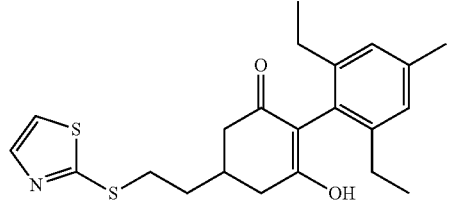
(1-151)
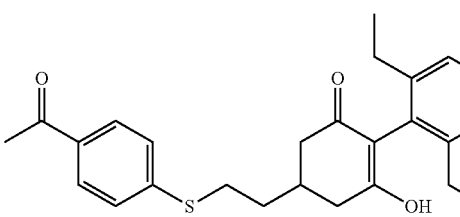
(1-152)
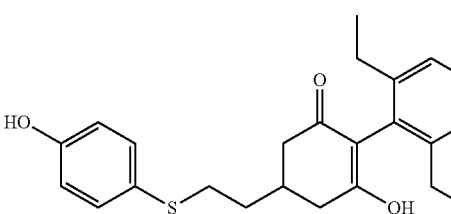
(1-153)
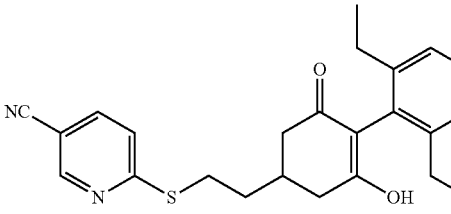

(1-154)
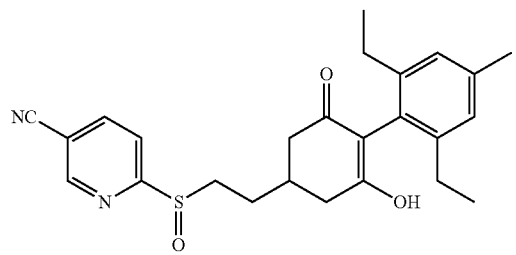
(1-155)
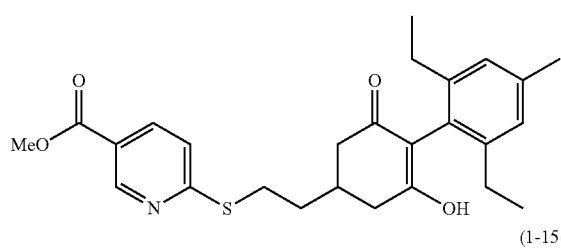
(1-156)
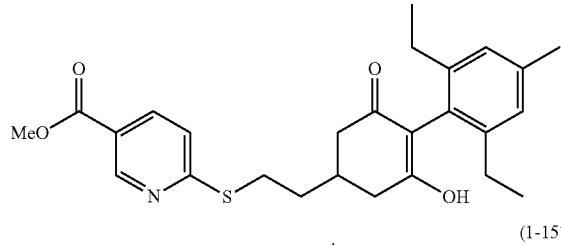
(1-157)
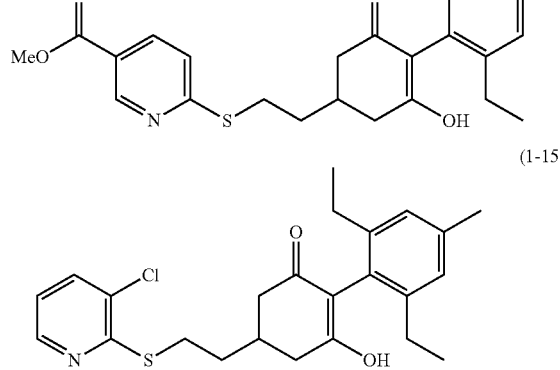
(1-158)
(1-159)
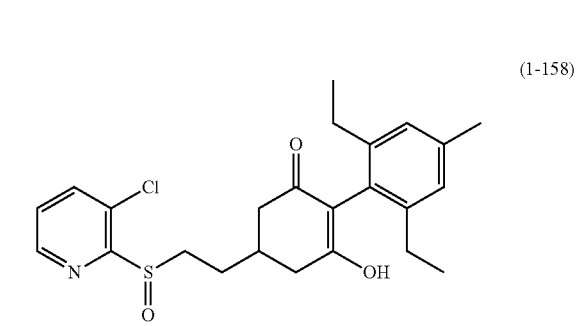
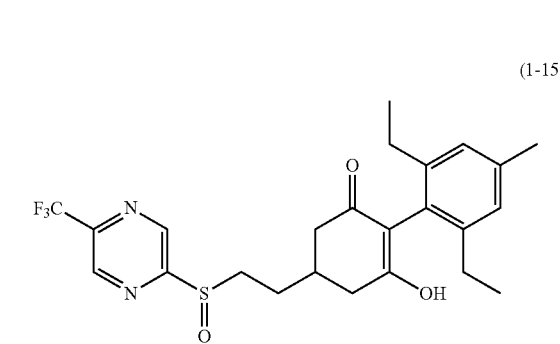
(1-160)
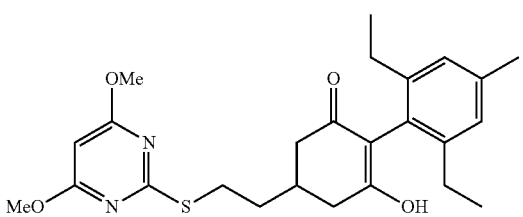
(1-161)
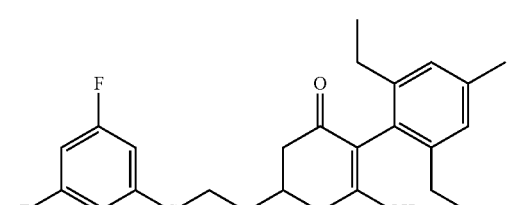
(1-162)
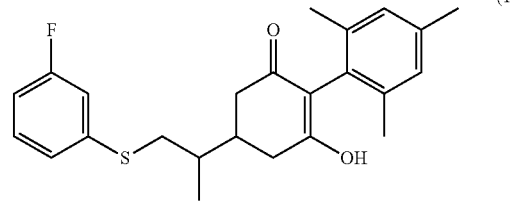
(1-163)
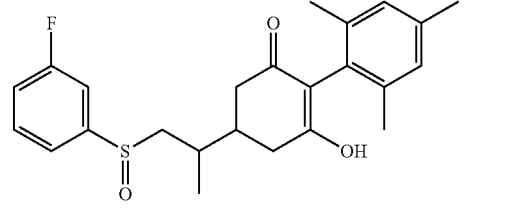
(1-164)
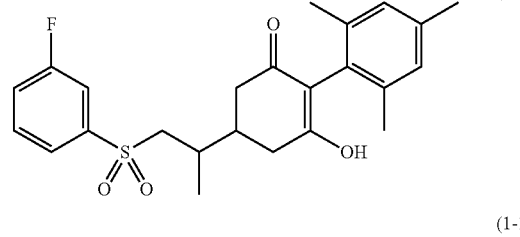
(1-165)
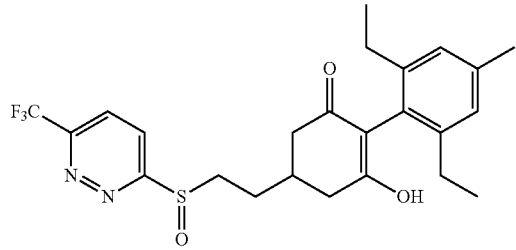
(1-166)
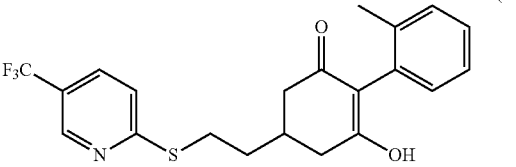

-continued

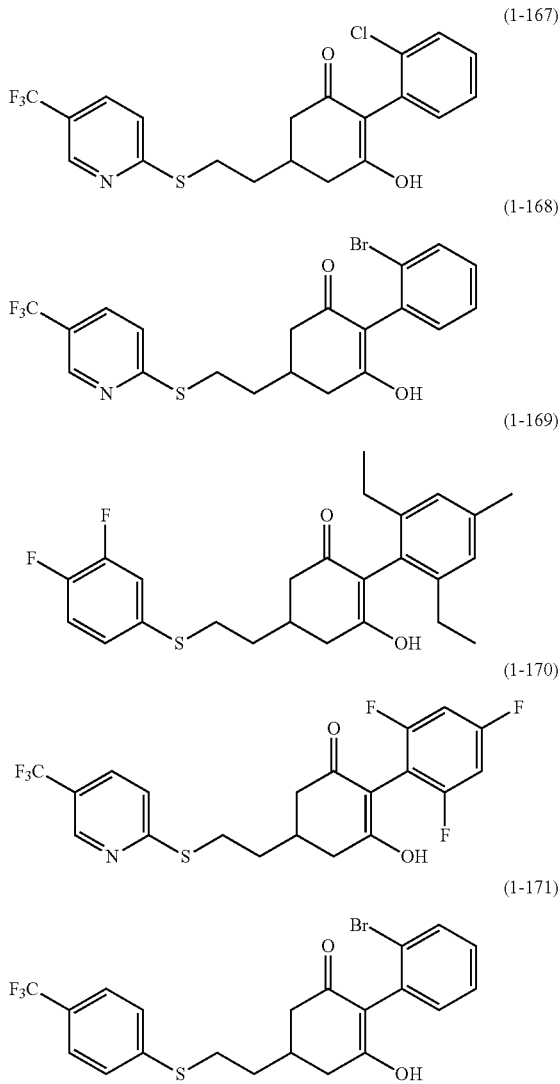

(1-167)
(1-168)
(1-169)
(1-170)
(1-171)

EXAMPLES

The present invention is described below in more detail with Preparation Examples, Reference Examples, Formulation Examples and Test Examples, but the present invention should not be construed to be limited thereto.

The "room temperature" (hereinafter sometimes abbreviated to as "RT") described in Preparation Example and Reference Example means usually 10 to 30° C. $^1$H NMR means a proton nuclear magnetic resonance spectrum and Tetramethyl silane is used as an internal standard and chemical shift (δ) is expressed in ppm.

The following abbreviations are sometimes used in Preparation Example and Reference Example.

CDCl$_3$: Deuterated chloroform, s: singlet, d: doublet, t: triplet, q: quartet, brs: broad singlet, m: multiplet, J: coupling constant, Me: methyl group, Et: ethyl group, Phe: phenyl group, OMe: methoxy group, OAc: acetoxy group, Pyr: pyridyl group, Bn: benzyl group, Ts: p-toluenesulfonyl group, TM: registered trademark.

Preparation Example 1-1

Preparation of the Compound of the Formula (1-1)

<Preparation of the Compound of the Formula 9-1>

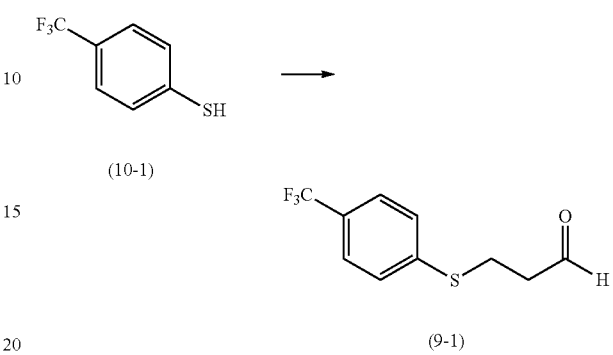

(10-1)

(9-1)

At room temperature, the compound of the formula (10-1) 10 g and tetrahydrofuran 15 ml were mixed and stirred and the resulting mixture was cooled to 0° C. and then thereto were added dropwise 95% acrolein 4.0 g and triethylamine 0.1 g. The resulting mixture was stirred under ice-cooling for 1.5 hours. Thereafter, the resulting mixture was added to water. The resulting mixture was extracted with tert-butyl methyl ether. The organic layer was washed with water, dried over anhydrous sodium sulfate and concentrated under reduced pressure to give the compound of the formula (9-1) 18.1 g.

$^1$H NMR (CDCl$_3$)

δ ppm: 9.77 (1H, s), 7.51 (2H, d), 7.36 (2H, d), 3.28-3.20 (2H, m), 2.87-2.80 (2H, m)

<Preparation of the Compound of the Formula 7-1>

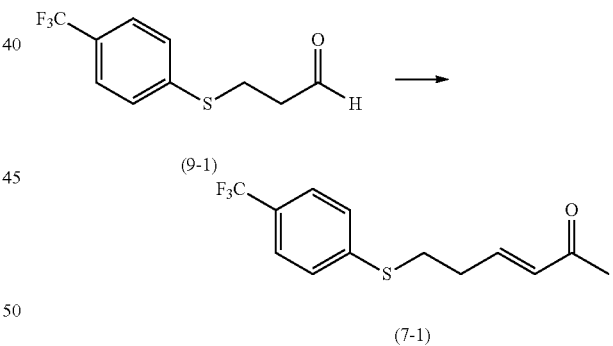

(9-1)

(7-1)

At room temperature, the compound of the formula (9-1) 65.7 g and triphenylphosphine acetylmethylene 100 g were dissolved in chloroform 330 ml. The resulting solution was stirred at 0° C. for 8 hours. Thereafter, under reduced pressure, chloroform was removed from the resulting reaction solutions. To the resulting residue were added tert-butyl methyl ether and hexane. The resulting mixtures were filtered and the resulting filtrates were concentrated under reduced pressure. The resulting oils were subjected to a silica gel column chromatography (eluates, ethyl acetate:hexane=1:4) to give the compound of the formula (7-1) 28.6 g.

$^1$H NMR (CDCl$_3$)

δ ppm: 7.52 (2H, d), 7.39 (2H, d), 6.82-6.74 (1H, m), 6.13 (1H, dd), 3.11 (2H, m), 2.63-2.56 (2H, m), 2.23 (3H, s)

<Preparation of the Compound of the Formula 6-1>

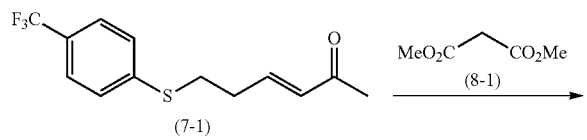

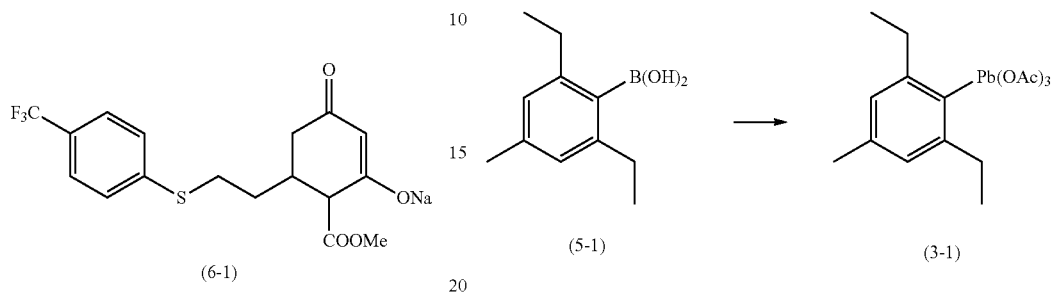

At RT, 28% sodium methoxide methanol solution 22 g and the compound of the formula (8-1) 7.6 g were dissolved in tetrahydrofuran 250 ml. The resulting solutions were heated under reflux for 15 minutes. Thereafter, heating was stopped and to the resulting mixtures were added the compound of the formula (7-1) 28.6 g. Thereafter, the resulting mixtures were heated under reflux for 30 minutes. The resulting reaction solutions were cooled to rt, and the precipitated crystals were collected by filtering and washed thoroughly with tert-butyl methyl ether and hexane sequentially to give the compound of the formula (6-1) 24.5 g.

$^1$H NMR (d-DMSO)

δ ppm: 7.63 (2H, d), 7.45 (2H, d), 4.39 (1H, s), 3.46 (3H, s), 3.11 (1H, m), 2.95 (1H, m), 2.83 (1H, d), 2.34-2.26 (1H, m), 2.12 (1H, dd), 1.78 (1H, dd), 1.53-1.47 (2H, m)

<Preparation of the Compound of the Formula 2-1>

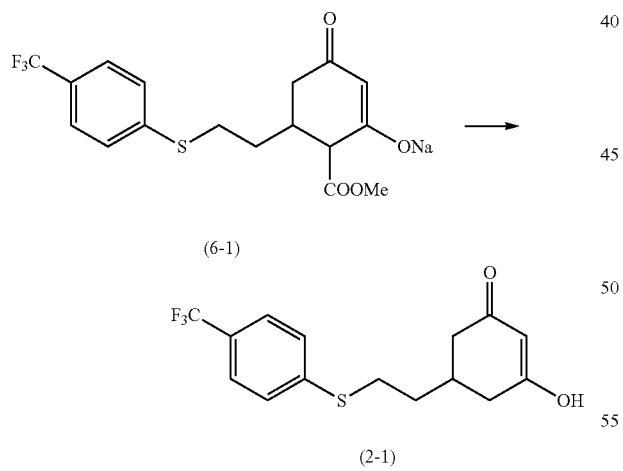

At RT, the compound of the formula (6-1) 12 g was dissolved in water 180 ml. To the resulting solutions were added anhydrous sodium carbonate 10 g. The resulting solutions were heated under reflux for 5 hours. The reaction solutions were cooled to rt and washed with tert-butyl methyl ether to remove impurities and then the aqueous layers were acidified with 2N hydrochloric acid and extracted with ethyl acetate. The ethyl acetate layers was concentrated under reduced pressure and the resulting crystals were washed with tert-butyl methyl ether and hexane sequentially to give the compound of the formula (2-1) 18 g.

$^1$H NMR (d-DMSO)

δ ppm: 11.07 (1H, s), 7.63 (2H, d), 7.48 (2H, d), 5.22 (1H, s), 3.16-3.05 (2H, m), 2.33-1.69 (7H, m)

<Preparation of the Compound of the Formula 3-1>

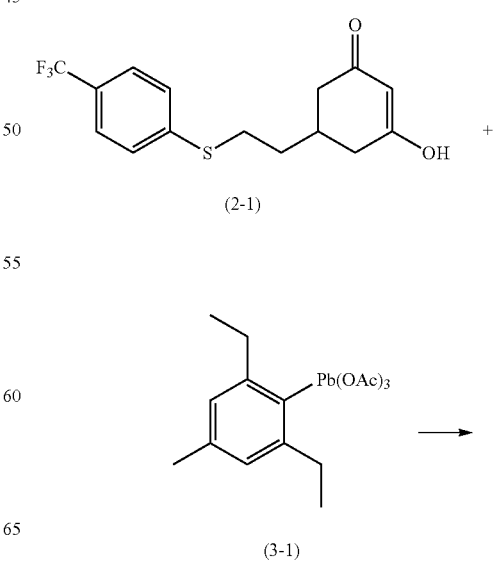

Under nitrogen atmosphere, at RT, lead tetraacetate 26.5 g, mercury acetate 0.83 g and the compound of the formula (5-1) 10 g were dissolved in chloroform 110 ml. The resulting solutions were stirred at RT under nitrogen atmosphere for 15 minutes. Thereafter, under nitrogen atmosphere, the reaction solutions were stirred at 40° C. for 4 hours. The reaction solutions were cooled to rt and filtered through Celite™. The resulting filtrates were concentrated under reduced pressure to give yellow oils. To the oils was added hexane and the resulting mixtures were concentrated under reduced pressure to yellow solids. Under nitrogen atmosphere, at RT, the resulting solids were dissolved in chloroform 260 ml. To the resulting solutions was added potassium carbonate 86.2 g and the resulting mixtures were stirred quickly for 10 minutes. Thereafter, the reaction solutions were filtered through Celite™. The resulting filtrates were concentrated under reduced pressure to give the compound of the formula (3-1) 21 g.

$^1$H NMR (CDCl$_3$)

δ ppm: 7.05 (2H, s), 2.90 (4H, m), 2.35 (3H, s), 2.06 (9H, s), 1.33-1.27 (6H, m)

<Preparation of the Compound of the Formula 1-1>

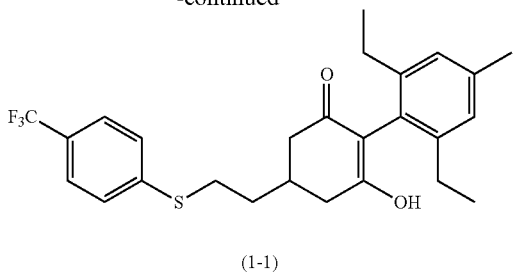

(1-1)

Under nitrogen atmosphere, at RT, the compound of the formula (2-1) 240 mg and dimethylaminopyridine 460 mg were dissolved in a mixture of chloroform 2.5 ml and toluene 0.5 ml. The resulting solutions were stirred at RT under nitrogen atmosphere for 15 minutes. Thereafter to the resulting solutions was added the compound of the formula (3-1) 440 mg under nitrogen atmosphere. Under nitrogen atmosphere, the resulting mixtures were stirred at 75° C. for 1 hour. The resulting reaction solutions were cooled to rt, adjusted to pH 1 with 2N hydrochloric acid and filtered through Celite™. The resulting filtrates were extracted with chloroform. The resulting chloroform layers were washed with water, dried over anhydrous sodium sulfate and filtered. The resulting filtrates were concentrated under reduced pressure to give yellow oils. The resulting oils were subjected to a silica gel column chromatography (eluates, ethyl acetate:hexane=1:3) to give the compound of the formula (1-1) 120 mg.

$^1$H NMR (CDCl$_3$)

δ ppm: 7.54 (2H, d), 7.38 (2H, d), 6.98 (2H, s), 5.50 (1H, s), 3.07 (2H, ddd), 2.71 (2H, td), 2.47-2.24 (10H, m), 1.88 (2H, q), 1.10-1.03 (6H, m)

Preparation Example 1-2

Preparation of the Compound of the Formula (1-2)

<Preparation of the Compound of the Formula 3-2>

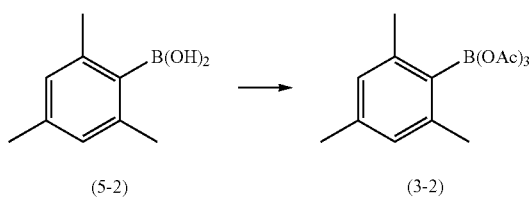

Under nitrogen atmosphere, at RT, lead tetraacetate 6.2 g, mercury acetate 194 mg and the compound of the formula (5-2) 2 g were dissolved in chloroform 25 ml. The resulting solutions were stirred at RT under nitrogen atmosphere for 15 minutes. Thereafter, under nitrogen atmosphere, the reaction solutions were stirred at 40° C. for 4 hours. The reaction solutions were cooled to rt and filtered through Celite™. The resulting filtrates were concentrated under reduced pressure to give yellow oils. To the resulting oils added hexane and the resulting mixtures were concentrated under reduced pressure to yellow oils. Under nitrogen atmosphere, at RT, the resulting solids were dissolved in chloroform 50 ml. To the resulting solutions was added potassium carbonate 20 g and the resulting mixtures were stirred quickly for 10 minutes. Thereafter, the reaction solutions were filtered through Celite™. The resulting filtrates were concentrated under reduced pressured to give the compound of the formula (3-2) 4 g.

$^1$H NMR (CDCl$_3$)

δ ppm: 6.99 (2H, s), 2.57 (6H s), 2.30 (3H, s), 2.06 (9H, s)

<Preparation of the Compound of the Formula 1-2>

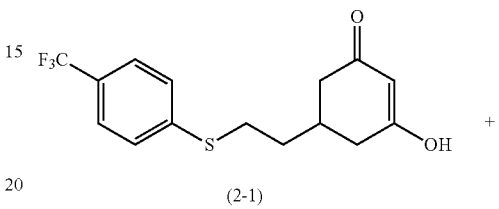

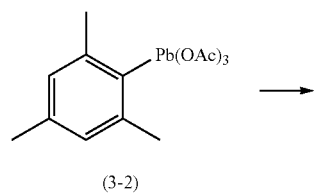

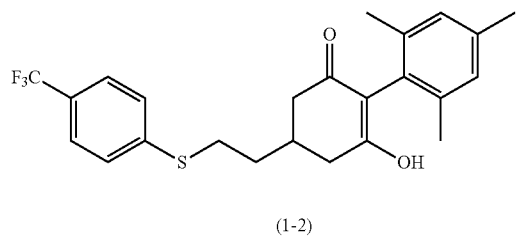

(1-2)

Under nitrogen atmosphere, at RT, the compound of the formula (2-1) 240 mg and dimethylaminopyridine 460 mg were dissolved in a mixture of chloroform 2.5 ml and toluene 0.5 ml. The resulting solutions were stirred at RT under nitrogen atmosphere for 15 minutes. Thereafter under nitrogen atmosphere, to the resulting solutions was added the compounds of the formula (3-2) 420 mg. Under nitrogen atmosphere, the resulting mixtures were stirred at 75° C. for 1 hour. The resulting solutions were cooled to rt, adjusted to pH 1 with 2N hydrochloric acid and filtered through Celite™. The resulting filtrates were extracted with chloroform. The resulting chloroform layers were wished with water, dried over anhydrous sodium sulfate and filtered. The resulting filtrates were concentrated under reduced pressure to give yellow oils. The resulting oils were subjected to silica gel column chromatography (eluates, ethyl acetate hexane=1:3) to give the compound of the formula (1-2) 125 mg.

$^1$H NMR (CDCl$_3$)

δ ppm: 7.54 (2H, d), 7.37 (2H, d), 6.94 (2H, s), 5.72 (1H, s), 3.11-3.01 (2H, m), 2.70 (2H, td), 2.44-2.01 (12H, m), 1.87 (2H, q)

Preparation Example 1-3

Preparation of the Compound of the Formula (1-3)

<Preparation of the Compound of the Formula 3-3>

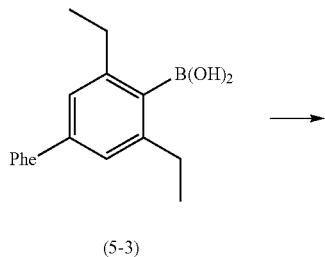

(5-3)

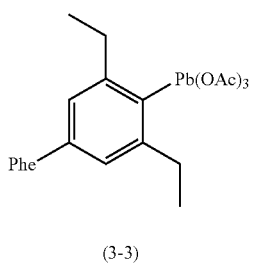

(3-3)

Under nitrogen atmosphere, at RT, lead tetraacetate 8.4 g, mercury acetate 263 mg and the compound of the formula (5-3) 4.2 g were dissolved in chloroform 35 ml. The resulting solutions were stirred at RT under nitrogen atmosphere for 15 minutes. Thereafter, under nitrogen atmosphere, the reactions solutions were stirred at 40° C. for 4 hours. The reaction solutions were cooled to rt and filtered through Celite™. The resulting filtrates were concentrated under reduced pressure to give yellow oils. To the resulting oils was added hexane and the resulting mixtures were concentrated under reduced pressure to give yellow solids. Under nitrogen atmosphere, at RT, the resulting solids were dissolved in chloroform 80 ml. To the resulting solutions was added potassium carbonate 27.4 g and the resulting mixtures were stirred quickly for 10 minutes. Thereafter, the reactions solutions were filtered through Celite™. The resulting filtrates were concentrated under reduced pressure to give the compound of the formula (3-3) 6.4 g.

$^1$H NMR (CDCl$_3$)

δ ppm: 7.60-7.31 (7H, m), 3.06-2.93 (4H, m), 2.07 (9H, s), 1.39-1.32 (6H, m)

<Preparation of the Compound of the Formula 1-3>

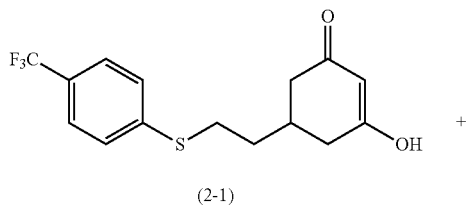

(2-1)

+

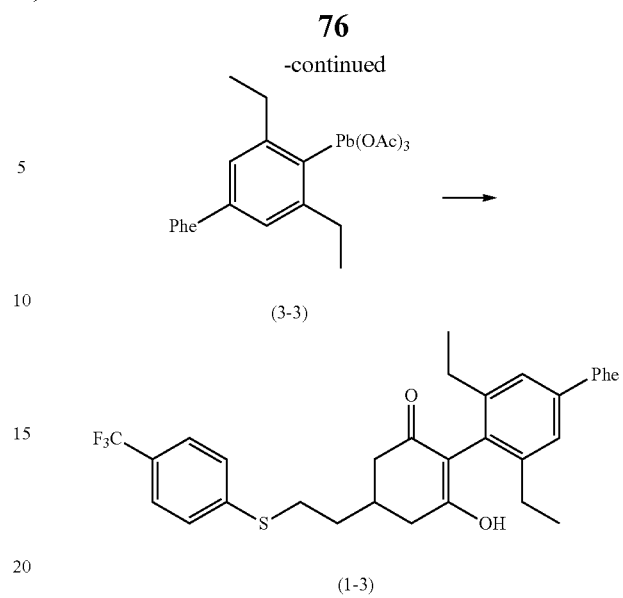

(3-3)

(1-3)

Under nitrogen atmosphere, at RT, the compound of the formula (2-1) 240 mg and dimethylaminopyridine 460 mg were dissolved in a mixture of chloroform 2.5 ml and toluene 0.5 ml. The resulting solutions were stirred at RT under nitrogen atmosphere for 15 minutes. Thereafter, under nitrogen atmosphere, to the resulting solutions was added the compound of the formula (3-3) 500 mg. Under nitrogen atmosphere, the resulting mixtures were stirred at 75° C. for 1 hour. The resulting solutions were cooled to rt, adjusted to pH 1 with 2N hydrochloric acid and filtered through Celite™. The resulting filtrates were extracted with chloroform. The resulting chloroform layers were washed with water, dried over anhydrous sodium sulfate and filtered. The resulting filtrates were concentrated under reduced pressure to give yellow oils. The resulting oils were subjected to a silica gel column chromatography (eluates, ethyl acetate hexane=1:3) to give the compound of the formula (1-3) 190 mg.

$^1$H NMR (CDCl$_3$)

δ ppm: 7.57 (4H, td), 7.45 (2H, dd), 7.40-7.34 (5H, m), 5.56 (1H, s), 3.10 (2H, dt), 2.78-2.71 (2H, m), 2.53-2.30 (7H, m), 1.90 (2H, q), 1.17-1.09 (6H, m)

Preparation Example 1-4

Preparation of the Compound of the Formula (1-4)

<Preparation of the Compound of the Formula 9-2>

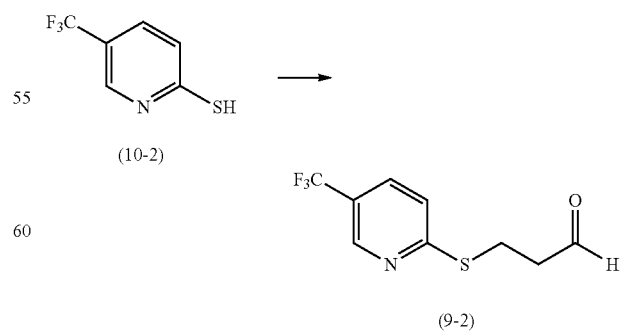

(10-2)

(9-2)

At RT, the compound of the formula (10-2) 10 g and tetrahydrofuran 30 ml were mixed and stirred, and the resulting mixtures were cooled to 0° C. and then thereto were added dropwise 95% acrolein 4.0 g and triethylamine 0.1 g. The resulting mixtures were stirred under ice-cooling for 1.5 hours. Thereafter, the resulting mixtures were added to water. The resulting mixtures were extracted with tert-butyl methyl ether. The organic layers were washed with water, dried over anhydrous sodium sulfate and concentrated under reduced pressure to give the compound of the formula (9-2) 13 g.

$^1$H NMR (CDCl$_3$)

δ ppm: 9.80 (1H, s), 8.67-8.66 (1H, m), 7.67 (1H, dd), 7.26 (1H, dd), 3.48 (2H, ddd), 2.98-2.95 (2H, m)

<Preparation of the Compound of the Formula 7-2>

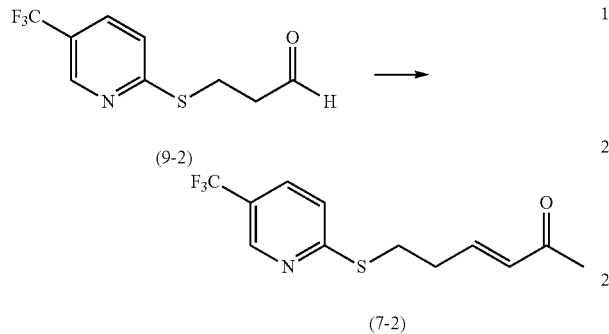

At RT, the compound of the formula (9-2)-13 g and triphenylphosphine acetylmethylene 20 g were dissolved in chloroform 65 ml. The resulting solutions were stirred at 0° C. for 8 hours. Thereafter, under reduced pressure, chloroform was removed from the resulting reaction solutions. To the resulting residues were added tert-butyl methyl ether and hexane. The resulting mixtures were filtered and the resulting filtrates were concentrated under reduced pressure. The resulting oils were subjected to a silica gel column chromatography (eluates, ethyl acetate:hexane=1:4) to give the compound of the formula (7-2) 13 g.

$^1$H NMR (CDCl$_3$)

δ ppm: 8.67 (1H, dd), 7.69-7.66 (1H, m), 7.29 (1H, d), 6.88-6.80 (1H, m), 6.16 (1H, dt), 3.36 (2H, t), 2.67 (2H, tt), 2.24 (3H, s)

<Preparation of the Compound of the Formula 6-2>

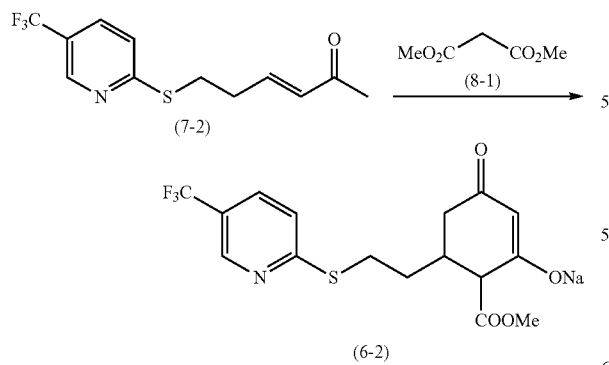

At RT, 28% sodium methoxide methanol solution 10 g and the compound of the formula (8-1) 6.7 g were dissolved in tetrahydrofuran 130 ml. The resulting solutions were heated under reflux for 15 minutes. Thereafter, the heating was stopped and to the resulting reaction mixtures was added the compound of the formula (7-2) 13 g. Thereafter, the resulting mixture solutions were heated under reflux for 30 minutes. The resulting reaction solutions were cooled to rt, and the precipitated crystals were collected by filtering and washed with tert-butyl methyl ether and hexane sequentially to give the compound of the formula (6-2) 15.4 g.

$^1$H NMR (d-DMSO)

δ ppm: 8.78 (1H, d), 7.98 (1H, dd), 7.50 (1H, d), 4.40 (1H, s), 3.49 (3H, s), 3.26 (1H, dq), 3.06 (1H, dt), 2.83 (1H, d), 2.34-2.24 (1H, m), 2.13 (1H, dd), 1.79 (1H, dt), 1.63-1.49 (2H, m)

<Preparation of the Compound of the Formula 2-2>

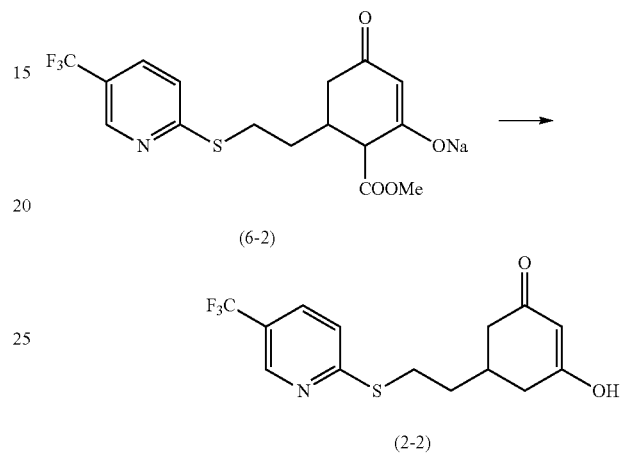

At RT, the compound of the formula (6-2) 5 g was dissolved in water 70 ml. To the resulting solutions was added anhydrous sodium carbonate 4 g. The resulting solutions were heated under reflux for 5 hours. The reaction solutions were cooled to rt and washed with tert-butyl methyl ether to remove impurities and then the aqueous layers were acidified with 2N hydrochloric acid and extracted with ethyl acetate. The ethyl acetate layers were concentrated under reduced pressure and the resulting crystals were washed with tert-butyl methyl ether and hexane sequentially to give the compound of the formula (2-2) 3.1 g.

$^1$H NMR (d-DMSO)

δ ppm: 11.07 (1H, s), 8.80 (1H, d), 7.98 (1H, dd), 7.52 (1H, d), 5.21 (1H, s), 3.23 (2H, t), 2.34 (2H, d), 2.13 (3H, m), 1.73 (2H, m)

<Preparation of the Compound of the Formula 1-4>

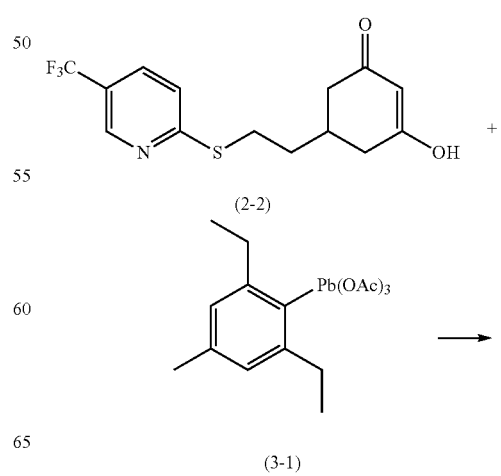

-continued

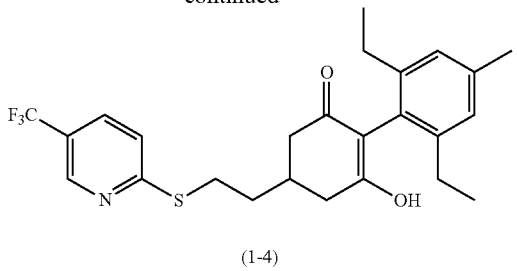

(1-4)

Under nitrogen atmosphere, at RT, the compound of the formula (2-2) 540 mg and dimethylaminopyridine 1.05 g were dissolved in a mixture of chloroform 4.8 ml and toluene 1.2 ml. The resulting solutions were stirred at RT under nitrogen atmosphere for 15 minutes. Thereafter, under nitrogen atmosphere, to the resulting solutions was added the compound of the formula (3-1) 1.0 g. Under nitrogen atmosphere, the resulting mixtures were stirred at 75° C. for 1 hour. The resulting reaction solutions were cooled to rt, adjusted to pH 1 with 2N hydrochloric acid and filtered through Celite™. The resulting filtrates were extracted with chloroform. The resulting chloroform layers were washed with water, dried over anhydrous sodium sulfate and filtered. The resulting filtrates were concentrated under reduced pressure to give yellow oils. The resulting oils were subjected to a silica gel column chromatography (eluates, ethyl acetate hexane=1:3) to give the compound of the formula (1-4) 320 mg.

$^1$H NMR (CDCl$_3$)

δ ppm: 8.68-8.67 (1H, m), 7.67 (1H, dd), 7.27 (1H, d), 6.98 (2H, s), 5.52 (1H, s), 3.31 (2H, tt), 2.75 (2H, ddd), 2.51-2.23 (10H, m), 1.92 (2H, ddd), 1.5 (6H, dt)

Preparation Example 1-5

Preparation of the Compound of the Formula (1-5)

<Preparation of the Compound of the Formula 1-5>

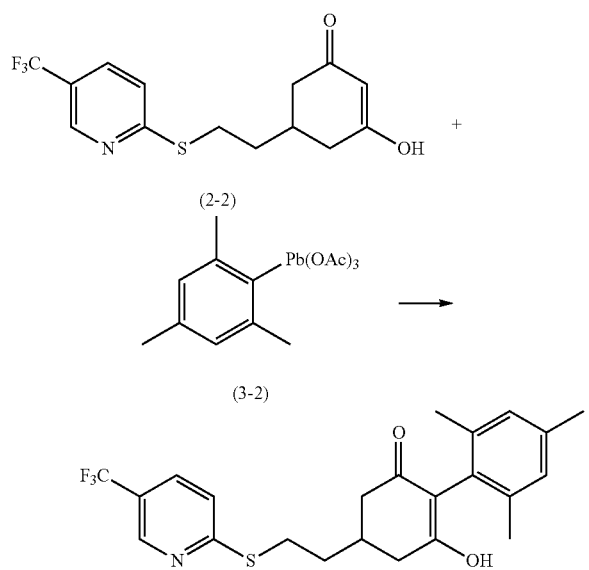

Under nitrogen atmosphere, at RT, the compound of the formula (2-2) 570 mg and dimethylaminopyridine 1.1 g were dissolved in a mixture of chloroform 4.8 ml and toluene 1.2 ml. The resulting solutions were stirred at RT under nitrogen atmosphere for 15 minutes. Thereafter, under nitrogen atmosphere, to the resulting solutions was added the compound of the formula (3-2) 1.0 g. Under nitrogen atmosphere, the resulting mixtures were stirred at 75° C. for 1 hour. The resulting reaction solutions were cooled to rt and, adjusted to pH 1 with 2N hydrochloric acid and filtered through Celite™. The resulting filtrates were extracted with chloroform. The resulting chloroform layers were washed with water, dried over anhydrous sodium sulfate and filtered. The resulting filtrates were concentrated under reduced pressure to give yellow oils. The resulting oils were subjected to a silica gel column chromatography (eluates, ethyl acetate hexane=1:3) to give the compound of the formula (1-5) 410 mg.

$^1$H NMR (CDCl$_3$)

δ ppm: 8.66 (1H, s), 7.66 (1H, dd), 7.26 (1H, d), 6.93 (2H, s), 5.66 (1H, s), 3.32-3.28 (2H, m), 2.74 (2H, t), 2.46-2.04 (12H, m), 1.91 (2H, m)

Preparation Example 1-6

Preparation of the Compound of the Formula (1-6)

<Preparation of the Compound of the Formula 9-3>

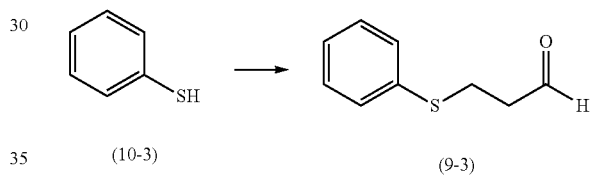

At RT, the compound of the formula (10-3) 10 g and tetrahydrofuran 30 ml were mixed and stirred and the resulting mixtures were cooled to 0° C. and then thereto were added dropwise 95% acrolein 6.6 g and triethylamine 0.2 g. The resulting mixtures were stirred under ice-cooling for 1.5 hours. Thereafter, the resulting mixtures were added to water. The resulting mixtures were extracted with tert-butyl methyl ether. The organic layers were washed with water, dried over anhydrous sodium sulfate and concentrated under reduced pressure to give the compound of the formula (9-3) 15 g.

$^1$H NMR (CDCl$_3$)

δ ppm: 9.74 (1H, s), 7.36-7.17 (5H, m), 3.17 (2H, t), 2.75 (2H, t)

<Preparation of the Compound of the Formula 7-3>

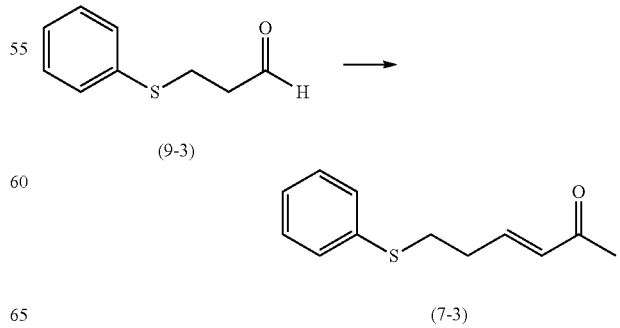

At RT, the compound of the formula (9-3) 10 g and triphenylphosphine acetylmethylene 21 g were dissolved in chloroform 70 ml. The resulting solutions were stirred at 0° C. for 8 hours. Thereafter, under reduced pressure, chloroform was removed from the resulting reaction solutions. To the resulting residues were added tert-butyl methyl ether and hexane. The resulting mixtures were filtered and the resulting filtrates were concentrated under reduced pressure. The resulting oils were subjected to a silica gel column chromatography (eluates, ethyl acetate:hexane=1:4) to give the compound of the formula (7-3) 7.2 g.

$^1$H NMR (CDCl$_3$)

δ ppm: 7.35-7.25 (4H, m), 7.18 (1H, m), 6.80-6.71 (1H, m), 6.07 (1H, dt), 3.01 (2H, tt), 2.51 (2H, ddd), 2.23 (3H, s)

<Preparation of the Compound of the Formula 6-3>

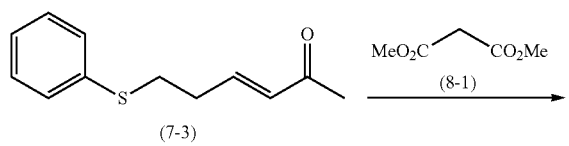

(7-3)      (8-1)

At RT, 28% sodium methoxide methanol solution 7.5 g and the compound of the formula (8-1) 5 g were dissolved in tetrahydrofuran 100 ml. The resulting solutions were heated under reflux for 15 minutes. Thereafter, the heating was stopped and to the resulting reaction mixtures was added the compound of the formula (7-3) 7.2 g. Thereafter, the resulting mixture solutions were heated under reflux for 30 minutes. The resulting reaction solutions were cooled to rt, and the precipitated crystals were collected by filtering, washed with tert-butyl methyl ether and hexane sequentially to give the compound of the formula (6-3) 10 g.

$^1$H NMR (d-DMSO)

δ ppm: 7.33-7.27 (4H, m), 7.17 (1H, dq), 4.37 (1H, s), 3.48 (3H, s), 3.02-2.96 (1H, m), 2.87-2.78 (2H, m), 2.33-2.23 (1H, m), 2.08 (1H, dd), 1.74 (1H, dd), 1.44 (2H, m)

<Preparation of the Compound of the Formula 2-3>

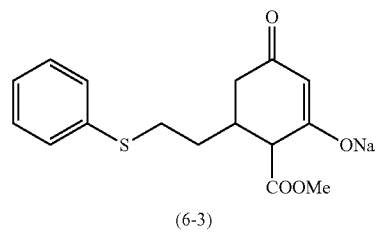

(6-3)

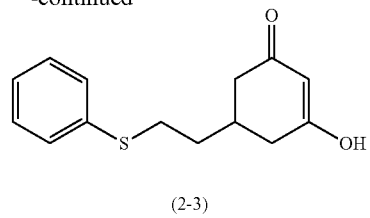

(2-3)

At RT, the compound of the formula (6-3) 5 g was dissolved in water 80 ml. To the resulting solutions was added anhydrous sodium carbonate 4.8 g. The resulting solutions were heated under reflux for 5 hours. The reaction solutions were cooled to rt and washed with tert-butyl methyl ether to remove impurities and then the aqueous layers were acidified with 2N hydrochloric acid and extracted with ethyl acetate. The ethyl acetate layers were concentrated under reduced pressure and the resulting crystals were washed with tert-butyl methyl ether and hexane sequentially to give the compound of the formula (2-3) 3.4 g.

$^1$H NMR (d-DMSO)

δ ppm: 11.05 (1H, s), 7.31 (4H, m), 7.18 (1H, m), 5.19 (1H, s), 3.00 (2H, t), 2.33-1.99 (5H, m), 1.63 (2H, m)

<Preparation of the Compound of the Formula 1-6>

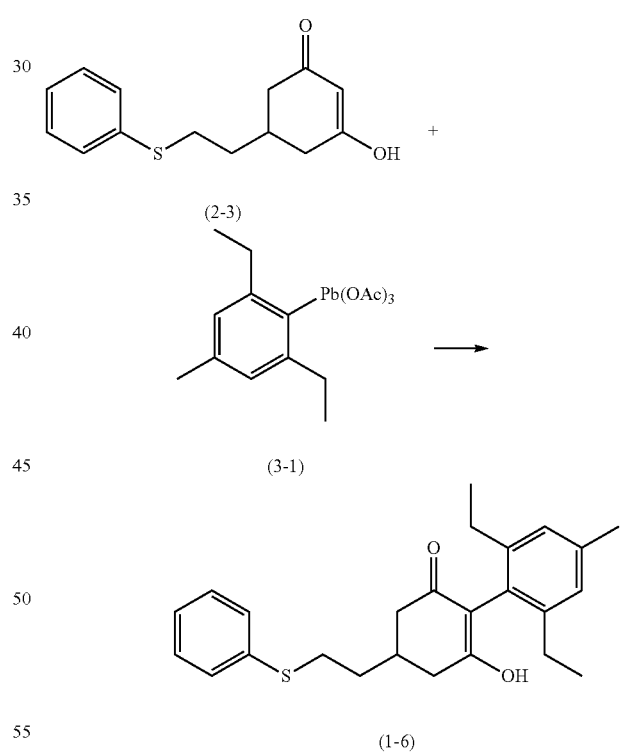

Under nitrogen atmosphere, at RT, the compound of the formula (2-3) 430 mg and dimethylaminopyridine 1.05 g were dissolved in a mixture of chloroform 4.8 ml and toluene 1.2 ml. The resulting solutions were stirred at RT under nitrogen atmosphere for 15 minutes. Thereafter, under nitrogen atmosphere, to the resulting solutions was added the compound of the formula (3-1) 1.0 g. Under nitrogen atmosphere, the resulting mixtures were stirred at 75° C. for 1 hour. The resulting reaction solutions were cooled to rt, adjusted to pH 1 with 2N hydrochloric acid and filtered through Celite™.

The resulting filtrates were extracted with chloroform. The resulting chloroform layers were washed with water, dried over anhydrous sodium sulfate and filtered. The resulting filtrates were concentrated under reduced pressure to give yellow oils. The resulting oils were subjected to a silica gel column chromatography (eluates, ethyl acetate:hexane=1:4) to the compound of the formula (1-6) 310 mg.

$^1$H NMR (CDCl$_3$)

δ ppm: 7.36-7.20 (5H, m), 6.97 (2H, s), 5.59 (1H, s), 3.00 (2H, ddd), 2.67 (2H, ddt), 2.47-2.20 (10H, m), 1.82 (2H, q), 1.10-1.02 (6H, m)

Preparation Example 1-7

Preparation of the Compound of the Formula (1-7)

<Preparation of the Compound of the Formula 9-4>

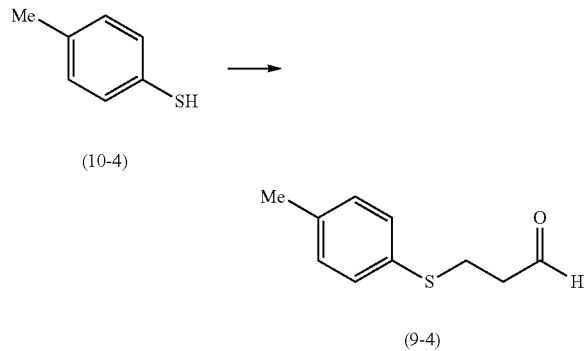

At RT, the compound of the formula (10-4) 5 g and tetrahydrofuran 15 ml were mixed and stirred and the resulting mixtures were cooled to 0° C. and then thereto were added dropwise 95% acrolein 3.0 g and triethylamine 0.1 g. The resulting mixtures were stirred under ice-cooling for 1.5 hours. Thereafter, the resulting mixtures were added to water. The resulting mixtures were extracted with tert-butyl methyl ether. The organic layers were washed with water, dried over anhydrous sodium sulfate and concentrated under reduced pressure to give the compound of the formula (9-4) 7.4 g.

$^1$H NMR (CDCl$_3$)

δ ppm: 9.72 (1H, s), 7.24 (2H, d), 7.18 (2H, d), 3.12 (2H, t), 2.71 (2H, t), 2.31 (3H, s)

<Preparation of the Compound of the Formula 6-4>

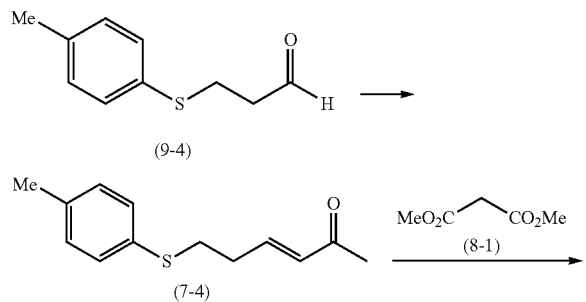

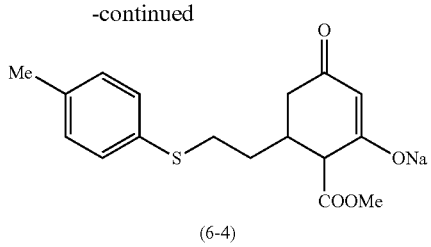

At RT, the compound of the formula (9-4) 7.4 g and triphenylphosphine acetylmethylene 14.4 g were dissolved in chloroform 50 ml. The resulting solutions were stirred at 0° C. for 8 hours. Thereafter, under reduced pressure, chloroform was removed from the resulting reaction solutions. To the resulting residues were added tert-butyl methyl ether and hexane. The resulting mixtures were filtered and the resulting filtrates were concentrated under reduced pressure. The resulting oils were subjected to a silica gel column chromatography (eluates, ethyl acetate:hexane=1:4) to the compound of the formula (7-4) 6.0 g.

Continuously, at RT, 28% sodium methoxide methanol solution 5.8 g and the compound of the formula (8-1) 4.0 g were dissolved in tetrahydrofuran 80 ml. The resulting solutions were heated under reflux for 15 minutes. Thereafter, the heating was stopped and to the resulting reaction mixtures was added the compound of the formula (7-4) 6.0 g. Thereafter, the resulting mixture solutions were heated under reflux for 30 minutes. The resulting reaction solutions were cooled to rt, and the precipitated crystals were collected by filtering and washed with tert-butyl methyl ether and hexane sequentially to give the compound of the formula (6-4) 6.7 g.

$^1$H NMR (d-DMSO)

δ ppm: 7.19 (2H, d), 7.12 (2H, d), 4.39 (1H, s), 3.48 (3H, s), 2.97-2.90 (1H, m), 2.82-2.75 (2H, m), 2.24 (3H, s), 2.10-2.04 (1H, m), 1.72 (1H, dd), 1.49-1.35 (2H, m)

<Preparation of the Compound of the Formula 2-4>

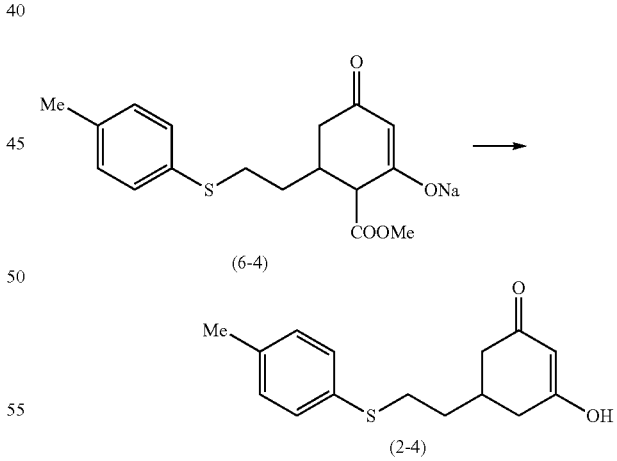

At RT, the compound of the formula (6-4) 5 g was dissolved in water 80 ml. To the resulting solution was added anhydrous sodium carbonate 4.6 g. The resulting solutions were heated under reflux for 5 hours. The reaction solutions were cooled to rt and washed with tert-butyl methyl ether to remove impurities and then the aqueous layers were acidified with 2N hydrochloric acid and extracted with ethyl acetate. The ethyl acetate layers were concentrated under reduced pressure and the resulting crystals were washed with tert-butyl methyl ether and hexane sequentially to give the compound of the formula (2-4) 2.9 g.

¹H NMR (d-DMSO)

δ ppm: 11.04 (1H, s), 7.23 (2H, d), 7.13 (2H, d), 5.19 (1H, s), 2.95 (2H, t), 2.42-1.99 (8H, m), 1.60-1.58 (2H, m)

<Preparation of the Compound of the Formula 1-7>

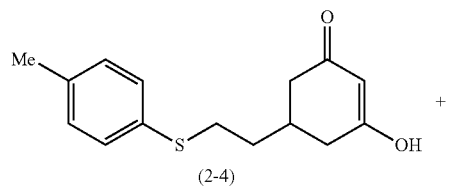

(2-4)

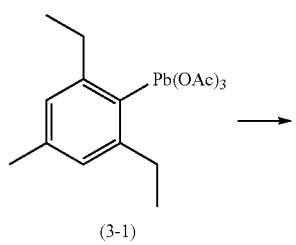

(3-1)

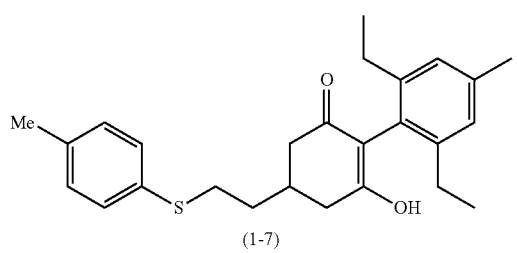

(1-7)

Under nitrogen atmosphere, at RT, the compound of the formula (2-4) 450 mg and dimethylaminopyridine 1.05 g were dissolved in a mixture of chloroform 4.8 ml and toluene 1.2 ml. The resulting solutions were stirred at RT under nitrogen atmosphere for 15 minutes. Thereafter, under nitrogen atmosphere, to the resulting solutions was added the compound of the formula (3-1) 1.0 g. Under nitrogen atmosphere, the resulting mixtures were stirred at 75° C. for 1 hour. The resulting reaction solutions were cooled to rt, adjusted to pH 1 with 2N hydrochloric acid and filtered through Celite™. The resulting filtrates were extracted with chloroform. The resulting chloroform layers were washed with water, dried over anhydrous sodium sulfate and filtered. The resulting filtrates were concentrated under reduced pressure to give yellow oils. The resulting oils were subjected to a silica gel column chromatography (eluates, ethyl acetate hexane=1:4) to give the compound of the formula (1-7) 340 mg.

¹H NMR (CDCl₃)

δ ppm: 7.27 (2H, d), 7.12 (2H, d), 6.98 (2H, s), 5.47 (1H, s), 2.96 (2H, dt), 2.67 (2H, ddd), 2.45-2.21 (13H, m), 1.80 (2H, q), 1.06 (6H, dt)

Preparation Example 1-8

Preparation of the Compound of the Formula (1-8)

<Preparation of the Compound of the Formula 9-5>

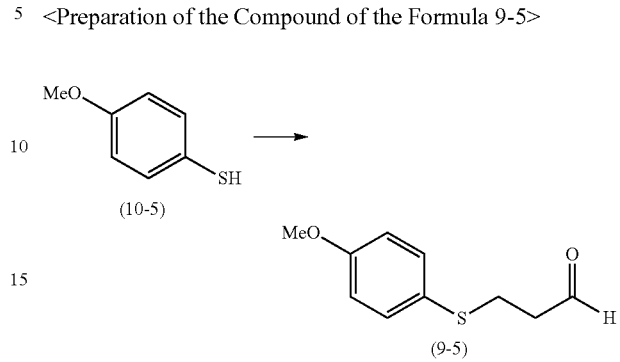

At RT, the compound of the formula (10-5) 4 g and tetrahydrofuran 15 ml were mixed and stirred and the resulting mixtures were cooled to 0° C. and then thereto were added dropwise 95% acrolein 2.5 g and triethylamine 0.1 g. The resulting mixtures were stirred under ice-cooling for 1.5 hours. Thereafter, the resulting mixtures were added to water. The resulting mixtures were extracted with tert-butyl methyl ether. The organic layers were washed with water, dried over anhydrous sodium sulfate and concentrated under reduced pressure to give the compound of the formula (9-5) 5.5 g.

¹H NMR (CDCl₃)

δ ppm: 9.73 (1H, s), 7.36 (2H, d), 6.85 (2H, d), 3.80 (3H, s), 3.06 (2H, t), 2.68 (2H, t)

<Preparation of the Compound of the Formula 6-5>

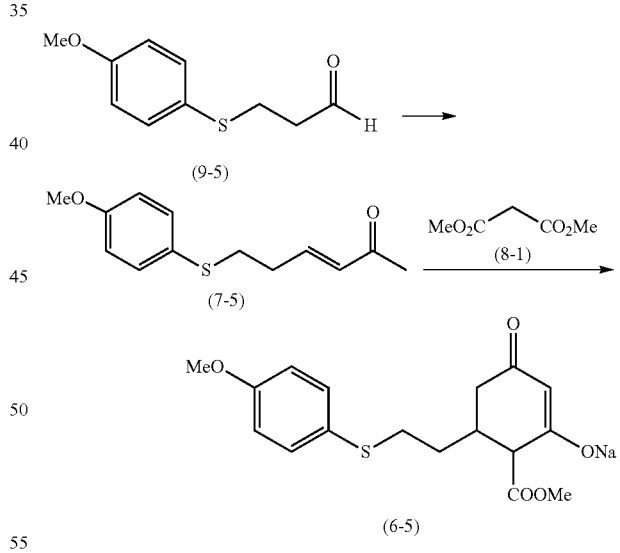

At RT, the compound of the formula (9-5) 5.5 g and triphenylphosphine acetylmethylene 10 g were dissolved in chloroform 40 ml. The resulting solutions were stirred at 0° C. for 8 hours. Thereafter, under reduced pressure, chloroform was removed from the resulting reaction solutions. To the resulting residues were added tert-butyl methyl ether and hexane. The resulting mixtures were filtered and the resulting filtrates were concentrated under reduced pressure. The resulting oils were subjected to a silica gel column chromatography (eluates, ethyl acetate:hexane=1:4) to give the compound of the formula (7-5) 5.4 g.

Continuously, at RT, 28% sodium methoxide methanol solution 4.8 g and the compound of the formula (8-1) 3.3 g were dissolved in tetrahydrofuran 70 ml. The resulting solutions were heated under reflux for 15 minutes. Thereafter, the heating was stopped and to the resulting reaction mixtures was added the compound of the formula (7-5) 5.4 g. Thereafter, the resulting mixture solutions were heated under reflux for 30 minutes. The resulting reaction solutions were cooled to rt, and the precipitated crystals were collected by filtering and washed with tert-butyl methyl ether and hexane sequentially to give the compound of the formula (6-5) 5.7 g.

$^1$H NMR (d-DMSO)

δ ppm: 7.28 (2H, d), 6.90 (2H, d), 4.38 (1H, s), 3.75 (3H, s), 3.47 (3H, s), 2.90-2.69 (3H, m), 2.30-2.22 (1H, m), 2.04 (1H, dd), 1.74-1.66 (1H, m), 1.45-1.33 (2H, m)

<Preparation of the Compound of the Formula 1-8>

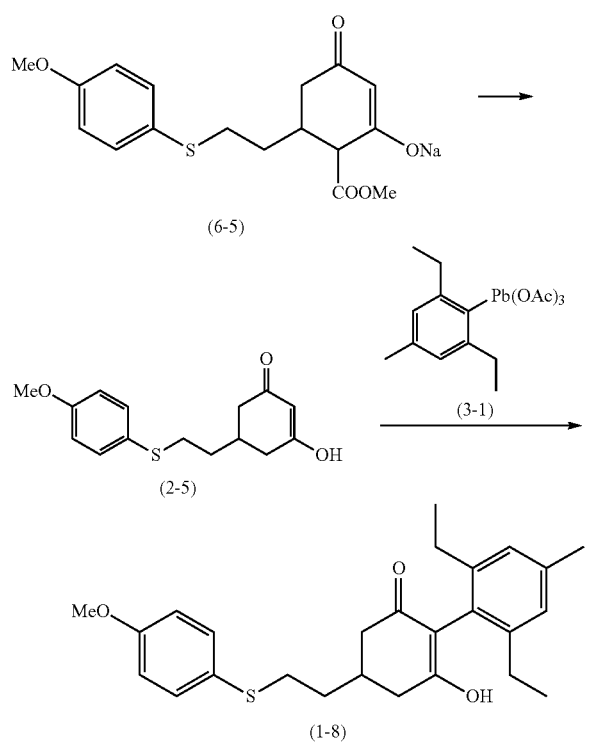

At RT, the compound of the formula (6-5) 5 g was dissolved in water 80 ml. To the resulting solutions was added anhydrous sodium carbonate 4.4 g. The resulting solutions were heated under reflux for 5 hours. The reaction solutions were cooled to rt and washed with tert-butyl methyl ether to remove impurities and then the aqueous layers were acidified with 2N hydrochloric acid and extracted with ethyl acetate. The ethyl acetate layers were concentrated under reduced pressure, and the resulting crystals were washed with tert-butyl methyl ether and hexane sequentially to give the compound of the formula (2-5) 3.8 g.

Continuously, under nitrogen atmosphere, at RT, the compound of the formula (2-5) 480 mg and dimethylaminopyridine 1.05 g were dissolved in a mixture of chloroform 4.8 ml and toluene 1.2 ml. The resulting solutions were stirred at RT under nitrogen atmosphere for 15 minutes. Thereafter, under nitrogen atmosphere, to the resulting solutions was added the compound of the formula (3-1) 1.0 g. Under nitrogen atmosphere, the resulting mixtures were stirred at 75° C. for 1 hour. The resulting reaction solutions were cooled to rt, adjusted to pH 1 with 2N hydrochloric acid and filtered through Celite™. The resulting filtrates were extracted with chloroform. The resulting chloroform layers were washed with water, dried over anhydrous sodium sulfate and filtered. The resulting filtrates were concentrated under reduced pressure to give yellow oils. The resulting oils were subjected to a silica gel column chromatography (eluates, ethyl acetate:hexane=1:3) to give the compound of the formula (1-8) 174 mg.

$^1$H NMR (CDCl$_3$)

δ ppm: 7.36 (2H, dd), 6.97 (2H, d), 6.86 (2H, dd), 5.57 (1H, s), 3.80 (3H, 3H), 2.92-2.88 (2H, m), 2.69-2.60 (2H, m), 2.44-2.19 (10H, m), 1.75 (2H, dd), 1.06 (6H, dt)

Preparation Example 1-9

Preparation of the Compound of the Formula (1-9)

<Preparation of the Compound of the Formula 9-6>

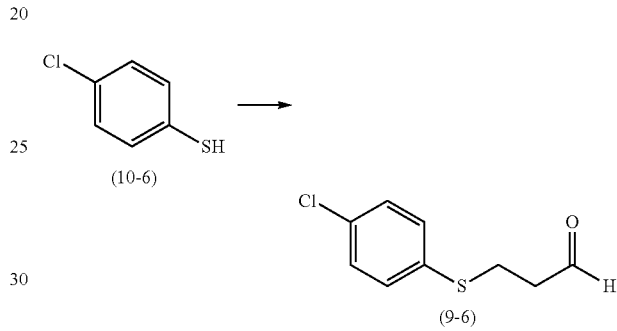

At RT, the compound of the formula (10-6) 10 g and tetrahydrofuran 20 ml were mixed and stirred and the resulting mixtures were cooled to 0° C. and then thereto were added dropwise 95% acrolein 5.6 g and triethylamine 0.2 g. The resulting mixtures were stirred under ice-cooling for 1.5 hours. Thereafter, the resulting mixtures were added to water. The resulting mixtures were extracted with tert-butyl methyl ether. The organic layers were washed with water, dried over anhydrous sodium sulfate and concentrated under reduced pressure to give the compound of the formula (9-6) 13 g.

$^1$H NMR (CDCl$_3$)

δ ppm: 9.73 (1H, s), 7.29-7.20 (4H, m), 3.14 (2H, t), 2.75 (2H, t)

<Preparation of the Compound of the Formula 7-6>

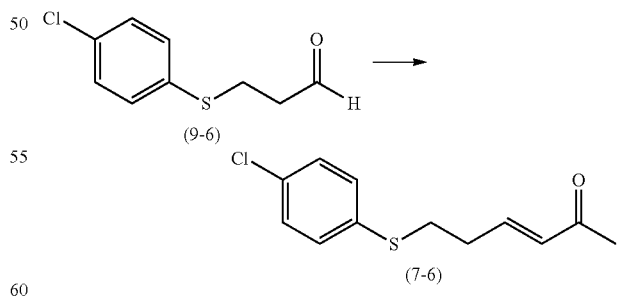

At RT, the compound of the formula (9-6) 10 g and triphenylphosphine acetylmethylene 17.4 g were dissolved in chloroform 60 ml. The resulting solutions were stirred at 0° C. for 8 hours. Thereafter, under reduced pressure, chloroform was removed from the resulting reaction solutions. To the resulting residues were added tert-butyl methyl ether and hexane. The resulting mixtures were filtered and the resulting filtrates were concentrated under reduced pressure. The resulting oils were subjected to a silica gel column chromatography (eluates, ethyl acetate:hexane=1:4) to give the compound of the formula (7-6) 9.4 g.

$^1$H NMR (CDCl$_3$)

δ ppm: 7.31-7.22 (4H, m), 6.80-6.70 (1H, m), 6.08 (1H, d), 3.00 (2H, m), 2.52 (2H, m), 2.23 (3H, s)

<Preparation of the Compound of the Formula 6-6>

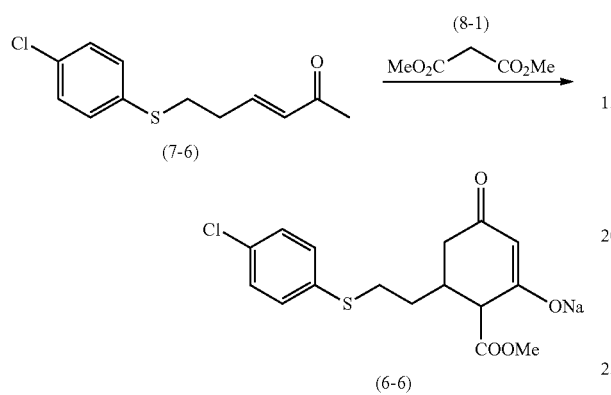

At RT, 28% sodium methoxide methanol solution 8.3 g and the compound of the formula (8-1) 5.7 g were dissolved in tetrahydrofuran 100 ml. The resulting solutions were heated under reflux for 15 minutes. Thereafter, the heating was stopped and to the resulting mixtures was added the compound of the formula (7-6) 9.4 g. Thereafter, the resulting mixture solutions were heated under reflux for 30 minutes. The resulting reaction solutions were cooled to rt, and the precipitated crystals were collected by filtering and washed with tert-butyl methyl ether and hexane sequentially to give the compound of the formula (6-6) 10 g.

$^1$H NMR (d-DMSO)

δ ppm: 7.36 (2H, d), 7.30 (2H, d), 4.38 (1H, s), 3.48 (3H, s), 3.00 (1H, m), 2.84 (2H, m), 2.32-2.22 (1H, m), 2.09 (1H, m), 1.78-1.71 (1H, m), 1.44 (2H, m)

<Preparation of the Compound of the Formula 2-6>

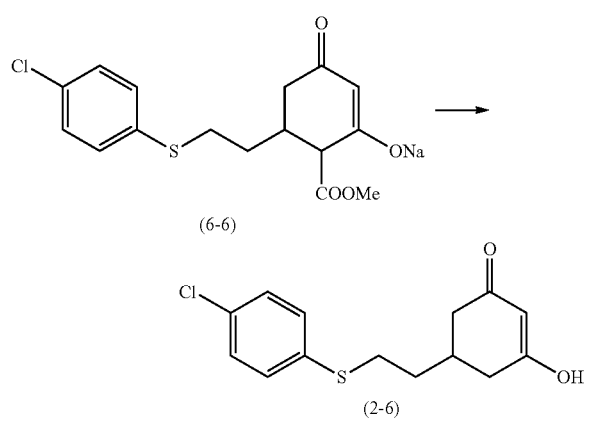

At RT, the compound of the formula (6-6) 5 g was dissolved in water 80 ml. To the resulting solutions was added anhydrous sodium carbonate 4.4 g. The resulting solutions were heated under reflux for 5 hours. The reaction solutions were cooled to rt and washed with tert-butyl methyl ether to remove impurities and then the aqueous layers were acidified with 2N hydrochloric acid and extracted with ethyl acetate. The ethyl acetate layers were concentrated under reduced pressure and the resulting crystals were washed with tert-butyl methyl ether and hexane sequentially to give the compound of the formula (2-6) 2.9 g.

$^1$H NMR (d-DMSO)

δ ppm: 11.06 (1H, s), 7.36 (4H, m), 5.19 (1H, s), 3.01 (2H, t), 2.32-1.99 (5H, m), 1.62 (2H, m)

<Preparation of the Compound of the Formula 1-9>

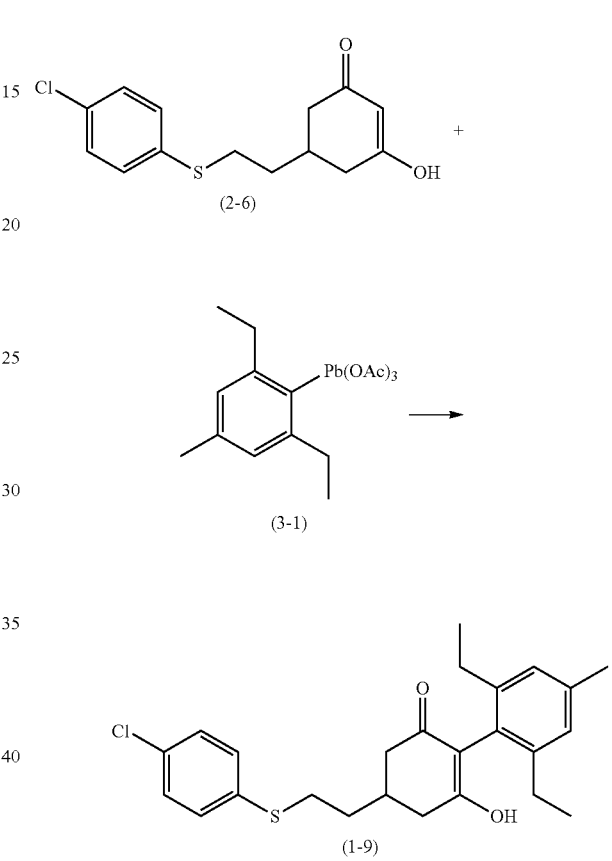

Under nitrogen atmosphere, at RT, the compound of the formula (2-6) 490 mg and dimethylaminopyridine 1.05 g were dissolved in a mixture of chloroform 4.8 ml and toluene 1.2 ml. The resulting solutions were stirred at RT under nitrogen atmosphere for 15 minutes. Thereafter, under nitrogen atmosphere, to the resulting solutions was added the compound of the formula (3-1) 1.0 g. Under nitrogen atmosphere, the resulting mixtures were stirred at 75° C. for 1 hour. The resulting reaction solutions were cooled to rt, adjusted to pH 1 with 2N hydrochloric acid and filtered through Celite™. The resulting filtrates were extracted with chloroform. The resulting chloroform layers were washed with water, dried over anhydrous sodium sulfate and filtered. The resulting filtrates were concentrated under reduced pressure to give yellow oils. The resulting oils were subjected to a silica gel column chromatography (eluates, ethyl acetate:hexane=1:4) to give the compound of the formula (1-9) 350 mg.

$^1$H NMR (CDCl$_3$)

δ ppm: 7.29-7.24 (4H, m), 6.97 (2H, s), 5.66 (1H, s), 3.02-2.93 (2H, m), 2.66 (2H, tt), 2.45-2.21 (10H, m), 1.80 (2H, q), 1.10-1.01 (6H, m)

Preparation Example 1-10

Preparation of the Compound of the Formula 1-10

<Preparation of the Compound of the Formula 6-7>

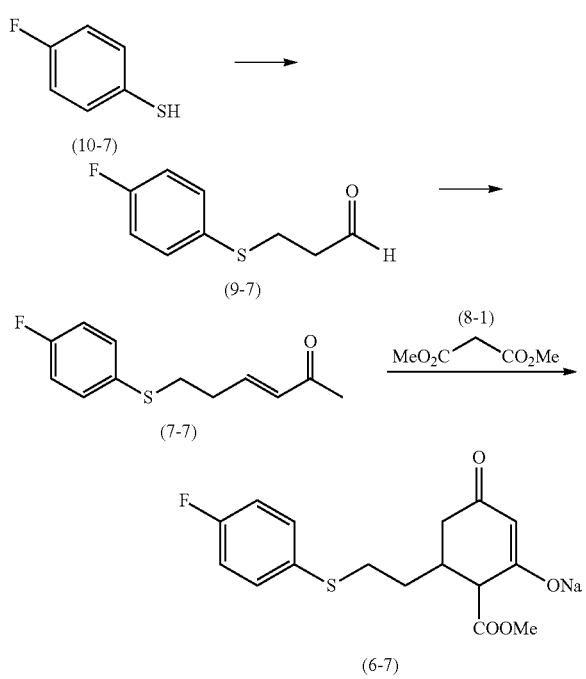

At RT, the compound of the formula (10-7) 10 g and tetrahydrofuran 25 ml were mixed ad stirred and the resulting mixtures were cooled to 0° C. and then thereto were added dropwise 95% acrolein 6.7 g and triethylamine 0.2 g. The resulting mixtures were stirred under ice-cooling for 1.5 hours. Thereafter, the resulting mixtures were added to water. The resulting mixtures were extracted with tert-butyl methyl ether. The organic layers were washed with water, dried over anhydrous sodium sulfate and concentrated under reduced pressure to give the compound of the formula (9-7) 14 g.

Continuously, at RT, the compound of the formula (9-7) 14 g and triphenylphosphine acetylmethylene 30 g were dissolved in chloroform 100 ml. The resulting solutions were stirred at 0° C. for 8 hours. Thereafter, under reduced pressure, chloroform was removed from the resulting reaction solutions. To the resulting residues were added tert-butyl methyl ether and hexane. The resulting mixtures were filtered and the resulting filtrates were concentrated under reduced pressure. The resulting oils were subjected to a silica gel column chromatography (eluates, ethyl acetate:hexane=1:4) to give the compound of the formula (7-7) 13 g.

Continuously, at RT, 28% sodium methoxide methanol solution 12 g and the compound of the formula (8-1) 8.4 g were dissolved in tetrahydrofuran 150 ml. The resulting solutions were heated under reflux for 15 minutes. Thereafter, the heating was stopped and to the resulting reaction mixtures was added the compound of the formula (7-7) 13 g. Thereafter, the resulting mixture solutions were heated under reflux for 30 minutes. The resulting reaction solutions were cooled to rt, and the precipitated crystals were collected by filtering and washed with tert-butyl methyl ether and hexane sequentially to give the compound of the formula (6-7) 14.2 g.

$^1$H NMR (d-DMSO)

δ ppm: 7.36 (2H, ddd), 7.17 (2H, tt), 4.37 (1H, s), 3.49 (3H, s), 3.00-2.93 (1H, m), 2.85-2.77 (2H, m), 2.27 (1H, tdd), 2.06 (1H, dd), 1.73 (1H, dt), 1.42 (2H, tt)

<Preparation of the Compound of the Formula 2-7>

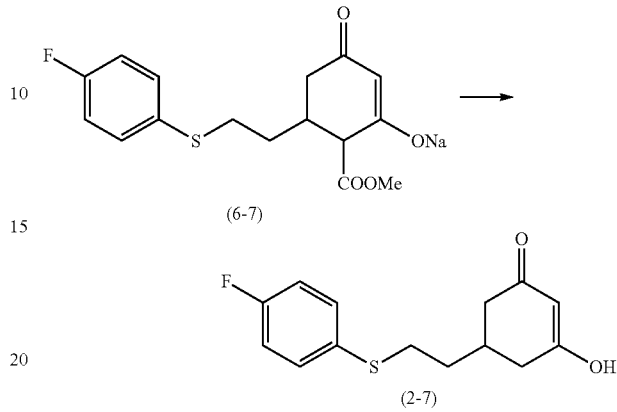

At RT, the compound of the formula (6-7) 5 g was dissolved in water 80 ml. To the resulting solutions was added anhydrous sodium carbonate 4.6 g. The resulting solutions were heated under reflux for 5 hours. The reaction solutions were cooled to rt and washed with tert-butyl methyl ether to remove impurities and then the aqueous layers were acidified with 2N hydrochloric acid and extracted with ethyl acetate. The ethyl acetate layers were concentrated under reduced pressure, and the resulting crystals were washed with tert-butyl methyl ether and hexane sequentially to the compound of the formula (2-7) 2.4 g.

$^1$H NMR (d-DMSO)

δ ppm: 11.04 (1H, s), 7.40 (2H, ddd), 7.17 (2H, tt), 5.19 (1H, s), 2.98 (2H, t), 2.28-1.91 (5H, m), 1.60 (2H, dd)

<Preparation of the Compound of the Formula 1-10>

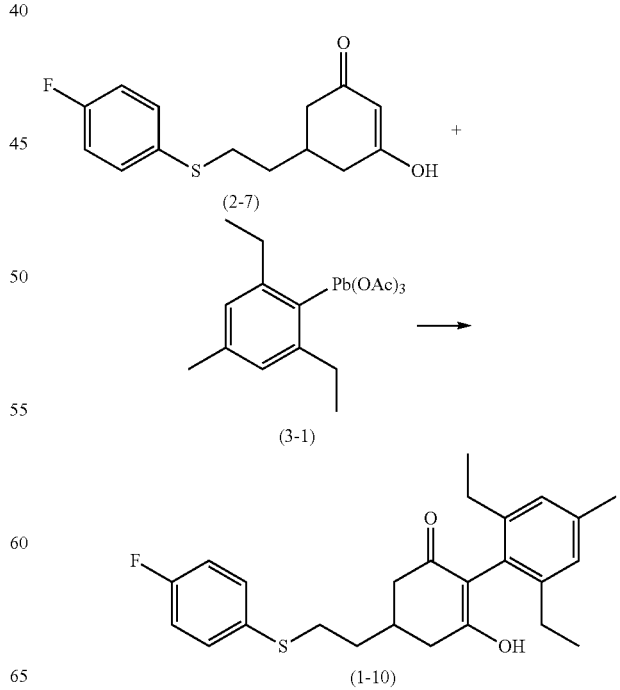

Under nitrogen atmosphere, at RT, the compound of the formula (2-7) 460 mg and dimethylaminopyridine 1.05 g were dissolved in a mixture of chloroform 4.8 ml and toluene 1.2 ml. The resulting solutions were stirred at RT under nitrogen atmosphere for 15 minutes. Thereafter, under nitrogen atmosphere, to the resulting solutions was added the compound of the formula (3-1) 1.0 g. Under nitrogen atmosphere, the resulting mixtures were stirred at 75° C. for 1 hour. The resulting reaction solutions were cooled to rt, adjusted to pH 1 with 2N hydrochloric acid and filtered through Celite™. The resulting filtrates were extracted with chloroform. The resulting chloroform layers were washed with water, dried over anhydrous sodium sulfate and filtered. The resulting filtrates were concentrated under reduced pressure to give yellow oils. The resulting oils were subjected to a silica gel column chromatography (eluates, ethyl acetate:hexane=1:4) to give the compound of the formula (1-10) 330 mg.

$^1$H NMR (CDCl$_3$)

δ ppm: 7.39-7.33 (2H, m), 7.04-6.98 (2H, m), 6.97 (2H, s), 5.62 (1H, s), 2.95 (2H, ddd), 2.65 (2H, dd), 2.45-2.21 (10H, m), 1.78 (2H, q), 1.06 (6H, ddd)

Preparation Example 1-11

Preparation of the Compound of the Formula (1-11)

<Preparation of the Compound of the Formula 9-8>

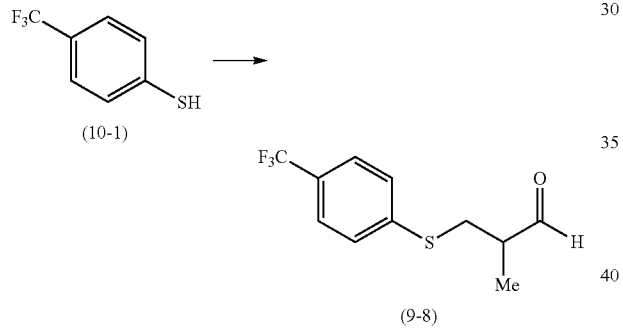

At RT, the compound of the formula (10-1) 5 g and tetrahydrofuran 15 ml were mixed and stirred, and the resulting mixtures were cooled to 0° C. and then thereto were added dropwise methacrolein 2.6 g and triethylamine 0.1 g. The resulting mixtures were stirred under ice-cooling for 1.5 hours. Thereafter, the resulting mixtures were added to water. The resulting mixtures were extracted with tert-butyl methyl ether. The organic layers were washed with water, dried over anhydrous sodium sulfate and concentrated under reduced pressure to the compound of the formula (9-8) 6.9 g.

$^1$H NMR (CDCl$_3$)

δ ppm: 9.69 (1H, s), 7.53 (2H, d), 7.40 (2H, d), 3.42-3.35 (1H, m), 3.00-2.95 (1H, m), 2.67 (1H, dd), 1.28 (3H, dd)

<Preparation of the Compound of the Formula 7-8>

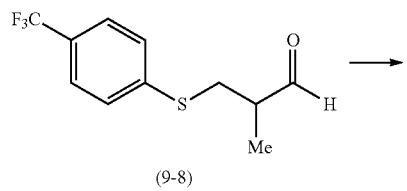

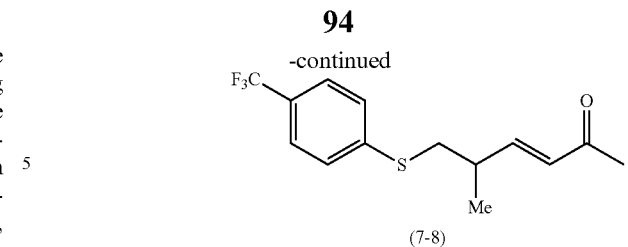

At RT, the compound of the formula (9-8) 6.9 g and triphenylphosphine acetylmethylene 10 g were dissolved in chloroform 50 ml. The resulting solutions were stirred at 0° C. for 8 hours. Thereafter, under reduced pressure, chloroform was removed from the resulting reaction solutions. To the resulting residues were added tert-butyl methyl ether and hexane. The resulting mixtures were filtered and the resulting filtrates were concentrated under reduced pressure. The resulting oils were subjected to a silica gel column chromatography (eluates, ethyl acetate:hexane=1:4) to give the compound of the formula (7-8) 5.3 g.

$^1$H NMR (CDCl$_3$)

δ ppm: 7.52 (2H, d), 7.36 (2H, d), 6.72 (1H, dd), 6.09 (1H, dd), 3.03 (2H, ddd), 2.67 (1H, dt), 2.24 (3H, s), 1.25 (3H, d)

<Preparation of the Compound of the Formula 2-8>

At RT, 28% sodium methoxide methanol solution 3.9 g and the compound of the formula (8-1) 2.7 g were dissolved in tetrahydrofuran 60 ml. The resulting solutions were heated under reflux for 15 minutes. Thereafter, the heating was stopped and to the resulting reaction mixture was added the compound of the formula (7-8) 5.3 g. Thereafter, the resulting mixture solutions were heated under reflux for 30 minutes. The resulting reaction solutions were cooled to rt and thereto was added hexane. Thereafter, the reaction solutions were ice-cooled and the precipitated crystals were collected by filtering and washed thoroughly with hexane to give the compound of the formula (6-8) 4.4 g.

Continuously, at RT, the compound of the formula (6-8) 1.6 g was dissolved in water 30 ml. To the resulting solution was added anhydrous sodium carbonate 1.3 g. The resulting solutions were heated under reflux for 5 hours. The reaction solutions were cooled to rt and washed with tert-butyl methyl ether to remove impurities and then the aqueous layers were acidified with 2N hydrochloric acid and extracted with ethyl acetate. The ethyl acetate layers were concentrated under reduced pressure to give the compound of the formula (2-8) 1.3 g.

$^1$H NMR (d-DMSO)

δ ppm: 7.52 (2H, t), 7.35 (2H, d), 5.51 (1H, s), 3.42 (1H, s), 3.09-2.82 (2H, m), 2.67 (1H, d), 2.46 (2H, dt), 2.25 (2H, ddd), 1.90-1.84 (1H, m), 1.09 (3H, dd)

<Preparation of the Compound of the Formula 1-11>

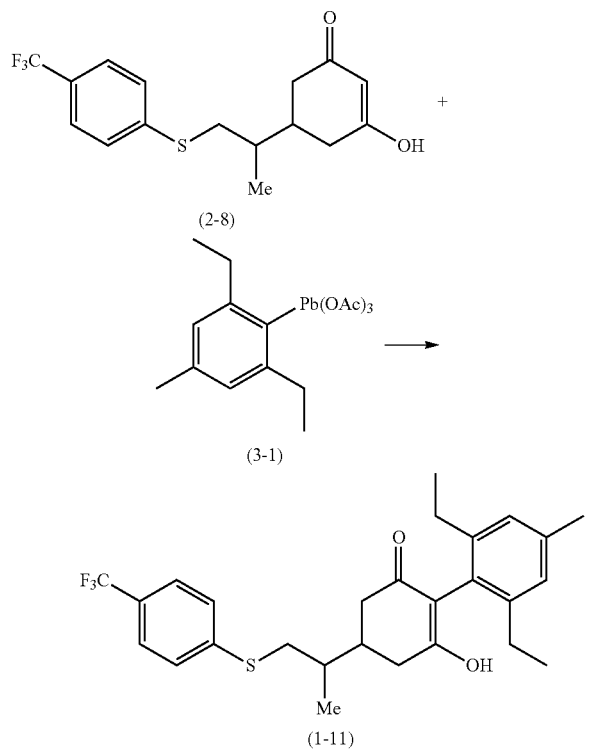

Under nitrogen atmosphere, at RT, the compound of the formula (2-8) 570 mg and dimethylaminopyridine 1.05 g were dissolved in a mixture of chloroform 4.8 ml and toluene 1.2 ml. The resulting solutions were stirred at RT under nitrogen atmosphere for 15 minutes. Thereafter, under nitrogen atmosphere, to the resulting solutions was added the compound of the formula (3-1) 1.0 g. Under nitrogen atmosphere, the resulting mixtures were stirred at 75° C. for 1 hour. The resulting reaction solutions were cooled to rt, adjusted to pH 1 with 2N hydrochloric acid and filtered through Celite™. The resulting filtrates were extracted with chloroform. The resulting chloroform layers were washed with water, dried over anhydrous sodium sulfate and filtered. The resulting filtrates were concentrated under reduced pressure to give yellow oils. The resulting oils were subjected to a silica gel column chromatography (eluates, ethyl acetate hexane=1:4) to give the compound of the formula (1-11) 480 mg.

$^1$H NMR (CDCl$_3$)

δ ppm: 7.53 (2H, d), 7.38 (2H, d), 6.98 (2H, s), 5.54 (1H, s), 3.22-3.14 (1H, m), 2.87 (1H, ddd), 2.67-2.23 (12H, m), 1.95-1.88 (1H, m), 1.16 (3H, dd), 1.11-1.04 (6H, m)

Preparation Example 1-12

Preparation of the Compound of the Formula (1-12)

<Preparation of the Compound of the Formula 1-12>

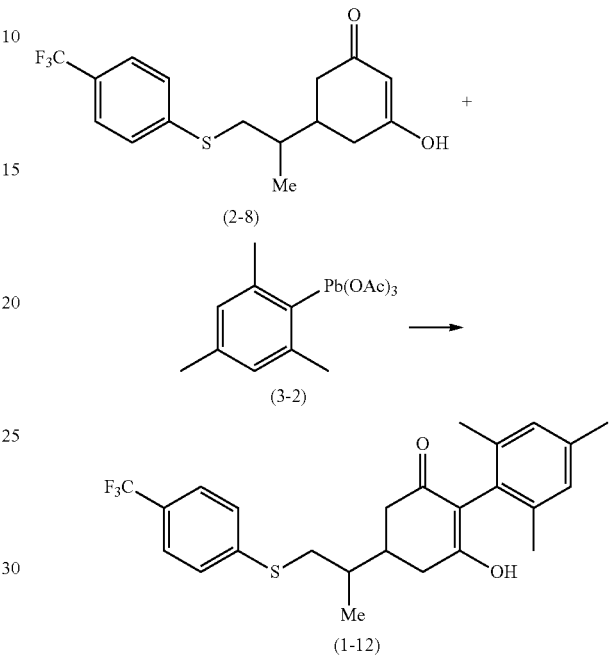

In a flask, under nitrogen atmosphere, at RT, the compound of the formula (2-8) 600 mg and dimethylaminopyridine 1.1 g were dissolved in a mixture of chloroform 4.8 ml and toluene 1.2 ml. The resulting solutions were stirred at RT under nitrogen atmosphere for 15 minutes. Thereafter, under nitrogen atmosphere, to the resulting solutions was added the compound of the formula (3-2) 1.0 g. Under nitrogen atmosphere, the resulting mixtures were stirred at 75° C. for 1 hour. The resulting reaction solutions were cooled to rt, adjusted to pH 1 with 2N hydrochloric acid and filtered through Celite™. The resulting filtrates were extracted with chloroform. The resulting chloroform layers were washed with water, dried over anhydrous sodium sulfate and filtered. The resulting filtrates were concentrated under reduced pressure to give yellow oils. The resulting oils were subjected to a silica gel column chromatography (eluates, ethyl acetate:hexane=1:4) to give the compound of the formula (1-12) 540 mg.

$^1$H NMR (CDCl$_3$)

δ ppm: 7.53 (2H, d), 7.38 (2H, d), 6.94 (2H, s), 5.56 (1H, s), 3.16 (1H, ddd), 2.87 (1H, ddd), 2.65-2.25 (8H, m), 2.08 (3H, d), 2.01 (3H, s), 1.90 (1H, td), 1.15 (3H, dd)

The present compound prepared according to preparation Example 1-12 is shown below.

<Compound of the Formula 1-162>

$^1$H NMR (CDCl$_3$)

δ ppm: 7.28-7.22 (1H, m), 7.09 (1H, d), 7.03 (1H, dt), 6.93 (2H, s), 6.90-6.85 (1H, m), 5.73 (1H, s), 3.10 (1H, s), 2.83 (1H, dt), 2.60-2.22 (8H, m), 2.06-1.97 (6H, m), 1.86 (1H, s), 1.13 (3H, d)

Preparation Example 1-13

Preparation of the Compound of the Formula (1-13)

<Preparation of the Compound of the Formula 9-9>

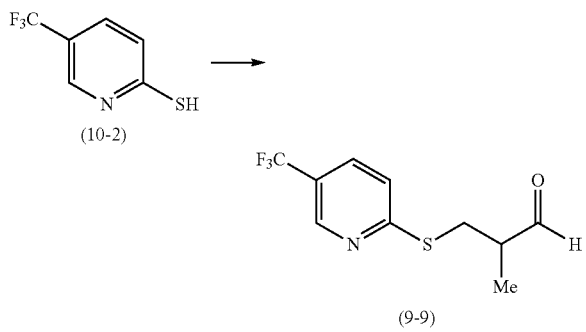

At RT, the compound of the formula (10-2) 5 g and tetrahydrofuran 15 ml were mixed and stirred and the resulting mixtures were cooled to 0° C. and then thereto were added dropwise methacrolein 2.6 g and triethylamine 0.1 g. The resulting mixtures were stirred under ice-cooling for 1.5 hours. Thereafter, the resulting mixtures were added to water. The resulting mixtures were extracted with tert-butyl methyl ether. The organic layers were washed with water, dried over anhydrous sodium sulfate and concentrated under reduced pressure to give the compound of the formula (9-9) 6.3 g.

$^1$H NMR (CDCl$_3$)

δ ppm: 9.72 (1H, s), 8.66 (1H, s), 7.66 (1H, d), 7.27 (1H, d), 3.56 (1H, ddd), 3.38-3.31 (1H, m), 2.84 (1H, dd), 1.27-1.25 (3H, m)

<Preparation of the Compound of the Formula 7-9>

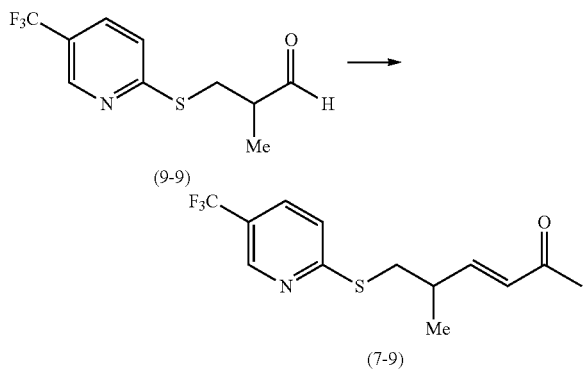

At RT, the compound of the formula (9-9) 6.6 g and triphenylphosphine acetylmethylene 9 g were dissolved in chloroform 40 ml. The resulting solutions were stirred at 0° C. for 8 hours. Thereafter, under reduced pressure, chloroform was removed from the resulting reaction solutions. To the resulting residues were added tert-butyl methyl ether and hexane. The resulting mixtures were filtered and the resulting filtrates were concentrated under reduced pressure. The resulting oils were subjected to a silica gel column chromatography (eluates, ethyl acetate:hexane=1:4) to give the compound of the formula (7-9) 2.8 g.

$^1$H NMR (CDCl$_3$)

δ ppm: 8.66 (1H, s), 7.67-7.65 (1H, m), 7.28 (1H, d), 6.77 (1H, dd), 6.10 (1H, dd), 3.32 (2H, ddd), 2.79-2.72 (1H, m), 2.22 (3H, s), 1.25 (3H, d)

<Preparation of the Compound of the Formula 2-9>

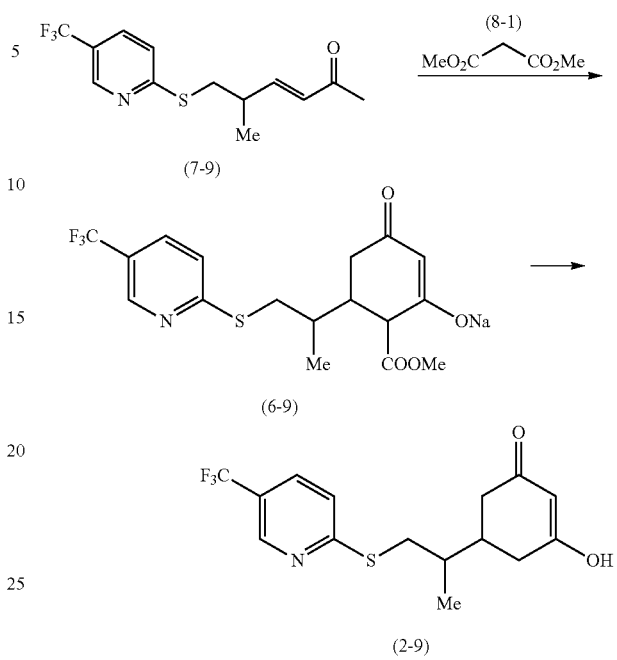

At RT, 28% sodium methoxide methanol solution 2.1 g and the compound of the formula (8-1) 1.4 g were dissolved in tetrahydrofuran 40 ml. The resulting solutions were heated under reflux for 15 minutes. Thereafter, the heating was stopped and to the resulting reaction mixture was added the compound of the formula (7-9) 2.8 g. Thereafter, the resulting mixture solutions were heated under reflux for 30 minutes. The resulting reaction solutions were cooled to rt and there was added hexane. Thereafter, the reaction solutions were ice-cooled, and the precipitated crystals were collected by filtering and washed with hexane thoroughly to give the compound of the formula (6-9) 2.0 g.

Continuously, in the flask, at RT, the compound of the formula (6-9) 1.8 g was dissolved in water 25 ml. To the resulting solutions was added anhydrous sodium carbonate 1.5 g. The resulting solutions were heated under reflux for 5 hours. The reaction solutions were cooled to rt and washed with tert-butyl methyl ether to remove impurities and then the aqueous layers were acidified with 2N hydrochloric acid and extracted with ethyl acetate. The ethyl acetate layers were concentrated under reduced pressure to give the compound of the formula (2-9) 1.3 g.

$^1$H NMR (CDCl$_3$)

δ ppm: 8.66 (1H, s), 7.67-7.64 (1H, m), 7.25-7.19 (1H, m), 5.52 (1H, s), 3.49-3.41 (1H, m), 3.05-2.96 (1H, m), 2.75 (1H, dd), 2.58-2.45 (2H, m), 2.37-2.18 (2H, m), 1.98-1.88 (1H, m), 1.06 (3H, dd)

<Preparation of the Compound of the Formula 1-13>

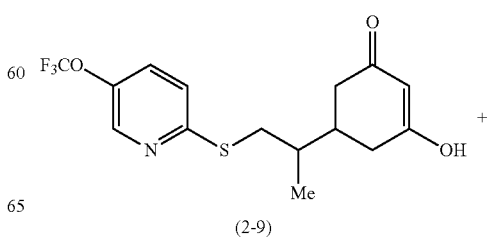

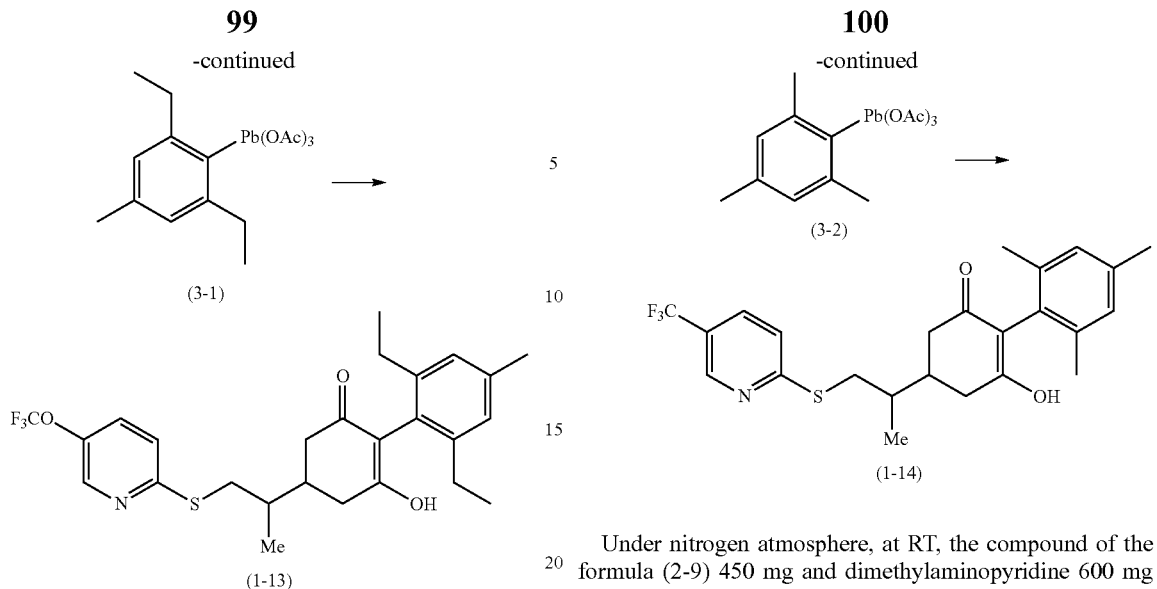

Under nitrogen atmosphere, at RT, the compound of the formula (2-9) 570 mg and dimethylaminopyridine 1.05 g were dissolved in a mixture of chloroform 4.8 ml and toluene 1.2 ml. The resulting solutions were stirred at RT under nitrogen atmosphere for 15 minutes. Thereafter, under nitrogen atmosphere, to the resulting solutions was added the compound of the formula (3-1) 1.0 g. Under nitrogen atmosphere, the resulting mixtures were stirred at 75° C. for 1 hour. The resulting reaction solutions were cooled to rt, adjusted to pH 1 with 2N hydrochloric acid and filtered through Celite™. The resulting filtrates were extracted with chloroform. The resulting chloroform layers were washed with water, dried over anhydrous sodium sulfate and filtered. The resulting filtrates were concentrated under reduced pressure to give yellow oils. The resulting oils were subjected to a silica gel column chromatography (eluates, ethyl acetate hexane=1:4) to give the compound of the formula (1-13) 570 mg. Continuously, Compound of the formula (1-13) were subjected to a chiral column chromatography (condition: CHIRALPAK IC-3, temperature 40° C., CO$_2$: 2.0 ml/min, MeOH: 0.15 ml/min) to give the compound of retention time 13 min (1-13-A) and the compound of retention time 16 min (1-13-B).

$^1$H NMR (CDCl$_3$)

δ ppm: 8.67 (1H, s), 7.66 (1H, dd), 7.28 (1H, d), 6.98 (2H, s), 5.54 (1H, s), 3.59 (1H, ddd), 3.02 (1H, dddd), 2.76-2.26 (12H, m), 1.95 (1H, t), 1.15 (3H, dt), 1.09-1.02 (6H, m)

Preparation Example 1-14

Preparation of the Compound of the Formula (1-14)

<Preparation of the Compound of the Formula 1-14>

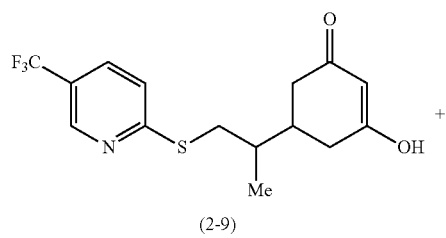

Under nitrogen atmosphere, at RT, the compound of the formula (2-9) 450 mg and dimethylaminopyridine 600 mg were dissolved in a mixture of chloroform 2.5 ml and toluene 0.5 ml. The resulting solutions were stirred at RT under nitrogen atmosphere for 15 minutes. Thereafter, under nitrogen atmosphere, to the resulting solutions was added the compound of the formula (3-2) 500 mg. Under nitrogen atmosphere, the resulting mixtures were stirred at 75° C. for 1 hour. The resulting reaction solutions were cooled to rt, adjusted to pH 1 with 2N hydrochloric acid and filtered through Celite™. The resulting filtrates were extracted with chloroform. The resulting chloroform layers were washed with water, dried over anhydrous sodium sulfate and filtered. The resulting filtrates were concentrated under reduced pressure to give yellow oils. The resulting oils were subjected to a silica gel column chromatography (eluates, ethyl acetate hexane=1:3) to give the compound of the formula (1-14) 320 mg.

$^1$H NMR (CDCl$_3$)

δ ppm: 8.66 (1H, s), 7.66 (1H, dd), 7.27 (1H, d), 6.93 (2H, s), 5.65 (1H, s), 3.57 (1H, ddd), 3.07-2.96 (1H, m), 2.74-2.27 (6H, m), 2.07-1.94 (9H, m), 1.17-1.10 (3H, m)

Preparation Example 1-15

Preparation of the Compound of the Formula (1-15)

<Preparation of the Compound of the Formula 7-10>

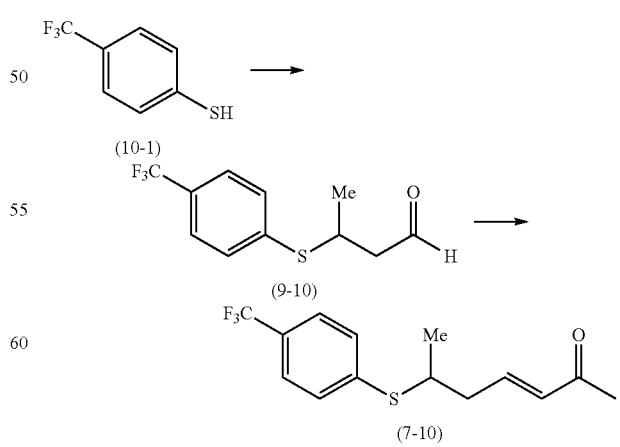

At RT, the compound of the formula (10-1) 3 g and tetrahydrofuran 10 ml were mixed and stirred and the resulting mixtures were cooled to 0° C. and then thereto were added dropwise crotonaldehyde 1.5 g and triethylamine 0.1 g. The resulting mixtures were stirred under ice-cooling for 1.5 hours. Thereafter, the resulting mixtures were added to water. The resulting mixtures were extracted with tert-butyl methyl ether. The organic layers were washed with water, dried over anhydrous sodium sulfate and concentrated under reduced pressure to give the compound of the formula (9-10) 4.4 g.

Continuously, at RT, the compound of the formula (9-10) 4.4 g and triphenylphosphine acetylmethylene 6.2 g were dissolved in chloroform 25 ml. The resulting solutions were stirred at 0° C. for 8 hours. Thereafter, under reduced pressure, chloroform was removed from the resulting reaction solutions. To the resulting residues were added tert-butyl methyl ether and hexane. The resulting mixtures were filtered and the resulting filtrates were concentrated under reduced pressure. The resulting oils were subjected to a silica gel column chromatography (eluates, ethyl acetate:hexane=1:4) to give the compound of the formula (7-10) 3.7 g.

$^1$H NMR (CDCl$_3$)

δ ppm: 7.54 (2H, d), 7.45 (2H, d), 6.79 (1H, dt), 6.14-6.10 (1H, m), 3.51 (1H, q), 2.60-2.45 (2H, m), 2.24 (3H, s), 1.36 (3H, d)

<Preparation of the Compound of the Formula 2-10>

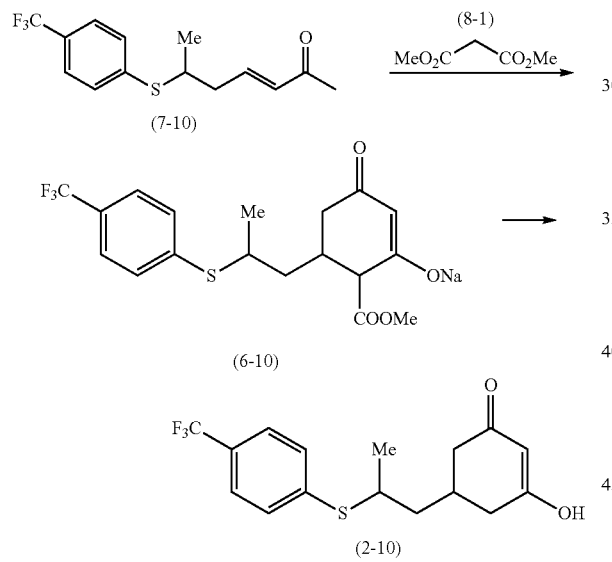

At RT, 28% sodium methoxide methanol solution 2.7 g and the compound of the formula (8-1) 1.8 g were dissolved in tetrahydrofuran 40 ml. The resulting solutions were heated under reflux for 15 minutes. Thereafter, the heating was stopped and to the resulting reaction mixtures was added the compound of the formula (7-10) 3.7 g. Thereafter, the resulting mixture solutions were heated under reflux for 30 minutes. The resulting reaction solutions were cooled to rt and thereto was added hexane. Thereafter, the reaction solutions were ice-cooled and the precipitated crystals were collected by filtering and washed with hexane thoroughly to give the compound of the formula (6-10) 2.9 g.

Continuously, at RT, the compound of the formula (6-10) 2.9 g was dissolved in water (40 ml). To the resulting solutions was added anhydrous sodium carbonate 2.3 g. The resulting solutions were heated under reflux for 5 hours. The reaction solutions were cooled to rt and washed with tert-butyl methyl ether to remove impurities and then the aqueous layers were acidified with 2N hydrochloric acid and extracted with ethyl acetate. The ethyl acetate layers were concentrated under reduced pressure to give the compound of the formula (2-10) 2.1 g.

$^1$H NMR (CDCl$_3$)

δ ppm: 7.54 (2H, t), 7.42 (2H, dd), 5.48 (1H, s), 3.36 (2H, tt), 2.78 (2H, d), 2.53-2.34 (2H, m), 2.13 (1H, dd), 1.75-1.53 (2H, m), 1.34-1.29 (3H, m)

<Preparation of the Compound of the Formula 1-15>

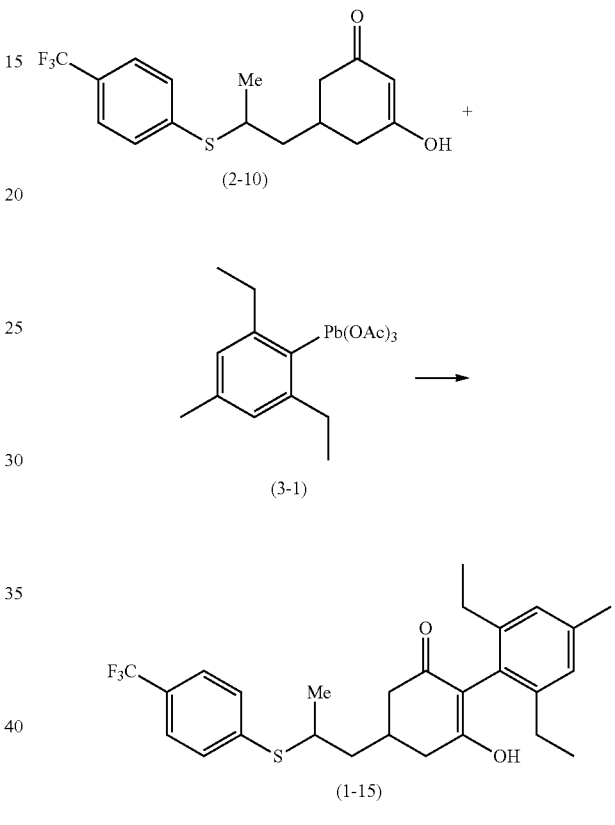

Under nitrogen atmosphere, at RT, the compound of the formula (2-10) 570 mg and dimethylaminopyridine 1.05 g were dissolved in a mixture of chloroform 4.8 ml and toluene 1.2 ml. The resulting solutions were stirred at RT under nitrogen atmosphere for 15 minutes. Thereafter, under nitrogen atmosphere, to the resulting solutions was the compound of the formula (3-1) 1.0 g. Under nitrogen atmosphere, the resulting mixtures were stirred at 75° C. for 1 hour. The resulting reaction solutions were cooled to rt, adjusted to pH 1 with 2N hydrochloric acid and filtered through Celite™. The resulting filtrates were extracted with chloroform. The resulting chloroform layers were washed with water, dried over anhydrous sodium sulfate and filtered. The resulting filtrates were concentrated under reduced pressure to give yellow oils. The resulting oils were subjected to a silica gel column chromatography (eluates, ethyl acetate:hexane=1:4) to give the compound of the formula (1-15) 360 mg.

$^1$H NMR (CDCl$_3$)

δ ppm: 7.56-7.52 (2H, m), 7.46-7.41 (2H, m), 6.98 (2H, s), 5.53 (1H, s), 3.49-3.42 (1H, m), 2.76-2.23 (12H, m), 1.83-1.71 (2H, m), 1.38 (3H, dd), 1.06 (6H, tt)

Preparation Example 1-16

Preparation of the Compound of the Formula (1-16)

<Preparation of the Compound of the Formula 9-11>

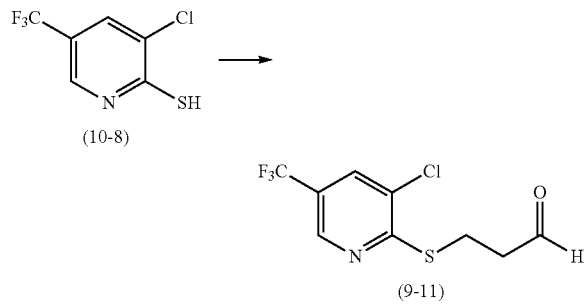

At RT, the compound of the formula (10-8) 2 g and tetrahydrofuran 10 ml were mixed and stirred and the resulting mixtures were cooled to 0° C. and then thereto were added dropwise 95% acrolein 0.8 g and triethylamine 0.1 g. The resulting mixtures were stirred under ice-cooling for 1.5 hours. Thereafter, the resulting mixtures were added to water. The resulting mixtures were extracted with tert-butyl methyl ether. The organic layers were washed with water, dried over anhydrous sodium sulfate and concentrated under reduced pressure to give the compound of the formula (9-11) 2.5 g.

$^1$H NMR (CDCl$_3$)

δ ppm: 9.84 (1H, s), 8.59 (1H, s), 7.76 (1H, s), 3.49 (2H, t), 2.96 (2H, t)

<Preparation of the Compound of the Formula 7-11>

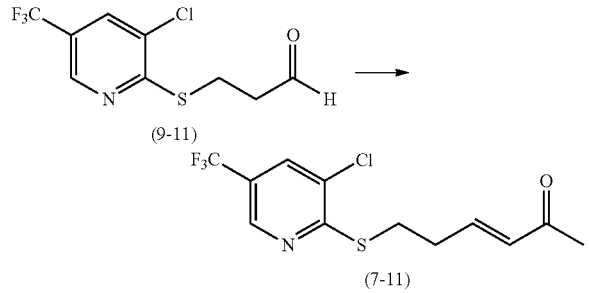

At RT, the compound of the formula (9-11) 2.5 g and triphenylphosphine acetylmethylene 3.4 g were dissolved in chloroform 15 ml. The resulting solutions were stirred at 0° C. for 8 hours. Thereafter, under reduced pressure, chloroform was removed from the resulting reaction solutions. To the resulting residues were added tert-butyl methyl ether and hexane. The resulting mixtures were filtered and the resulting filtrates were concentrated under reduced pressure. The resulting oils were subjected to a silica gel column chromatography (eluates, ethyl acetate:hexane=1:4) to give the compound of the formula (7-11) 1.2 g.

$^1$H NMR (CDCl$_3$)

δ ppm: 8.60 (1H, s), 7.76 (1H, s), 6.84 (1H, dt), 6.16 (1H, dt), 3.36 (2H, t), 2.68 (2H, ddd), 2.26 (3H, s)

<Preparation of the Compound of the Formula 6-11>

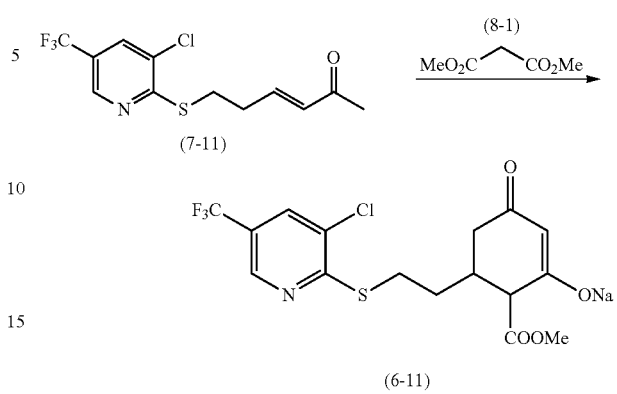

At RT, 28% sodium methoxide methanol solution 0.8 g and the compound of the formula (8-1) 0.56 g were dissolved in tetrahydrofuran 15 ml. The resulting solutions were heated under reflux for 15 minutes. Thereafter, the heating was stopped and to the resulting reaction mixtures was added the compound of the formula (7-11) 1.2 g. Thereafter, the resulting mixture solutions were heated under reflux for 30 minutes. The resulting reaction solutions were cooled to rt and the precipitated crystals were collected by filtering and washed with tert-butyl methyl ether and hexane sequentially to give the compound of the formula (6-11) 0.8 g.

$^1$H NMR (d-DMSO)

δ ppm: 8.81 (1H, s), 8.34 (1H, s), 4.38 (1H, s), 3.50 (3H, s), 3.42-3.25 (1H, m), 3.15-3.07 (1H, m), 2.82 (1H, d), 2.33-2.23 (1H, m), 2.12 (1H, dd), 1.79 (1H, dt), 1.63-1.50 (2H, m)

<Preparation of the Compound of the Formula 2-11>

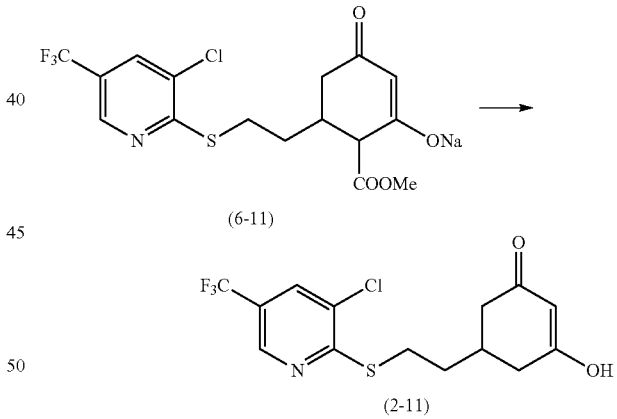

In the flask, at RT, the compound of the formula (6-11) 0.8 g was dissolved in water 10 ml. To the resulting solutions was added anhydrous sodium carbonate 0.6 g. The resulting solutions were heated under reflux for 5 hours. The reaction solutions were cooled to rt and washed with tert-butyl methyl ether to remove impurities and then the aqueous layers were acidified with 2N hydrochloric acid and extracted with ethyl acetate. The ethyl acetate layers were concentrated under reduced pressure and the resulting crystals were washed with tert-butyl methyl ether and hexane sequentially to give the compound of the formula (2-11) 0.6 g.

$^1$H NMR (d-DMSO)

δ ppm: 11.06 (1H, s), 8.81 (1H, d), 8.35 (1H, d), 5.20 (1H, s), 3.27 (2H, t), 2.51-1.91 (5H, m), 1.74 (2H, d)

105

<Preparation of the Compound of the Formula 1-16>

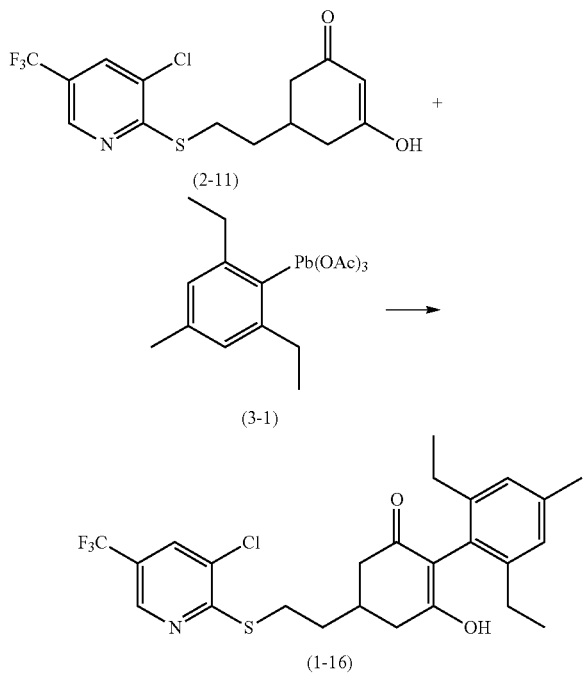

Under nitrogen atmosphere, at RT, the compound of the formula (2-11) 600 mg and dimethylaminopyridine 1.05 g were dissolved in a mixture of chloroform 4.8 ml and toluene 1.2 ml. The resulting solutions were stirred at RT under nitrogen atmosphere for 15 minutes. Thereafter, under nitrogen atmosphere, to the resulting solutions was added dropwise the compound of the formula (3-1) 1.0 g. Under nitrogen atmosphere, the resulting mixtures were stirred at 75° C. for 1 hour. The resulting reaction solutions were cooled to rt, adjusted to pH 1 with 2N hydrochloric acid and filtered through Celite™. The resulting filtrates were extracted with chloroform. The resulting chloroform layers were washed with water, dried over anhydrous sodium sulfate and filtered. The resulting filtrates were concentrated under reduced pressure to give yellow oils. The resulting oils were subjected to a silica gel column chromatography (eluates, ethyl acetate:hexane=1:4) to give the compound of the formula (1-16) 360 mg.

$^1$H NMR (CDCl$_3$)

δ ppm: 8.60 (1H, s), 7.75 (1H, d), 6.97 (2H, s), 5.71 (1H, s), 3.31 (2H, ddd), 2.75 (2H, t), 2.51-2.23 (10H, m), 1.94-1.88 (2H, m), 1.09-1.00 (6H, m)

Preparation Example 1-17

Preparation of the Compound of the Formula (1-17)

<Preparation of the Compound of the Formula 7-12>

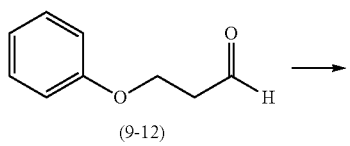

106

-continued

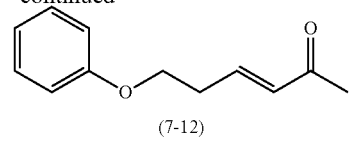

At RT, the compound of the formula (9-12) 9.3 g and triphenylphosphine acetylmethylene 22 g were dissolved in chloroform 90 ml. The resulting solutions were stirred at 0° C. for 8 hours. Thereafter, under reduced pressure, chloroform was removed from the resulting reaction solutions. To the resulting residues were added tert-butyl methyl ether and hexane. The resulting mixtures were filtered and the resulting filtrates were concentrated under reduced pressure. The resulting oils were subjected to a silica gel column chromatography (eluates, ethyl acetate:hexane=1:4) to give the compound of the formula (7-12) 2.1 g.

$^1$H NMR (CDCl$_3$)

δ ppm: 7.31-7.23 (2H, m), 6.95 (1H, tt), 6.92-6.82 (3H, m), 6.21-6.14 (1H, m), 4.09 (2H, t), 2.69 (2H, q), 2.24 (3H, s)

<Preparation of the Compound of the Formula 6-12>

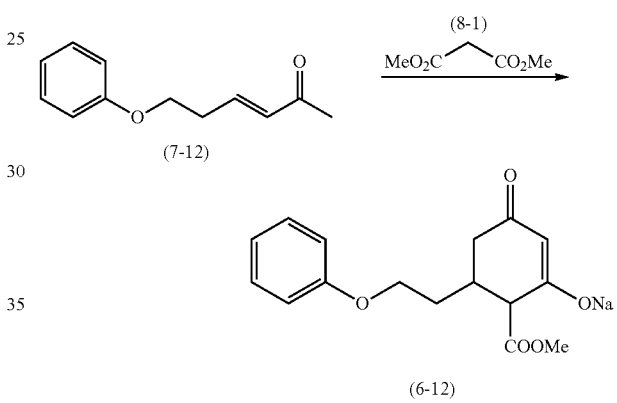

At RT, 28% sodium methoxide methanol solution 2.3 g and the compound of the formula (8-1) 1.6 g were dissolved in tetrahydrofuran 40 ml. The resulting solutions were heated under reflux for 15 minutes. Thereafter, the heating was stopped and to the resulting reaction mixtures was added the compound of the formula (7-12) 2.1 g. Thereafter, the resulting mixture solutions were heated under reflux for 30 minutes. The resulting reaction solutions were cooled to rt and, the precipitated crystals were collected by filtering and washed with tert-butyl methyl ether and hexane sequentially to give the compound of the formula (6-12) 2.6 g.

$^1$H NMR (d-DMSO)

δ ppm: 7.27 (2H, t), 6.92-6.89 (3H, m), 4.40 (1H, s), 4.38-3.89 (2H, m), 3.54 (3H, s), 2.87 (1H, d), 2.40-2.30 (1H, m), 2.08 (1H, dd), 1.81 (1H, dd), 1.72-1.64 (1H, m), 1.60-1.51 (1H, m)

<Preparation of the Compound of the Formula 2-12>

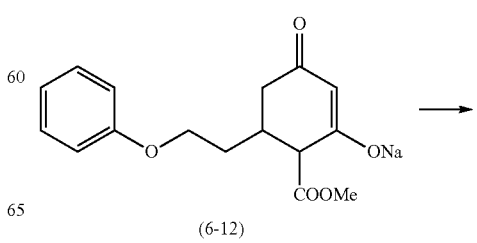

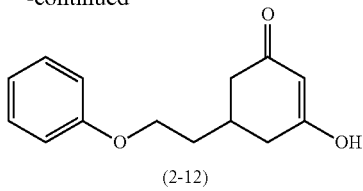

(2-12)

At RT, the compound of the formula (6-12) 2.0 g was dissolved in water 40 ml. To the resulting solutions was added anhydrous sodium carbonate 2.0 g. The resulting solutions were heated under reflux for 5 hours. The reaction solutions were cooled to rt and washed with tert-butyl methyl ether to remove impurities, and then the aqueous layers were acidified with 2N hydrochloric acid and extracted with ethyl acetate. The ethyl acetate layers were concentrated under reduced pressure, and the resulting crystals were washed with tert-butyl methyl ether and hexane sequentially to give the compound of the formula (2-12) 1.2 g.

$^1$H NMR (d-DMSO)

δ ppm: 11.06 (1H, s), 7.28 (2H, t), 6.92 (2H, dd), 5.20 (1H, s), 4.02 (2H, t), 2.50-1.99 (5H, m), 1.79 (2H, d)

<Preparation of the Compound of the Formula 1-17>

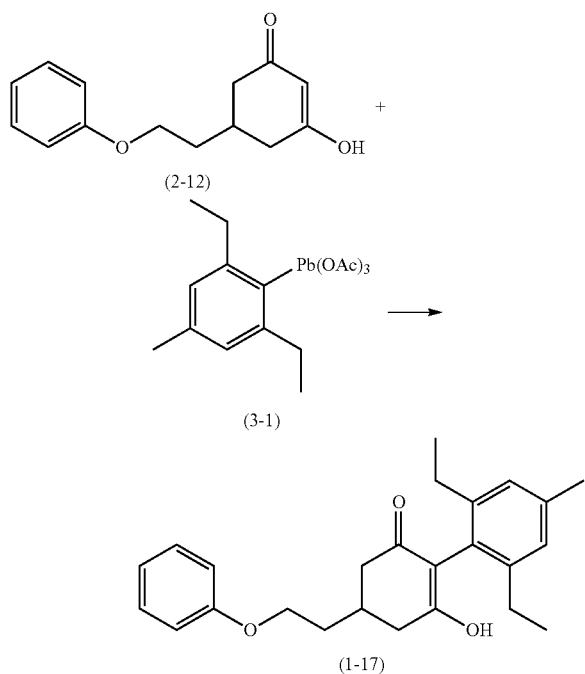

Under nitrogen atmosphere, at RT, the compound of the formula (2-12) 400 mg and dimethylaminopyridine 1.05 g were dissolved in a mixture of chloroform 4.8 ml and toluene 1.2 ml. The resulting solutions were stirred at RT under nitrogen atmosphere for 15 minutes. Thereafter, under nitrogen atmosphere, to the resulting solutions was added the compound of the formula (3-1) 1.0 g. Under nitrogen atmosphere, the resulting mixtures were stirred at 75° C. for 1 hour. The resulting reaction solutions were cooled to rt, adjusted to pH 1 with 2N hydrochloric acid and filtered through Celite™. The resulting filtrates were extracted with chloroform. The resulting chloroform layers were washed with water, dried over anhydrous sodium sulfate and filtered. The resulting filtrates were concentrated under reduced pressure to give yellow oils. The resulting oils were subjected to a silica gel column chromatography (eluates, ethyl acetate hexane=1:3) to give the compound of the formula (1-17) 380 mg.

$^1$H NMR (CDCl$_3$)

δ ppm: 7.32-7.27 (2H, m), 6.97-6.89 (5H, m), 5.68 (1H, s), 4.11-4.06 (2H, m), 2.78-2.69 (2H, m), 2.60-2.25 (10H, m), 1.97 (2H, ddd), 1.11-1.05 (6H, m)

Preparation Example 1-18

Preparation of the Compound of the Formula (1-18)

<Preparation of the Compound of the Formula 7-13>

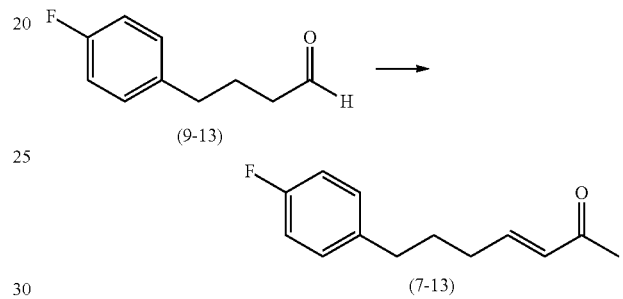

At RT, the compound of the formula (9-13) 3.5 g and triphenylphosphine acetylmethylene 7.5 g were dissolved in chloroform 30 ml. The resulting solutions were stirred at 0° C. for 8 hours. Thereafter, under reduced pressure, chloroform was removed from the resulting reaction solutions. To the resulting residues were added tert-butyl methyl ether and hexane. The resulting mixtures were filtered and the resulting filtrates were concentrated under reduced pressure. The resulting oils were subjected to a silica gel column chromatography (eluates, ethyl acetate:hexane=1:4) to give the compound of the formula (7-13) 1.1 g.

$^1$H NMR (CDCl$_3$)

δ ppm: 7.14-7.09 (2H, m), 6.99-6.93 (2H, m), 6.79 (1H, dt), 6.08 (1H, dt), 2.62 (2H, t), 2.27-2.20 (5H, m), 1.82-1.74 (2H, m)

<Preparation of the Compound of the Formula 2-13>

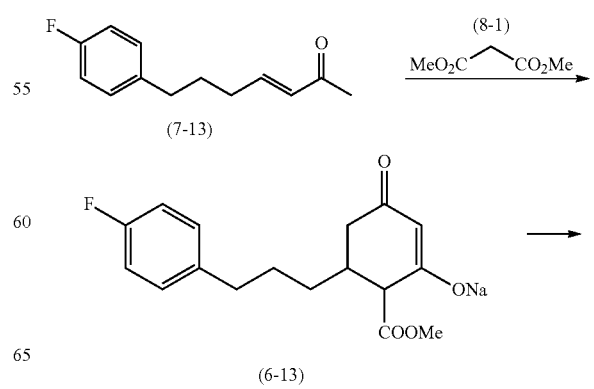

-continued

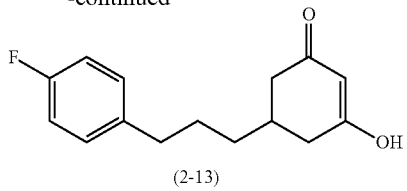

(2-13)

At RT, 28% sodium methoxide methanol solution 1.1 g and the compound of the formula (8-1) 0.8 g were dissolved in tetrahydrofuran 20 ml. The resulting solutions were heated under reflux for 15 minutes. Thereafter, the heating was stopped and to the resulting reaction mixtures was added the compound of the formula (7-13) 1.1 g. Thereafter, the resulting mixture solutions were heated under reflux for 30 minutes. The resulting reaction solutions were cooled to rt and the precipitated crystals were collected by filtering and washed with tert-butyl methyl ether and hexane sequentially to give the compound of the formula (6-13) 1.0 g.

Continuously, at RT, the compound of the formula (6-13) 1.0 g was dissolved in water 20 ml. To the resulting solutions was added anhydrous sodium carbonate 1.0 g. The resulting solutions were heated under reflux for 5 hours. The reaction solutions were cooled to rt and washed with tert-butyl methyl ether to remove impurities and then the aqueous layers were acidified with 2N hydrochloric acid and extracted with ethyl acetate. The ethyl acetate layers were concentrated under reduced pressure and the resulting crystals were washed with tert-butyl methyl ether and hexane sequentially to give the compound of the formula (2-13) 650 mg.

$^1$H NMR (d-DMSO)

δ ppm: 10.99 (1H, s), 7.25-7.21 (2H, m), 7.11-7.05 (2H, m), 5.18 (1H, s), 2.55 (2H, t), 2.43-1.91 (5H, m), 1.61-1.53 (2H, m), 1.35-1.32 (2H, m)

<Preparation of the Compound of the Formula 1-18>

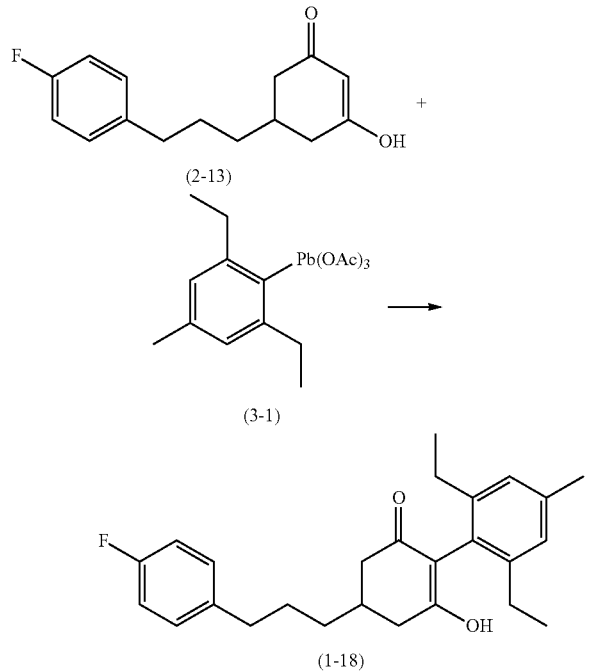

Under nitrogen atmosphere, at RT, the compound of the formula (2-13) 430 mg and dimethylaminopyridine 1.05 g were dissolved in a mixture of chloroform 4.8 ml and toluene 1.2 ml. The resulting solutions were stirred at RT under nitrogen atmosphere for 15 minutes. Thereafter, under nitrogen atmosphere, to the resulting solutions was added the compound of the formula (3-1) 1.0 g. Under nitrogen atmosphere, the resulting mixtures were stirred at 75° C. for 1 hour. The resulting reaction solutions were cooled to rt, adjusted to pH 1 with 2N hydrochloric acid and filtered through Celite™. The resulting filtrates were extracted with chloroform. The resulting chloroform layers were washed with water, dried over anhydrous sodium sulfate and filtered. The resulting filtrates were concentrated under reduced pressure to give yellow oils. The resulting oils were subjected to a silica gel column chromatography (eluates, ethyl acetate hexane=1:4) to give the compound of the formula (1-18) 440 mg.

$^1$H NMR (CDCl$_3$)

δ ppm: 7.15-7.11 (2H, m), 6.99-6.93 (4H, m), 5.60 (1H, s), 2.67-2.61 (4H, m), 2.40-2.19 (10H, m), 1.74-1.66 (2H, m), 1.52-1.46 (2H, m), 1.08-1.00 (6H, m)

Preparation Example 1-19

Preparation of the Compound of the Formula (1-69)

<Preparation of the Compound of the Formula 7-14>

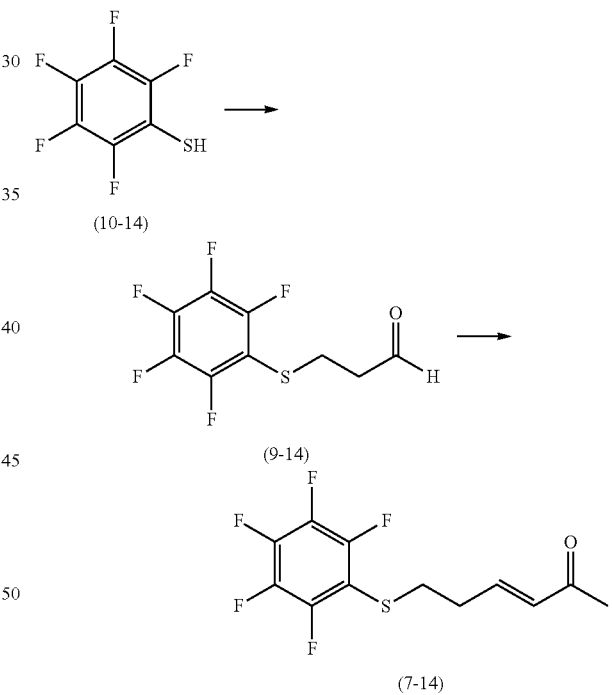

At RT, the compound of the formula (10-14) 9.0 g and tetrahydrofuran 30 ml were mixed and stirred, and the resulting mixtures were cooled to 0° C. and then thereto were added dropwise 95% acrolein 3.6 g and triethylamine 0.1 g. The resulting mixtures were stirred under ice-cooling for 1.5 hours. Thereafter, the resulting mixtures were added to water. The resulting mixtures were extracted with tert-butyl methyl ether. The organic layers were washed with water, dried over anhydrous sodium sulfate and concentrated under reduced pressure to give the compound of the formula (9-14) 11 g.

Continuously, at RT, the compound of the formula (9-14) 11 g and triphenylphosphine acetylmethylene 15.8 g were dissolved in chloroform 50 ml. The resulting solutions were stirred at 0° C. for 8 hours. Thereafter, under reduced pressure, chloroform was removed from the resulting reaction solutions. To the resulting residues were added tert-butyl methyl ether and hexane. The resulting mixtures were filtered and the resulting filtrates were concentrated under reduced pressure. The resulting oils were subjected to a silica gel column chromatography (eluates, ethyl acetate:hexane=1:5) to give the compound of the formula (7-14) 2.65 g.

¹H NMR (CDCl₃)

δ ppm: 6.79-6.71 (1H, m), 6.11 (1H, dt), 3.02 (2H, td), 2.51 (2H, dt), 2.25 (3H, dd)

<Preparation of the Compound of the Formula 6-14>

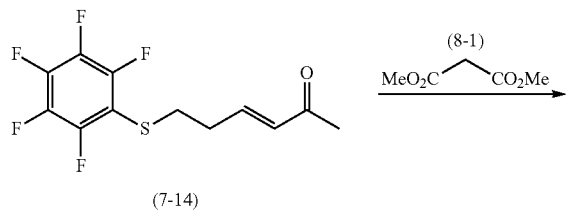
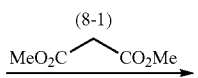

(7-14)

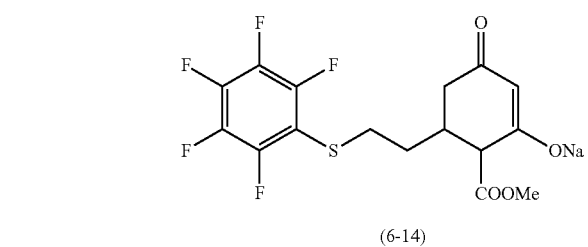

(6-14)

At RT, 28% sodium methoxide methanol solution 1.9 g and the compound of the formula (8-1) 1.3 g were dissolved in tetrahydrofuran 35 ml. The resulting solutions were heated under reflux for 15 minutes. Thereafter, the heating was stopped and to the resulting reaction mixtures was added the compound of the formula (7-14) 2.65 g. Thereafter, the resulting mixture solutions were heated under reflux for 30 minutes. The resulting reaction solutions were cooled to rt and the precipitated crystals were collected by filtering and washed with tert-butyl methyl ether and hexane sequentially to give the compound of the formula (6-14) 1.1 g.

¹H NMR (d-DMSO)

δ ppm: 4.39 (1H, s), 3.49 (3H, s), 2.99-2.92 (1H, m), 2.86-2.76 (2H, m), 2.28-2.19 (1H, m), 2.05-1.99 (1H, m), 1.76-1.65 (1H, m), 1.44-1.33 (2H, m)

<Preparation of the Compound of the Formula 1-69>

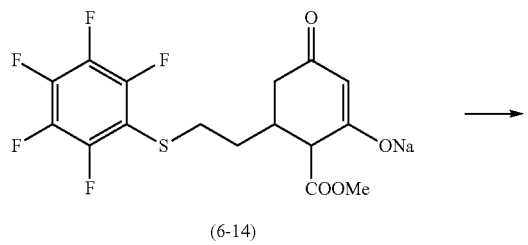

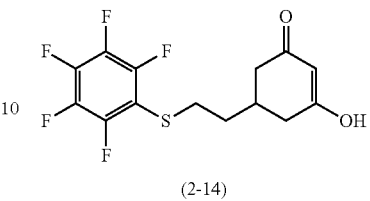
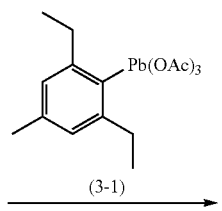

(2-14)

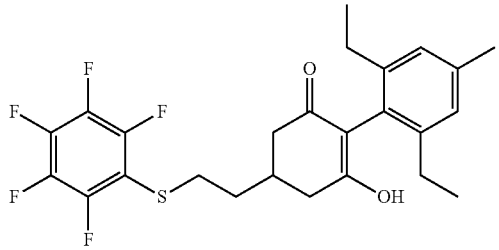

(1-69)

At RT, the compound of the formula (6-14) 1.1 g was dissolved in water 20 ml. To the resulting solutions was added anhydrous sodium carbonate 840 mg. The resulting solutions were heated under reflux for 5 hours. The reaction solutions were cooled to rt, washed with tert-butyl methyl ether to remove impurities and then acidified with 2N hydrochloric acid and extracted with ethyl acetate. The ethyl acetate layers were concentrated under reduced pressure and the resulting crystals were washed with tert-butyl methyl ether and hexane sequentially to give the compound of the formula (2-14) 800 mg.

Continuously, under nitrogen atmosphere, at RT, the compound of the formula (2-14) 580 mg and dimethylaminopyridine 1.05 g were dissolved in a mixture of chloroform 4.8 ml and toluene 1.2 ml. The resulting solutions were stirred at RT under nitrogen atmosphere for 15 minutes. Thereafter, under nitrogen atmosphere, to the resulting solutions was added the compound of the formula (3-1) 1.0 g. Under nitrogen atmosphere, the resulting mixtures were stirred at 75° C. for 1 hour. The resulting reaction solutions were cooled to rt, adjusted to pH 1 with 2N hydrochloric acid and filtered through Celite™. The resulting filtrates were extracted with chloroform. The resulting chloroform layers were washed with water, dried over anhydrous sodium sulfate and filtered. The resulting filtrates were concentrated under reduced pressure to give yellow oils. The resulting oils were subjected to a silica gel column chromatography (eluates, ethyl acetate:hexane=1:4) to give the compound of the formula (1-69) 150 mg.

¹H NMR (CDCl₃)

δ ppm: 6.99 (2H, s), 5.56 (1H, s), 3.00-2.95 (2H, m), 2.71-2.62 (2H, m), 2.47-2.22 (10H, m), 1.75 (2H, dd), 1.10-1.04 (6H, m)

Preparation Example 1-20

Preparation of the Compound of the Formula (1-31)

<Preparation of the Compound of the Formula 9-15>

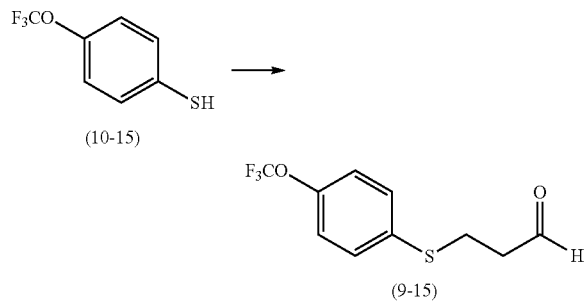

At RT, the compound of the formula (10-15) 3.3 g and tetrahydrofuran 15 ml were mixed and stirred and the resulting mixtures were cooled to 0° C. and then thereto were added dropwise 95% acrolein 1.4 g and triethylamine 0.1 g. The resulting mixtures were stirred under ice-cooling for 1.5 hours. Thereafter, the resulting mixtures were added to water. The resulting mixtures were extracted with tert-butyl methyl ether. The organic layers were washed with water, dried over anhydrous sodium sulfate and concentrated under reduced pressure to give the compound of the formula (9-15) 4.2 g.

$^1$H NMR (CDCl$_3$)

δ ppm: 9.76 (1H, s), 7.52 (2H, d), 7.37 (2H, d), 3.21-3.16 (2H, m), 2.80-2.76 (2H, m)

<Preparation of the Compound of the Formula 7-15>

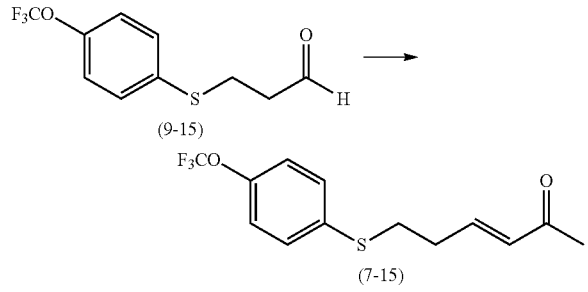

At RT, the compound of the formula (9-15) 4.2 g and triphenylphosphine acetylmethylene 6.0 g were dissolved in chloroform 20 ml. The resulting solutions were stirred at 0° C. for 8 hours. Thereafter, under reduced pressure, chloroform was removed from the resulting reaction solutions. To the resulting residues were added tert-butyl methyl ether and hexane. The resulting mixtures were filtered and the resulting filtrates were concentrated under reduced pressure. The resulting oils were subjected to a silica gel column chromatography (eluates, ethyl acetate:hexane=1:4) to give the compound of the formula (7-15) 2.7 g.

$^1$H NMR (CDCl$_3$)

δ ppm: 7.37 (2H, d), 7.16 (2H, d), 6.77 (1H, dt), 6.09 (1H, d), 3.04 (2H, t), 2.58-2.52 (2H, m), 2.23 (3H, s)

<Preparation of the Compound of the Formula 6-15>

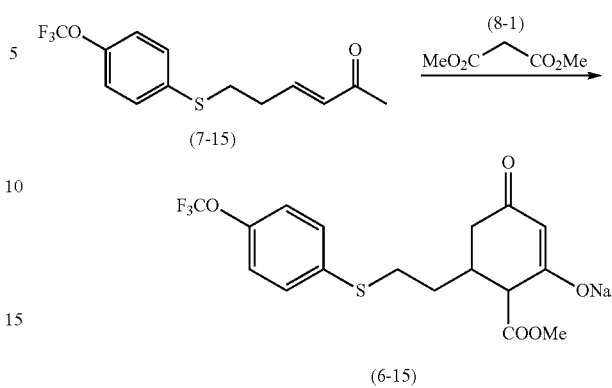

At RT, 28% sodium methoxide methanol solution 2 g and the compound of the formula (8-1) 1.4 g were dissolved in tetrahydrofuran 40 ml. The resulting solutions were heated under reflux for 15 minutes. Thereafter, the heating was stopped and to the resulting reaction mixtures was added the compound of the formula (7-15) 2.7 g. Thereafter, the resulting mixture solutions were heated under reflux for 30 minutes. The resulting reaction solutions were cooled to rt, and the precipitated crystals were collected by filtering and washed with tert-butyl methyl ether and hexane sequentially to give the compound of the formula (6-15) 1.8 g.

$^1$H NMR (d-DMSO)

δ ppm: 7.39 (2H, d), 7.31 (2H, d), 4.40 (1H, s), 3.47 (3H, s), 3.07-3.01 (1H, m), 2.92-2.80 (2H, m), 2.34-2.24 (1H, m), 2.09 (1H, dd), 1.75 (1H, dd), 1.51-1.40 (2H, m)

<Preparation of the Compound of the Formula 1-31>

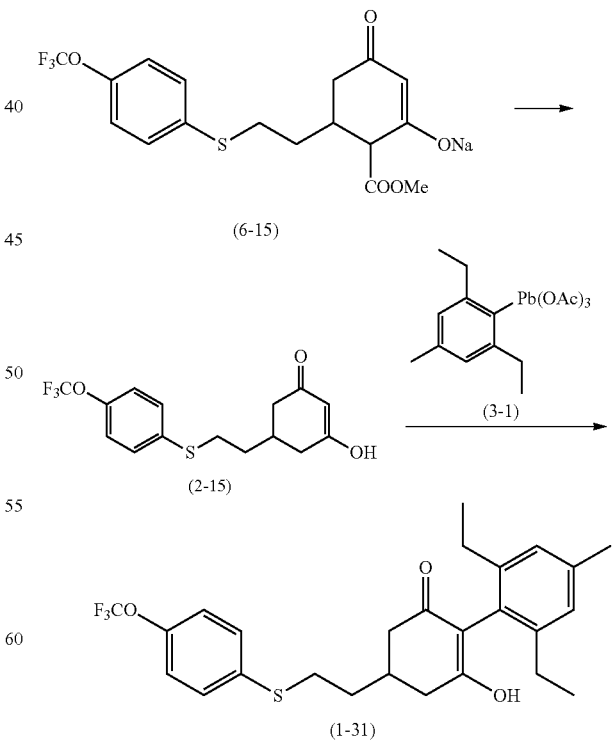

At RT, the compound of the formula (6-15) 1.8 g was dissolved in water 35 ml. To the resulting solutions was added anhydrous sodium carbonate 1.4 g. The resulting solutions were heated under reflux for 5 hours. The reaction solutions were cooled to rt, washed with tert-butyl methyl ether to remove impurities and then acidified with 2N hydrochloric acid and extracted with ethyl acetate. The ethyl acetate layers were concentrated under reduced pressure and the resulting crystals were washed with tert-butyl methyl ether and hexane sequentially to give the compound of the formula (2-15) 1.6 g.

Continuously, under nitrogen atmosphere, at RT, the compound of the formula (2-15) 570 mg and dimethylaminopyridine 1.05 g were dissolved in a mixture of chloroform 4.8 ml and toluene 1.2 ml. The resulting solutions were stirred at RT under nitrogen atmosphere for 15 minutes. Thereafter, under nitrogen atmosphere, to the resulting solution was added the compound of the formula (3-1) 1.0 g. Under nitrogen atmosphere, the resulting mixtures were stirred at 75° C. for 1 hour. The resulting reaction solutions were cooled to rt, adjusted to pH 1 with 2N hydrochloric acid and filtered through Celite™. The resulting filtrates were extracted with chloroform. The resulting chloroform layers were washed with water, dried over anhydrous sodium sulfate and filtered. The resulting filtrates were concentrated under reduced pressure to give oils. The resulting oils were subjected to a silica gel column chromatography (eluates, ethyl acetate:hexane=1:4) to give the compound of the formula (1-31) 290 mg.

$^1$H NMR (CDCl$_3$)

δ ppm: 7.36 (2H, d), 7.15 (2H, d), 6.98 (2H, s), 5.59 (1H, s), 3.00 (2H, ddd), 2.71-2.65 (2H, m), 2.48-2.22 (10H, m), 1.83 (2H, q), 1.10-1.03 (6H, m)

Preparation Example 1-21

Preparation of the Compound of the Formula (1-73)

<Preparation of the Compound of the Formula 7-16>

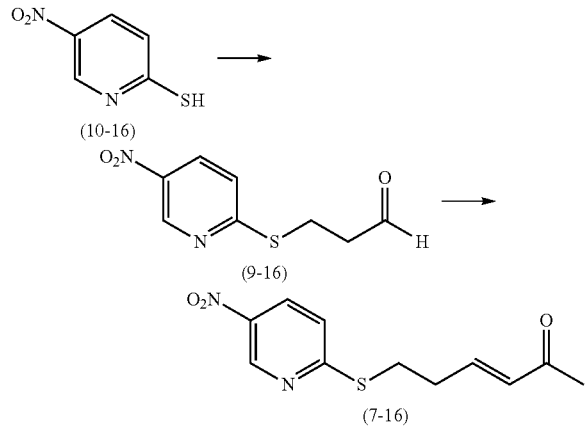

At RT, the compound of the formula (10-16) 5.0 g and tetrahydrofuran 30 ml were mixed and stirred, and the resulting mixtures were cooled to 0° C. and then thereto were added dropwise 95% acrolein 2.8 g and triethylamine 0.1 g. The resulting mixtures were stirred under ice-cooling for 1.5 hours. Thereafter, the resulting mixtures were added to water. The resulting mixtures were extracted with tert-butyl methyl ether. The organic layers were washed with water, dried over anhydrous sodium sulfate and concentrated under reduced pressure to give the compound of the formula (9-16) 6.7 g.

Continuously, at RT, the compound of the formula (9-16) 6.7 g and triphenylphosphine acetylmethylene 11.2 g were dissolved in chloroform 40 ml. The resulting solutions were stirred at 0° C. for 8 hours. Thereafter, under reduced pressure, chloroform was removed from the resulting reaction solutions. To the resulting residues were added tert-butyl methyl ether and hexane. The resulting mixtures were filtered and the resulting filtrates were concentrated under reduced pressure. The resulting oils were subjected to a silica gel column chromatography (eluates, ethyl acetate:hexane=1:3) to give the compound of the formula (7-16) 5.0 g.

$^1$H NMR (CDCl$_3$)

δ ppm: 9.23 (1H, d), 8.25-8.21 (1H, m), 7.32-7.28 (1H, m), 6.83 (1H, dt), 6.16 (1H, d), 3.41 (2H, t), 2.72-2.67 (2H, m), 2.24 (3H, s)

<Preparation of the Compound of the Formula 6-14>

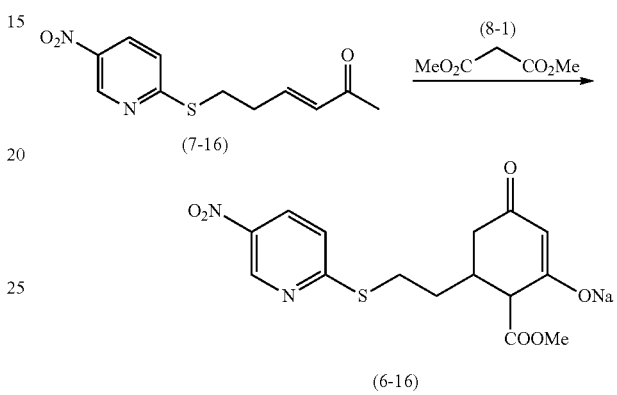

At RT, 28% sodium methoxide methanol solution 4.2 g and the compound of the formula (8-1) 2.9 g were dissolved in tetrahydrofuran 80 ml. The resulting solutions were heated under reflux for 15 minutes. Thereafter, the heating was stopped and to the resulting reaction mixture was added the compound of the formula (7-16) 5.0 g. Thereafter, the resulting mixture solutions were heated under reflux for 30 minutes. The resulting reaction solutions were cooled to rt, and the precipitated crystals were collected by filtering and washed with tert-butyl methyl ether and hexane sequentially to give the compound of the formula (6-16) 4.9 g.

$^1$H NMR (d-DMSO)

δ ppm: 9.21 (1H, d), 8.36 (1H, dd), 7.54 (1H, dd), 4.38 (1H, s), 3.52 (3H, s), 3.34-2.82 (3H, m), 2.33-2.24 (1H, m), 2.16-2.11 (1H, m), 1.83-1.74 (1H, m), 1.61-1.53 (2H, m)

<Preparation of the Compound of the Formula 1-73>

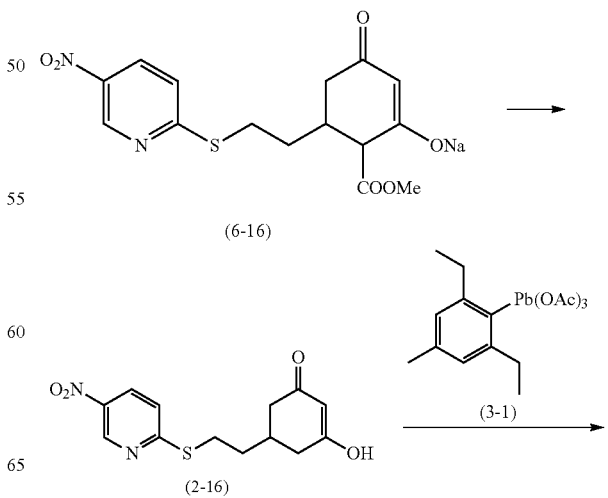

-continued

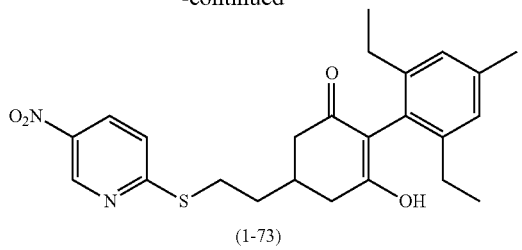

(1-73)

At RT, the compound of the formula (6-16) 3.0 g was dissolved in water 65 ml. To the resulting solutions was added anhydrous sodium carbonate 2.7 g. The resulting solutions were heated under reflux for 5 hours. The reaction solutions were cooled to rt and washed with tert-butyl methyl ether to remove impurities, and then the aqueous layers were acidified with 2N hydrochloric acid and extracted with ethyl acetate. The ethyl acetate layers were concentrated under reduced pressure and the resulting crystals were washed with tert-butyl methyl ether and hexane sequentially to give the compound of the formula (2-16) 1.1 g.

Continuously, under nitrogen atmosphere, at RT, the compound of the formula (2-16) 500 mg and dimethylaminopyridine 1.05 g were dissolved in a mixture of chloroform 4.8 ml and toluene 1.2 ml. The resulting solutions were stirred at RT under nitrogen atmosphere for 15 minutes. Thereafter, under nitrogen atmosphere, to the resulting solutions was added the compound of the formula (3-1) 1.0 g. Under nitrogen atmosphere, the resulting mixtures were stirred at 75° C. for 1 hour. The resulting reaction solutions were cooled to rt, adjusted to pH 1 with 2N hydrochloric acid and filtered through Celite™. The resulting filtrates were extracted with chloroform. The resulting chloroform layers were washed with water, dried over anhydrous sodium sulfate and filtered. The resulting filtrates were concentrated under reduced pressure to give oils. The resulting oils were subjected to a silica gel column chromatography (eluates, ethyl acetate:hexane=2:3) to give the compound of the formula (1-73) 50 mg.

$^1$H NMR (CDCl$_3$)

δ ppm: 9.25 (1H, d), 8.23 (1H, dt), 7.30 (1H, d), 6.98 (2H, s), 5.58 (1H, s), 3.36 (2H, t), 2.80-2.71 (2H, m), 2.52-2.25 (10H, m), 1.96-1.90 (2H, m), 1.09-1.03 (6H, m)

Preparation Example 1-22

Preparation of the Compound of the Formula (1-74)

<Preparation of the Compound of the Formula 7-17>

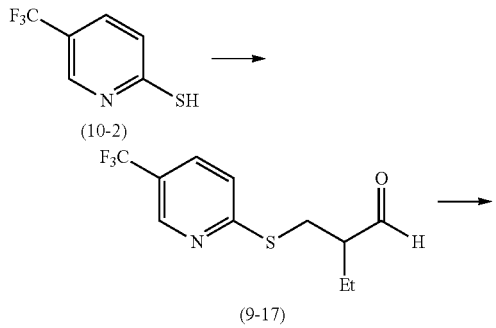

-continued

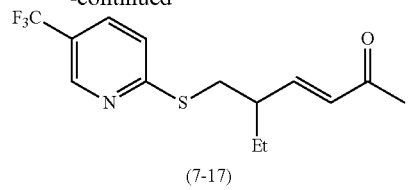

(7-17)

At RT, the compound of the formula (10-2) 3.0 g and tetrahydrofuran 15 ml were mixed and stirred, and the resulting mixtures were cooled to 0° C. and then thereto were added dropwise 2-ethylacrolein 1.85 g and triethylamine 0.1 g. The resulting mixtures were stirred under ice-cooling for 1.5 hours. Thereafter, the resulting mixtures were added to water. The resulting mixtures were extracted with tert-butyl methyl ether. The organic layers were washed with water, dried over anhydrous sodium sulfate and concentrated under reduced pressure to give the compound of the formula (9-17) 4.3 g.

Continuously, at RT, the compound of the formula (9-17) 4.3 g and triphenylphosphine acetylmethylene 5.8 g were dissolved in chloroform 20 ml. The resulting solutions were stirred at 0° C. for 8 hours. Thereafter, under reduced pressure, chloroform was removed from the resulting reaction solutions. To the resulting residues were added tert-butyl methyl ether and hexane. The resulting mixtures were filtered and the resulting filtrates were concentrated under reduced pressure. The resulting oils were subjected to a silica gel column chromatography (eluates, ethyl acetate:hexane=1:4) to give the compound of the formula (7-17) 1.1 g.

$^1$H NMR (CDCl$_3$)

δ ppm: 8.66 (1H, s), 7.67-7.64 (1H, m), 7.28-7.24 (1H, m), 6.66-6.59 (1H, m), 6.10 (1H, dd), 3.45-3.24 (2H, m), 2.53-2.47 (1H, m), 2.20 (3H, s), 1.79-1.46 (2H, m), 0.96-0.92 (3H, m)

<Preparation of the Compound of the Formula 1-74>

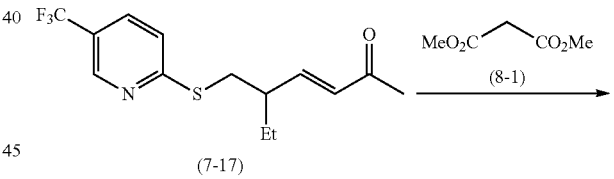

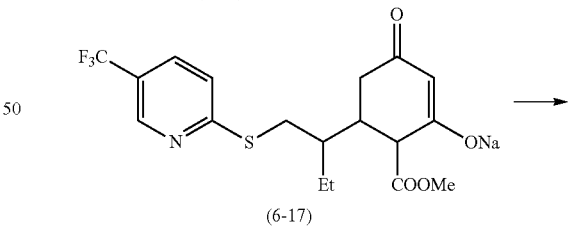

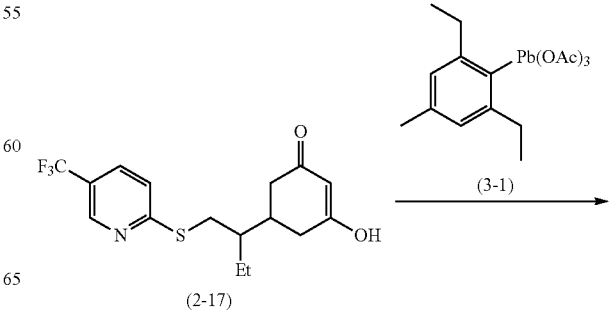

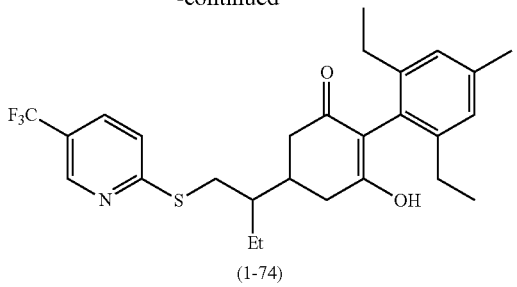

(1-74)

At RT, 28% sodium methoxide methanol solution 810 mg and the compound of the formula (8-1) 560 mg were dissolved in tetrahydrofuran 15 ml. The resulting solutions were heated under reflux for 15 minutes. Thereafter, the heating was stopped and to the resulting reaction mixtures was added the compound of the formula (7-17) 1.1 g. Thereafter, the resulting mixture solutions were heated under reflux for 30 minutes. The resulting reaction solutions were cooled to rt, and the precipitated crystals were collected by filtering and washed with tert-butyl methyl ether and hexane sequentially to give the compound of the formula (6-17) 1.6 g.

Continuously, at RT, the compound of the formula (6-17) 1.6 g was dissolved in water (30 ml). To the resulting solutions was added anhydrous sodium carbonate 1.2 g. The resulting solutions were heated under reflux for 5 hours. The reaction solutions were cooled to rt, washed with tert-butyl methyl ether to remove impurities and then acidified with 2N hydrochloric acid and extracted with ethyl acetate. The ethyl acetate layers were concentrated under reduced pressure and the resulting crystals were washed with tert-butyl methyl ether and hexane sequentially to give the compound of the formula (2-17) 1.2 g.

Continuously, under nitrogen atmosphere, at RT, the compound of the formula (2-17) 600 mg and dimethylaminopyridine 1.05 g were dissolved in a mixture of chloroform 4.8 ml and toluene 1.2 ml. The resulting solutions were stirred at RT under nitrogen atmosphere for 15 minutes. Thereafter, under nitrogen atmosphere, to the resulting solutions was added the compound of the formula (3-1) 1.0 g. Under nitrogen atmosphere, the resulting mixtures were stirred at 75° C. for 1 hour. The resulting reaction solutions were cooled to rt, adjusted to pH 1 with 2N hydrochloric acid and filtered through Celite™. The resulting filtrates were extracted with chloroform. The resulting chloroform layers were washed with water, dried over anhydrous sodium sulfate and filtered. The resulting filtrates were concentrated under reduced pressure to give oils. The resulting oils were subjected to a silica gel column chromatography (eluates, ethyl acetate:hexane=1:5) to give the compound of the formula (1-74) 200 mg.

$^1$H NMR (CDCl$_3$)

δ ppm: 8.67 (1H, s), 7.66 (1H, dd), 7.27 (1H, d), 6.98 (2H, s), 5.52 (1H, s), 3.57-3.46 (1H, m), 3.31-3.17 (1H, m), 2.71-2.58 (3H, m), 2.44-2.25 (10H, m), 1.75-1.62 (2H, m), 1.08-1.00 (9H, m)

Preparation Example 1-23

Preparation of the Compound of the Formula (1-21)

<Preparation of the Compound of the Formula 12-1>

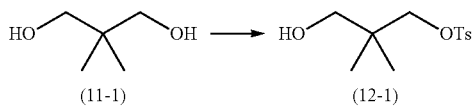

At RT, the compound of the formula (1-11) 31 g, pyridine 17 ml and methylene chloride 100 ml were mixed and stirred, and the resulting mixtures were cooled to 0° C. and then added dropwise to mixture solutions that were prepared by dissolving para-toluenesulphonylchloride 11.4 g into methylenechloride 60 ml. The resulting mixture solutions were stirred at 0° C. under ice-cooling for three hours. The resulting reaction mixture solutions were diluted with ethyl acetate and washed with a saturated sodium hydrogen carbonate aqueous solution. The resulting ethyl acetate layers were washed with saturated saline, dried over anhydrous sodium sulfate and then filtered. The resulting filtrates were concentrated under reduced pressure to give oils. The resulting oils were subjected to a silica gel column chromatography (eluates, ethyl acetate:hexane=3:2) to give the compound of the formula (12-1) (colorless oils) 16 g.

$^1$H NMR (CDCl$_3$)

δ ppm: 7.80-7.78 (2H, m), 7.34-7.30 (2H, m), 3.82 (2H, s), 3.37 (2H, s), 2.45 (3H, s), 0.88 (6H, s)

<Preparation of the Compound of the Formula 13-1>

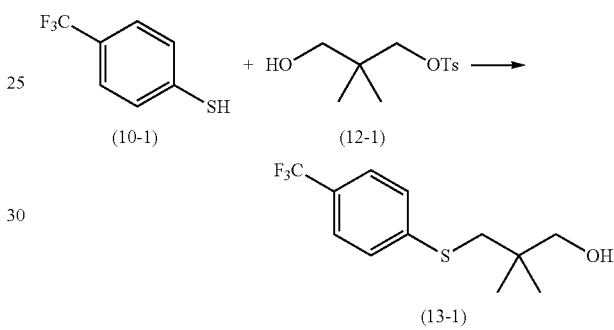

Under nitrogen atmosphere, to 60% sodium hydrate 1.55 g was added anhydrous N,N-dimethylformamide 30 ml. To the resulting mixtures was added dropwise the compound of the formula (10-1) 7.2 g under ice-cooling. The resulting mixtures were stirred under ice-cooling for 25 minutes and then thereto was added dropwise a solution of the compound of the formula (12-1) 8 g in anhydrous DMF 15 ml and the resulting mixtures were stirred at RT for 1 hour, then heated so as to increase the reaction temperature to 90° C. and stirred for 8 hours. The resulting reaction mixtures were extracted with t-butylmethylether. The organic layers were combined, washed with water, dried over anhydrous sodium sulfate and concentrated under reduced pressure to give crude products. The crude products were subjected to a silica gel column chromatography (eluates, ethyl acetate:hexane=1:4→2:3) to give the compound of the formula (13-1) (oils) 7.6 g.

$^1$H NMR (CDCl$_3$)

δ ppm: 7.48 (2H, d), 7.39 (2H, d), 3.45 (2H, s), 3.02 (2H, s), 2.03 (1H, s), 1.01 (6H, s)

<Preparation of the Compound of the Formula 9-18>

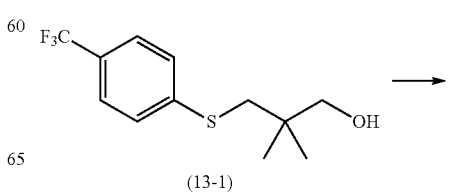

-continued

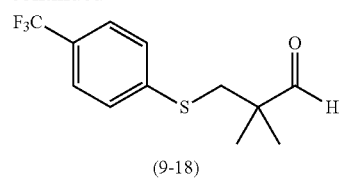

(9-18)

Under nitrogen atmosphere, a mixture solution of oxalyl chloride 3.4 ml and methylene chloride 120 ml was cooled to −78° C. and then thereto was added dropwise dimethyl sulfoxide 5.7 ml slowly and the resulting mixtures were stirred for 10 minutes. Thereafter, to the resulting mixture solutions was added dropwise a solution of the compound of the formula (13-1) 7.6 g in methylene chloride 50 ml and the resulting mixtures were stirred for 30 minutes. Thereafter, to the resulting mixture solutions was added triethylamine 11.6 g and the resulting mixtures were stirred at −78° C. for 1 hour and then at 0° C. under ice-cooling for another 6 hours. The resulting reactions were diluted with chloroform and washed with 1N aqueous sodium hydroxide solution. The resulting chloroform layers were washed with saturated saline, dried over anhydrous sodium sulfate and then filtered. The resulting filtrates were concentrated under reduced pressure to give the compound of the formula (9-18) (oils) 6.7 g.

$^1$H NMR (CDCl$_3$)

δ ppm: 9.50 (1H, s), 7.51 (2H, d), 7.40 (2H, d), 3.16 (2H, s), 1.24 (6H, s)

<Preparation of the Compound of the Formula 7-18>

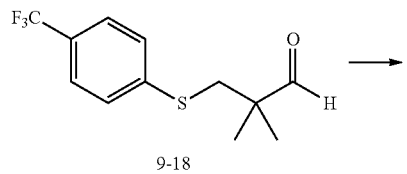

9-18

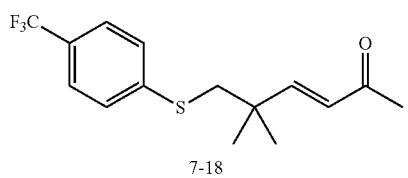

7-18

At RT, the compound of the formula (9-18) 4.2 g and triphenylphosphine acetylmethylene 5.6 g were dissolved in xylene 20 ml. The resulting solutions were heated under reflux for 8 hours. Thereafter, under reduced pressure, xylene was removed from the resulting reaction solutions. To the resulting residues were added tert-butyl methyl ether and hexane. The resulting mixtures were filtered and the resulting filtrates were concentrated under reduced pressure. The resulting oils were subjected to a silica gel column chromatography (eluates, ethyl acetate:hexane=1:4) to give the compound of the formula (7-18) 4.1 g.

$^1$H NMR (CDCl$_3$)

δ ppm: 7.50 (2H, d), 7.38 (2H, d), 6.73 (1H, dd), 6.05 (1H, dd), 3.06 (2H, s), 2.17 (3H, s), 1.23 (6H, s)

<Preparation of the Compound of the Formula 1-21>

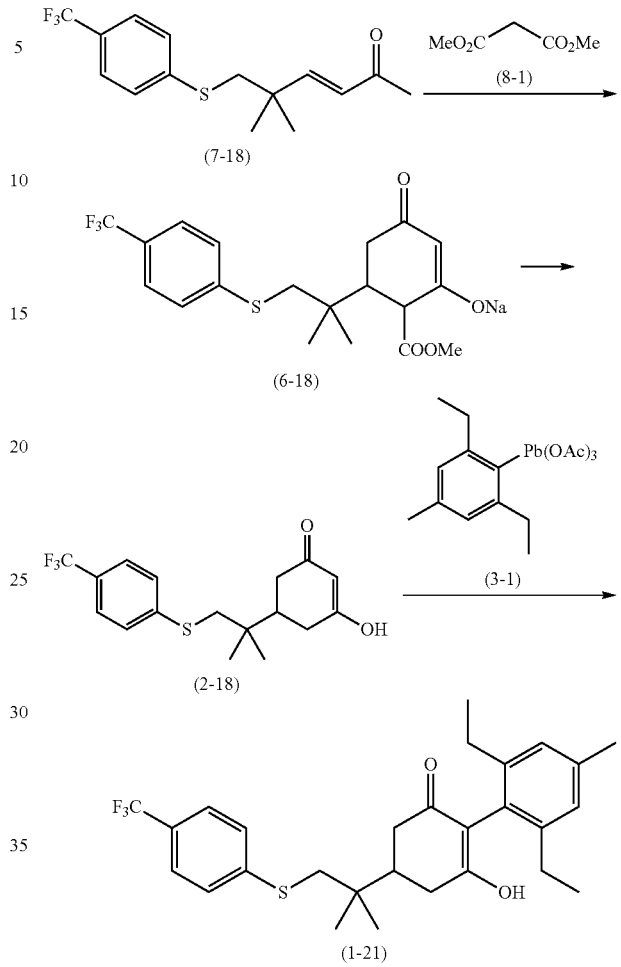

At RT, 28% sodium methoxide methanol solution 2.9 g and the compound of the formula (8-1) 2.0 g were dissolved in 1,4-dioxane 35 ml. The resulting solutions were heated under reflux for 15 minutes. Thereafter, the heating was stopped and to the resulting reaction mixtures was added the compound of the formula (7-18) 4.1 g. Thereafter, the resulting mixture solutions were heated under reflux for 1 hour. The resulting reaction solutions were cooled to rt and concentrated under reduced pressure and the crude crystals precipitated were washed with tert-butyl methyl ether and hexane sequentially to give the compound of the formula (6-18) 5.7 g.

Continuously, at RT, the compound of the formula (6-18) 5.7 g was dissolved in water 25 ml. To the resulting solutions was added anhydrous sodium carbonate 1.05 g. The resulting solutions were heated under reflux for 5 hours. The reaction solutions were cooled to rt and washed with tert-butyl methyl ether to remove impurities and then the aqueous layers were acidified with 2N hydrochloric acid and extracted with ethyl acetate. The ethyl acetate layers were concentrated under reduced pressure and the resulting crystals were washed with tert-butyl methyl ether and hexane sequentially to give the compound of the formula (2-18) 970 mg.

Continuously, under nitrogen atmosphere, at RT, the compound of the formula (2-18) 970 mg and dimethylaminopyridine 1.7 g were dissolved in a mixture of chloroform 7.5 ml and toluene 2 ml. The resulting solutions were stirred at RT under nitrogen atmosphere for 15 minutes. Thereafter, under nitrogen atmosphere, to the resulting solution was added the compound of the formula (3-1) 1.5 g. Under nitrogen atmosphere, the resulting mixtures were stirred at 75° C. for 1 hour. The resulting reaction solutions were cooled to rt, adjusted to pH 1 with 2N hydrochloric acid and filtered through Celite™. The resulting filtrates were extracted with chloroform. The resulting chloroform layers were washed with water, and dried over anhydrous sodium sulfate and filtered. The resulting filtrates were concentrated under reduced pressure to give oils. The resulting oils were subjected to a silica gel column chromatography (eluates, ethyl acetate:hexane=1:4) to give the compound of the formula (1-21) (white solids) 300 mg.

$^1$H NMR (CDCl$_3$)

δ ppm: 7.52 (2H, d), 7.41 (2H, d), 6.99 (2H, s), 5.54 (1H, s), 3.04 (2H, dd), 2.67-2.24 (12H, m), 1.13-1.06 (12H, m)

Preparation Example 1-24

Preparation of the Compound of the Formula (1-22)

<Preparation of the Compound of the Formula 13-2>

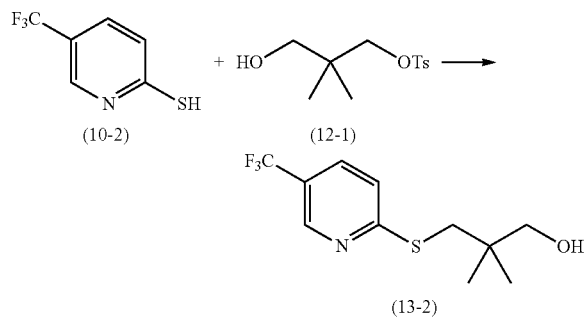

Under nitrogen atmosphere, to 60% sodium hydrate 1.55 g was added dropwise anhydrous N,N-dimethylformamide 30 ml. To the resulting mixtures was added dropwise the compound of the formula (10-2) 7.2 g under ice-cooling. The resulting mixtures were stirred under ice-cooling for 25 minutes, and then thereto was added dropwise a solution of the compound of the formula (12-1) 8 g in anhydrous N,N-dimethylformamide 15 ml, and the resulting mixtures were stirred at RT for 1 hour and then heated so as to increase the reaction temperature to 90° C. and stirred for 8 hours. The resulting reaction mixtures were extracted with tert-butyl methyl ether. The organic layers were combined, washed with water, dried over anhydrous sodium sulfate and then concentrated under reduced pressure to give crude products. The crude products were subjected to a silica gel column chromatography (eluates, ethyl acetate:hexane=1:3) to give the compound of the formula (13-2) 6.7 g.

$^1$H NMR (CDCl$_3$)

δ ppm: 8.61 (1H, s), 7.70-7.67 (1H, m), 7.36-7.32 (2H, m), 3.30 (2H, d), 3.23 (2H, d), 1.04 (6H, s)

<Preparation of the Compound of the Formula 9-19>

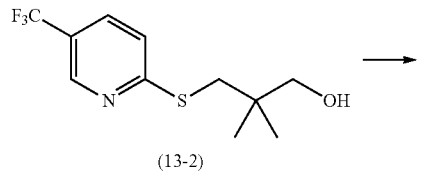

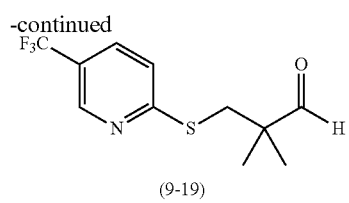

Under nitrogen atmosphere, a mixture of oxalyl chloride 3.1 ml and methylene chloride 120 ml was cooled to −78° C. and then thereto was added dropwise dimethyl sulfoxide 5.0 ml slowly and the resulting mixtures were stirred for 10 minutes. Thereafter, to the resulting mixture solutions was added triethylamine 10.3 g and the resulting mixtures were stirred at −78° C. for 1 hour and at 0° C. under ice-cooling for 6 hours. The resulting reaction solutions were diluted with chloroform and washed with 1N aqueous sodium hydroxide solution. The resulting chloroform layers were washed with saturated saline, dried over anhydrous sodium sulfate and then filtered. The resulting filtrates were concentrated under reduced pressure to give the compound of the formula (9-19) 6.2 g.

$^1$H NMR (CDCl$_3$)

δ ppm: 9.51 (1H, s), 8.64 (1H, s), 7.65 (1H, d), 7.27 (1H, d), 3.52 (2H, s), 1.24 (6H, s)

<Preparation of the Compound of the Formula 7-19>

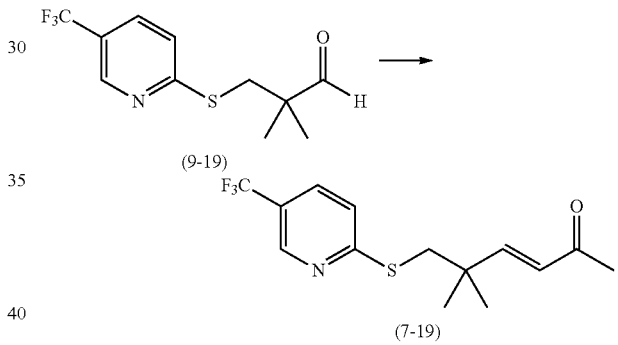

At RT, the compound of the formula (9-19) 4.6 g and triphenylphosphine acetylmethylene 6.2 g were dissolved in xylene 25 ml. The resulting solutions were heated under reflux for 8 hours. Thereafter, xylene was removed from the resulting reaction solutions under reduced pressure. To the resulting residues were added tert-butyl methyl ether and hexane. Continuously, the resulting mixtures were filtered and the resulting filtrates were concentrated under reduced pressure. The resulting oils were subjected to a silica gel column chromatography (eluates, ethyl acetate:hexane=1:4) to give the compound of the formula (7-19) 3.8 g.

$^1$H NMR (CDCl$_3$)

δ ppm: 8.64 (1H, s), 7.64 (1H, dd), 7.27 (1H, d), 6.04 (1H, d), 6.04 (1H, d), 3.43 (2H, s), 2.17 (3H, s), 1.22 (6H, s)

<Preparation of the Compound of the Formula 1-22>

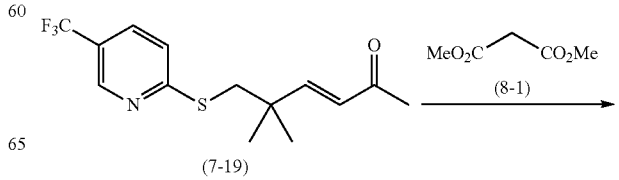

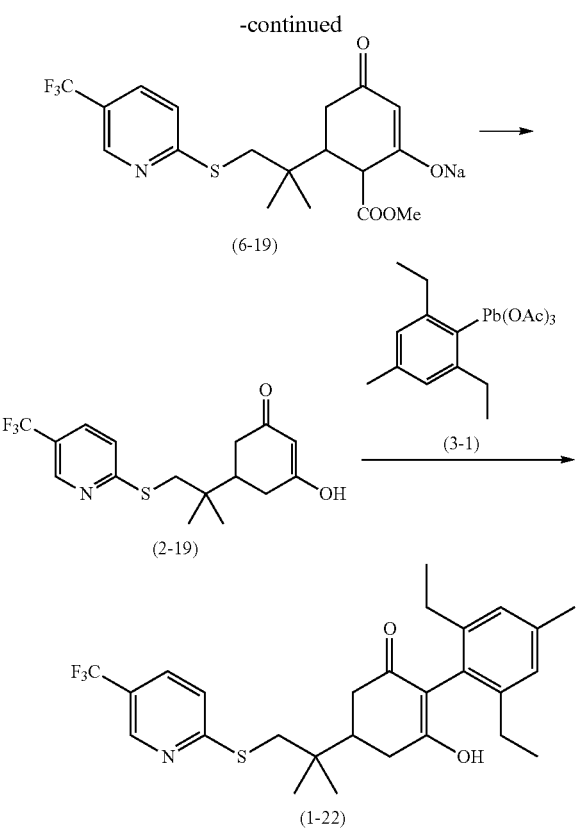

At RT, 28% sodium methoxide methanol solution 2.7 g and the compound of the formula (8-1) 1.8 g were dissolved in 1,4-dioxane 35 ml. The resulting solutions were heated under reflux for 15 minutes. Thereafter, the heating was stopped and to the resulting reaction mixtures was added the compound of the formula (7-19) 3.8 g. Thereafter, the resulting mixtures were heated under reflux for 1 hour. The resulting reaction solutions were cooled to rt and concentrated under reduced pressure and the crude crystals precipitated were washed with tert-butyl methyl ether and hexane sequentially to give the compound of the formula (6-19) 5.3 g.

Continuously, at RT, the compound of the formula (6-19) 5.3 g was dissolved in water 95 ml. To the resulting solutions was added anhydrous sodium carbonate 4.0 g. The resulting solutions were heated under reflux for 5 hours. The reaction solutions were cooled to rt and washed with tert-butyl methyl ether to remove impurities and then the aqueous layers were acidified with 2N hydrochloric acid and extracted with ethyl acetate. The ethyl acetate layers were concentrated under reduced pressure and the resulting crystals were washed with tert-butyl methyl ether and hexane sequentially to give the compound of the formula (2-19) 2.8 g.

Continuously, under nitrogen atmosphere, at RT, the compound of the formula (2-19) 600 mg and dimethylaminopyridine 1.05 g were dissolved in a mixture of chloroform 4.8 ml and toluene 1.2 ml. The resulting solutions were stirred at RT under nitrogen atmosphere for 15 minutes. Thereafter, under nitrogen atmosphere, to the resulting solutions was added the compound of the formula (3-1) 1.0 g. Under nitrogen atmosphere, the resulting mixtures were stirred at 75° C. for 1 hour. The resulting reaction solutions were cooled to rt, adjusted to pH 1 with 2N hydrochloric acid and filtered through Celite™. The resulting filtrates were extracted with chloroform. The resulting chloroform layers were washed with water, dried over anhydrous sodium sulfate and filtered. The resulting filtrates were concentrated under reduced pressure to give oils. The resulting oils were subjected to a silica gel column chromatography (eluates, ethyl acetate:hexane=1:5) to give the compound of the formula (1-22) (white solids) 290 mg.

$^1$H NMR (CDCl$_3$)

δ ppm: 8.65 (1H, s), 7.65 (1H, dd), 7.30 (1H, d), 6.98 (2H, s), 5.54 (1H, s), 3.41 (2H, dd), 2.78-2.51 (3H, m), 2.48-2.26 (9H, m), 1.18-1.00 (12H, m)

Preparation Example 1-25

Preparation of the Compound of the Formula (1-40)

<Preparation of the Compound of the Formula 3-3>

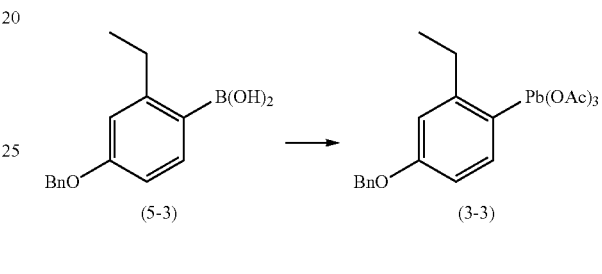

Under nitrogen atmosphere, at RT, lead tetraacetate 10 g, mercury acetate 310 mg and the compound of the formula (5-3) 5 g were dissolved in chloroform 40 ml. The resulting solutions were stirred at RT under nitrogen atmosphere for 15 minutes. Thereafter, under nitrogen atmosphere, the reaction solutions were stirred at 40° C. for 4 hours. The reaction solutions were cooled to rt and filtered through Celite™. The resulting filtrates were concentrated under reduced pressure to give red oils. To the resulting oils was added hexane and the resulting mixtures were concentrated under reduced pressure to give the compound of the formula (3-3) (red solids) 10.2 g.

$^1$H NMR (CDCl$_3$)

δ ppm: 7.61-7.59 (1H, m), 7.41-7.34 (5H, m), 7.00-6.97 (2H, m), 5.08 (2H, s), 2.83 (2H, q), 2.09 (9H, s), 1.29 (3H, t)

<Preparation of the Compound of the Formula 34-1>

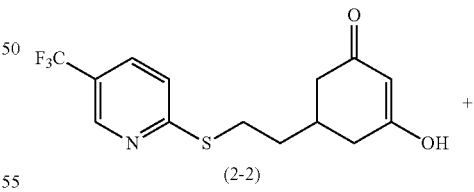

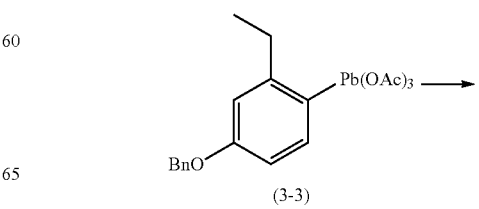

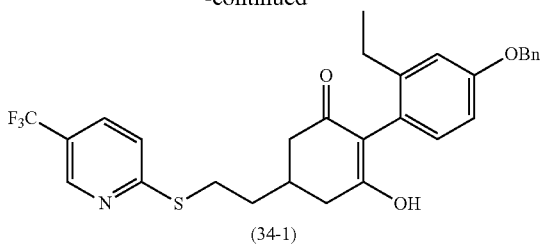

Under nitrogen atmosphere, rt, the compound of the formula (2-2) 540 mg and dimethylaminopyridine 1.05 g were dissolved in a mixture of chloroform 4.8 ml and toluene 1.2 ml. The resulting solutions were stirred at RT under nitrogen atmosphere for 15 minutes. Thereafter, under nitrogen atmosphere, to the resulting solutions was added the compound of the formula (3-3) 1.1 g. Under nitrogen atmosphere, the resulting mixtures were stirred at 75° C. for 1 hour. The resulting reaction solutions were cooled to rt, adjusted to pH 1 with 2N hydrochloric acid and filtered through Celite™. The resulting filtrates were extracted with chloroform. The resulting chloroform layers were washed with water, dried over anhydrous sodium sulfate and filtered. The resulting filtrates were concentrated under reduced pressure to give oils. The resulting oils were subjected to a silica gel column chromatography (eluates, ethyl acetate:hexane=1:2) to give the compound of the formula (34-1) 386 mg.

$^1$H NMR (CDCl$_3$)

δ ppm: 8.67 (1H, s), 7.67 (1H, dd), 7.46-7.26 (6H, m), 6.98-6.92 (2H, m), 6.86 (1H, dt), 5.74 (1H, s), 5.08 (2H, s), 3.30 (2H, t), 2.79-2.67 (2H, m), 2.50-2.24 (5H, m), 1.93-1.87 (2H, m), 1.08 (3H, dt)

<Preparation of the Compound of the Formula 1-40>

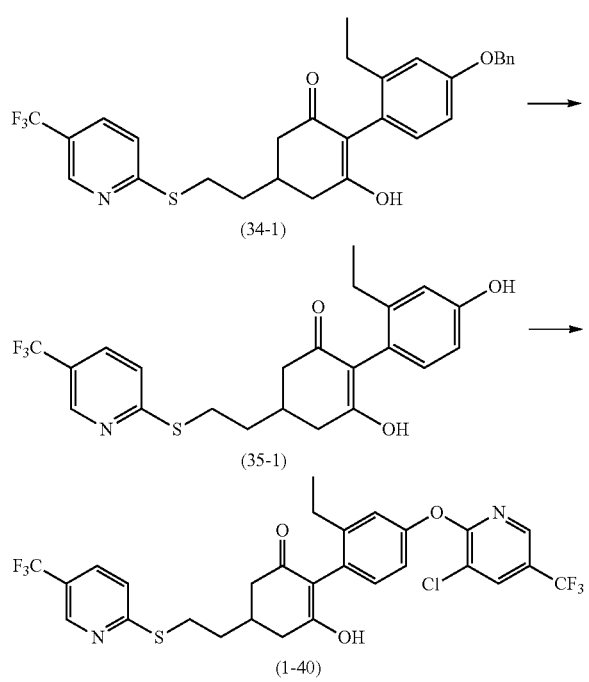

At RT, the compound of the formula (34-1) 300 mg was dissolved in acetic acid 2.2 ml and to the resulting mixtures was added dropwise 47% hydrogen bromide 0.7 ml. The resulting reaction solutions were heated to 100° C. and stirred for 30 minutes. To the resulting reaction solutions was iced water 10 ml and the resulting mixtures were extracted with ethyl acetate. The resulting ethyl acetate layers were washed with water, dried over anhydrous sodium sulfate and then filtered. The resulting filtrates were concentrated under reduced pressure to give the compound of the formula (35-1) 240 mg.

Continuously, at RT, the compound of the formula (35-1) 240 mg, cesium carbonate 200 mg and 2,3-dichloro-5-trifluoromethylpyridine 118 mg were dissolved in N,N-dimethylformamide 2 ml. The resulting reaction solutions were heated to 70° C. and stirred for 2 hours. The resulting reaction solutions were extracted with ethyl acetate and the resulting ethyl acetate layers were washed with saturated saline, dried over anhydrous sodium sulfate and then filtered. The resulting filtrates were concentrated under reduced pressure and then subjected to a silica gel column chromatography (eluates, ethyl acetate:hexane=1:2) to give the compound of the formula (1-40) 80 mg.

$^1$H NMR (CDCl$_3$)

δ ppm: 8.68 (1H, s), 8.24 (1H, dd), 8.00 (1H, d), 7.67 (1H, dd), 7.28-7.26 (1H, m), 7.14-7.03 (3H, m), 6.33 (1H, s), 3.31 (2H, t), 2.79-2.68 (2H, m), 2.52-2.26 (5H, m), 1.94-1.89 (2H, m), 1.10 (3H, dt)

Preparation Example 1-26

Preparation of the Compound of the Formula (1-75)

<Preparation of the Compound of the Formula 7-20>

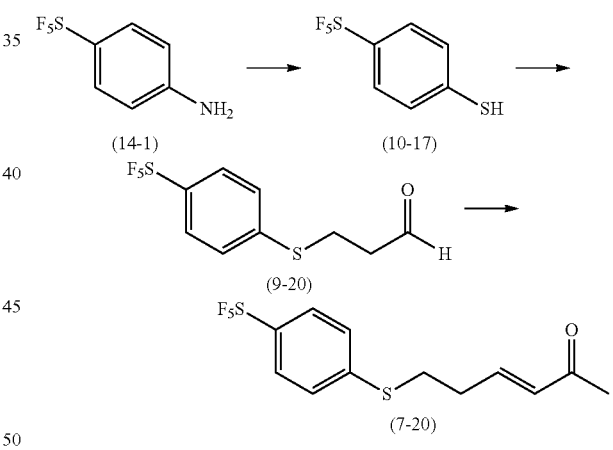

At RT, the compound of the formula (7-20) 10 g was dissolved in acetic acid 33 ml. To the resulting mixtures was added 35% sulfuric acid 100 ml. Thereafter, the resulting reaction mixtures were cooled to 0° C. and then thereto were added dropwise a mixture of sodium nitrite 3.3 g and water 25 ml and the resulting mixtures were stirred at 0° C. for 10 minutes.

Thereafter, the resulting reaction solutions were added dropwise to a mixture of sodium sulfide 15 g, sulfur 2 g and sodium hydroxide 3.3 g dissolved in water 100 ml at 60° C., and the resulting mixtures were stirred for 30 minutes. The reaction solutions were cooled to rt, extracted with tert-butyl methyl ether, washed with 10% hydrochloric acid, dried over anhydrous sodium sulfate and then filtered. The resulting filtrates were concentrated under reduced pressure, dissolved in diethyl ether 300 ml and thereto was added dropwise lithium aluminium hydride 1.8 g at 0° C. under nitrogen atmosphere, and then the resulting mixture solutions were stirred at RT for 1 hour. To the resulting reaction mixtures was added 10% hydrochloric acid 500 ml and the resulting mixtures were extracted with diethyl ether. The resulting organic layers were washed with saturated saline, dried over anhydrous sodium sulfate and then filtered. The resulting filtrates were concentrated under reduced pressure to give the compound of the formula (10-17) as crude products. The resulting crude products were subjected to a silica gel column chromatography (eluates, ethyl acetate:hexane=1:4) to give the compound of the formula (10-17) 3.1 g.

Thereafter, at RT. the compound of the formula (10-17) 3.0 g and tetrahydrofuran 10 ml were mixed and stirred and the resulting mixtures were cooled to 0° C. and then thereto were added dropwise acrolein 1.05 g and triethylamine 0.1 g. The resulting mixtures were stirred under ice-cooling for 2 hours. Thereafter, to the resulting mixtures was added water and the resulting mixtures were extracted with tert-butyl methyl ether. The organic layers were washed with water, dried over anhydrous sodium sulfate and concentrated under reduced pressure to give the compound of the formula (9-20) 1.2 g.

Continuously, at RT, the compound of the formula (9-20) 1.2 g and triphenylphosphine acetylmethylene 1.4 g were dissolved in chloroform 5 ml. The resulting solutions were stirred at 0° C. for 8 hours. Thereafter, under reduced pressure, chloroform was removed from the resulting reaction solutions. To the resulting residues were added tert-butyl methyl ether and hexane. The resulting mixtures were filtered and the resulting filtrates were concentrated under reduced pressure. The resulting oils were subjected to a silica gel column chromatography (eluates, ethyl acetate:hexane=1:4) to give the compound of the formula (7-20) 340 mg.

$^1$H NMR (CDCl$_3$)

δ ppm: 7.66 (2H, d), 7.32 (2H, d), 6.78 (1H, dt), 6.14 (1H, d), 3.12 (2H, t), 2.61 (2H, q), 2.25 (3H, s)

<Preparation of the Compound of the Formula 6-20>

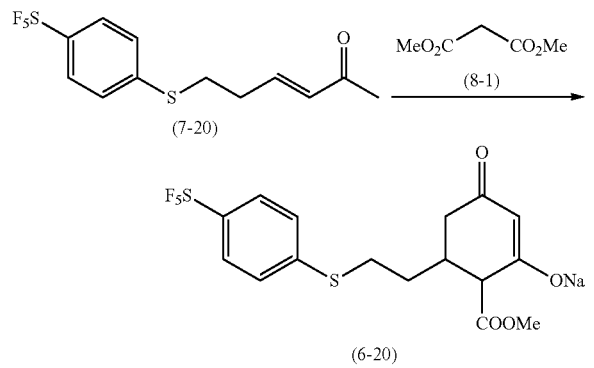

At RT, 28% sodium methoxide methanol solution 220 g and the compound of the formula (8-1) 150 mg were dissolved in tetrahydrofuran 4 ml. The resulting solutions were heated under reflux for 15 minutes. Thereafter, the heating was stopped and to the resulting reaction mixture was added the compound of the formula (7-20) 340 mg. Thereafter, the resulting mixture solutions were heated under reflux for 30 minutes. The resulting reaction solutions were cooled to 0° C. and thereto was added hexane, and the precipitated crystals were collected by filtering and washed with tert-butyl methyl ether and hexane sequentially to give the compound of the formula (6-20) 460 mg.

$^1$H NMR (d-DMSO)

δ ppm: 7.80 (2H, d), 7.44 (2H, d), 4.39 (1H, s), 3.65-3.48 (4H, m), 3.17-3.10 (1H, m), 2.99-2.91 (1H, m), 2.83 (1H, d), 2.32-2.25 (1H, m), 2.15-2.03 (1H, m), 1.85-1.74 (1H, m), 1.53-1.47 (1H, m)

<Preparation of the Compound of the Formula 1-75>

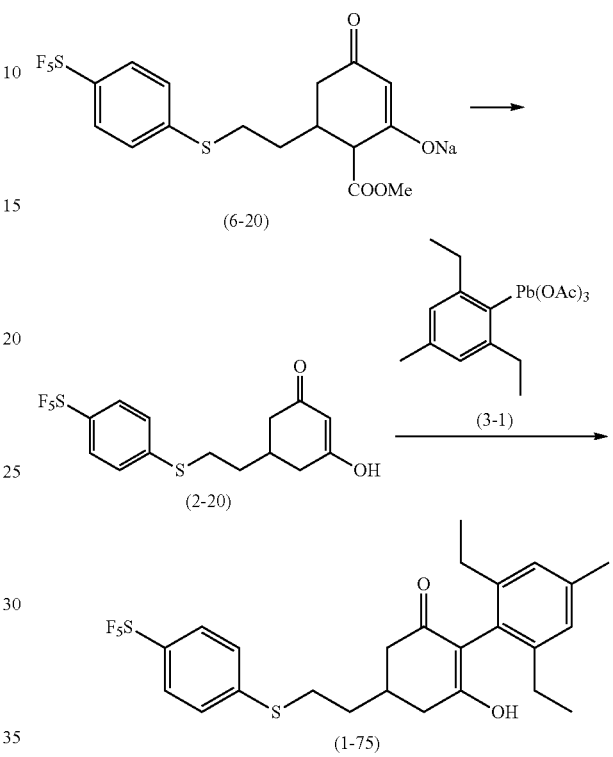

At RT, the compound of the formula (6-20) 460 mg was dissolved in water 10 ml. To the resulting solutions was added anhydrous sodium carbonate 323 mg. The resulting solutions were heated under reflux for 5 hours. The reaction solutions were cooled to rt, washed with tert-butyl methyl ether and then to the aqueous layers was added 2N hydrochloric acid and the resulting mixtures were extracted with ethyl acetate. The ethyl acetate layers were concentrated under reduced pressure and the resulting crystals were washed with tert-butyl methyl ether and hexane sequentially to give the compound of the formula (2-20) 400 mg.

Continuously, under nitrogen atmosphere, at RT, the compound of the formula (2-20) 400 mg and dimethylaminopyridine 620 mg were dissolved in a mixture of chloroform 3 ml and toluene 1 ml. The resulting solutions were stirred at RT under nitrogen atmosphere for 15 minutes. Thereafter, under nitrogen atmosphere, to the resulting solutions was added the compound of the formula (3-1) 600 mg. Under nitrogen atmosphere, the resulting mixtures were stirred at 75° C. for 1 hour. The resulting reaction solutions were cooled to rt, adjusted to pH 1 with 2N hydrochloric acid and filtered through Celite™. The resulting filtrates were extracted with chloroform. The resulting chloroform layers were washed with water, dried over anhydrous sodium sulfate and filtered. The resulting filtrates were concentrated under reduced pressure to give yellow oils. The resulting oils were subjected to a silica gel column chromatography (eluates, ethyl acetate:hexane=1:3) to give the compound of the formula (1-75) 150 mg.

$^1$H NMR (CDCl$_3$)

δ ppm: 7.66 (2H, d), 7.32 (2H, d), 6.98 (2H, s), 5.57 (1H, s), 3.13-3.01 (2H, m), 2.77-2.68 (2H, m), 2.49-2.22 (10H, m), 1.88 (2H, q), 1.06 (6H, ddd)

Preparation Example 1-27

Preparation of the Compound of the Formula (1-23)

<Preparation of the Compound of the Formula 21-1>

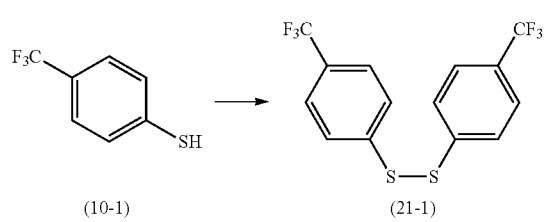 [SMILES: FC(F)(F)c1ccc(S)cc1 ; FC(F)(F)c1ccc(SSc2ccc(C(F)(F)F)cc2)cc1]

At RT, the compound of the formula (10-1) 10 g was dissolved in dimethylformamide 50 ml. To the resulting mixtures was added triethylamine 5.7 g at RT and the resulting mixture solutions were stirred under ultrasonication for 6 hours. The resulting reaction mixtures were extracted with tert-methylethylether and the resulting organic layers were washed with water, dried over anhydrous sodium sulfate and then filtered. The resulting filtrates were concentrated under reduced pressure to give the compound of the formula (21-1) (colorless solid) 9.3 g.

¹H NMR (CDCl₃)

δ ppm: 7.60-7.53 (8H, m)

<Preparation of the Compound of the Formula 13-3>

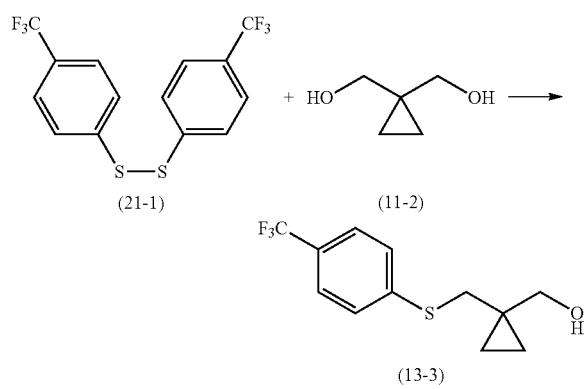

The compound of the formula (1-12) 5 g and the compound of the formula (21-1) 9.3 g were dissolved in tetrahydrofuran 250 ml. Under nitrogen atmosphere, at RT, to the resulting mixture solutions was added dropwise tributylphosphine 5.8 g and the resulting mixtures were stirred for 2 hours. The resulting reaction mixture solutions were concentrated under reduced pressure and the resulting crude products were subjected to a silica gel column chromatography (eluates, ethyl acetate:hexane=1:4) to give the compound of the formula (13-3) (colorless solids) 4.5 g.

¹H NMR (CDCl₃)

δ ppm: 7.50 (2H, d), 7.41 (2H, d), 3.58 (2H, s), 3.17 (2H, s), 0.58 (4H, s)

<Preparation of the Compound of the Formula 7-21>

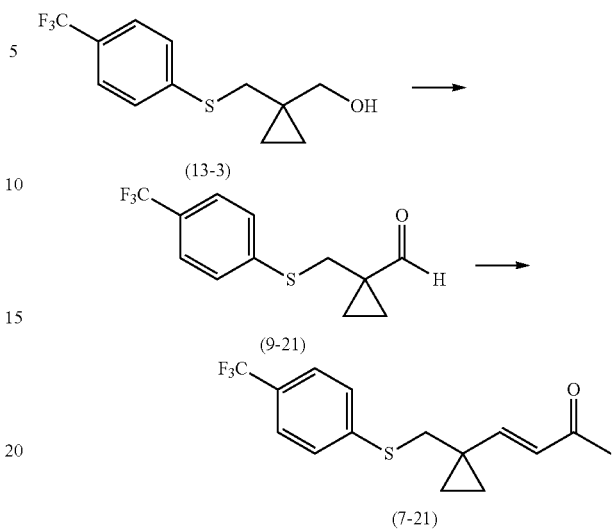

Under nitrogen atmosphere, a mixture of oxalyl chloride 2.5 g and methylene chloride 45 ml was cooled to −78° C. and then thereto was added dropwise a solution of dimethyl sulfoxide 2.7 g in methylene chloride 20 ml and the resulting mixtures were stirred for 10 minutes. Thereafter, to the resulting mixture solutions was added dropwise a solution of the compound of the formula (13-3) 4.5 g in methylene chloride 5 ml and the resulting mixtures were stirred for 30 minutes. Thereafter, to the resulting mixture solutions was added triethylamine 8.8 g and the resulting mixtures were warmed to rt and stirred for 3 hours. The resulting reaction solutions were poured into 1N hydrochloric acid 60 ml and extracted with chloroform. The resulting organic layers were dried over anhydrous sodium sulfate and then filtered. The resulting filtrates were concentrated under reduced pressure to give the compound of the formula (9-21) 4.5 g as crude products.

Continuously, at RT, the compound of the formula (9-21) 4.5 g as crude products and triphenylphosphine acetylmethylene 6.1 g were dissolved in xylene 45 ml. The resulting reaction mixture solutions were heated under reflux for 8 hours. Thereafter, the resulting reaction solutions were concentrated under reduced pressure to remove xylene. To the resulting residues were added tert-butyl methyl ether and hexane. Continuously, the resulting mixtures were filtered and the resulting filtrates were concentrated under reduced pressure. The resulting oils were subjected to a silica gel column chromatography (eluates, ethyl acetate hexane=1:4) to give the compound of the formula (7-21) 3.8 g.

¹H NMR (CDCl₃)

δ ppm: 7.52 (2H, d), 7.35 (2H, d), 6.49 (1H, d), 6.17 (1H, d), 3.19 (2H, s), 2.22 (3H, s), 1.10-1.00 (4H, m)

<Preparation of the Compound of the Formula 6-21>

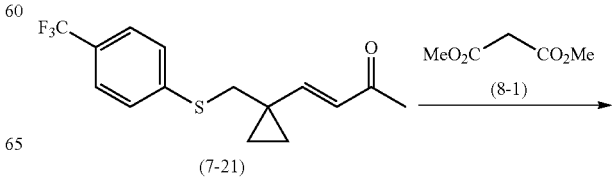

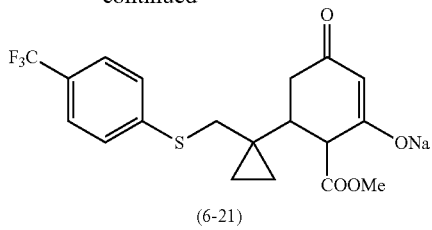

(6-21)

At RT, 28% sodium methoxide methanol solution 2.7 g and the compound of the formula (8-1) 1.8 g were dissolved in 1,4-dioxane 30 ml. The resulting solutions were heated under reflux for 15 minutes. Thereafter, the heating was stopped and to the resulting reaction mixture was added the compound of the formula (7-21) 3.8 g. Thereafter, the resulting mixture solutions were heated under reflux for 1 hour. The resulting reaction solutions were cooled to 0° C. and thereto was added hexane, and the precipitated crystals were filtered and washed with tert-butyl methyl ether and hexane sequentially to give the compound of the formula (6-21) 4.5 g.

¹H NMR (CDCl₃)
δ ppm: 7.62 (2H, d), 7.45 (2H, d), 4.42 (1H, s), 3.57 (3H, s), 3.39-3.35 (1H, m), 3.23 (1H, d), 3.07 (1H, d), 2.32 (1H, t), 1.93 (1H, dd), 1.76 (1H, td), 0.46-0.34 (4H, m)

<Preparation of the Compound of the Formula 1-23>

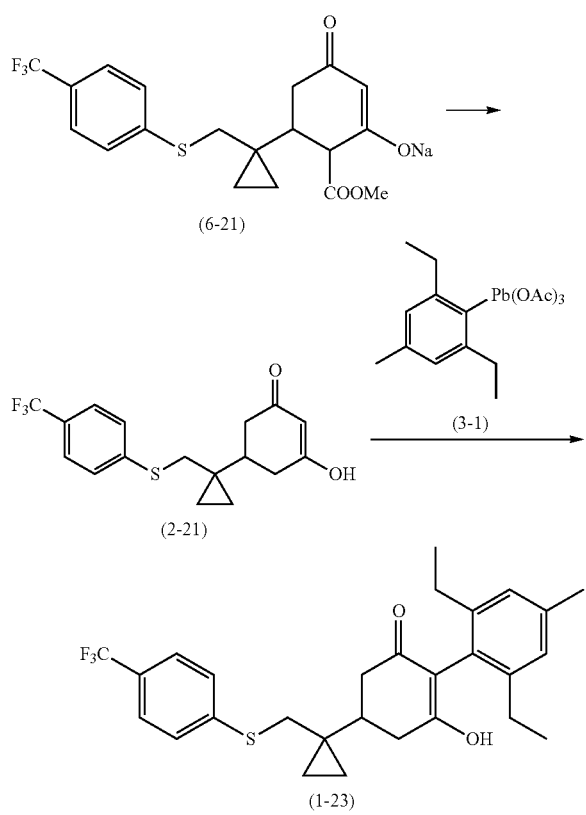

At RT, the compound of the formula (6-21) 4.5 g was dissolved in water 100 ml. To the resulting solutions was added anhydrous sodium carbonate 3.37 g. The resulting solutions were heated under reflux for 5 hours. The reaction solutions were cooled to rt and washed with tert-butyl methyl ether and then to the aqueous layers was added 2N hydrochloric acid, and the resulting mixtures were extracted with ethyl acetate. The ethyl acetate layers were dried over anhydrous sodium sulfate, filtered and concentrated under reduced pressure to give the compound of the formula (2-21) 3.4 g.

Continuously, under nitrogen atmosphere, at RT, the compound of the formula (2-21) 1.75 g as crude products and dimethylaminopyridine 3.13 g were dissolved in a mixture of chloroform 14 ml and toluene 4 ml. The resulting solutions were stirred at RT under nitrogen atmosphere for 15 minutes. Thereafter, under nitrogen atmosphere, to the resulting solutions was added the compound of the formula (3-1) 3 g. Under nitrogen atmosphere, the resulting mixtures were stirred at 75° C. for 1 hour. The resulting reaction solutions were cooled to rt and, adjusted to pH 1 with 2N hydrochloric acid and filtered through Celite™. The resulting filtrates were extracted with chloroform. The resulting chloroform layers were washed with water, dried over anhydrous sodium sulfate and filtered. The resulting filtrates were concentrated under reduced pressure to give yellow oils. The resulting oils were subjected to a silica gel column chromatography (eluates, ethyl acetate:hexane=1:4) to give the compound of the formula (1-23) 1.9 g.

¹H NMR (CDCl₃)
δ ppm: 7.52 (2H, d), 7.35 (2H, d), 6.97 (2H, s), 5.99 (1H, s), 3.12 (2H, dd), 2.65-2.58 (3H, m), 2.46-2.13 (9H, m), 1.07 (6H, t), 0.64 (4H, s)

Preparation Example 1-28

Preparation of the Compound of the Formula (1-36)

<Preparation of the Compound of the Formula 27-1>

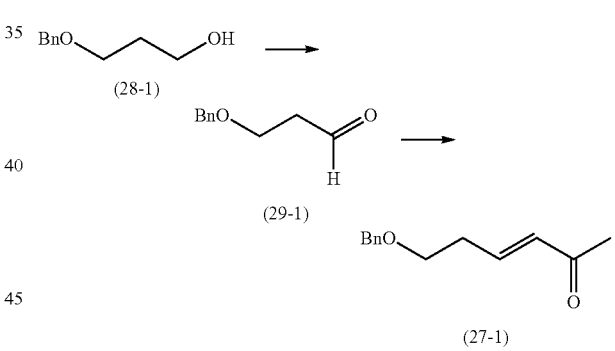

Under nitrogen atmosphere, a mixture of oxalyl chloride 8.6 g and methylene chloride 150 ml was cooled to −78° C. and to the resulting mixture solutions was added dropwise a solution of dimethyl sulfoxide 9.4 g in methylene chloride 60 ml and the resulting mixtures were stirred for 10 minutes. Thereafter, to the resulting mixture solutions was added dropwise a solution of the compound of the formula (28-1) 10 g in methylene chloride 20 ml and the resulting mixtures were stirred for 30 minutes. Thereafter, to the resulting mixture solutions was added triethylamine 30.4 g and the resulting mixtures were warmed to rt and stirred for 1 hour. The resulting reaction solutions were poured into 1N hydrochloric acid 200 ml and the resulting mixtures were extracted with chloroform. The resulting organic layers were dried over anhydrous sodium sulfate and then filtered. The resulting filtrates were concentrated under reduced pressure to give the compound of the formula (29-1) 9.8 g as crude products.

Continuously, at RT, the compound of the formula (29-1) 9.8 g as crude products and 1-triphenylphosphoranylidene-2- propanone 22.6 g were dissolved in chloroform 80 ml. The resulting reaction mixture solutions were heated under reflux for 8 hours. Thereafter, the resulting reaction solutions were concentrated under reduced pressure to remove chloroform. To the resulting residues were added tert-butyl methyl ether and hexane. Continuously, the resulting mixtures were filtered and the resulting filtrates were concentrated under reduced pressure. The resulting oils were subjected to a silica gel column chromatography (eluates, ethyl acetate:hexane=1:4) to give the compound of the formula (27-1) (colorless oils) 7.4 g.

$^1$H NMR (CDCl$_3$)

δ ppm: 7.38-7.26 (5H, m), 6.82 (1H, dt), 6.13 (1H, dt), 4.51 (2H, s), 3.63-3.57 (2H, m), 2.53 (2H, ddd), 2.24 (3H, s)

<Preparation of the Compound of the Formula 25-1>

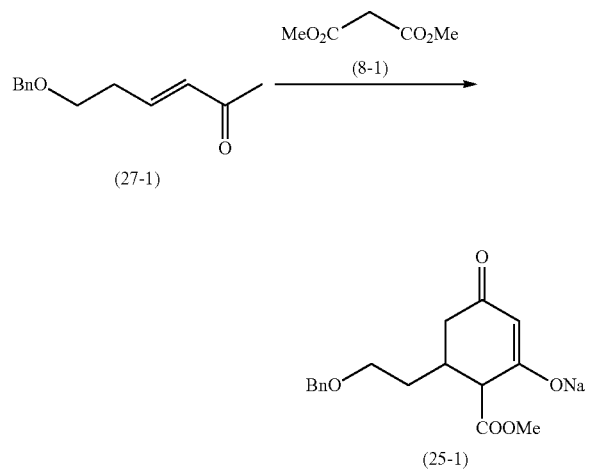

At RT, 28% sodium methoxide methanol solution 7.7 g and the compound of the formula (8-1) 5.3 g were dissolved in tetrahydrofuran 100 ml. The resulting solutions were heated under reflux for 15 minutes. Thereafter, the heating was stopped and to the resulting reaction mixture was added the compound of the formula (27-1) 7.4 g. Thereafter, the resulting mixture solutions were heated under reflux for 1 hour. The resulting reaction solutions were cooled to 0° C. and thereto was added hexane, and the precipitated crystals were filtered and washed with tert-butyl methyl ether and hexane sequentially to give the compound of the formula (25-1) 7.2 g.

$^1$H NMR (CDCl$_3$)

δ ppm: 7.37-7.26 (5H, m), 4.50-4.38 (3H, m), 3.59 (3H, s), 3.43-3.40 (3H, m), 2.84 (1H, d), 2.32-2.24 (1H, m), 2.08 (1H, dd), 1.76 (1H, dd), 1.57-1.36 (2H, m)

<Preparation of the Compound of the Formula 24-1>

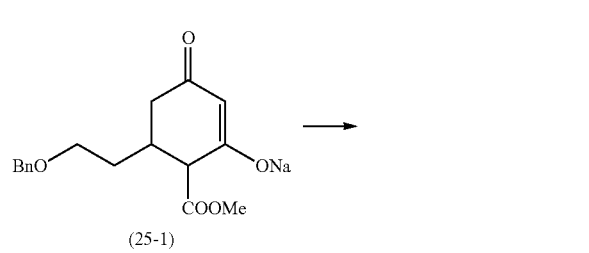

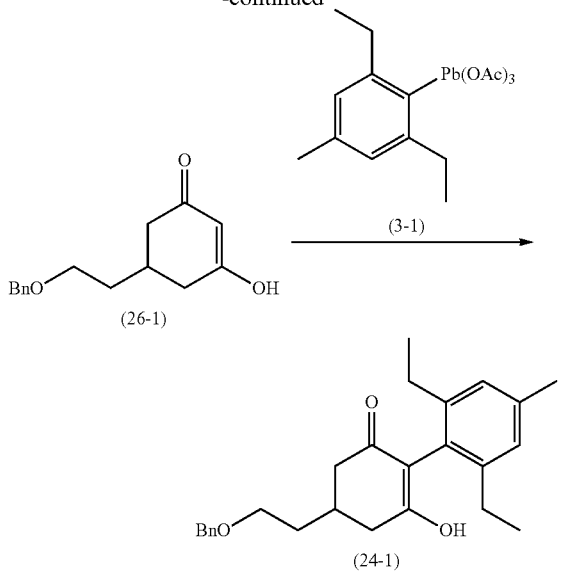

At RT, the compound of the formula (25-1) 3 g was dissolved in water 90 ml. To the resulting solutions was added anhydrous sodium carbonate 2.9 g. The resulting solutions were heated under reflux for 5 hours. The reaction solutions were cooled to rt and washed with tert-butyl methyl ether and then to the aqueous layers was added 2N hydrochloric acid and the resulting mixtures were extracted with ethyl acetate. The ethyl acetate layers were dried over anhydrous sodium sulfate, filtered and concentrated under reduced pressure to give the compound of the formula (26-1) (yellow solids) 2 g as crude products.

Continuously, under nitrogen atmosphere, at RT, the compound of the formula (26-1) 730 mg as crude products and dimethylaminopyridine 1.8 g were dissolved in a mixture of chloroform 8 ml and toluene 2 ml. The resulting solutions were stirred at RT under nitrogen atmosphere for 15 minutes. Thereafter, under nitrogen atmosphere, to the resulting solutions was added the compound of the formula (3-1) 1.7 g. Under nitrogen atmosphere, the resulting mixtures were stirred at 75° C. for 1 hour. The resulting reaction solutions were cooled to rt, adjusted to pH 1 with 2N hydrochloric acid and filtered through Celite™. The resulting filtrates were extracted with chloroform. The resulting chloroform layers were washed with water, dried over anhydrous sodium sulfate and filtered. The resulting filtrates were concentrated under reduced pressure to give oils. The resulting oils were subjected to a silica gel column chromatography (eluates, ethyl acetate:hexane=1:2) to give the compound of the formula (24-1) 890 mg.

$^1$H NMR (CDCl$_3$)

δ ppm: 7.39-7.27 (5H, m), 6.97 (2H, s), 5.70 (1H, s), 4.53 (2H, s), 3.62-3.53 (2H, m), 2.69-2.62 (2H, m), 2.52-2.22 (10H, m), 1.83-1.74 (2H, m), 1.08 (6H, ddd)

<Preparation of the Compound of the Formula 23-1>

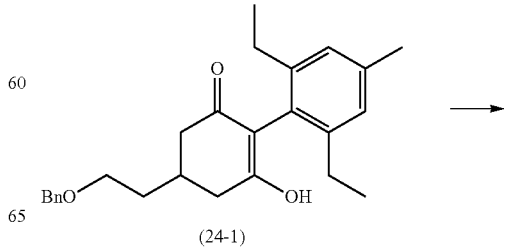

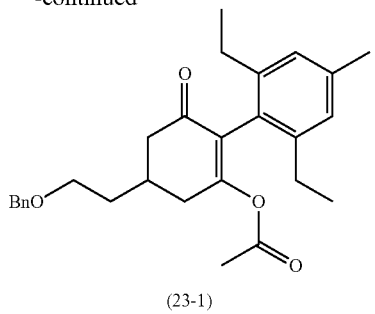

(23-1)

To the compound of the formula (24-1) 4.5 g was added a solution of triethylamine 1.8 g in anhydrous tetrahydrofuran 30 ml. To the resulting mixtures was added a solution of acetyl chloride 1.8 g in anhydrous tetrahydrofuran 10 ml under ice-cooling. The resulting mixtures were stirred at RT for 12 hours. To the reaction mixtures was added water and the resulting mixtures were extracted with chloroform. The chloroform layers extracted were dried over anhydrous sodium sulfate, then concentrated under reduced pressure and subjected to a silica gel column chromatography (eluates, ethyl acetate:hexane=1:4) to give the compound of the formula (23-1) (colorless oils) 3.7 g.

$^1$H NMR (CDCl$_3$)

δ ppm: 7.35-7.24 (5H, m), 6.88 (2H, s), 4.50 (2H, dd), 3.56 (2H, t), 2.72-2.28 (12H, m), 1.86-1.73 (5H, m), 1.12-1.03 (6H, m)

<Preparation of the Compound of the Formula 23-1>

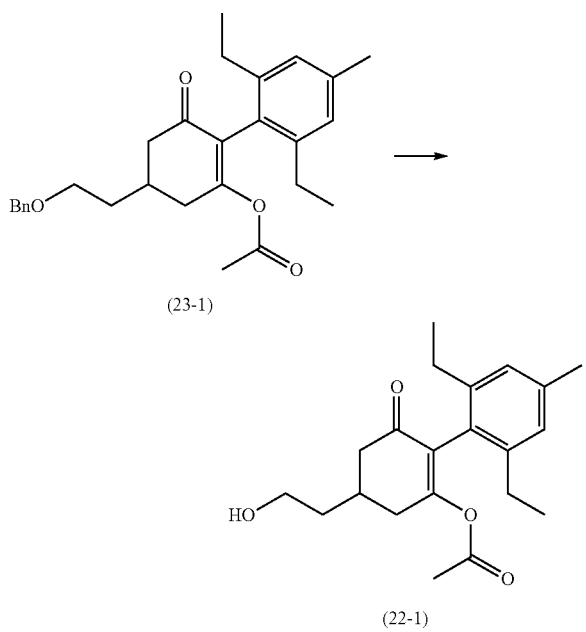

The compound of the formula (23-1) 3.7 g were dissolved in ethyl acetate 150 ml. To the resulting mixture solutions was added 10% palladium-carbon 1.5 g and the resulting mixtures were stirred at 35° C. under hydrogen atmosphere for 4 hours.

The resulting reaction mixture solutions were filtered through Celite™ and the resulting filtrates were concentrated under reduced pressure to give the compound of the formula (22-1) (colorless solids) 2.4 g.

$^1$H NMR (CDCl$_3$)

δ ppm: 6.89 (2H, s), 3.79 (2H, d), 2.79-2.69 (3H, m), 2.60-2.53 (1H, m), 2.42-2.25 (7H, m), 1.88 (3H, s), 1.82-1.73 (2H, m), 1.63-1.61 (2H, m), 1.07 (6H, q)

<Preparation of the Compound of the Formula 1-36>

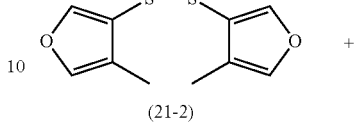

(21-2)

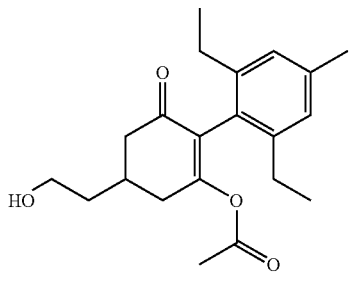

(22-1)

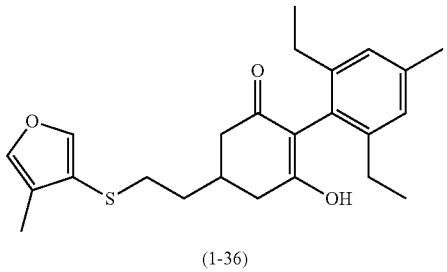

(1-36)

The compound of the formula (22-1) 344 mmg and the compound of the formula (21-2) 227 mg were dissolved in tetrahydrofuran 5 ml. Under nitrogen atmosphere, at RT, to the resulting mixture solutions was added dropwise tributylphosphine 223 mg, and the resulting mixtures were stirred for 2 hours. The resulting reaction mixture solutions were concentrated under reduced pressure and the resulting crude products were subjected to a silica gel column chromatography (eluates, ethyl acetate:hexane=1:4) to give the compound of the formula (1-36) (colorless oils) 400 mg.

$^1$H NMR (CDCl$_3$)

δ ppm: 7.29 (1H, d), 6.96 (2H, s), 6.34 (1H, d), 5.88 (1H, s), 2.71-2.60 (4H, m), 2.44-2.16 (13H, m), 1.70 (2H, dd), 1.10-1.01 (6H, m)

Preparation Example 1-29

Preparation of the Compound of the Formula (1-33)

<Preparation of the Compound of the Formula 1-33>

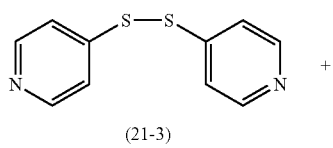

(21-3)

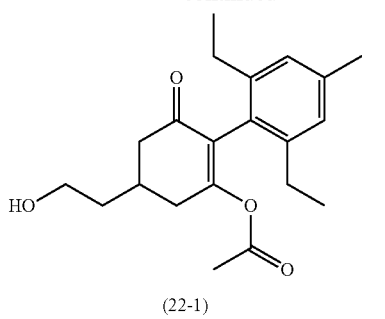

(22-1)

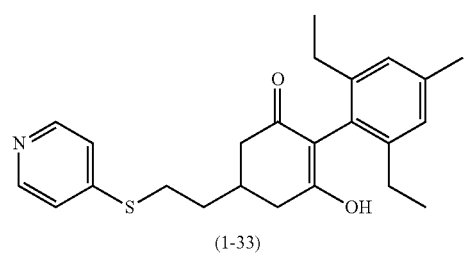

(1-33)

The compound of the formula (22-1) 344 mg and the compound of the formula (21-3) 121 mg were dissolved in tetrahydrofuran 5 ml. Under nitrogen atmosphere, at RT, to the resulting mixture solutions was added dropwise tributylphosphine 121 mg and the resulting mixtures were stirred for 2 hours. The resulting reaction mixture solutions were concentrated under reduced pressure and the resulting crude products were subjected to a silica gel column chromatography (eluates, ethyl acetate:hexane=1:2) to give the compound of the formula (1-33) 80 mg.

$^1$H NMR (CDCl$_3$)

δ ppm: 8.41 (2H, dd), 7.13 (2H, dd), 6.90 (1H, s), 3.08 (2H, t), 2.82-2.67 (3H, m), 2.58-2.24 (9H, m), 1.95-1.84 (3H, m), 1.13-1.03 (6H, m)

Preparation Example 1-30

Preparation of the Compound of the Formula (1-76)

<Preparation of the Compound of the Formula 1-76>

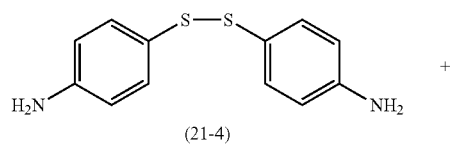

(21-4)

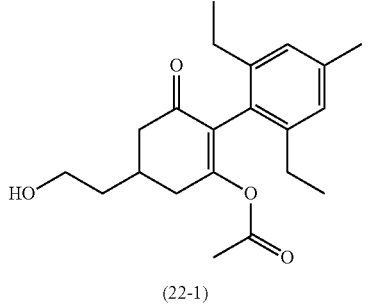

(22-1)

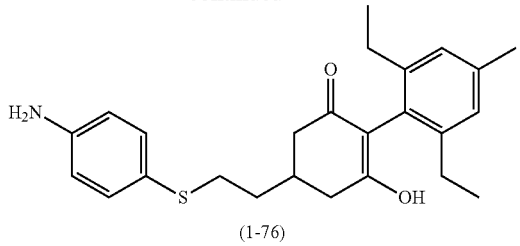

(1-76)

The compound of the formula (22-1) 172 mg and the compound of the formula (21-4) 124 mg were dissolved in tetrahydrofuran 2.5 ml. Under nitrogen atmosphere, at RT, to the resulting mixture solutions was added dropwise tributylphosphine 0.14 ml and the resulting mixtures were stirred for 2 hours. The resulting reaction mixture solutions were concentrated under reduced pressure and the resulting crude products were subjected to a silica gel column chromatography (eluates, ethyl acetate:hexane=1:3→1:2→1:1) to give the compound of the formula (1-76) 160 mg.

$^1$H NMR (CDCl$_3$)

δ ppm: 7.26-7.22 (2H, m), 6.97 (2H, s), 6.61 (2H, dt), 2.86-2.82 (2H, m), 2.67-2.59 (2H, m), 2.44-2.18 (10H, m), 1.73 (2H, dd), 1.11-1.02 (6H, m)

Preparation Example 1-31

Preparation of the Compound of the Formula (1-77)

<Preparation of the Compound of the Formula 1-77>

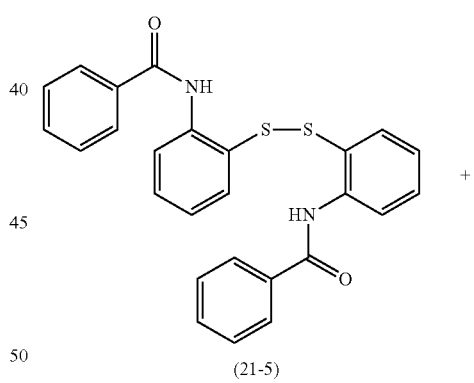

(21-5)

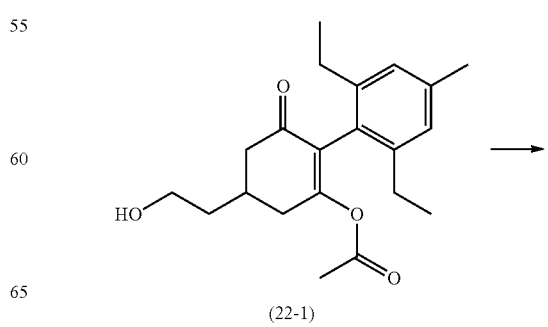

(22-1)

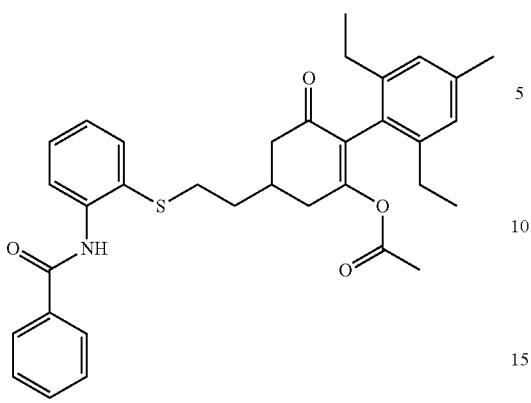

(1-77)

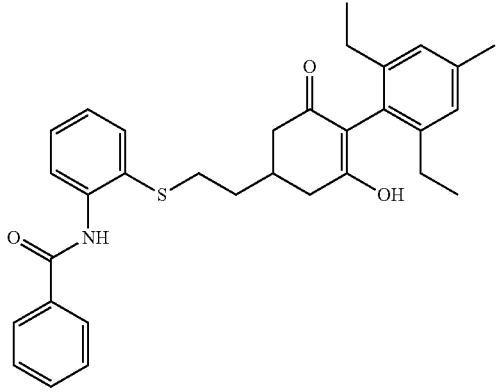

(1-78)

The compound of the formula (22-1) 344 mg and the compound of the formula (21-5) 456 mg were dissolved in tetrahydrofuran 5 ml. Under nitrogen atmosphere, at RT, to the resulting mixture solutions was added dropwise tributylphosphine 111 mg and the resulting mixtures were stirred for 2 hours. The resulting reaction mixture solutions were concentrated under reduced pressure and the resulting crude products were subjected to a silica gel column chromatography (eluates, ethyl acetate:hexane=1:4→1:2) to give the compound of the formula (1-77) 210 mg.

$^1$H NMR (CDCl$_3$)

δ ppm: 9.40 (1H, s), 8.61 (1H, dd), 7.98-7.95 (2H, m), 7.61-7.51 (4H, m), 7.42 (1H, td), 7.11 (1H, td), 6.87 (2H, s), 2.87-2.83 (2H, m), 2.68-2.54 (3H, m), 2.46-2.22 (9H, m), 1.85 (3H, s), 1.79-1.73 (2H, m), 1.04 (6H, dt)

Preparation Example 1-32

Preparation of the Compound of the Formula (1-78)

<Preparation of the Compound of the Formula 1-78>

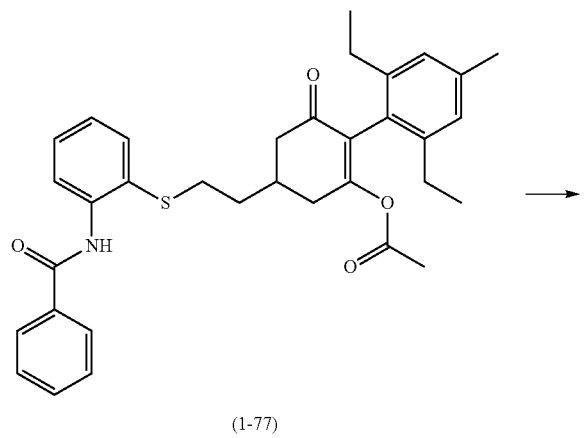

(1-77)

At RT, the compound of the formula (1-77) 150 mg was dissolved in methanol 20 ml and thereto was added potassium carbonate 100 mg and the resulting mixtures were stirred for 1 hour. The resulting reaction solutions were concentrated under reduced pressure to give the compound of the formula (1-78) as crude products. Thereafter, the resulting crude products were subjected to a silica gel column chromatography (eluates, ethyl acetate:hexane=1:4) to give the compound of the formula (1-78) 160 mg.

$^1$H NMR (CDCl$_3$)

δ ppm: 9.39 (1H, s), 8.59 (1H, dd), 7.95 (2H, m), 7.60-7.51 (4H, m), 7.44-7.39 (1H, m), 7.11 (1H, td), 6.94 (2H, s), 5.91 (1H, s), 2.88-2.83 (2H, m), 2.60-2.57 (2H, m), 2.32-2.15 (9H, m), 1.76-1.71 (2H, m), 1.06-0.97 (6H, dt)

Preparation Example 1-33

Preparation of the Compound of the Formula (1-97)

<Preparation of the Compound of the Formula 31-1>

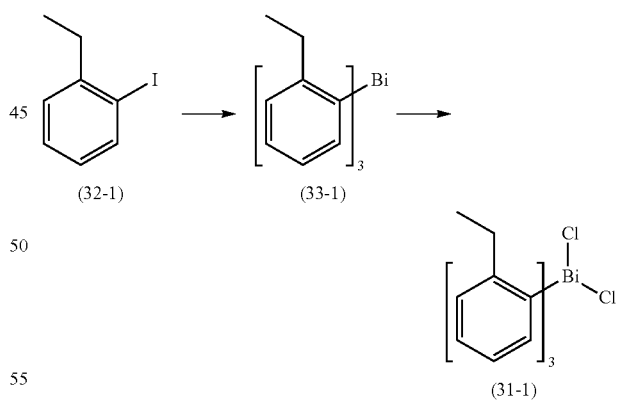

Under nitrogen atmosphere, at 0° C., to tetramethylethylenediamine 3.2 ml was added n-butyllithium 16 ml (1.6M hexane solution) and the resulting mixtures were stirred for 10 minutes. Thereafter, at 0° C. under ice-cooling, thereto was added the compound of the formula (32-1) 5 g. Thereafter, the resulting solutions were cooled to −78° C. and then thereto was added a suspension of trichlorobismuth 2.3 g in tetrahydrofuran 15 ml and the resulting mixtures were stirred for 1 hour with heating to rt. Thereafter, to the resulting reaction solutions was added water 20 ml and the aqueous layers were extracted with chloroform. The resulting chloroform layers were washed with saturated saline, dried over anhydrous sodium sulfate and filtered, and the resulting filtrates were concentrated under reduced pressure to give the compound of the formula (33-1) 2.6 g as crude products.

Continuously, at RT, the compound of the formula (33-1) 2.6 g as crude products were dissolved in dehydrated chloroform 25 ml and cooled to 0° C. and then thereto was added sulfuryl chloride 0.4 ml. Thereafter, the resulting mixtures were warmed to rt and stirred four 1 hour. The resulting reaction solutions were concentrated under reduced pressure, and to the resulting oils was added hexane to precipitate crystals and the crystals were filtered to give the compound of the formula (31-1) 1.3 g.

$^1$H NMR (CDCl$_3$)

δ ppm: 8.00 (1H, dd), 7.66 (1H, dd), 7.54-7.46 (2H, m), 3.03 (2H, q), 1.38 (3H, t)

<Preparation of the Compound of the Formula 1-97>

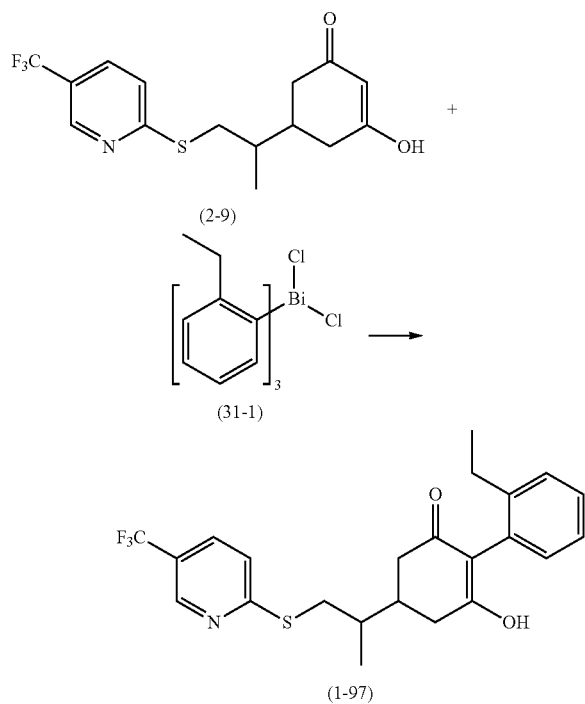

Under nitrogen atmosphere, at RT, the compound of the formula (31-1) 550 mg and the compound of the formula (2-9) 290 mg were dissolved in a mixture of chloroform 1 ml and toluene 4 ml. The resulting solutions were stirred at RT under nitrogen atmosphere for 15 minutes. Thereafter, under nitrogen atmosphere, to the resulting solution was added diazabicycloundecene 0.17 ml. Under nitrogen atmosphere, at RT, the resulting mixtures were stirred for 12 hours. The resulting reaction solutions were diluted with chloroform. The resulting diluted solutions were washed with hydrochloric acid adjusted to pH 1 to 2 and continuously, washed with saturated saline. Thereafter, the resulting organic layers were dried over anhydrous sodium sulfate and filtered, and the resulting filtrates were concentrated under reduced pressure to give oils. The resulting oils were subjected to a silica gel column chromatography (eluates, ethyl acetate:hexane=1:3) to give the compound of the formula (1-97) 240 mg.

$^1$H NMR (CDCl$_3$)

δ ppm: 8.67 (1H, s), 7.66 (1H, dd), 7.36-7.23 (4H, m), 7.04-7.01 (1H, m), 5.91-5.87 (1H, m), 3.61-3.51 (1H, m), 3.08-2.98 (1H, m), 2.74-2.28 (7H, m), 2.04-1.95 (1H, m), 1.17-1.03 (6H, m)

Preparation Example 1-34

Preparation of the Compound of the Formula (1-19)

<Preparation of the Compound of the Formula 1-19>

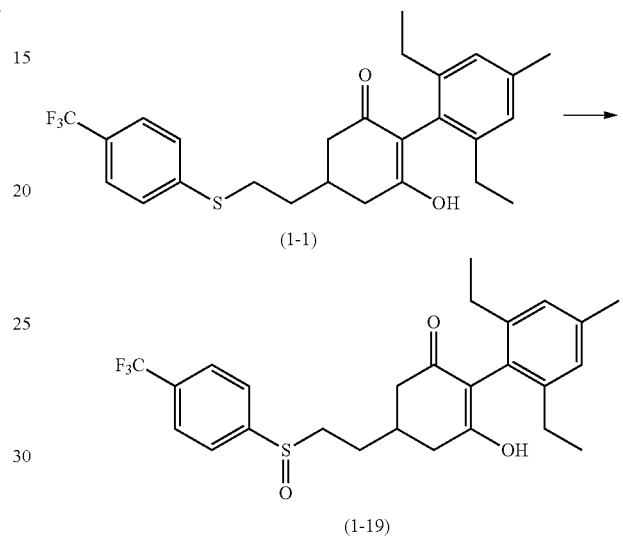

At RT, to the compound of the formula (1-1) 250 mg was added chloroform 3 ml. The resulting mixtures were cooled to 0° C. with stirring and thereto was added dropwise a mixture of meta-chloroperbenzoic acid 120 mg dissolved in chloroform 2 ml. The resulting mixtures were stirred for 1 hour. Thereafter, the resulting mixtures were warmed to rt and stirred at RT overnight. The reaction solutions were diluted with chloroform and washed with 10% sodium sulfite aqueous solution. The resulting chloroform layers were washed with saturated saline, dried over anhydrous sodium sulfate and then filtered. The resulting filtrates were concentrated under reduced pressure to give oils. The resulting oils were subjected to a silica gel column chromatography (eluates, ethyl acetate:hexane=9:1) to give the compound of the formula (1-19) 154 mg.

$^1$H NMR (CDCl$_3$)

δ ppm: 7.83-7.75 (4H, m), 6.97 (2H, s), 5.53 (1H, s), 3.03-2.94 (1H, m), 2.89-2.62 (3H, m), 2.46-2.19 (10H, m), 2.13-1.78 (2H, m), 1.08-1.00 (6H, m)

The present compounds prepared according to preparation Example 1-34 are shown below.

<Compound of the Formula 1-79>

$^1$H NMR (CDCl$_3$)

δ ppm: 11.51 (1H, s), 8.72 (1H, d), 8.05 (2H, d), 7.60-7.50 (4H, m), 7.31 (1H, d), 7.19 (1H, t), 6.94 (2H, s), 5.82 (1H, s), 3.34-3.24 (1H, m), 3.09-3.01 (1H, m), 2.62-2.55 (2H, m), 2.36-2.14 (10H, m), 1.96-1.80 (2H, m), 1.05-1.01 (6H, m)

<Compound of the Formula 1-81>

$^1$H NMR (CDCl$_3$)

δ ppm: 7.83-7.77 (4H, m), 6.90-6.88 (2H, m), 2.99-2.19 (15H, m), 1.35-1.02 (9H, m)

<Compound of the Formula 1-83>

¹H NMR (CDCl₃)

δ ppm: 8.89 (1H, s), 8.23-8.16 (2H, m), 6.96 (2H, d), 3.36-3.28 (1H, m), 3.01-2.84 (1H, m), 2.70-2.21 (13H, m), 1.37-1.17 (3H, m), 1.11-1.03 (6H, m)

<Compound of the Formula 1-85>

¹H NMR (CDCl₃)

δ ppm: 8.99 (1H, s), 8.04 (1H, s), 6.97 (2H, s), 5.78 (1H, s), 3.21-3.13 (2H, m), 2.76-2.65 (2H, m), 2.48-1.82 (12H, m), 1.06-1.02 (6H, m)

<Compound of the Formula 1-87>

¹H NMR (CDCl₃)

δ ppm: 7.80 (4H, dd), 6.98 (2H, s), 3.00-2.92 (1H, m), 2.76-2.22 (13H, m), 1.36-1.33 (6H, m), 1.11-1.05 (6H, m)

<Compound of the Formula 1-89>

¹H NMR (CDCl₃)

δ ppm: 8.90 (1H, s), 8.24-8.18 (2H, m), 6.98 (2H, s), 3.24 (1H, dd), 2.89 (1H, dd), 2.76-2.67 (2H, m), 2.57-2.23 (10H, m), 1.40-1.35 (6H, m), 1.11-1.05 (6H, m)

<Compound of the Formula 1-91>

¹H NMR (CDCl₃)

δ ppm: 7.84-7.76 (4H, m), 6.98 (1H, s), 5.86 (1H, s), 2.95-2.25 (14H, m), 1.11-1.06 (6H, m), 1.00-0.94 (1H, m), 0.86-0.74 (2H, s), 0.64-0.59 (1H, s)

<Compound of the Formula 1-98>

¹H NMR (CDCl₃)

δ ppm: 7.96-7.93 (4H, m), 6.92 (1H, d), 3.01-2.84 (2H, m), 2.66-2.26 (9H, m), 2.09-1.97 (6H, m), 1.40-1.15 (3H, m)

<Compound of the Formula 1-154>

¹H NMR (CDCl₃)

δ ppm: 8.90 (1H, s), 8.24 (1H, dt), 8.18 (1H, dd), 6.98 (2H, s), 5.50 (1H, d), 3.35-3.19 (1H, m), 3.11-2.99 (1H, m), 2.73-2.64 (2H, m), 2.44-2.23 (12H, m), 1.08-1.03 (6H, m)

<Compound of the Formula 1-156>

¹H NMR (CDCl₃)

δ ppm: 9.21 (1H, s), 8.55 (1H, d), 8.12 (1H, dd), 6.97 (2H, s), 5.48 (1H, d), 4.00 (3H, s), 3.34-3.24 (1H, m), 3.11-3.00 (1H, m), 2.68-2.63 (2H, m), 2.38-2.06 (12H, m), 1.08-1.01 (6H, m)

<Compound of the Formula 1-158>

¹H NMR (CDCl₃)

δ ppm: 8.76 (1H, d), 7.79 (1H, d), 7.45 (1H, dd), 6.97 (2H, s), 5.50 (1H, d), 3.18-3.14 (2H, m), 2.72-2.65 (2H, m), 2.47-2.24 (11H, m), 2.05-2.01 (1H, m), 1.09-1.02 (6H, m)

<Compound of the Formula 1-159>

¹H NMR (CDCl₃)

δ ppm: 9.33 (1H, d), 8.98 (1H, s), 6.98 (2H, s), 5.53 (1H, d), 3.36-3.28 (1H, m), 3.20-3.11 (1H, m), 2.75-2.66 (2H, m), 2.49-2.20 (11H, m), 1.84-1.63 (1H, m), 1.08-1.01 (6H, m)

<Compound of the Formula 1-165>

¹H NMR (CDCl₃)

δ ppm: 8.39 (1H, dd), 8.12 (1H, dd), 6.97 (2H, s), 5.52 (1H, d), 3.49-3.42 (1H, m), 3.27-3.20 (1H, m), 2.74-2.64 (2H, m), 2.46-2.14 (11H, m), 1.76-1.66 (1H, m), 1.08-1.02 (6H, m)

Preparation Example 1-35

Preparation of the Compound of the Formula (1-20)

<Preparation of the Compound of the Formula 1-20>

At RT, to the compound of the formula (1-1) 250 mg was added chloroform 3 ml. The resulting mixtures were cooled to 0° C. with stirring and thereto was added dropwise a mixture of meta-chloroperbenzoic acid 440 mg dissolved in chloroform 2 ml. The resulting mixtures were stirred for 1 hour. Thereafter, the resulting mixtures were warmed to rt and stirred at RT overnight. The reaction solutions were diluted with chloroform and the resulting diluted solutions were washed with 10% sodium sulfite aqueous solution. The resulting chloroform layers were washed with saturated saline, dried over anhydrous sodium sulfate and then filtered. The resulting filtrates were concentrated under reduced pressure to give oils. The resulting oils were subjected to a silica gel column chromatography (eluates, ethyl acetate:hexane=1:2) to give the compound of the formula (1-20) 154 mg.

¹H NMR (CDCl₃)

δ ppm: 8.08 (2H, d), 7.88 (2H, d), 6.97 (2H, s), 5.52 (1H, s), 3.27-3.15 (2H, m), 2.73-2.60 (2H, m), 2.45-2.21 (10H, m), 2.02-1.90 (2H, m), 1.08-1.00 (6H, m)

The present compounds prepared according to preparation Example 1-35 are shown below.

<Compound of the Formula 1-80>

¹H NMR (CDCl₃)

δ ppm: 10.46 (1H, s), 8.69 (1H, d), 8.05-7.91 (2H, m), 7.73 (1H, td), 7.64-7.52 (4H, m), 7.34 (1H, td), 6.95 (2H, s), 3.26-3.16 (2H, m), 2.61-2.52 (2H, m), 2.35-2.11 (10H, m), 1.93-1.87 (2H, m), 1.03 (6H, dd)

<Compound of the Formula 1-82>

¹H NMR (CDCl₃)

δ ppm: 8.09 (2H, d), 7.88 (2H, d), 6.98 (2H, s), 3.28-2.99 (2H, m), 2.61-2.21 (13H, m), 1.28-1.22 (3H, m), 1.08-1.04 (6H, m)

<Compound of the Formula 1-84>

¹H NMR (CDCl₃)

δ ppm: 9.02 (1H, s), 8.27 (2H, s), 6.98 (2H, s), 5.67 (1H, s), 3.69 (1H, dt), 3.32 (1H, ddd), 2.66-2.21 (13H, m), 1.28-1.24 (3H, m), 1.10-1.02 (6H, m)

<Compound of the Formula 1-86>
 $^1$H NMR (CDCl$_3$)
  δ ppm: 8.79 (1H, s), 8.18 (1H, s), 6.99 (2H, s), 3.86-3.66 (2H, m), 2.86-2.72 (2H, m), 2.54-2.09 (12H, m), 1.10-1.01 (6H, m)
<Compound of the Formula 1-88>
 $^1$H NMR (CDCl$_3$)
  δ ppm: 8.09 (2H, d), 7.86 (2H, d), 6.99 (2H, d), 3.11 (2H, dd), 2.68-2.24 (12H, m), 1.35 (6H, d), 1.08 (6H, dt)
<Compound of the Formula 1-90>
 $^1$H NMR (CDCl$_3$)
  δ ppm: 9.01 (1H, s), 8.27-8.22 (2H, m), 6.98 (2H, s), 3.59-3.49 (2H, m), 2.59-2.48 (2H, m), 2.59-2.48 (2H, m), 2.42-2.27 (8H, m), 1.33-1.27 (6H, m), 1.08 (6H, td)
<Compound of the Formula 1-92>
 $^1$H NMR (CDCl$_3$)
  δ ppm: 8.08 (2H, d), 7.86 (2H, d), 6.98 (2H, d), 5.86 (1H, s), 3.26-3.08 (2H, m), 2.88-2.73 (1H, m), 2.68-2.52 (2H, m), 2.47-2.17 (9H, m), 1.12-1.05 (6H, m), 0.83-0.53 (4H, m)
<Compound of the Formula 1-99>
 $^1$H NMR (CDCl$_3$)
  δ ppm: 8.09 (2H, d), 7.88 (2H, d), 6.93 (2H, s), 5.59 (1H, s), 3.23 (1H, td), 3.05-2.98 (1H, m), 2.59-2.23 (9H, m), 2.06-1.97 (6H, m), 1.21 (3H, dt)

Preparation Example 1-36

Preparation of the Compound of the Formula (1-59)

<Preparation of the Compound of the Formula 1-59>

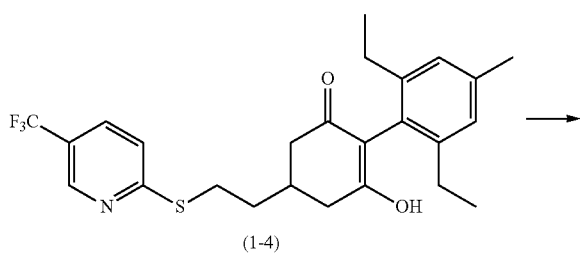

(1-4)

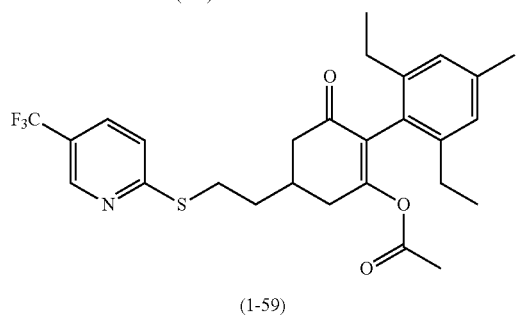

(1-59)

To the compound of the formula (1-4) 500 mg added a solution of triethylamine 175 mg in anhydrous tetrahydrofuran 3 ml. To the resulting mixtures was added a solution of acetyl chloride 170 mg in anhydrous tetrahydrofuran 1 ml under ice-cooling. The resulting mixtures were stirred at RT for 12 hours. To the reaction mixtures was added water 5 ml and the resulting mixtures were extracted with chloroform. The resulting chloroform layers were dried over anhydrous sodium sulfate, concentrated under reduced pressure and subjected to a silica gel column chromatography (eluates, ethyl acetate:hexane=1:6) to give the compound of the formula (1-59) (colorless oils) 530 mg.

$^1$H NMR (CDCl$_3$)
  δ ppm: 8.67 (1H, m), 7.67 (1H, dd), 7.27 (1H, d), 6.89 (2H, s), 3.30 (2H, t), 2.84-2.25 (12H, m), 1.98-1.89 (5H, m), 1.09-1.02 (6H, m)

The present compounds prepared according to preparation Example 1-36 are shown below.
<Compound of the Formula 1-60>
 $^1$H NMR (CDCl$_3$)
  δ ppm: 8.67 (1H, m), 7.67 (1H, dd), 7.27 (1H, d), 6.88 (2H, s), 3.31 (2H, t), 2.77-2.23 (12H, m), 2.17-2.11 (2H, m), 1.98-1.88 (2H, m), 1.05 (6H, ddd), 0.84 (3H, t)
<Compound of the Formula 1-61>
 $^1$H NMR (CDCl$_3$)
  δ ppm: 8.67 (1H, m), 7.67 (1H, dd), 7.27 (1H, d), 6.87 (2H, s), 3.31 (2H, td), 2.84-2.25 (12H, m), 1.94 (2H, dt), 1.05 (6H, dt), 0.88 (9H, s)
<Compound of the Formula 1-62>
 $^1$H NMR (CDCl$_3$)
  δ ppm: 8.67 (1H, dd), 7.67 (1H, dd), 7.27 (1H, d), 6.90 (2H, s), 3.70 (3H, s), 3.31 (2H, t), 2.92-2.26 (12H, m), 1.99-1.89 (2H, m), 1.09-1.02 (6H, m)
<Compound of the Formula 1-63>
 $^1$H NMR (CDCl$_3$)
  δ ppm: 8.67 (1H, dd), 7.67 (1H, dd), 7.27 (1H, d), 6.90 (2H, s), 4.12-4.07 (2H, m), 3.34-3.27 (2H, m), 2.91-2.27 (12H, m), 1.99-1.88 (2H, m), 1.18 (3H, t), 1.09-1.00 (6H, m)
<Compound of the Formula 1-66>
 $^1$H NMR (CDCl$_3$)
  δ ppm: 8.67 (1H, dd), 7.66 (1H, dd), 7.26 (1H, d), 6.90 (2H, s), 5.80-5.71 (1H, m), 5.21-5.15 (2H, m), 4.52-4.50 (2H, m), 3.30 (2H, t), 2.82-2.26 (12H, m), 1.97-1.88 (2H, m), 1.09-1.00 (6H, m)
<Compound of the Formula 1-67>
 $^1$H NMR (CDCl$_3$)
  δ ppm: 8.67 (1H, t), 7.66 (1H, dd), 7.35-7.18 (4H, m), 6.95 (2H, s), 6.87-6.83 (2H, m), 3.31 (2H, t), 2.99-2.29 (12H, m), 2.00-1.90 (2H, m), 1.08-1.03 (6H, m)
<Compound of the Formula 1-68>
 $^1$H NMR (CDCl$_3$)
  δ ppm: 8.69 (1H, t), 7.67 (1H, dd), 7.27 (1H, d), 6.93 (2H, s), 3.66-3.27 (2H, m), 3.06 (1H, dd), 2.84-2.76 (2H, m), 2.56-2.26 (12H, m), 1.99-1.88 (2H, m), 1.14-1.04 (6H, m)
<Compound of the Formula 1-93>
 $^1$H NMR (CDCl$_3$)
  δ ppm: 8.91 (1H, s), 8.24-8.18 (2H, m), 6.90 (2H, d), 4.13-4.05 (2H, m), 3.33 (1H, ddd), 3.07-2.24 (14H, m), 1.39-1.02 (12H, m)

Preparation Example 1-37

Preparation of the Compound of the Formula (1-64)

<Preparation of the Compound of the Formula 1-64>

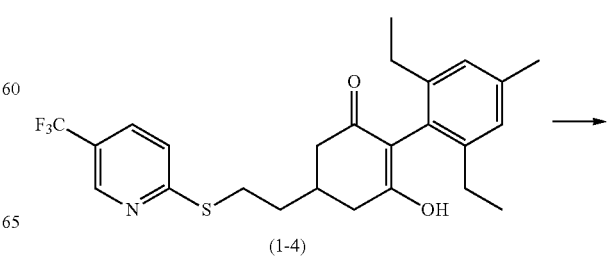

(1-4)

-continued

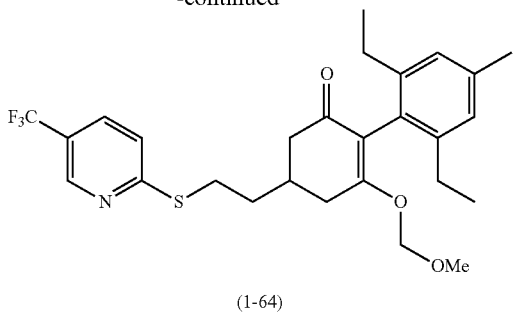
(1-64)

To 60% sodium hydrate 110 mg was added anhydrous N,N-dimethylformamide 1 ml. To the resulting mixtures was added dropwise a solution of the compound of the formula (1-4) 500 mg in anhydrous N,N-dimethylformamide 3 ml under ice-cooling. The resulting mixtures were stirred under ice-cooling for 10 minutes and then thereto was added dropwise a solution of chloromethyl methyl ether 200 mg in anhydrous N,N-dimethylformamide 1 ml and the resulting mixtures were stirred at RT for 2 hours. To the reaction mixtures was added water 5 ml and the resulting mixtures were extracted with ethyl acetate. The resulting ethyl acetate layers were washed with water, dried over anhydrous sodium sulfate and then concentrated under reduced pressure and subjected to a silica gel column chromatography (eluates, ethyl acetate:hexane=1:4) to give the compound of the formula (1-64) (yellow oils) 208 mg.

$^1$H NMR (CDCl$_3$)

δ ppm: 8.67 (1H, m), 7.67 (1H, dd), 7.27 (1H, d), 6.90 (2H, s), 4.98 (2H, s), 3.39-3.22 (5H, m), 3.03-2.25 (12H, m), 1.99-1.89 (2H, m), 1.08-1.02 (6H, m)

The present compounds prepared according to preparation Example 1-37 are shown below.

<Compound of the Formula 1-65>

$^1$H NMR (CDCl$_3$)

δ ppm: 8.67 (1H, m), 7.67 (1H, dd), 7.27 (1H, d), 6.91 (2H, s), 5.05-4.99 (2H, m), 3.56-3.51 (2H, m), 3.37-3.28 (2H, m), 3.04-2.23 (12H, m), 1.97-1.90 (2H, m), 1.17-0.99 (9H, m)

Preparation Example 1-38

Preparation of the Compound of the Formula (1-30)

<Preparation of the Compound of the Formula 9-30>

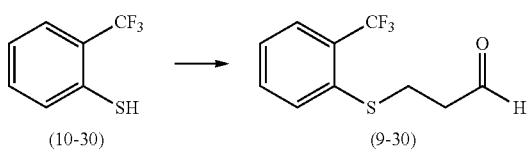 [SMILES: FC(F)(F)c1ccccc1S ; O=CCCSc1ccccc1C(F)(F)F]

At RT, the compound of the formula (10-30) 7.10 g and tetrahydrofuran 60 ml were mixed and stirred and to the resulting mixtures were added dropwise 95% acrolein 3.64 g and triethylamine 1.21 g. The resulting mixtures were stirred at RT for 5.5 hours. Thereafter, the resulting reaction solutions were concentrated under reduced pressure to give the compound of the formula (9-30) 9.32 g.

$^1$H NMR (CDCl$_3$)

δ ppm: 9.78 (1H, s), 7.67 (1H, d), 7.54-7.46 (2H, m), 7.35-7.31 (1H, m), 3.24 (2H, t), 2.80 (2H, dt)

<Preparation of the Compound of the Formula 7-30>

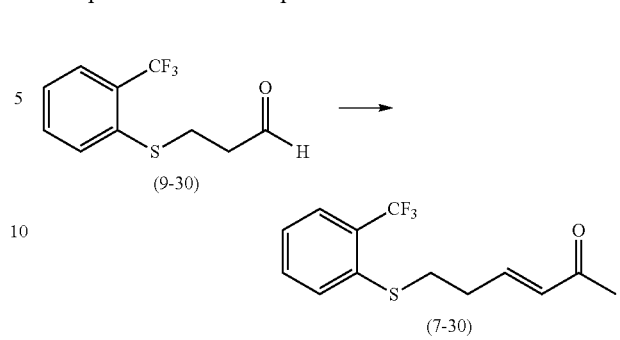

At RT, the compound of the formula (9-30) 9.32 g was dissolved in chloroform 40 ml. To the resulting solutions was added triphenylphosphine acetylmethylene 16.5 g under ice-cooling. The resulting solutions were stirred at RT for 17 hours. Thereafter, under reduced pressure, chloroform was removed from the resulting reaction solutions. To the resulting residues were added tert-butyl methyl ether and hexane. The resulting mixtures were filtered and the resulting filtrates were concentrated under reduced pressure. The resulting oils were subjected to a silica gel column chromatography (eluates, ethyl acetate:hexane=1:4) to give the compound of the formula (7-30) 9.76 g.

$^1$H NMR (CDCl$_3$)

δ ppm: 7.67 (1H, d), 7.52-7.43 (2H, m), 7.34-7.30 (1H, m), 6.79 (1H, dt), 6.11 (1H, dt), 3.10 (2H, t), 2.57 (2H, qd), 2.24 (3H, s)

<Preparation of the Compound of the Formula 6-30>

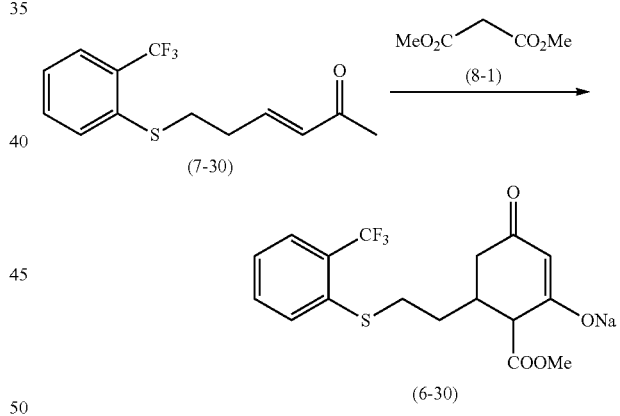

At RT, 28% sodium methoxide methanol solution 7.55 g and the compound of the formula (8-1) 5.17 g were dissolved in tetrahydrofuran 70 ml. The resulting solutions were heated under reflux for 10 minutes. Thereafter, the heating was stopped and to the resulting reaction mixtures was added the compound of the formula (7-30) 9.76 g. Thereafter, the resulting mixture solutions were heated under reflux for 2 hours. The resulting reaction solutions were cooled to rt, and the precipitated crystals were collected by filtering and washed with tert-butyl methyl ether and hexane sequentially to give the compound of the formula (6-30) 6.80 g.

$^1$H NMR (d-DMSO)

δ ppm: 7.70 (1H, d), 7.61 (2H, dd), 7.36 (1H, q), 4.39 (1H, s), 3.47 (3H, s), 3.15-3.08 (1H, m), 3.00-2.93 (1H, m), 2.83 (1H, d), 2.33-2.23 (1H, m), 2.11 (1H, dd), 1.77 (1H, dd), 1.53-1.44 (2H, m)

151

<Preparation of the Compound of the Formula 1-30>

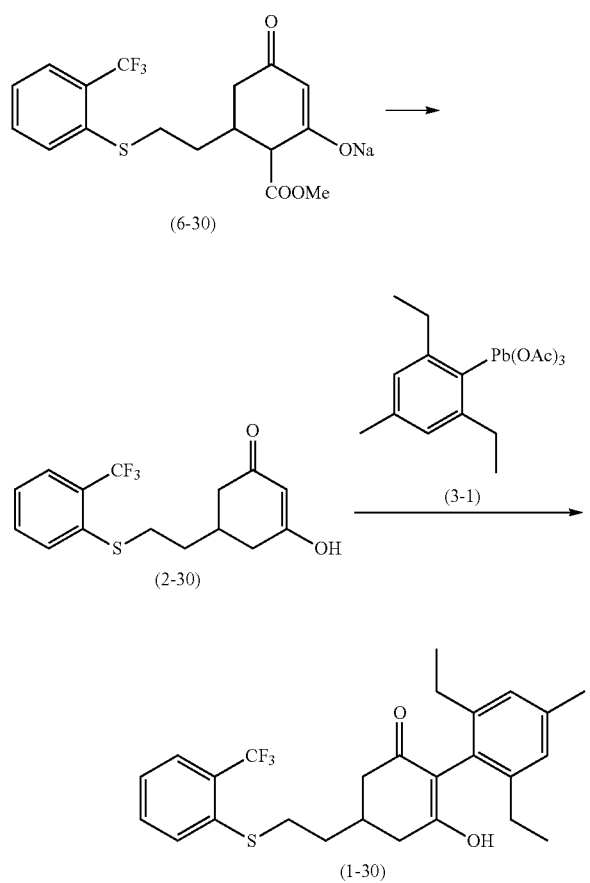

At RT, the compound of the formula (6-30) 6.80 g was dissolved in water 90 ml. To the resulting solutions was added anhydrous sodium carbonate 5.78 g. The resulting solutions were heated under reflux for 5 hours. The reaction solutions were cooled to rt and acidified with 2N hydrochloric acid. The resulting reaction solutions were extracted with ethyl acetate to give the compound of the formula (2-30) 6.01 g.

Under nitrogen atmosphere, at RT, the compound of the formula (2-30) 541 mg and dimethylaminopyridine 1.04 g were dissolved in a mixture of chloroform 5.0 ml and toluene 2.0 ml. The resulting solutions were stirred at RT under nitrogen atmosphere for 15 minutes. Thereafter, under nitrogen atmosphere, to the resulting solutions was added the compound of the formula (3-1) 1.00 g. Under nitrogen atmosphere, the resulting mixtures were stirred at 75° C. for 1.5 hours. The resulting reaction solutions were cooled to rt, adjusted to pH 1 with 2N hydrochloric acid and filtered through Celite™. The resulting filtrates were extracted with chloroform. The resulting chloroform layers were washed with water, dried over anhydrous sodium sulfate and filtered. The resulting filtrates were concentrated under reduced pressure to give yellow oils. The resulting oils were subjected to a silica gel column chromatography (eluates, ethyl acetate hexane=1:4) to give the compound of the formula (1-30) 387 mg.

$^1$H NMR (CDCl$_3$)

δ ppm: 7.67 (1H, d), 7.49 (2H, t), 7.32-7.28 (1H, m), 6.98 (2H, s), 5.54 (1H, s), 3.07 (2H, ddd), 2.69 (2H, td), 2.48-2.24 (10H, m), 1.85 (2H, q), 1.08 (3H, t), 1.05 (3H, t)

152

Preparation Example 1-39

Preparation of the Compound of the Formula (1-29)

<Preparation of the Compound of the Formula 7-29>

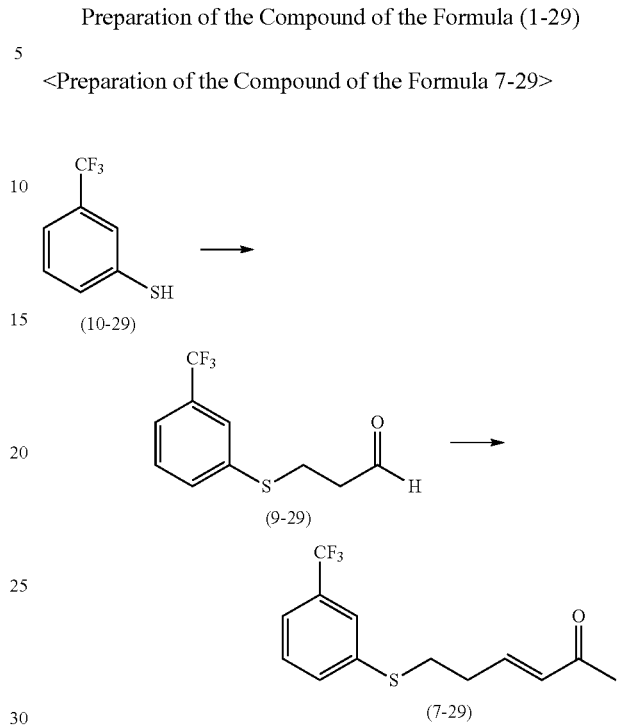

At RT, the compound of the formula (10-29) 5.0 g and tetrahydrofuran 56 ml were mixed and stirred and to the resulting mixtures were added dropwise 95% acrolein 2.56 g and triethylamine 852 mg. The resulting mixtures were stirred at RT for 2 hours. Thereafter, the resulting reaction solutions were concentrated under reduced pressure to give the compound of the formula (9-29) 6.61 g.

At RT, the compound of the formula (9-29) 6.61 g and triphenylphosphine acetylmethylene 11.6 g were dissolved in tetrahydrofuran 28 ml. The resulting solutions were stirred at RT for 5 hours. Thereafter, under reduced pressure, tetrahydrofuran was removed from the resulting reaction solutions. To the resulting residues were added tert-butyl methyl ether and hexane. The resulting mixtures were filtered and the resulting filtrates were concentrated under reduced pressure. The resulting oils were subjected to a silica gel column chromatography (eluates, ethyl acetate:hexane=1:4) to give the compound of the formula (7-29) 1.01 g.

$^1$H NMR (CDCl$_3$)

δ ppm: 7.56 (1H, s), 7.51-7.40 (3H, m), 6.78 (1H, dt), 6.13 (1H, dt), 3.10 (2H, t), 2.59 (2H, qd), 2.25 (3H, s)

<Preparation of the Compound of the Formula 6-29>

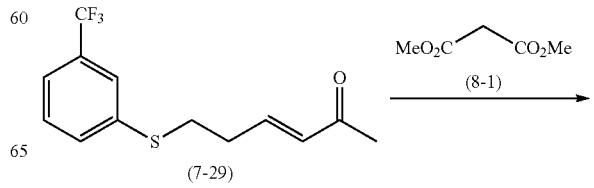

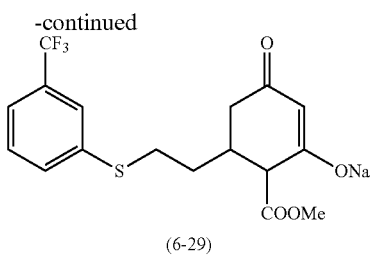

At RT, 28% sodium methoxide methanol solution 781 mg and the compound of the formula (8-1) 464 mg were dissolved in tetrahydrofuran 7 ml. The resulting solutions were heated under reflux for 10 minutes. Thereafter, the heating was stopped and to the resulting reaction mixtures was added the compound of the formula (7-29) 1.01 g. Thereafter, the resulting mixture solutions were heated under reflux for 1 hour. The resulting reaction solutions were cooled to rt and the precipitated crystals were collected by filtering and washed with tert-butyl methyl ether and hexane sequentially to give the compound of the formula (6-29) 873 mg.

$^1$H NMR (CDCl$_3$)

δ ppm: 7.57-7.51 (4H, m), 4.38 (1H, s), 3.45 (3H, s), 3.10 (1H, m), 2.96 (1H, m), 2.81 (1H, d), 2.28 (1H, m), 2.11 (1H, d), 1.75 (1H, t), 1.47 (2H, m)

<Preparation of the Compound of the Formula 1-29>

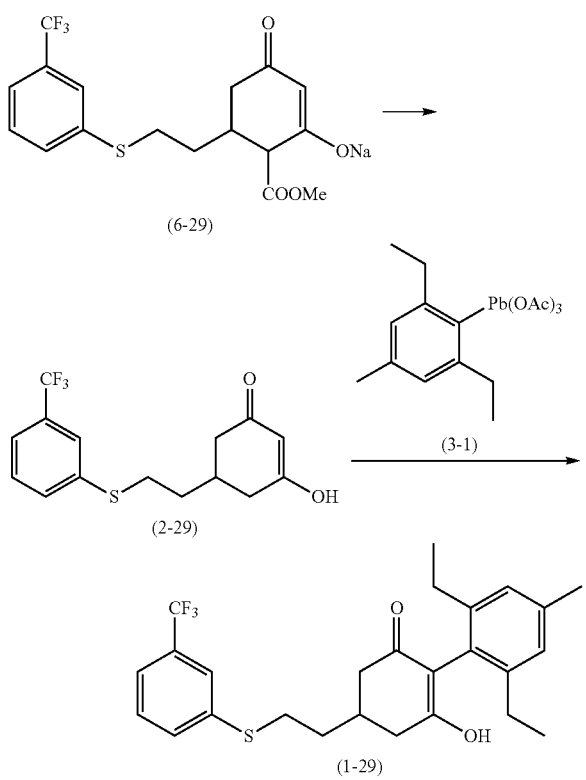

At RT, the compound of the formula (6-29) 873 mg was dissolved in water 12 ml. To the resulting solutions was added anhydrous sodium carbonate 741 mg. The resulting solutions were heated under reflux for 6.5 hours. The reaction solutions were cooled to rt and acidified with 2N hydrochloric acid. The resulting reaction solutions were extracted with ethyl acetate. The ethyl acetate layers were concentrated under reduced pressure and the resulting crystals were washed with tert-butyl methyl ether and hexane sequentially to give the compound of the formula (2-29) 434 mg.

Under nitrogen atmosphere, at RT, the compound of the formula (2-29) 430 mg and dimethylaminopyridine 831 mg were dissolved in a mixture of chloroform 4 ml and toluene 1 ml. The resulting solutions were stirred at RT under nitrogen atmosphere for 15 minutes. Thereafter, under nitrogen atmosphere, to the resulting solutions was added the compound of the formula (3-1) 795 mg. Under nitrogen atmosphere, the resulting mixtures were stirred at 80° C. four 1 hour. The resulting reaction solutions were cooled to rt, adjusted to pH 1 with 2N hydrochloric acid and filtered through Celite™. The resulting filtrates were extracted with chloroform. The resulting chloroform layers were washed with water, dried over anhydrous magnesium sulfate and filtered. The resulting filtrates were concentrated under reduced pressure to give yellow oils. The resulting oils were subjected to a silica gel column chromatography (eluates, ethyl acetate:hexane=15:85) to give the compound of the formula (1-29) 144 mg.

$^1$H NMR (CDCl$_3$)

δ ppm: 7.56 (1H, s), 7.50-7.40 (3H, m), 6.98 (2H, s), 5.54 (1H, s), 3.10-3.01 (2H, m), 2.70 (2H, t), 2.47-2.24 (10H, m), 1.86 (2H, q), 1.10-1.03 (6H, m)

Preparation Example 1-40

Preparation of the Compound of the Formula (1-41)

<Preparation of the Compound of the Formula 3-1>

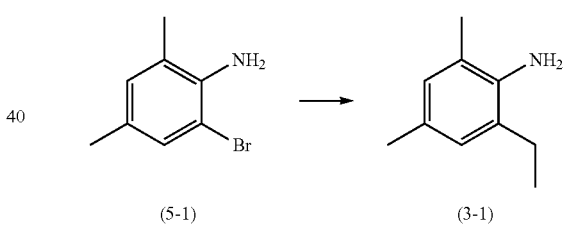

Under nitrogen atmosphere, at RT, 1,1'-bis(diphenylphosphino)ferrocene-palladium(II)dichloride-dichloromethane complex 2.04 g, cesium carbonate 48.8 g and the compound of the formula (5-1) 10 g were dissolved in N,N-dimethylformamide 125 ml. To the resulting solutions was added dropwise triethylborane (32.5 ml) (1.0M hexane solution) and the resulting mixtures were stirred at RT under nitrogen atmosphere for 16 hours. The reaction solutions were filtered through Celite™ and then to the filtrates was added water and the resulting mixtures were extracted with tert-butyl methyl ether, and the organic layers were washed with saturated saline and dried over anhydrous magnesium sulfate. The resulting organic layers were concentrated under reduced pressure and subjected to a silica gel column chromatography (eluates, ethyl acetate hexane=1:19→1:9) to give the compound of the formula (3-1) 3.18 g.

$^1$H NMR (CDCl$_3$)

δ ppm: 6.78 (2H, s), 3.49 (2H, s), 2.51 (2H, q), 2.23 (3H, s), 2.16 (3H, s), 1.24 (3H, t)

155
<Preparation of the Compound of the Formula 11-4>

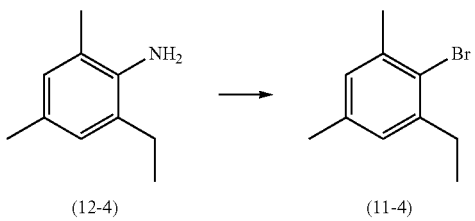

(12-4)  (11-4)

At RT, the compound of the formula (12-4) 3.18 g was dissolved in water 25 ml. To the resulting solutions was added 48% hydrogen bromide 26.6 ml and the resulting mixtures were stirred at 40° C. for 15 minutes. To the resulting reaction solutions was added dropwise 2.34M sodium nitrite aqueous solution 10 ml at 0° C. and the resulting mixtures were stirred under ice-cooling for 20 minutes. The resulting mixtures were added dropwise to a mixture that was prepared by adding 48% hydrogen bromide 26.6 ml to copper sulfate (II) pentahydrate 3.19 g and copper (powder) 1.27 g followed by cooling the resulting mixtures to 0° C. The resulting solutions were stirred at RT for 3.5 hours. The resulting reaction solutions were filtered through Celite™ and the resulting filtrates were extracted with ethyl acetate. The organic layers were washed with saturated saline and then dried over anhydrous magnesium sulfate. The resulting organic layers were concentrated under reduced pressure and subjected to a silica gel column chromatography (eluates, hexane) to give the compound of the formula (11-4) 1.91 g.

$^1$H NMR (CDCl$_3$)

δ ppm: 6.90 (1H, s), 6.88 (1H, s), 2.74 (2H, q), 2.38 (3H, s), 2.25 (3H, s), 1.21 (3H, t)

<Preparation of the Compound of the Formula 3-4>

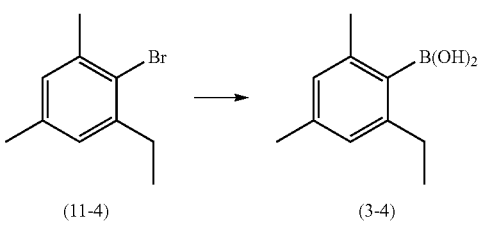

(11-4)  (3-4)

Under nitrogen atmosphere, at RT, the compound of the formula (11-4) 1.91 g were dissolved in tetrahydrofuran 23 ml. The resulting solutions were cooled to −78° C. and thereto was added dropwise n-butyllithium (1.63M hexane solution) under nitrogen atmosphere. Thereafter, under nitrogen atmosphere, the reaction solutions were stirred at 40° C. for 4 hours. The resulting solutions were cooled to −78° C. and thereto was added dropwise trimethoxyborane 1.12 g under nitrogen atmosphere and the resulting mixtures were stirred at RT for 23 hours. The resulting solutions were cooled to 0° C. and acidified with 1N hydrochloric acid. The resulting reaction solutions were extracted with chloroform, and the organic layers were washed with saturated saline and then dried over anhydrous magnesium sulfate. The organic layers were concentrated under reduced pressure and filtered and the residues were washed with hexane to give the compound of the formula (3-4) 654 mg.

$^1$H NMR (CDCl$_3$)

δ ppm: 6.86 (1H, s), 6.85 (1H, s), 4.58 (2H, d), 2.63 (2H, q), 2.35 (3H, s), 2.29 (3H, s), 1.23 (3H, t)

156
<Preparation of the Compound of the Formula 1-41>

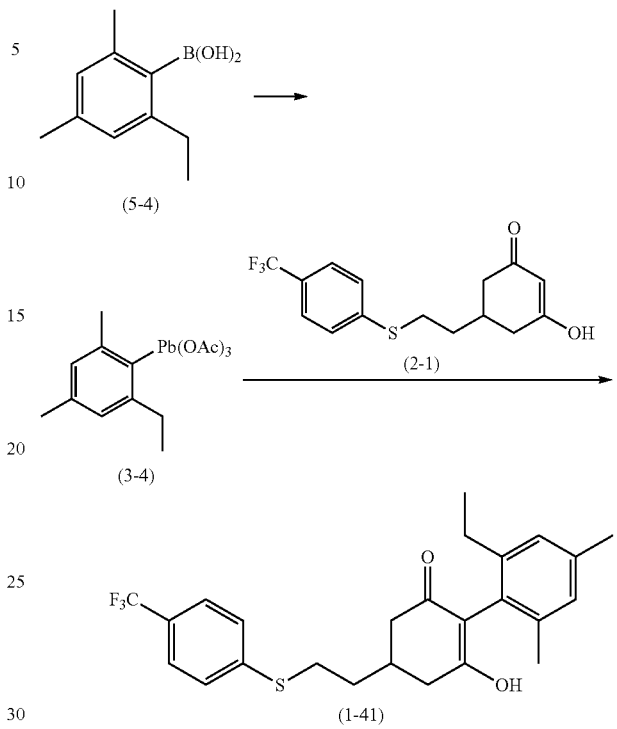

Under nitrogen atmosphere, at RT, lead tetraacetate 1.87 g, mercury acetate 58.5 mg and the compound of the formula (5-4) 654 mg were dissolved in chloroform 7 ml. The resulting solutions were stirred at RT under nitrogen atmosphere for 15 minutes. Thereafter, under nitrogen atmosphere, the reaction solutions were stirred at 45° C. for 4 hours. The reaction solutions were cooled to rt and filtered through Celite™. The resulting filtrates were concentrated under reduced pressure to give yellow oils. To the resulting oils was added hexane and the resulting mixtures were concentrated under reduced pressure to give yellow solids. Under nitrogen atmosphere, at RT, the resulting solids were dissolved in chloroform 16 ml. To the resulting solutions was added potassium carbonate 6.09 g and the resulting mixtures were stirred for 15 minutes. Thereafter, the reaction solutions were filtered through Celite™. The resulting filtrates were concentrated under reduced pressure to give the compound of the formula (3-4) 21 g.

Under nitrogen atmosphere, at RT, the compound of the formula (2-1) 332 mg and dimethylaminopyridine 644 mg were dissolved in a mixture of chloroform 3 ml and toluene 1 ml. The resulting solutions were stirred at RT under nitrogen atmosphere for 15 minutes. Thereafter, under nitrogen atmosphere, to the resulting solutions were added the compound of the formula (3-4) 600 mg. Under nitrogen atmosphere, the resulting mixtures were heated under reflux for 2 hours. The resulting reaction solutions were cooled to rt, adjusted to pH 1 with 2N hydrochloric acid and filtered through Celite™. The resulting filtrates were extracted with chloroform. The resulting chloroform layers were washed with water, dried over anhydrous magnesium sulfate and filtered. The resulting filtrates were concentrated under reduced pressure to give yellow oils. The resulting oils were subjected to a silica gel column chromatography (eluates, ethyl acetate:hexane=1: 9→3:17) to give the compound of the formula (1-41) 361 mg.

¹H NMR (CDCl₃)

δ ppm: 7.54 (2H, d), 7.37 (2H, d), 6.96 (2H, s), 5.50 (1H, s), 3.13-3.03 (2H, m), 2.71 (2H, t), 2.47-2.25 (8H, m), 2.06-2.00 (3H, m), 1.90-1.85 (2H, m), 1.10-1.02 (3H, m)

The present compounds prepared according to preparation Example 1-40 are shown below.

<Compound of the Formula 1-128>

¹H NMR (CDCl₃)

δ ppm: 7.53 (2H, d), 7.37 (3H, d), 7.23-7.12 (3H, m), 3.05 (2H, td), 2.69 (2H, d), 2.47-2.30 (3H, m), 1.87-1.81 (2H, m)

<Compound of the Formula 1-167>

¹H NMR (CDCl₃)

δ ppm: 7.55-7.49 (3H, m), 7.38-7.26 (4H, m), 7.19-7.14 (1H, m), 5.62 (1H, s), 3.07-3.06 (2H, m), 2.72-2.63 (2H, m), 2.48-2.21 (3H, m), 1.87 (2H, dt)

<Compound of the Formula 1-168>

¹H NMR (CDCl₃)

δ ppm: 8.67 (1H, s), 7.70-7.65 (2H, m), 7.38 (1H, tt), 7.29-7.23 (2H, m), 7.16 (1H, ddd), 5.58 (1H, d), 3.31 (2H, t), 2.81-2.67 (2H, m), 2.55-2.24 (3H, m), 1.97-1.88 (2H, m)

<Compound of the Formula 1-170>

¹H NMR (CDCl₃)

δ ppm: 8.63 (1H, s), 7.66 (1H, dd), 7.25 (1H, d), 6.61 (2H, s), 3.25-3.21 (2H, m), 2.69 (2H, d), 2.37-2.31 (3H, m), 1.86-1.83 (2H, m)

<Compound of the Formula 1-171>

¹H NMR (CDCl₃)

δ ppm: 7.69 (1H, ddd), 7.54 (2H, d), 7.38 (3H, d), 7.28-7.13 (2H, m), 5.58 (1H, s), 3.07 (2H, q), 2.77-2.25 (5H, m), 1.91-1.85 (2H, m)

Preparation Example 1-41

Preparation of the Compound of the Formula (1-105)

<Preparation of the Compound of the Formula 31-2>

Under nitrogen atmosphere, at RT, the compound of the formula (32-2) 2.52 g was dissolved in tetrahydrofuran 15 ml. The resulting solutions were cooled to −78° C. and thereto was added n-butyllithium 10 ml (1.6M hexane solution) and the resulting mixtures were stirred for 1 hour. Thereafter, thereto was added a suspension of trichlorobismuth 1.44 g in tetrahydrofuran 10 ml and the resulting mixtures were stirred for about 1 hour with heating to rt. To the resulting reaction solutions was added water 20 ml and the resulting mixtures were filtered through Celite™. The filtrates were extracted with chloroform. The resulting chloroform layers were washed with saturated saline, dried over anhydrous magnesium sulfate and then filtered, and the resulting filtrates were concentrated under reduced pressure to give the compound of the formula (33-2) as crude products 2.18 g.

Continuously, at RT, the compound of the formula (33-2) 2.18 g as crude products were dissolved in dehydrated chloroform 5 ml and the resulting mixtures were cooled to 0° C. and then thereto was added sulfuryl chloride 0.55 ml. Thereafter, the resulting mixtures were warmed to rt and stirred for 30 minutes. To the resulting reaction solutions was added tert-butyl methyl ether to precipitate crystals and then the resulting mixtures were concentrated under reduced pressure and filtered to give the compound of the formula (31-2) 1.86 g.

¹H NMR (d-DMSO)

δ ppm: 8.03 (3H, dd), 7.62 (3H, t), 7.51 (3H, d), 7.34 (3H, t), 3.82 (9H, s)

<Preparation of the Compound of the Formula 1-105>

Under nitrogen atmosphere, at RT, the compound of the formula (2-9) 475 mg, diazabicyclo[5.4.0]undeca-7-ene 274 mg and the compound of the formula (31-2) 1.08 g were dissolved in a mixture of chloroform 1 ml and toluene 5 ml and the resulting mixtures were stirred at RT under nitrogen atmosphere for 24 hours. The resulting reaction solutions were diluted with chloroform and washed with hydrochloric acid adjusted to pH 1 to 2, and continuously, washed with saturated saline. Thereafter, the resulting organic layers were dried over anhydrous magnesium sulfate and then filtered, and the resulting filtrates were concentrated under reduced pressure to give oils. The resulting oils were subjected to a silica gel column chromatography (eluates, ethyl acetate:hexane=1:9→3:7) to give the compound of the formula (1-105) 72.4 mg.

¹H NMR (CDCl₃)

δ ppm: 7.53 (2H, d), 7.38-7.34 (3H, m), 7.14-6.98 (3H, m), 6.30 (1H, s), 3.80 (3H, s), 3.10-3.02 (2H, m), 2.73-2.65 (2H, m), 2.47-2.39 (2H, m), 2.31-2.24 (1H, m), 1.88-1.82 (2H, m)

Preparation Example 1-42

Preparation of the Compound of the Formula (1-96)

<Preparation of the Compound of the Formula 31-3>

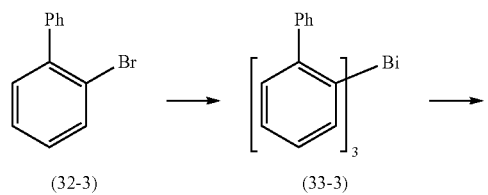

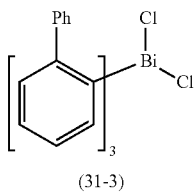

Under nitrogen atmosphere, at RT, the compound of the formula (32-3) 3.20 g were dissolved in tetrahydrofuran 15 ml. The resulting solutions were cooled to −78° C. and thereto was added n-butyllithium 10 ml (1.6M hexane solution) and the resulting mixtures were stirred for 1 hour. Thereafter, thereto was added a suspension of trichlorobismuth 1.44 g in tetrahydrofuran 10 ml and the resulting mixtures were stirred for 1 hour with heating to rt. To the resulting reaction solutions was added water 20 ml and the aqueous layers were extracted with chloroform. The resulting chloroform layers were washed with saturated saline, dried over anhydrous magnesium sulfate and then filtered, and the resulting filtrates were concentrated under reduced pressure to give the compound of the formula (33-3) 3.07 g.

Continuously, the resulting compound of the formula (33-3) 3.07 g as crude products was dissolved in dehydrated chloroform 5 ml at RT and the resulting mixtures were cooled to 0° C. and then thereto was added sulfuryl chloride 0.55 ml. Thereafter, the resulting mixtures were warmed to rt and stirred for 30 minutes. The resulting reaction solutions were concentrated under reduced pressure, and to the resulting oils was added hexane to precipitate crystals. The resulting crystals were filtered to give the compound of the formula (31-3) 1.25 g.

$^1$H NMR (CDCl$_3$)

δ ppm: 8.11 (3H, d), 7.51-7.45 (9H, m), 7.30 (6H, d), 7.19-7.15 (3H, m), 7.05 (6H, t)

<Preparation of the Compound of the Formula 1-96>

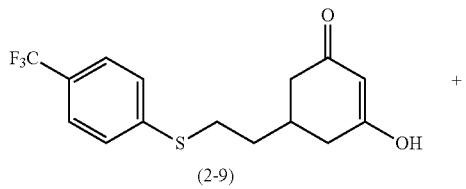

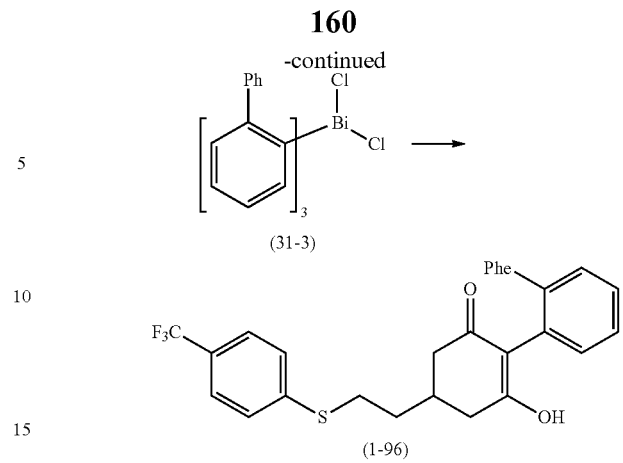

Under nitrogen atmosphere, at RT, the compound of the formula (2-9) 3.16 mg, 1,8-diazabicyblo[5.4.0]undeca-7-ene 183 mg and the compound of the formula (31-3) 887 mg were dissolved in a mixture of chloroform 1 ml and toluene 4 ml and the resulting mixtures were stirred at RT under nitrogen atmosphere for 24 hours. The resulting reaction solutions were diluted with chloroform and the resulting diluted solutions were washed with hydrochloric acid adjusted to pH 1 to 2 and continuously, washed with saturated saline. Thereafter, the resulting organic layers were dried over anhydrous magnesium sulfate and filtered, and the resulting filtrates were concentrated under reduced pressure to give oils. The resulting oils were subjected to a silica gel column chromatography (eluates, ethyl acetate:hexane=3:7) to give the compound of the formula (1-96) 99 mg.

$^1$H NMR (CDCl$_3$)

δ ppm: 7.54-7.17 (13H, m), 5.66 (1H, s), 3.02 (2H, m), 2.73 (2H, m), 2.59-2.17 (3H, m), 1.82-1.77 (2H, m)

The present compounds prepared according to preparation Example 1-42 are shown below.

<Compound of the Formula 1-42>

$^1$H NMR (CDCl$_3$)

δ ppm: 7.79 (1H, d), 7.63-7.53 (4H, m), 7.38 (2H, d), 7.20 (1H, dd), 5.40 (1H, s), 3.06 (2H, t), 2.75-2.25 (5H, m), 1.86 (2H, dt)

<Compound of the Formula 1-166>

$^1$H NMR (CDCl$_3$)

δ ppm: 7.54 (2H, d), 7.38 (2H, d), 7.31-7.06 (3H, m), 7.04 (1H, m), 5.65 (1H, d), 3.11-3.03 (2H, m), 2.75-2.65 (2H, m), 2.49-2.39 (2H, m), 2.32-2.23 (1H, m), 2.11 (3H, d), 1.87 (2H, q)

Preparation Example 1-43

Preparation of the Compound of the Formula (1-102)

<Preparation of the Compound of the Formula 32-4>

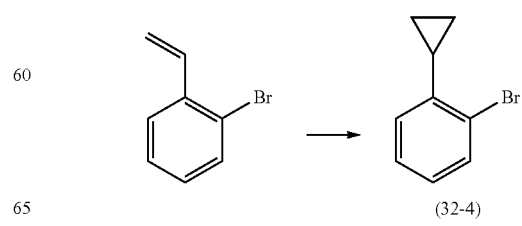

Under nitrogen atmosphere, under ice-cooling, diethylzinc 20 ml (1.0M hexane solution) was dissolved in dichloromethane 20 ml and thereto was added a solution of trifluoroacetic acid 2.28 g in dichloromethane 20 ml. The resulting mixture solutions were stirred under ice-cooling for 20 minutes and thereto was added a solution of diiodomethane 5.36 g in dichloromethane 20 ml and the resulting mixtures were stirred for 20 minutes. To resulting solutions was added a solution of 2-bromostyrene 1.83 g in dichloromethane 10 ml under ice-cooling and the resulting mixtures were stirred at RT for 6 hours. To the resulting reaction solutions was added 2N hydrochloric acid to make the mixtures pH 1 to 2 and then the resulting mixtures were extracted with hexane. The organic layers were washed with saturated saline, dried over anhydrous magnesium sulfate and filtered, and the resulting filtrates were concentrated under reduced pressure to give the compound of the formula (32-4) 1.76 g as crude products.

$^1$H NMR (CDCl$_3$)

δ ppm: 7.54 (1H, dd), 7.20 (1H, td), 7.02 (1H, td), 6.93 (1H, dd), 2.16 (1H, tt), 1.01 (2H, ddd), 0.68 (2H, dt)

<Preparation of the Compound of the Formula 31-4>

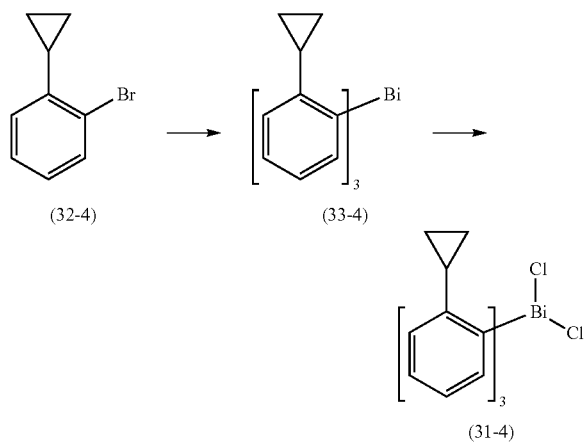

Under nitrogen atmosphere, at RT, the compound of the formula (32-4) 1.76 g was dissolved in tetrahydrofuran 9 ml. The resulting solutions were cooled to −78° C. and thereto added n-butyllithium 6.6 ml (1.6M hexane solution) and the resulting mixtures were stirred for 30 minutes. Thereafter, to the resulting mixtures was added a suspension of trichlorobismuth 939 mg in tetrahydrofuran 5 ml and the resulting mixtures were stirred for 1 hour with heating to rt. To the resulting reaction solutions was added water 20 ml and the resulting mixtures were extracted with chloroform. The resulting chloroform layers were washed with saturated saline, dried over anhydrous magnesium sulfate and then filtered, and the resulting filtrates were concentrated under reduced pressure to give the compound of the formula (33-4) 2.27 g as crude products.

Continuously, at RT, the resulting compound of the formula (33-4) 2.27 g as crude products was dissolved in dehydrated chloroform 5 ml and the resulting mixtures were cooled to 0° C., and thereto was added sulfuryl chloride 0.36 ml. Thereafter, the resulting mixtures were warmed to rt and stirred for 1 hour. To the resulting reaction solutions was added tert-butyl methyl ether to precipitate crystals and the resulting mixtures were concentrated under reduced pressure. The resulting crystals were filtered to give the compound of the formula (31-4) 1.05 g.

$^1$H NMR (d-DMSO)

δ ppm: 7.92 (3H, t), 7.58-7.52 (6H, m), 7.26 (3H, t), 2.36-2.28 (3H, m), 1.03-0.94 (12H, m)

<Preparation of the Compound of the Formula 1-102>

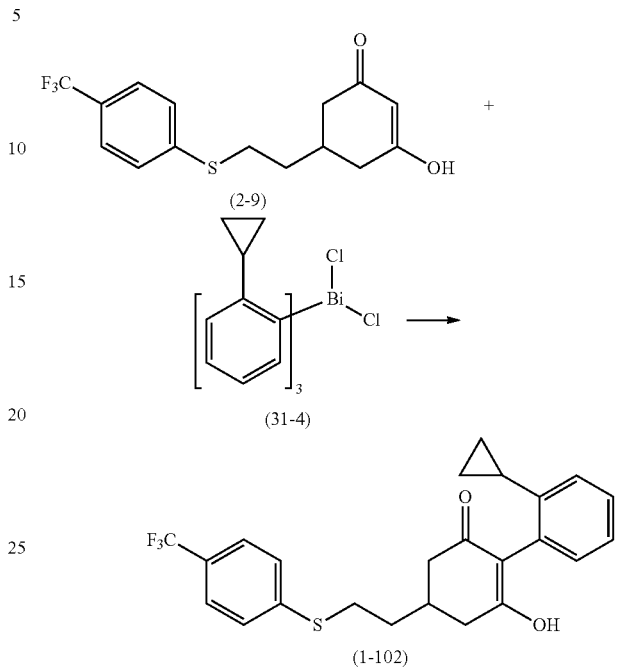

Under nitrogen atmosphere, at RT, the compound of the formula (2-9) 3.16 mg, 1,8-diazabicyclo[5.4.0]undeca-7-ene 183 mg and the compound of the formula (31-4) 887 mg were dissolved in a mixture of chloroform 1 ml and toluene 4 ml. Under nitrogen atmosphere, at RT, the resulting mixtures were stirred for about 24 hours. The resulting reaction solutions were diluted with chloroform and washed with hydrochloric acid adjusted to pH 1 to 2 and continuously, washed with saturated saline. Thereafter, the resulting organic layers were dried over anhydrous magnesium sulfate and filtered, and the resulting filtrates were concentrated under reduced pressure to give oils. The resulting oils were subjected to a silica gel column chromatography (eluates, ethyl acetate hexane=3:7) to give the compound of the formula (1-102) 56 mg.

$^1$H NMR (CDCl$_3$)

δ ppm: 7.54 (2H, d), 7.38-7.22 (4H, m), 7.06-7.00 (2H, m), 5.76 (1H, d), 3.08-3.02 (2H, m), 2.75-2.68 (2H, m), 2.55-2.10 (4H, m), 1.90-1.86 (2H, m), 0.87-0.65 (3H, m), 0.57-0.47 (1H, m)

Preparation Example 1-44

Preparation of the Compound of the Formula (1-71)

<Preparation of the Compound of the Formula 23-2>

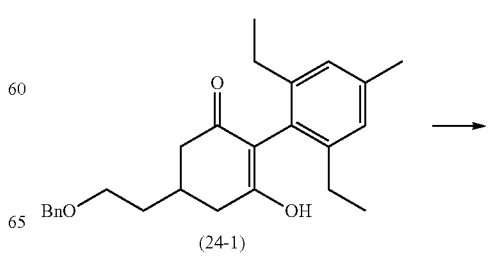

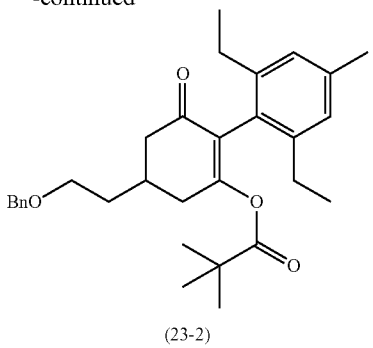

(23-2)

The compound of the formula (24-1) 6.60 g and diisopropylethylamine 5.43 g were dissolved in anhydrous N,N-dimethylformamide 50 ml. To the resulting mixtures was added dropwise pivaloyl chloride under ice-cooling, and the resulting mixtures were stirred at RT for 30 minutes. To the resulting reaction mixtures was added water and the resulting mixtures were extracted with tert-butyl methyl ether. The organic layers were dried over anhydrous magnesium sulfate, concentrated under reduced pressure to give crude products. These crude products were subjected to a silica gel column chromatography (eluates, ethyl acetate:hexane=3:17) to give the compound of the formula (23-2) 7.14 g.

$^1$H NMR (CDCl$_3$)

δ ppm: 7.38-7.26 (5H, m), 6.87 (2H, s), 4.53 (2H, dd), 3.63-3.54 (2H, m), 2.75-2.22 (12H, m), 1.86-1.76 (2H, m), 1.10-1.03 (6H, m), 0.87 (9H, s)

<Preparation of the Compound of the Formula 22-2>

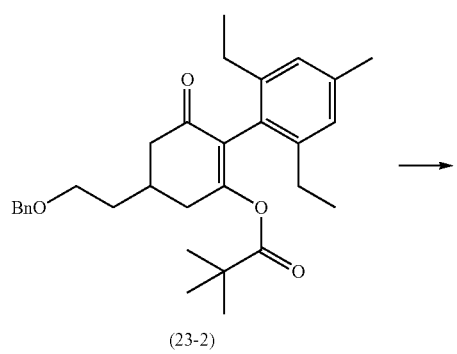

(23-2)

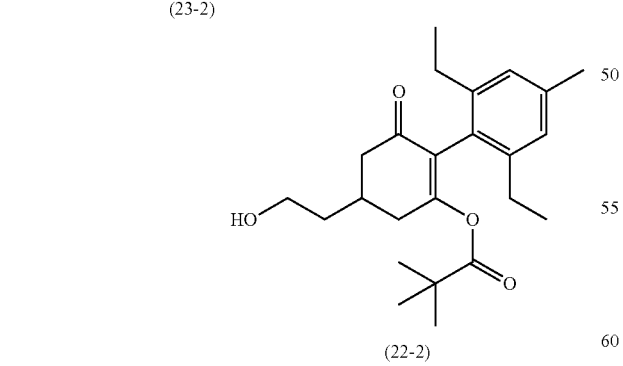

(22-2)

The compound of the formula (23-2) 7.14 g was dissolved in ethyl acetate 45 ml. To the resulting mixture solutions was added 10% palladium-carbon 3.57 g and the resulting mixtures were stirred at 35° C. under hydrogen atmosphere for 18 hours. The reaction mixture solutions were filtered through Celite™ and the resulting filtrates were concentrated under reduced pressure to give the compound of the formula (22-2) 5.10 g.

$^1$H NMR (CDCl$_3$)

δ ppm: 6.87 (2H, s), 3.81 (2H, d), 2.78-2.24 (12H, m), 1.83-1.73 (2H, m), 1.39-1.36 (1H, m), 1.10-1.04 (6H, m), 0.87 (9H, s)

<Preparation of the Compound of the Formula 21-1>

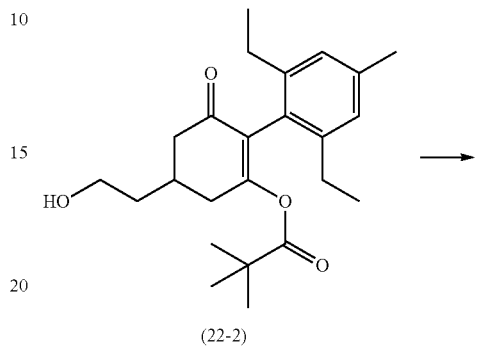

(22-2)

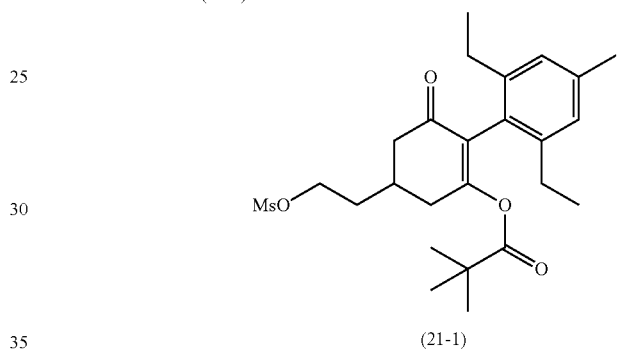

(21-1)

The compound of the formula (21-2) 193 mg and diisopropylethylamine 162 mg were dissolved in N,N-dimethylformamide 5 ml. To the resulting mixtures was added dropwise methanesulfonyl chloride 68.7 mg under ice-cooling and the resulting mixtures were stirred at RT for 1 hour. To the reaction mixtures was added water and the resulting mixtures were extracted with tert-butyl methyl ether. The organic layers were dried over anhydrous magnesium sulfate and concentrated under reduced pressure. To the residues added hexane and the resulting mixtures were filtered to give the compound of the formula (21-1) 208 mg.

$^1$H NMR (CDCl$_3$)

δ ppm: 6.87 (2H, s), 4.37 (2H, dd), 3.05 (3H, s), 2.74-2.25 (12H, m), 2.00-1.97 (2H, m), 1.10-1.04 (6H, m), 0.88 (9H, s)

<Preparation of the Compound of the Formula 1-71>

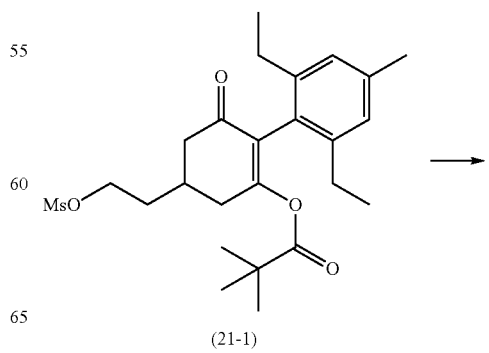

(21-1)

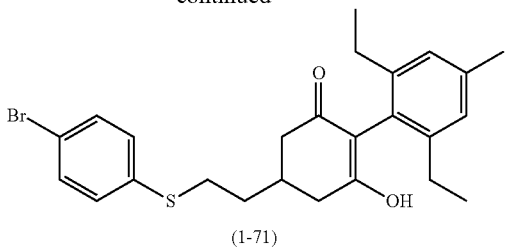

(1-71)

The compound of the formula (21-1) 200 mg and diisopropylethylamine 167 mg were dissolved in N,N-dimethylformamide 5 ml. To the resulting mixture solutions was added para-bromothiophenol 195 mg and the resulting mixtures were stirred at RT for 16 hours. The resulting mixtures were heated to 80° C. and stirred for 2 hours and then thereto was added water and the resulting mixtures were extracted with tert-butyl methyl ether. The resulting organic layers were washed with water, dried over anhydrous magnesium sulfate and filtered. The resulting filtrates were concentrated under reduced pressure and subjected to a silica gel column chromatography (eluates, ethyl acetate:hexane=0:100→1:4) to give the compound of the formula (1-71) 193 mg.

$^1$H NMR (CDCl$_3$)

δ ppm: 7.42 (2H, dt), 7.21 (2H, dt), 6.98 (2H, s), 5.61 (1H, s), 3.05-2.93 (2H, m), 2.73-2.64 (2H, m), 2.48-2.21 (10H, m), 1.81 (2H, q), 1.10-1.03 (6H, m)

Preparation Example 1-45

Preparation of the Compound of the Formula (1-132)

<Preparation of the Compound of the Formula 1-132>

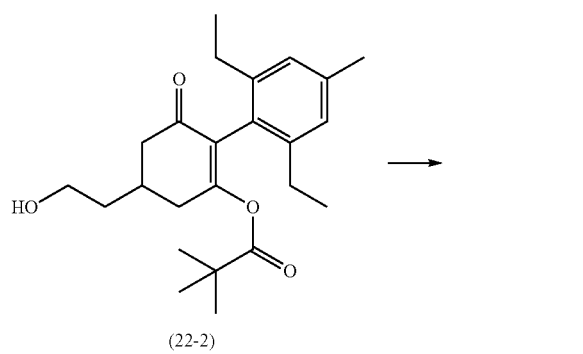

(22-2)

(1-132)

The compound of the formula (22-2) 193 mg and diisopropylethylamine 258 mg were dissolved in N,N-dimethylformamide 5 ml. To the resulting mixtures was added dropwise methanesulfonyl chloride 68.7 mg under ice-cooling and the resulting mixtures were stirred at RT for 30 minutes. To the resulting mixture solutions was added 2-mercaptopyridine 123 mg and the resulting mixtures were stirred at 80° C. for 9 hours. To the resulting reaction solutions was added 2N hydrochloric acid to adjust them to pH 1 and the resulting mixtures were extracted with tert-butyl methyl ether. The resulting organic layers were washed with water, dried over anhydrous magnesium sulfate and filtered. The resulting filtrates were concentrated under reduced pressure and subjected to a silica gel column chromatography (eluates, ethyl acetate:hexane=7:13) to give the compound of the formula (1-132) 171 mg.

$^1$H NMR (CDCl$_3$)

δ ppm: 8.52 (2H, dd), 6.98 (1H, dt), 6.87 (2H, d), 3.30-3.18 (2H, m), 2.85-2.67 (2H, m), 2.57-2.23 (10H, m), 1.96 (2H, q), 1.09-1.02 (6H, m), 0.87 (9H, s)

Preparation Example 1-46

Preparation of the Compound of the Formula (1-34)

<Preparation of the Compound of the Formula 1-34>

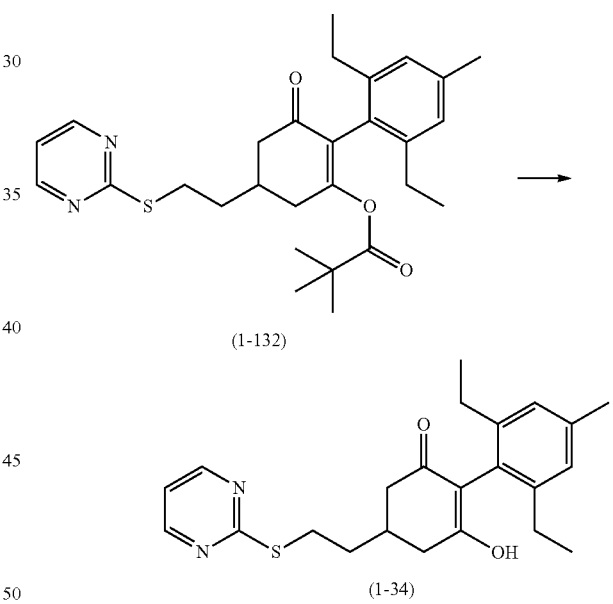

(1-132)

(1-34)

The compound of the formula (1-132) 170 mg was dissolved in a mixture solution of tetrahydrofuran 10 ml, methanol 10 ml and water 10 ml. To the resulting solutions was added lithium hydroxide monohydrate 44.5 mg and the resulting mixtures were stirred at RT for 10 minutes. The reaction solutions were concentrated under reduced pressure and adjusted with 2N hydrochloric acid to pH 1 and the resulting mixtures were extracted with tert-butyl methyl ether. The resulting organic layers were washed with water, dried over anhydrous magnesium sulfate and filtered. The resulting filtrates were concentrated under reduced pressure and subjected to a silica gel column chromatography (eluates, ethyl acetate:hexane=2:3) to give the compound of the formula (1-34) 126 mg.

$^1$H NMR (CDCl$_3$)

δ ppm: 8.53 (2H, d), 7.00-6.96 (3H, m), 5.57 (1H, s), 3.29-3.21 (2H, m), 2.81-2.73 (2H, m), 2.51-2.43 (2H, m), 2.41-2.25 (8H, m), 1.95 (2H, s), 1.09-1.03 (6H, m)

Preparation Example 1-47

Preparation of the Compound of the Formula (1-104)

<Preparation of the Compound of the Formula 1-104>

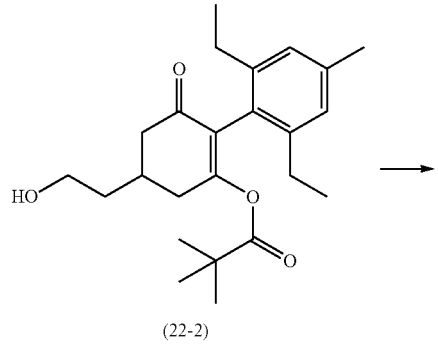

(22-2)

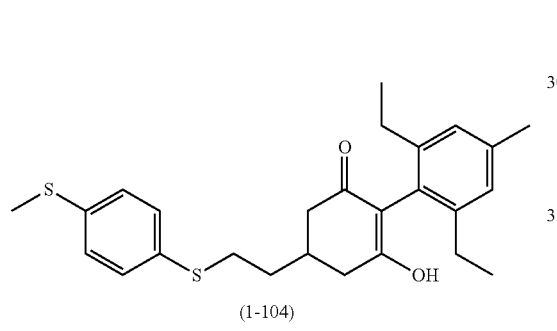

(1-104)

Preparation Example 1-48

Preparation of the Compound of the Formula (1-133)

<Preparation of the Compound of the Formula 1-133>

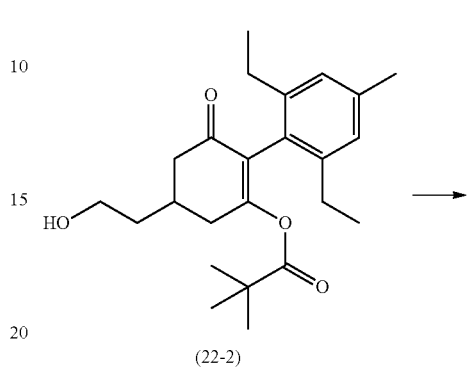

(22-2)

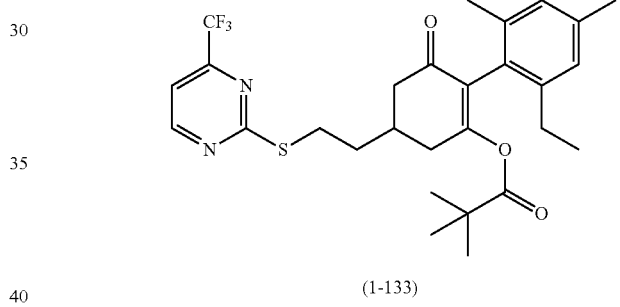

(1-133)

The compound of the formula (22-2) 178 mg and diisopropylethylamine 238 mg were dissolved in N,N-dimethylformamide 5 ml. To the resulting mixtures was added dropwise methanesulfonyl chloride 63.3 mg under ice-cooling and the resulting mixtures were stirred at RT for 30 minutes. To the resulting solutions was added para(methylthio)thiophenol 158 mg and the resulting mixtures were stirred at RT for 1.5 hours. To the resulting reaction solutions was added 2N hydrochloric acid to make them pH 1 and the resulting mixtures were extracted with tert-butyl methyl ether. The resulting organic layers were washed with water, dried over anhydrous magnesium sulfate and filtered. The filtrates were concentrated under reduced pressure and subjected to a silica gel column chromatography (eluates, ethyl acetate:hexane=1:9→7:13) to give the compound of the formula (1-104) 100 mg.

$^1$H NMR (CDCl$_3$)

δ ppm: 7.30 (2H, dt), 7.20 (2H, dt), 6.98 (2H, s), 5.58 (1H, s), 2.97 (2H, td), 2.70-2.64 (2H, m), 2.47 (3H, s), 2.45-2.22 (10H, m), 1.80 (2H, q), 1.10-1.03 (6H, m)

The compound of the formula (22-2) 387 mg and diisopropylethylamine 516 mg were dissolved in N,N-dimethylformamide 10 ml. To the resulting mixtures was added dropwise methanesulfonyl chloride 137 mg under ice-cooling and the resulting mixtures were stirred at RT for 1 hour. To the resulting mixture solutions was added 4-trifluoromethyl-2-pyrimidinethiol 396 mg and the resulting mixtures were stirred at 80° C. for 30 minutes. To the reaction solutions was added 2N hydrochloric acid to adjust them to pH 1 and then the resulting mixtures were extracted with tert-butyl methyl ether. The resulting organic layers were washed with water, dried over anhydrous magnesium sulfate and filtered. The resulting filtrates were concentrated under reduced pressure and subjected to a silica gel column chromatography (eluates, ethyl acetate:hexane=1:3) to give the compound of the formula (1-133) 546 mg.

$^1$H NMR (CDCl$_3$)

δ ppm: 8.76 (1H, d), 7.29 (1H, d), 6.87 (2H, d), 3.33-3.23 (2H, m), 2.82-2.68 (3H, m), 2.59-2.24 (9H, m), 1.97 (2H, q), 1.10-1.03 (6H, m), 0.88 (9H, s)

Preparation Example 1-49

Preparation of the Compound of the Formula (1-35)

<Preparation of the Compound of the Formula 1-35>

(1-133)

→

(1-35)

The compound of the formula (1-133) 546 mg was dissolved in a mixture solution of tetrahydrofuran 10 ml, methanol 10 ml and water 10 ml. To the resulting solutions was added lithium hydroxide monohydrate 126 mg, and the resulting mixtures were stirred at RT for 20 minutes. The reaction solutions were concentrated under reduced pressure and thereto was added 2N hydrochloric acid to make them pH 1 and then the resulting mixtures were extracted with tert-butyl methyl ether. The resulting organic layers were washed with water, dried over anhydrous magnesium sulfate and filtered. The resulting filtrates were concentrated under reduced pressure and subjected to a silica gel column chromatography (eluates, ethyl acetate:hexane=1:3) to give the compound of the formula (1-35) 435 mg.

$^1$H NMR (CDCl$_3$)

δ ppm: 8.76 (1H, d), 7.29 (1H, d), 6.99 (2H, d), 5.62 (1H, s), 3.27 (2H, td), 2.78-2.71 (2H, m), 2.51-1.93 (12H, m), 1.07 (6H, m)

The present compounds prepared according to preparation Example 1-49 are shown below.

<Compound of the Formula 1-136>

$^1$H NMR (CDCl$_3$)

δ ppm: 7.38 (1H, t), 7.26 (1H, m), 7.10 (2H, m), 6.98 (2H, s), 5.51 (1H, s), 3.00 (2H, t), 2.77 (2H, t), 2.50-2.20 (10H, m), 1.79 (2H, q), 1.06 (6H, q)

<Compound of the Formula 1-137>

$^1$H NMR (CDCl$_3$)

δ ppm: 7.37 (1H, d), 7.30-7.20 (2H, m), 7.15-7.06 (1H, m), 6.98 (2H, s), 5.51 (1H, s), 3.02 (2H, q), 2.71 (2H, t), 2.51-2.22 (10H, m), 1.87 (2H, q), 1.06 (6H, q)

<Compound of the Formula 1-138>

$^1$H NMR (CDCl$_3$)

δ ppm: 7.57 (1H, d), 7.55-7.25 (2H, m), 7.07-7.04 (1H, m), 6.98 (2H, s), 5.51 (1H, s), 3.04-3.00 (2H, m), 2.71 (2H, t), 2.50-2.28 (10H, m), 1.89 (2H, q), 1.06 (6H, q)

<Compound of the Formula 1-139>

$^1$H NMR (CDCl$_3$)

δ ppm: 7.28-7.26 (1H, d), 7.19-7.05 (3H, m), 6.97 (2H, s), 5.51 (1H, s), 2.98 (2H, t), 2.70 (2H, t), 2.50-2.20 (10H, m), 1.85 (2H, q), 1.06 (6H, q)

<Compound of the Formula 1-140>

$^1$H NMR (CDCl$_3$)

δ ppm: 7.30-7.18 (4H, m), 6.97 (2H, s), 5.46 (1H, s), 3.00 (2H, t), 2.78 (2H, q), 2.65 (2H, t), 2.50-2.21 (10H, m), 1.84 (2H, q), 1.23 (3H, t), 1.06 (6H, q)

<Compound of the Formula 1-141>

$^1$H NMR (CDCl$_3$)

δ ppm: 7.34-7.10 (4H, m), 6.97 (2H, s), 5.53 (1H, s), 3.55-3.45 (1H, m), 2.98 (2H, t), 2.70 (2H, t), 2.50-2.22 (10H, m), 1.85 (2H, q), 1.24 (6H, d), 1.06 (6H, q)

<Compound of the Formula 1-142>

$^1$H NMR (CDCl$_3$)

δ ppm: 7.32-7.19 (4H, m), 6.98-6.84 (4H, m), 5.53 (1H, s), 3.91 (3H, s), 3.08-2.94 (2H, m), 2.69 (2H, t), 2.48-2.20 (10H, m), 1.80 (2H, q), 1.24 (6H, d), 1.06 (6H, q)

<Compound of the Formula 1-143>

$^1$H NMR (CDCl$_3$)

δ ppm: 7.30-7.20 (1H, m), 7.10-6.98 (4H, m), 6.90-6.80 (1H, t), 5.52 (1H, s), 3.05-3.00 (2H, m), 2.70 (2H, t), 2.49-2.23 (10H, m), 1.83 (2H, q), 1.06 (6H, q)

<Compound of the Formula 1-144>

$^1$H NMR (CDCl$_3$)

δ ppm: 7.30-7.15 (4H, m), 6.97 (2H, s), 5.54 (1H, s), 3.05-3.00 (2H, m), 2.70 (2H, t), 2.48-2.22 (10H, m), 1.85 (2H, q), 1.06 (6H, q)

<Compound of the Formula 1-145>

$^1$H NMR (CDCl$_3$)

δ ppm: 7.48 (1H, s), 7.31-7.11 (3H, m), 6.95 (2H, s), 5.53 (1H, s), 3.09-3.00 (2H, m), 2.70 (2H, t), 2.47-2.25 (10H, m), 1.85 (2H, q), 1.06 (6H, q)

<Compound of the Formula 1-146>

$^1$H NMR (CDCl$_3$)

δ ppm: 7.20-7.10 (3H, m), 7.12-6.98 (3H, m), 5.51 (1H, s), 3.01-2.95 (2H, m), 2.65 (2H, t), 2.45-2.20 (13H, m), 1.82 (2H, q), 1.06 (6H, q)

<Compound of the Formula 1-147>

$^1$H NMR (CDCl$_3$)

δ ppm: 7.30-7.12 (3H, m), 6.98 (2H, s), 5.48 (1H, s), 3.10-3.00 (2H, m), 2.72 (2H, t), 2.52-2.22 (10H, m), 1.89 (2H, q), 1.06 (6H, q)

<Compound of the Formula 1-148>

$^1$H NMR (CDCl$_3$)

δ ppm: 7.12-7.05 (3H, m), 6.92 (2H, s), 5.50 (1H, s), 2.71 (2H, t), 2.55 (6H, s), 2.61 (2H, t), 2.42-2.17 (10H, m), 1.80 (2H, q), 1.06 (6H, q)

<Compound of the Formula 1-149>

$^1$H NMR (CDCl$_3$)

δ ppm: 7.36 (1H, dd), 7.14 (1H, dd), 6.99 (1H, dd), 6.96 (2H, s), 5.80 (1H, s), 2.86 (2H, t), 2.67-2.59 (2H, m), 2.47-2.18 (10H, m), 1.78 (2H, q), 1.07 (3H, t), 1.05 (3H, t)

<Compound of the Formula 1-150>

$^1$H NMR (CDCl$_3$)

δ ppm: 7.68 (1H, d), 7.24 (1H, d), 6.99 (2H, s), 5.49 (1H, s), 3.32 (2H, t), 2.76-2.68 (2H, m), 2.46-2.25 (10H, m), 1.97 (2H, q), 1.08 (3H, t), 1.05 (3H, t)

<Compound of the Formula 1-151>

$^1$H NMR (CDCl$_3$)

δ ppm: 7.88 (2H, d), 7.33 (2H, d), 6.99 (2H, s), 5.52 (1H, s), 3.10 (2H, dt), 2.75-2.69 (2H, m), 2.58 (3H, s), 2.47-2.24 (10H, m), 1.90 (2H, q), 1.09 (3H, t), 1.05 (3H, t)

<Compound of the Formula 1-152>

¹H NMR (CDCl₃)

δ ppm: 7.31 (2H, d), 6.97 (2H, s), 6.78 (2H, d), 5.57 (1H, s), 5.18 (1H, s), 2.89 (2H, t), 2.68-2.61 (2H, m), 2.43-2.18 (10H, m), 1.76 (2H, q), 1.08 (3H, t), 1.04 (3H, t)

<Compound of the Formula 1-153>

¹H NMR (CDCl₃)

δ ppm: 8.67 (1H, dd), 7.67 (1H, dd), 7.27-7.25 (1H, m), 6.99 (2H, s), 5.50 (1H, s), 3.33-3.29 (2H, m), 2.79-2.71 (2H, m), 2.51-2.24 (10H, m), 1.94-1.89 (2H, m), 1.07 (3H, t), 1.04 (3H, t)

<Compound of the Formula 1-155>

¹H NMR (CDCl₃)

δ ppm: 9.02-9.01 (1H, m), 8.04 (1H, dd), 7.23 (1H, dd), 6.98 (2H, s), 5.53 (1H, s), 3.93 (3H, s), 3.32 (2H, t), 2.76 (2H, t), 2.51-2.23 (10H, m), 1.92 (2H, q), 1.05 (6H, q)

<Compound of the Formula 1-157>

¹H NMR (CDCl₃)

δ ppm: 8.36 (1H, dd), 7.55 (1H, dd), 6.98-6.95 (3H, m), 5.46 (1H, s), 3.30 (2H, dt), 2.80-2.73 (2H, m), 2.52-2.25 (10H, m), 1.92 (2H, q), 1.07 (3H, t), 1.04 (3H, t)

<Compound of the Formula 1-160>

¹H NMR (CDCl₃)

δ ppm: 6.98 (2H, s), 5.75 (1H, s), 5.55 (1H, s), 3.94 (6H, s), 3.29-3.18 (2H, m), 2.76-2.69 (2H, m), 2.47-2.26 (10H, m), 1.96 (2H, q), 1.07 (6H, q)

<Compound of the Formula 1-161>

¹H NMR (CDCl₃)

δ ppm: 6.98 (2H, s), 6.84-6.78 (2H, m), 6.62 (1H, tt), 5.52 (1H, s), 3.03 (2H, ddd), 2.72 (2H, dt), 2.48-2.25 (10H, m), 1.87 (2H, dd), 1.07 (6H, dt)

<Compound of the Formula 1-70>

¹H NMR (CDCl₃)

δ ppm: 7.61 (2H, d), 7.07 (2H, d), 6.97 (2H, s), 5.72 (1H, s), 3.04-2.92 (2H, m), 2.72-2.63 (2H, m), 2.45-2.21 (10H, m), 1.81 (2H, q), 1.08 (3H, t), 1.04 (3H, t)

<Compound of the Formula 1-75>

¹H NMR (CDCl₃)

δ ppm: 7.34-7.28 (4H, m), 6.98 (2H, s), 5.46 (1H, s), 2.99 (2H, dt), 2.71-2.64 (2H, m), 2.43-2.23 (10H, m), 1.82 (2H, q), 1.31 (9H, s), 1.08 (3H, t), 1.04 (3H, t)

<Compound of the Formula 1-109>

¹H NMR (CDCl₃)

δ ppm: 8.74 (2H, d), 6.98 (2H, s), 5.50 (1H, s), 3.28 (2H, dt), 2.79-2.73 (2H, m), 2.52-2.25 (10H, m), 1.96 (2H, q), 1.09-1.03 (6H, m)

<Compound of the Formula 1-112>

¹H NMR (CDCl₃)

δ ppm: 8.62 (1H, d), 7.74 (1H, dd), 7.60 (1H, d), 6.98 (2H, s), 5.51 (1H, s), 3.15-3.07 (2H, m), 2.75-2.68 (2H, m), 2.47-2.24 (10H, m), 1.89 (2H, q), 1.09 (3H, t), 1.05 (3H, t)

<Compound of the Formula 1-115>

¹H NMR (CDCl₃)

δ ppm: 8.70 (1H, s), 8.51 (1H, s), 6.98 (2H, s), 5.49 (1H, s), 3.33 (2H, dt), 2.79-2.72 (2H, m), 2.51-2.24 (10H, m), 1.93 (2H, q), 1.07 (3H, t), 1.04 (3H, t)

<Compound of the Formula 1-118>

¹H NMR (CDCl₃)

δ ppm: 7.56 (1H, d), 7.49 (1H, d), 6.98 (2H, s), 5.48 (1H, s), 3.54-3.46 (2H, m), 2.79-2.70 (2H, m), 2.53-2.27 (10H, m), 2.06-1.99 (2H, m), 1.08 (3H, t), 1.06 (3H, t)

<Compound of the Formula 1-121>

¹H NMR (CDCl₃)

δ ppm: 8.61 (1H, d), 7.72 (1H, dd), 7.23 (1H, dd), 6.98 (2H, s), 3.29 (2H, ddd), 2.76 (2H, ddd), 2.52-2.23 (10H, m), 1.95-1.89 (2H, m), 1.06 (3H, dt)

<Compound of the Formula 1-169>

¹H NMR (CDCl₃)

δ ppm: 7.21-7.06 (3H, m), 6.95 (2H, s), 5.64 (1H, s), 2.97 (2H, ddd), 2.68 (2H, dt), 2.48-2.22 (10H, m), 1.83-1.74 (2H, m), 1.12-0.99 (6H, m)

Preparation Example 1-50

Preparation of the Compound of the Formula (1-134)

<Preparation of the Compound of the Formula 35-1>

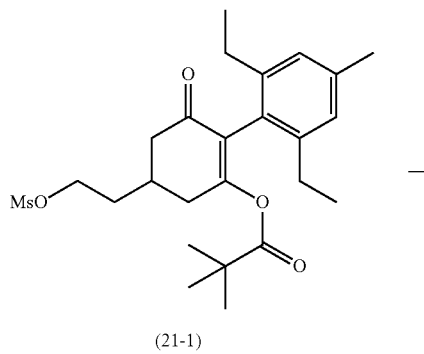

(21-1)

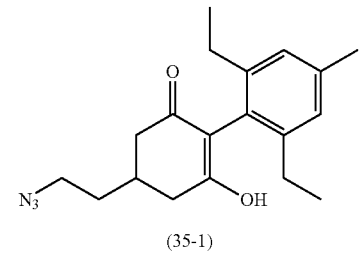

(35-1)

At RT, the compound of the formula (21-1) 360 mg was dissolved in N,N-dimethylformamide 4 ml and thereto were added sodium azide 500 mg and 15-crown-5-ether 0.015 ml. The resulting mixture solutions were heated to 100° C. and stirred for about 4 hours. Thereafter, the resulting reaction mixtures were concentrated under reduced pressure and subjected to a silica gel column chromatography (eluates, ethyl acetate:hexane=34:66) to give the compound of the formula (35-1) 180 mg.

¹H NMR (CDCl₃)

δ ppm: 6.98 (2H, s), 5.79 (1H, s), 3.44-3.40 (2H, m), 2.71-2.64 (2H, m), 2.44-2.24 (10H, m), 1.77 (2H, q), 1.07 (6H, td)

<Preparation of the Compound of the Formula 1-134>

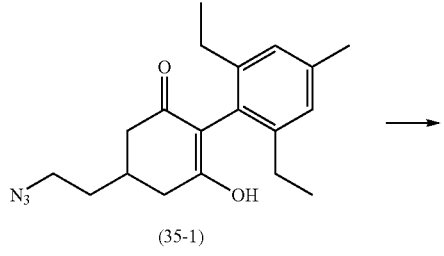

(35-1)

-continued (1-134)

At RT, the compound of the formula (35-1) 100 mg and 1-ethynyl-4-fluorobenzene 40 mg were dissolved in a mixture solution of acetonitrile 4 ml and dimethyl sulfoxide 1 ml and to the resulting mixture solutions were added sodium ascorbate 7 mg and cupper sulfate 3 mg and the resulting mixtures were heated under reflux for about 5 hours. Thereafter, the resulting reaction mixture solutions were concentrated under reduced pressure and subjected to a silica gel column chromatography (eluates, ethyl acetate:hexane 66:34) to give the compound of the formula (1-134) 54.1 mg.

$^1$H NMR (CDCl$_3$)

δ ppm: 7.83-7.78 (2H, m), 7.75 (1H, s), 7.13 (2H, t), 6.98 (2H, s), 5.77 (1H, s), 4.57-4.46 (2H, m), 2.80-2.67 (2H, m), 2.52-2.12 (12H, m), 1.04 (6H, q)

The present compounds prepared according to preparation Example 1-50 are shown below.

<Compound of the Formula 1-135>

$^1$H NMR (CDCl$_3$)

δ ppm: 7.95 (2H, d), 7.88 (1H, s), 7.69 (2H, d), 6.97 (2H, s), 5.79 (1H, s), 4.60-4.48 (2H, m), 2.80-2.68 (2H, m), 2.53-2.12 (12H, m), 1.04 (6H, q)

Next, the formulation examples are shown below. Here the present compound is expressed as the number of a structural formula.

Formulation 1
Wettable Powder

| | |
|---|---|
| Compound (1-1) | 50% by weight |
| Sodium ligninsulfonate | 5% by weight |
| Polyoxyethylene alkyl ether | 5% by weight |
| White carbon | 5% by weight |
| Clay | 35% by weight |

The ingredients shown above are mixed and ground to obtain a wettable powder.

The compound (1-1) is replaced with any of the compounds (1-2) to (1-171) to obtain respective formulations.

Formulation 2
Granules

| | |
|---|---|
| Compound (1-1) | 1.5% by weight |
| Sodium ligninsulfonate | 2% by weight |
| Talc | 40% by weight |
| Bentonite | 56.5% by weight |

The ingredients shown above are mixed, and the resulting mixtures is added water and fully kneaded, and then subjected to granulation and drying to obtain a granule.

The compound (1-1) is replaced with any of the compounds (1-2) to (1-171) to obtain respective formulations.

Formulation 3
Suspension Concentrates

| | |
|---|---|
| Compound (1-1) | 10% by weight |
| Mixture of polyoxyethylene alkylether sulfate ammonium salt and white carbon (weight ratio 1:1) | 35% by weight |
| Water | 55% by weight |

The ingredients shown above are mixed, and the resulting mixtures are then subjected to fine grinding according to wet grinding method, to obtain a suspension concentrate.

The compound (1-1) is replaced with any of the compounds (1-2) to (1-171) to obtain respective formulations.

Next, test examples are shown below.

Here an efficacy for controlling weeds on the present compound was visually observed and evaluated in 11 criteria of 0 to 10 (o represents no action, 10 represents complete death and the intermediate efficacy were evaluated in 1 to 9 criteria).

Test 1-1 Post-Emergence Treatment Test

Commercial soil for propagation was put in a pot measuring 8 cm in diameter and 6.5 cm in height, and in the pot, seeds of *Echinochloa crus-galli* were sown, and then covered with soil of about 0.5 cm thickness and the plants were grown in a greenhouse. When the plants were grown to 1-2 leaf stages, a predetermined amount of a chemical diluted solution containing a compound (1-1) was uniformly spayed on the whole plants. Here the chemical diluted solution was prepared by dissolving a predetermined amount of the compound (1-1) in dimethylformamide solution containing 2% of Tween 20 (polyoxyetylene sorbitan fatty acid ester) (manufactured by MP Biomedicals Inc.) and then diluting the solution with deionized water. After spraying, plants were grown in a greenhouse and after 20 days of the treatment, the efficacy for *Echinochloa crus-galli* was observed and the controlling effect was evaluated.

Similarly, the present compounds (1-2)~(1-23), (1-29)~(1-31), (1-33)~(1-36), (1-40)~(1-41), (1-44), (1-58)~(1-71), (1-73)~(1-75), (1-78), (1-83)~(1-84), (1-91)~(1-92), (1-94)~(1-95), (1-97)~(1-98), (1-100), (1-102)~(1-105), (1-107)~(1-109), (1-112), (1-115), (1-118), (1-121), (1-127)~(1-128), (1-134)~(1-162), (1-165)~(1-169), (1-171), (1-13-A) and (1-13-B) were also tested.

As a result, compounds (1-1)~(1-23), (1-29)~(1-31), (1-33)~(1-36), (1-40)~(1-41), (1-44), (1-58)~(1-71), (1-73)~(1-75), (1-78), (1-83)~(1-84), (1-91)~(1-92), (1-94)~(1-95), (1-97)~(1-98), (1-100), (1-102)~(1-105), (1-107)~(1-109), (1-112), (1-115), (1-118), (1-121), (1-127)~(1-128), (1-134)~(1-162), (1-165)~(1-169), (1-171), (1-13-A) and (1-13-B) were all shown an efficacy of 9 or more at a treatment amount of chemicals of 1.000 g/10000 m$^2$.

Test 1-2 Post-Emergence Treatment Test

Commercial soil for propagation was put in a pot measuring 8 cm in diameter and 6.5 cm in height, and in the pot, seeds of *Galium aparine* were sown, and then covered with soil of about 0.5 cm thickness and the plants were grown in a greenhouse. When the plants were grown to 1-2 leaf stages, a predetermined amount of a chemical diluted solution containing a compound (1-2) was uniformly spayed on the whole plants. Here the chemical diluted solution was prepared similarly to the test example 1-1. After spraying, plants were grown in a greenhouse and after 20 days of the treatment, the efficacy for *Galium aparine* was observed and evaluated.

Similarly, the present compounds (1-5), (1-12), (1-14), (1-98), (1-99), (1-100) and (1-162) were also tested.

As a result, compounds (1-5), (1-12), (1-14), (1-98), (1-99), (1-100) and (1-162) were all shown an efficacy of 7 or more at a treatment amount of chemicals of 1.000 g/10000 m².

Test 2-1 Pre-Emergence Treatment Test

Steam sterilized field soil was put in a pot measuring 8 cm in diameter and 6.5 cm in height, and in the pot, seeds of *Echinochloa crus-galli* were sown, and then covered with soil of about 0.5 cm thickness. Then a predetermined amount of a chemical diluted solution containing a compound (1-1) was uniformly spayed on the soil surface. Here the chemical diluted solution was prepared similarly to the test example 1-1. After chemical treatment, plants were grown in a greenhouse, and after 3 weeks of the spraying, the efficacy for *Echinochloa crus-galli* was observed and evaluated.

Similarly, the present compounds (1-2)~(1-20), (1-23), (1-29)~(1-31), (1-33)~(1-36), (1-40)~(1-41), (1-44), (1-58)~(1-71), (1-73)~(1-75), (1-78), (1-83)~(1-84), (1-91)~(1-92), (1-94)~(1-95), (1-97)~(1-98), (1-100), (1-102)~(1-104), (1-109), (1-112), (1-115), (1-118), (1-121), (1-127)~(1-128), (1-134)~(1-146), (1-148)~(1-162), (1-165)~(1-169), (1-13-A) and (1-13-B) were also tested.

As a result, compounds (1-1)~(1-20), (1-23), (1-29)~(1-31), (1-33)~(1-36), (1-40)~(1-41), (1-44), (1-58)~(1-71), (1-73)~(1-75), (1-78), (1-83)~(1-84), (1-91)~(1-92), (1-94)~(1-95), (1-97)~(1-98), (1-100), (1-102)~(1-104), (1-109), (1-112), (1-115), (1-118), (1-121), (1-127)~(1-128), (1-134)~(1-146), (1-148)~(1-162), (1-165)~(1-169), (1-13-A) and (1-13-B) were all shown an efficacy of 7 or more at a treatment amount of chemicals of 1.000 g/10000 m².

INDUSTRIAL APPLICABILITY

The present compound shows an efficacy for controlling weeds.

The invention claimed is:
1. A cyclohexanone compound of the formula (I):

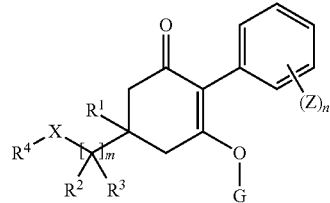

wherein
m is an integer of 1, 2 or 3;
n is an integer of any one of 1 to 5;
X represents $CH_2$, O, $NR^9$, S, S(O) or $S(O)_2$;
$R^1$ represents a hydrogen atom or a methyl group;
$R^2$ and $R^3$ represent independently of each other a hydrogen atom, a $C_{1-6}$ alkyl group, a $C_{1-6}$ haloalkyl group, a $C_{3-8}$ cycloalkyl group, a $C_{3-8}$ halocycloalkyl group, a $(C_{1-6}$ alkyl)$C_{3-8}$ cycloalkyl group, a $(C_{3-8}$ cycloalkyl)$C_{1-6}$ alkyl group, a $(C_{3-8}$ cycloalkyl)$C_{3-8}$ cycloalkyl group, a $(C_{3-8}$ halocycloalkyl)$C_{1-6}$ alkyl group or a $\{(C_{1-6}$ alkyl)$C_{3-8}$ cycloalkyl$\}C_{1-6}$ alkyl group, or $R^2$ and $R^3$ connect each other to represent a $C_{2-5}$ alkylene chain, or $R^2$ and $R^3$ combine each other to represent a $C_{1-3}$ alkylidene group optionally having one or more halogen atoms (with the proviso that when m is 2 or 3, two or three $R^2$ may be same or different to each other and two or three $R^3$ may be same or different to each other);

$R^4$ represents a $C_{6-10}$ aryl group or a five- to six-membered heteroaryl group (with the proviso that the $C_{6-10}$ aryl group and the five- or six-membered heteroaryl group may have one or more substituents selected from the group consisting of a halogen atom, a cyano group, a nitro group, an amino group, a $(C_{1-6}$ alkyl)amino group, a $(C_{1-6}$ alkyl)($C_{1-6}$ alkyl)amino group, a benzoylamino group, an aminocarbonyl group, a $(C_{1-6}$ alkyl)aminocarbonyl group, a $(C_{1-6}$ alkyl)($C_{1-6}$ alkyl)aminocarbonyl group, a pentafluorothio group, a $C_{1-6}$ alkyl group, a $C_{2-6}$ alkenyl group, a $C_{2-6}$ alkynyl group, a $C_{1-6}$ alkoxy group, a $C_{1-6}$ alkylthio group, a $C_{3-6}$ alkenyloxy group, a $C_{3-6}$ alkynyloxy group, a $C_{6-10}$ aryl group, a $C_{6-10}$ aryloxy group, a $C_{1-6}$ alkylsulfinyl group, a $C_{1-6}$ alkylsulfonyl group, a hydroxyl group, a $(C_{1-6}$ alkyl)carbonyl group, a hydroxycarbonyl group, a $(C_{1-6}$ alkoxy)carbonyl group and a $(C_{6-10}$ aryl)$C_{1-6}$ alkoxy group, and when two or more substituents exist, the substituents may be same or different to each other; and the $(C_{1-6}$ alkyl)amino group, the $(C_{1-6}$ alkyl)($C_{1-6}$ alkyl)amino group, the benzoylamino group, the $(C_{1-6}$ alkyl)aminocarbonyl group, the $(C_{1-6}$ alkyl)($C_{1-6}$ alkyl)aminocarbonyl group, the $C_{1-6}$ alkyl group, the $C_{2-6}$ alkenyl group, the $C_{2-6}$ alkynyl group, the $C_{1-6}$ alkoxy group, the $C_{1-6}$ alkylthio group, the $C_{3-6}$ alkenyloxy group, the $C_{3-6}$ alkynyloxy group, the $C_{6-10}$ aryl group, the $C_{6-10}$ aryloxy group, the $C_{1-6}$ alkylsulfinyl group, the $C_{1-6}$ alkylsulfonyl group, the $(C_{1-6}$ alkoxy)carbonyl group and the $(C_{6-10}$ aryl)$C_{1-6}$ alkoxy group may each have one or more halogen atoms or $C_{1-3}$ haloalkyl groups, and when two or more halogen atoms or $C_{1-3}$ haloalkyl groups exist, the halogen atoms or the $C_{1-3}$ haloalkyl groups may be same or different to each other respectively);

G represents a hydrogen atom or a group of any one of the following formulae:

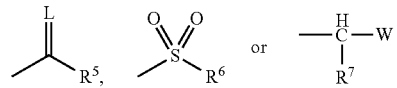

{wherein
L represents an oxygen atom or a sulfur atom;
$R^5$ represents a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a $(C_{6-10}$ aryl)$C_{1-6}$ alkyl group, a $C_{1-6}$ alkoxy group, a $C_{3-8}$ cycloalkoxy group, a $C_{3-6}$ alkenyloxy group, a $C_{3-6}$ alkynyloxy group, a $C_{6-10}$ aryloxy group, a $(C_{6-10}$ aryl)$C_{1-6}$ alkoxy group, a $(C_{1-6}$ alkyl)($C_{1-6}$ alkyl)amino group, a $(C_{3-6}$ alkenyl)($C_{3-6}$ alkenyl)amino group, a $(C_{1-6}$ alkyl)($C_{6-10}$ aryl)amino group or a five- to six-membered heteroaryl group (with the proviso that these groups may each one or more halogen atom, and when two or more halogen atoms exist, the halogen atoms may be same or different to each other; and the $C_{3-8}$ cycloalkyl group, the $C_{6-10}$ aryl group, an aryl moiety of the $(C_{6-10}$ aryl)$C_{1-6}$ alkyl group, a $C_{3-8}$ cycloalkoxy group, a $C_{6-10}$ aryloxy group, an aryl moiety of the $(C_{6-10}$ aryl)$C_{1-6}$ alkoxy group, an aryl moiety of the $(C_{1-6}$ alkyl)($C_{6-10}$ aryl)amino group and a five- to six-membered heteroaryl group may each have one or more $C_{1-6}$ alkyl groups, and when two or more $C_{1-6}$ alkyl groups exist, the alkyl groups may be same or different to each other);

$R^6$ represents a $C_{1-6}$ alkyl group, a $C_{6-10}$ aryl group or a ($C_{1-6}$ alkyl)($C_{1-6}$ alkyl)amino group (with the proviso that these groups may each have one or more halogen atoms and when two or more halogen atoms exist, the halogen atoms may be same or different to each other; and the $C_{6-10}$ aryl group may have one or more $C_{1-6}$ alkyl groups and when two or more $C_{1-6}$ alkyl groups exist, the alkyl groups may be same or different to each other);

$R^7$ represents a hydrogen atom or a $C_{1-6}$ alkyl group;

W represents a $C_{1-6}$ alkoxy group, a $C_{1-6}$ alkylthio group, a $C_{1-6}$ alkylsulfinyl group or a $C_{1-6}$ alkylsulfonyl group (with the proviso that these groups may each have one or more halogen atoms and when two or more halogen atoms exist, the halogen atoms may be same or different to each other)};

$R^9$ represents a hydrogen atom, a $C_{1-6}$ alkyl group, a $C_{6-10}$ aryl group, a $C_{6-10}$ arylthio group, a $C_{6-10}$ arylsulfinyl group, a $C_{6-10}$ arylsulfonyl group (with the proviso that the $C_{1-6}$ alkyl group may have one or more halogen atoms, and when two or more halogen atoms exist, the halogen atoms may be same or different to each other; the $C_{6-10}$ aryl group, the $C_{6-10}$ arylthio group, the $C_{6-10}$ arylsulfinyl group and the $C_{6-10}$ arylsulfonyl group may have one or more substituents selected from the group consisting of a halogen atom, a cyano group, a nitro group and an amino group);

Z represents a halogen atom, a cyano group, a nitro group, a $C_{1-6}$ alkyl group, a $C_{2-6}$ alkenyl group, a $C_{2-6}$ alkynyl group, a $C_{1-6}$ alkoxy group, a ($C_{1-6}$ alkyl)carbonyl group, a $C_{1-6}$ alkylthio group, a $C_{6-10}$ aryloxy group, a five- or six-membered heteroaryloxy group, a $C_{3-8}$ cycloalkyl group, a $C_{6-10}$ aryl group or a five- to six-membered heteroaryl group (with the proviso that the $C_{1-6}$ alkyl group, the $C_{2-6}$ alkenyl group, the $C_{2-6}$ alkynyl group, the $C_{1-6}$ alkoxy group, the ($C_{1-6}$ alkyl)carbonyl group and the $C_{1-6}$ alkylthio group may each have one or more halogen atoms, and when two or more halogen atoms exist, the halogen atoms may be same or different to each other; and the $C_{6-10}$ aryl group, a five- to six-membered heteroaryl group, a $C_{6-10}$ aryloxy group and the five- to six-membered heteroaryloxy group may each have one or more substituents selected from the group consisting of a halogen atom, a $C_{1-6}$ alkyl group and a $C_{1-6}$ haloalkyl group, and when two or more substituents exist, the substituents may be same or different to each other; and the $C_{3-8}$ cycloalkyl group may have one or more substituents selected from the group consisting of a halogen atom and a $C_{1-6}$ alkyl group, and when two or more substituents exist, the substituents may be same or different to each other; when n is an integer of 2 or more, Z may be same or different to each other).

2. The cyclohexanone compound according to claim 1 wherein n is an integer of any one of 1 to 3;

X represents $CH_2$, O, $NR^9$, S, S(O) or $S(O)_2$;

$R^1$ represents a hydrogen atom;

$R^2$ and $R^3$ represent independently of each other a hydrogen atom or a $C_{1-3}$ alkyl group, or $R^2$ and $R^3$ connect each other to represent a $C_{2-5}$ alkylene chain (with the proviso that when m is 2 or 3, two or three $R^2$ may be same or different to each other and two or three $R^3$ may be same or different to each other);

$R^4$ represents a phenyl group, a 2-pyridyl group, a 3-pyridyl group, a 4-pyridyl group, a 2-pyrimidinyl group, a 2-pyrazinyl group, a 3-pyridazinyl group, a 3-furyl group, a 2-thienyl group, a 2-thiazolyl group or a 1,2,3-triazolyl group (with the proviso that the phenyl group, the 2-pyridyl group, the 3-pyridyl group, the 4-pyridyl group, the 2-pyrimidinyl group, the 2-pyrazinyl group, the 3-pyridazinyl group and the 3-furyl group, the 2-thienyl group and the 2-thiazolyl group may each have one or more substituents selected from the group consisting of a halogen atom, a $C_{1-3}$ alkyl group, a hydroxyl group, a ($C_{1-3}$ alkyl)carbonyl group, a ($C_{1-3}$ alkoxy)carbonyl group, a $C_{1-3}$ alkoxy group, a $C_{1-3}$ haloalkyl group, a $C_{1-3}$ alkylthio group, a $C_{1-3}$ haloalkylthio group, a cyano group, a nitro group, an amino group, a pentafluorothio group, a benzoylamino group and a $C_{1-3}$ haloalkoxy group, and when two or more substituents exist, the substituents may be same or different to each other; and the 1,2,3-triazolyl group may be substituted with a $C_{6-10}$ aryl group and the $C_{6-10}$ aryl group may have one or more halogen atoms or $C_{1-3}$ haloalkyl groups, and when two or more halogen atoms or $C_{1-3}$ haloalkyl groups exist, the halogen atoms or the $C_{1-3}$ haloalkyl groups may be same or different respectively);

G represents a hydrogen atom or a group of any one of the following formulae:

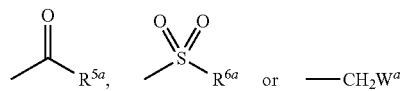

{wherein $R^{5a}$ represents a $C_{1-6}$ alkyl group, a $C_{6-10}$ aryl group, a $C_{1-6}$ alkoxy group, a $C_{3-6}$ alkenyloxy group, a $C_{3-6}$ alkynyloxy group or a $C_{6-10}$ aryloxy group;

$R^{6a}$ represents a $C_{1-6}$ alkyl group;

$W^a$ represents a $C_{1-3}$ alkoxy group};

$R^9$ represents a hydrogen atom, a $C_{1-6}$ alkyl group or a $C_{6-10}$ arylsulfonyl group (with the proviso that the $C_{1-6}$ alkyl group may have one or more halogen atoms, and when two or more halogen atoms exist, the halogen atoms may be same or different to each other; and the $C_{6-10}$ arylsulfonyl group may have one or more substituents selected from the group consisting of a halogen atom and a nitro group, and when two or more substituents exist, the substituents may be same or different to each other);

Z represents a halogen atom, a $C_{1-3}$ alkyl group, a $C_{2-6}$ alkenyl group, a $C_{2-6}$ alkynyl group, a $C_{1-3}$ alkoxy group, a $C_{3-8}$ cycloalkyl group, a nitro group, a phenyl group or a five- to six-membered heteroaryloxy group (with the proviso that the $C_{1-3}$ alkyl group, the $C_{2-6}$ alkenyl group, the $C_{2-6}$ alkynyl group, the $C_{1-3}$ alkoxy group, the phenyl group and the five- to six-membered heteroaryloxy group may have one or more halogen atoms, and when two or more halogen atoms exist, the halogen atoms may be same or different to each other.

3. The cyclohexanone compound according to claim 2 wherein m is 2;

X represents $CH_2$, O, $NR^9$, S, S(O) or $S(O)_2$;

$R^2$ and $R^3$ represents independently of each other a hydrogen atom, a methyl group or an ethyl group, or $R^2$ and $R^3$ connect each other to represent an ethylene chain (with the proviso that two $R^2$ may be same or different to each other and two $R^3$ may be same or different to each other);

$R^4$ represents a phenyl group, a 2-pyridyl group, a 3-pyridyl group, a 4-pyridyl group, a 2-pyrimidinyl group, a 2-pyrazinyl group, a 3-pyridazinyl group, a 3-furyl group, a 2-thienyl group, a 2-thiazolyl group or a 1,2,3-triazolyl group (with the proviso that the phenyl group, the 2-pyridyl group, the 3-pyridyl group, the 4-pyridyl group, the 2-pyrimidinyl group, the 2-pyrazinyl group, the 3-pyridazinyl group and the 3-furyl group, the 2-thienyl group and the 2-thiazolyl group have each one or more substituents selected from the group consisting of a chlorine atom, a bromine atom, an iodine atom, a fluorine atom, a methyl group, an ethyl group, an isopropyl group, a tert-butyl group, a methoxy group, a nitro group, an amino group, a cyano group, a hydroxyl group, an acetyl group, a methoxycarbonyl group, a pentafluorothio group, a pentafluoroethyl group, a difluoroethyl group, a heptafluoroisopropyl group, a trifluoromethylthio group, a benzoylamino group, a trifluoromethoxy group and a trifluoromethyl group; and the 1,2,3-triazolyl group may be substituted with a phenyl group, and the phenyl group has one or more substituents selected from the group consisting of a chlorine atom, a bromine atom, an iodine atom, a fluorine atom and a trifluoromethyl group);

G represents a hydrogen atom, an acetyl group, a propionyl group, a butyryl group, a benzoyl group, a methylsulfonyl group, a methoxycarbonyl group, an ethoxycarbonyl group, an allyoxycarbonyl group, a phenoxycarbonyl group, a methoxymethyl group or an ethoxymethyl group;

$R^9$ represents a hydrogen atom, a 2-nitrophenylsulfonyl group or a methyl group;

Z represents a methyl group, an ethyl group, a phenyl group, a vinyl group, a cyclopropyl group, a nitro group, a fluorine atom, a chlorine atom, a bromine atom, a methoxy group, a trifluoromethyl group, a 5-trifluoromethyl-2-chloropyridyloxy group or an ethynyl group.

4. A cyclohexanone compound of the formula (II):

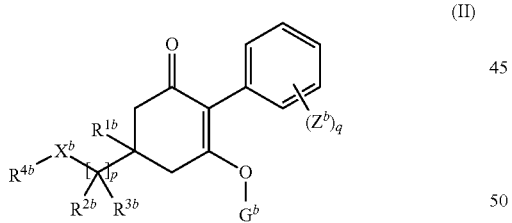

(II)

wherein
p is an integer of 1, 2 or 3;
q is an integer of any one of 1 to 5;
$X^b$ represents $CH_2$, O, S, S(O) or $S(O)_2$;
$R^{1b}$ represents a hydrogen atom or a methyl group;
$R^{2b}$ and $R^{3b}$ represent independently of each other a hydrogen atom, a $C_{1-6}$ alkyl group, a $C_{1-6}$ haloalkyl group, a $C_{3-8}$ cycloalkyl group, a $C_{3-8}$ halocycloalkyl group, a $(C_{1-6}$ alkyl$)C_{3-8}$ cycloalkyl group, a $(C_{3-8}$ cycloalkyl$)C_{1-6}$ alkyl group, a $(C_{3-8}$ cycloalkyl$)C_{3-8}$ cycloalkyl group, a $(C_{3-8}$ halocycloalkyl$)C_{1-6}$ alkyl group or a $\{(C_{1-6}$ alkyl$)C_{3-8}$ cycloalkyl$\}C_{1-6}$ alkyl group, or $R^{2b}$ and $R^{3b}$ connect each other to represent a $C_{2-5}$ alkylene chain, or $R^{2b}$ and $R^{3b}$ combine each other to represent a $C_{1-3}$ alkylidene group optionally having one or more halogen atoms (with the proviso that when p is 2 or 3, two or three $R^{2b}$ may be same or different to each other and $R^{3b}$ may be same or different to each other);

$R^{4b}$ represents a $C_{6-10}$ aryl group or a five- to six-membered heteroaryl group (with the proviso that the $C_{6-10}$ aryl group and the five- to six-membered heteroaryl group may have one or more substituents selected from the group consisting of a halogen atom, a cyano group, a nitro group, a pentafluorothio group, a $C_{1-6}$ alkyl group, a $C_{2-6}$ alkenyl group, a $C_{2-6}$ alkynyl group, a $C_{1-6}$ alkoxy group, a $C_{1-6}$ alkylthio group, a $C_{3-6}$ alkenyloxy group, a $C_{3-6}$ alkynyloxy group and a $(C_{6-10}$ aryl$)C_{1-6}$ alkoxy group, and when two or more substituents exist, the substituents may be same or different to each other; and the $C_{1-6}$ alkyl group, the $C_{2-6}$ alkenyl group, the $C_{2-6}$ alkynyl group, the $C_{1-6}$ alkoxy group, the $C_{1-6}$ alkylthio group, the $C_{3-6}$ alkenyloxy group, the $C_{3-6}$ alkynyloxy group and the $(C_{6-10}$ aryl$)C_{1-6}$ alkoxy group may have one or more halogen atoms, and when two or more halogen atoms exist, the halogen atoms may be same or different to each other);

$G^b$ represents a hydrogen atom or a group of any one of the following formulae:

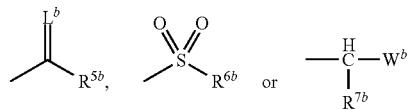

{wherein
$L^b$ represents an oxygen atom or a sulfur atom;
$R^{5b}$ represents a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a $(C_{6-10}$ aryl$)C_{1-6}$ alkyl group, a $C_{1-6}$ alkoxy group, a $C_{3-8}$ cycloalkoxy group, a $C_{3-6}$ alkenyloxy group, a $C_{3-6}$ alkynyloxy group, a $C_{6-10}$ aryloxy group, a $(C_{6-10}$ aryl$)C_{1-6}$ alkoxy group, a $(C_{1-6}$ alkyl$)(C_{1-6}$ alkyl)amino group, a $(C_{3-6}$ alkenyl$)(C_{3-6}$ alkenyl)amino group, a $(C_{1-6}$ alkyl$)(C_{6-10}$ aryl)amino group or a five- to six-membered heteroaryl group (with the proviso that these groups may each have one or more halogen atoms, when two or more halogen atoms exist, the halogen atoms may be same or different to each other; and the $C_{3-8}$ cycloalkyl group, the $C_{6-10}$ aryl group, an aryl moiety of the $(C_{6-10}$ aryl$)C_{1-6}$ alkyl group, the $C_{3-8}$ cycloalkoxy group, the $C_{6-10}$ aryloxy group, an aryl moiety of the $(C_{6-10}$ aryl$)C_{1-6}$ alkoxy group, an aryl moiety of the $(C_{1-6}$ alkyl$)(C_{6-10}$ aryl)amino group and a five- to six-membered heteroaryl group may each one or more $C_{1-6}$ alkyl groups, and when two or more $C_{1-6}$ alkyl groups exist, the alkyl groups may be same or different to each other);

$R^{6b}$ represents a $C_{1-6}$ alkyl group, a $C_{6-10}$ aryl group or a $(C_{1-6}$ alkyl$)(C_{1-6}$ alkyl)amino group (with the proviso that these groups may have one or more halogen atoms, and when two or more halogen atoms exist, the halogen atoms may be same or different to each other; and the $C_{6-10}$ aryl group may have one or more $C_{1-6}$ alkyl groups, and when two or more $C_{1-6}$ alkyl groups exist, the alkyl groups may be same or different to each other);

$R^{7b}$ represents a hydrogen atom or a $C_{1-6}$ alkyl group;

$W^b$ represents a $C_{1-6}$ alkoxy group, a $C_{1-6}$ alkylthio group, a $C_{1-6}$ alkylsulfinyl group or a $C_{1-6}$ alkylsulfonyl group (with the proviso that these groups may each have one or more halogen atoms, and when two or more halogen atoms exist, the halogen atoms may be same or different to each other)};

$Z^b$ represents a halogen atom, a cyano group, a nitro group, a phenyl group, a $C_{1-6}$ alkyl group, a $C_{2-6}$ alkenyl group, a $C_{2-6}$ alkynyl group, a $C_{1-6}$ alkoxy group, a $C_{1-6}$ alkylthio group, a $C_{6-10}$ aryloxy group, a five- to six-membered heteroaryloxy group or a $C_{3-8}$ cycloalkyl group (with the proviso that the $C_{1-6}$ alkyl group, the $C_{2-6}$ alkenyl group, the $C_{2-6}$ alkynyl group, the $C_{1-6}$ alkoxy group and the $C_{1-6}$ alkylthio group may have one or more halogen atoms, and when two or more halogen atoms exist, the halogen atoms may be same or different to each other; and the phenyl group, the $C_{6-10}$ aryloxy group and the five- to six-membered heteroaryloxy group may have one or more substituents selected from the group consisting of a halogen atom, a $C_{1-6}$ alkyl group and a $C_{1-6}$ haloalkyl group, and when two or more substituents exist, the substituents may be same or different to each other; and the $C_{3-8}$ cycloalkyl group may have one or more substituents selected from the group consisting of a halogen atom and a $C_{1-6}$ alkyl group, and when two or more substituents exist, the substituents may be same or different to each other; when q is an integer of 2 or more, $Z^b$ may be same or different to each other).

5. The cyclohexanone compound according to claim 4 wherein n is an integer of any one of 1 to 3;

$R^{1b}$ represents a hydrogen atom;

$R^{2b}$ and $R^{3b}$ represent independently of each other a hydrogen atom or a $C_{1-3}$ alkyl group (with the proviso that when p is 2 or 3, two or three $R^{2b}$ may be same or different to each other and two or three $R^{3b}$ may be same or different to each other);

$R^{4b}$ represents a phenyl group or a 2-pyridyl group (with the proviso that the phenyl group and the 2-pyridyl group may have one or more substituents selected from the group consisting of a halogen atom, a $C_{1-3}$ alkyl group, a $C_{1-3}$ alkoxy group, a $C_{1-3}$ haloalkyl group, a nitro group, a pentafluorothio group and a $C_{1-3}$ haloalkoxy group, and when two or more substituents exist, the substituents may be same or different to each other;

$G^b$ represents a hydrogen atom or a group of any one of the following formulae:

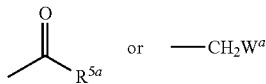

{wherein $R^{5a}$ represents a $C_{1-6}$ alkyl group, a $C_{6-10}$ aryl group, a $C_{1-6}$ alkoxy group, a $C_{3-6}$ alkenyloxy group, a $C_{3-6}$ alkynyloxy group or a $C_{6-10}$ aryloxy group; and $W^a$ represents a $C_{1-3}$ alkoxy group}; and $Z^b$ represents a $C_{1-3}$ alkyl group.

6. The cyclohexanone compound according to claim 5 wherein p is 2;

$R^{2b}$ and $R^{3b}$ represent independently of each other a hydrogen atom or a methyl group (with the proviso that two $R^{2b}$ may be same or different to each other and two $R^{3b}$ may be same or different to each other);

$R^{4b}$ represents a phenyl group or a 2-pyridyl group (with the proviso that the phenyl group and the 2-pyridyl group have one or more substituents selected from the group consisting of a chlorine atom, a fluorine atom, a methyl group, a methoxy group and a trifluoromethyl group);

$G^b$ represents a hydrogen atom, an acetyl group, a propionyl group, a benzoyl group, a methoxycarbonyl group, an ethoxycarbonyl group, an allyloxycarbonyl group, a phenoxycarbonyl group, a methoxymethyl group or an ethoxymethyl group; and $Z^b$ represents a methyl group or an ethyl group.

7. The cyclohexanone compound of claim 1 wherein G represents a hydrogen atom.

8. A herbicide comprising a cyclohexanone compound of claim 1 as an active ingredient.

9. A method for controlling weeds comprising applying an effective amount of the cyclohexanone compound of claim 1 to weeds or soil where weeds grow.

* * * * *